US012465578B2

(12) United States Patent
Daley et al.

(10) Patent No.: US 12,465,578 B2
(45) Date of Patent: Nov. 11, 2025

(54) SUBSTITUTED ALPHA-ETHYL PHENYLALKYLAMINES

(71) Applicant: Alexander Shulgin Research Institute, Inc., Lafayette, CA (US)

(72) Inventors: Paul F. Daley, El Sobrante, CA (US); Nicholas V. Cozzi, Slinger, WI (US)

(73) Assignee: Alexander Shulgin Research Institute, Inc., Lafayette, CA (US)

( * ) Notice: Subject to any disclaimer, the term of this patent is extended or adjusted under 35 U.S.C. 154(b) by 0 days.

(21) Appl. No.: 18/695,071

(22) PCT Filed: Sep. 26, 2022

(86) PCT No.: PCT/US2022/044771
§ 371 (c)(1),
(2) Date: Mar. 25, 2024

(87) PCT Pub. No.: WO2023/049480
PCT Pub. Date: Mar. 30, 2023

(65) Prior Publication Data
US 2024/0408038 A1 Dec. 12, 2024

Related U.S. Application Data

(60) Provisional application No. 63/248,450, filed on Sep. 25, 2021.

(51) Int. Cl.

| | |
|---|---|
| ***A61K 31/137*** | (2006.01) |
| ***A61K 45/06*** | (2006.01) |
| ***C07C 217/60*** | (2006.01) |

(52) U.S. Cl.
CPC ............ *A61K 31/137* (2013.01); *A61K 45/06* (2013.01); *C07C 217/60* (2013.01); *C07B 2200/05* (2013.01)

(58) Field of Classification Search
CPC ....... A61K 31/137; A61K 45/06; A61P 25/16; A61P 25/24; A61P 25/30; C07B 2200/05; C07B 59/002; C07C 217/60
See application file for complete search history.

(56) References Cited

U.S. PATENT DOCUMENTS 4,327,725 A 5/1982 Cortese et al.
4,624,848 A 11/1986 Lee (Continued)

FOREIGN PATENT DOCUMENTS

EP 2007397 B1 12/2008
EP 3565550 B1 11/2019

(Continued)

OTHER PUBLICATIONS

Marcher-Rørsted et al., Investigation of the 2,5-Dimethoxy Motif in Phenethylamine Serotonin 2A Receptor Agonists, ACS Chem. Neurosci., 2020, 11, pp. 1238-1244 (Year: 2020).*

(Continued)

*Primary Examiner* — Renee Claytor
*Assistant Examiner* — Andrew P Lee
(74) *Attorney, Agent, or Firm* — CALYX LAW; Graham Pechenik

(57) ABSTRACT

Provided are phenylalkylamines, such as 2,5-disubstituted and 2,4,5-trisubstituted phenylalkylamines. In some embodiments, the phenylalkylamines are asymmetrically substituted. In some embodiments, such compounds modulate the activity of monoamine receptors and/or monoamine transporters. Also provided are methods for the preparation of phenylalkylamines and pharmaceutical compositions thereof. Methods of using the phenylalkylamines, alone or in combination with other therapeutic agents, are provided. In some embodiments, phenylalkylamines are used to treat CNS disorders, such as mental health conditions and neu- (Continued)

rodegenerative disorders, or are used for the improvement of mental health or functioning.

20 Claims, 6 Drawing Sheets

(56) References Cited

U.S. PATENT DOCUMENTS

| | | | |
|---|---|---|---|
| 4,871,549 | A | 10/1989 | Ueda et al. |
| 4,933,504 | A | 6/1990 | Correale et al. |
| 4,968,509 | A | 11/1990 | Radebaugh et al. |
| 5,011,692 | A | 4/1991 | Fujioka et al. |
| 5,017,381 | A | 5/1991 | Maruyama et al. |
| 5,229,135 | A | 7/1993 | Philippon et al. |
| 5,260,068 | A | 11/1993 | Chen |
| 5,260,069 | A | 11/1993 | Chen |
| 5,456,923 | A | 10/1995 | Nakamichi et al. |
| 5,461,140 | A | 10/1995 | Heller et al. |
| 5,508,040 | A | 4/1996 | Chen |
| 5,516,527 | A | 5/1996 | Curatolo |
| 5,567,441 | A | 10/1996 | Chen |
| 5,622,721 | A | 4/1997 | Dansereau et al. |
| 5,686,105 | A | 11/1997 | Kelm et al. |
| 5,700,410 | A | 12/1997 | Nakamichi et al. |
| 5,837,284 | A | 11/1998 | Mehta et al. |
| 5,840,329 | A | 11/1998 | Bai |
| 5,977,175 | A | 11/1999 | Lin |
| 6,465,014 | B1 | 10/2002 | Moroni et al. |
| 6,875,751 | B2 | 4/2005 | Imbach et al. |
| 6,932,983 | B1 | 8/2005 | Straub et al. |
| 7,585,851 | B2 | 9/2009 | Bryant et al. |
| 7,964,580 | B2 | 6/2011 | Sofia et al. |
| 10,034,832 | B2 | 7/2018 | Salce, Jr. et al. |
| 2015/0367091 | A1 | 12/2015 | Djupesland et al. |
| 2020/0009067 | A1 | 1/2020 | Hoffman et al. |

FOREIGN PATENT DOCUMENTS

| | | | |
|---|---|---|---|
| WO | 2022038170 | A1 | 2/2022 |
| WO | 2023023351 | A1 | 2/2023 |

OTHER PUBLICATIONS

Harbeson, Deuterium in Drug Discovery and Development, Annual Reports in Medicinal Chemistry, 2011, 46, pp. 403-417 (Year: 2011).*

Holze et al. Safety pharmacology of acute LSD administration in healthy subjects [published correction appears in Psychopharmacology (Berl). Feb. 2022;239(2):661]. Psychopharmacology (Berl). 2022;239(6):1893-1905.

Huang RY, et al., Sobologram Analysis: A Comprehensive Review of Methodology and Current Research. Front in Pharmacology, 2019; 10:1222.

Izumi et al. Effects of co-administration of a selective serotonin reuptake inhibitor and monoamine oxidase inhibitors on 5-HT-related behavior in rats. European Journal of Pharmacology. 2006;532(2):258-264.

Jaiswal M, et al., Nanoemulsion: an advanced mode of drug delivery system. Biotech., 2015; 3(5):123-7.

Janssen et al. 5-HT2B receptor antagonists inhibit fibrosis and protect from RV heart failure. Biomed Res Int. 2015;2015:438403.

Johnson M, Richards W & Griffiths R, Human hallucinogen research: guidelines for safety. J Psychopharmacology, 2008;22: 603-20.

Jovel et al. Delirium due to intoxication from the novel synthetic tryptamine 5-MeO-DALT. J Forensic Sci. 2014;59(3):844-846.

Karlsson. Drugs that induce delirium. Dement Geriatr Cogn Disord. 1999; 10(5):412-415.

Katritzky et al. Preparation of 2-alkoxy-5-methoxybenzaldehydes and 2-ethoxy-5-alkoxybenzaldehydes. ARKIVOC, 2000 (vi), 868-875.

Katz et al. Characterizing the psychological state produced by LSD. J Abnorm Psychol. 1968;73(1):1-14.

Kedrowski Sma, et al., 1-Oxo-5-hydroxytryptamine: A Surprisingly Potent Agonist of the 5-HT3 (Serotonin) Receptor. Organic Letters, 2007; 9(17):3205-7.

Keri RP, et al., An overview of benzo[b]thiophene-based medicinal chemistry. European J Med Chem, 2017; 138:1002-33.

Kim et al. Critical evaluation of human oral bioavailability for pharmaceutical drugs by using various cheminformatics approaches. Pharm Res. 2014;31(4):1002-1014.

Klein et al. Investigation of the Structure-Activity Relationships of Psilocybin Analogues. ACS Pharmacol Transl Sci. 2020;4(2):533-542.

Klein et al. Receptor binding profiles and behavioral pharmacology of ring-substituted N, N-diallyltryptamine analogs. Neuropharmacology. 2018;142:231-239.

Knights et al. In Vitro Drug Metabolism Using Liver Microsomes. Curr Protoc Pharmacol. 2016;74:7.8.1-7.8.24.

Ko JW, et al. In vitro inhibition of the cytochrome P450 (CYP450) system by the antiplatelet drug ticlopidine: potent effect on CYP2C19 and CYP2D6, Br J Clin Pharmacol, 2000;29(4):343-451.

Kroenke K, et al., The PHQ9: Validity of a brief depression severity measure. Journal of General Internal Medicine. 2001;16(9):606-13.

Kushner DJ, Baker A & Dunstall TG, Pharmacological uses and perspectives of heavy water and deuterated compounds, Can. J. Physiol. Pharmacol. 1999;77:79.

Larock. Comprehensive Organic Transformations: A Guide to Functional Group Preparations. VCH Publishers. 1989.

Leth-Petersen et al. Metabolic Fate of Hallucinogenic NBOMes. Chem Res Toxicol. 2016;29(1):96-100.

Liechti ME et al., Gender Differences in the Subjective Effects of MDMA. Psychopharmacology (Berl) 2001; 154(2):161-8.

Lima et al. Acute kidney injury due to rhabdomyolysis. Saudi J Kidney Dis Transpl. 2008; 19(5):721-729.

Lin T, et al., In vitro assessment of cytochrome P450 inhibition: Strategies for increasing LC/MS based assay throughput using a one point IC50 method and multiplexing high performance liquid chromatograpy. J Pharm Sci. 2007;96(9):2485-95.

Liu & Li. TAAR1 in Addiction: Looking Beyond the Tip of the Iceberg. Front Pharmacol. 2018;9:279.

Lofdahl et al. 5-HT2B receptor antagonists attenuate myofibroblast differentiation and subsequent fibrotic responses in vitro and in vivo. Physiol Rep. 2016;4(15):e12873.

Lopez-Gimenez et al. Hallucinogens and Serotonin 5-HT2A Receptor-Mediated Signaling Pathways. Curr Top Behav Neurosci. 2018;36:45-73.

Luethi D & Liechti ME, Designer drugs: mechanism of action and adverse effects, Arch. Toxicol., 2020; 94, 1085-133.

Lukasiewicz et al. Serotonergic Psychedelics in Neural Plasticity. Front Mol Neurosci. 2021; 14:748359.

Luo et al. Normal Reference Intervals of Neutrophil-To-Lymphocyte Ratio, Platelet-To-Lymphocyte Ratio, Lymphocyte-To-Monocyte Ratio, and Systemic Immune Inflammation Index in Healthy Adults: a Large Multi-Center Study from Western China . Clin Lab. 2019 1;65(3).

Lynch T & Price A, The Effect of Cytochrome P450 Metabolism on Drug Response, Interactions, and Adverse Effects, Am Fam Physician. 2007;76(3):391-6.

Martin et al. Relation of the therapeutic alliance with outcome and other variables: a meta-analytic review. J Consult Clin Psychol. 2000;68(3):438-450.

Mas M, et al. Cardiovascular and neuroendocrine effects and pharmacokinetics of 3,4-methylenedioxymethamphetamine in humans. J Pharmacol Exp. Ther 1999;290(1):136-45.

Mitchell J, et al., Reply to: Caution at psychiatry's psychedelic frontier and Challenges with benchmarking of MDMA-assisted psychotherapy. Nat Med. 2021;27(6):1025-33.

Mithoefer MC, et al., A Manual for MDMA-Assisted Therapy in the Treatment of Postraumatic Stress Disorder. 2017 Ver 8.1.

Mithoefer MC, et al., The safety and efficacy of ±3,4-methylenedioxymethamphetamine-assisted psychotherapy in subjects with chronic, treatment-resistant posttraumatic stress disorder: the first randomized controlled pilot study. J. of Psychopharmacology. 2010;25(4):439-452.

(56) References Cited

OTHER PUBLICATIONS

Muller DM & Rentsch KM, Generation of metabolites by an automated online metabolism method using human liver microsomes with subsequent identification by LC-MS(n), and metabolism of 11 cathinones. Anal Bioanal Chem. 2012;402:2141-51.
Mundt JC, et al., Prediciton of Suicidal Behavior in Clinical Research by Lifetime Suicidal Ideation and Behavior Ascertained by the Electronic Columbia-Suicide Severity Rating Scale. The Journal of Clinical Psychiatry. 2013;74(9):887-93.
Nakagawasi et al. Monoamine oxidase and head-twitch response in mice. Mechanisms of alpha-methylated substrate derivatives. Neurotoxicology. 2004;25(1-2):223-232.
Neff KD, The Development and Validation of a Scale to Measure Self-Compassion. Self and Identity. 2003;2(3):223-50.
Nichols DE, et al., 2,3-Dihydrobenzofuran Analogues of Hallucinogenic Phenethylamines. J Med Chem, 1991; 34(1):276-81.
Nichols DE, Psychedelics, Pharmacological Reviews, 2016; 68(2):264-355.
Nichols et al. N-Benzyl-5-methoxytryptamines as Potent Serotonin 5-HT2 Receptor Family Agonists and Comparison with a Series of Phenethylamine Analogues. ACS Chem Neurosci. 2015;6(7):1165-1175.
Nichols et al. Psychedelics as Medicines: An Emerging New Paradigm. Clin Pharmacol Ther. 2017; 101(2):209-219.
Nuutinen & Panula. Histamine in neurotransmission and brain diseases. Adv Exp Med Biol. 2010;709:95-107.
Oehen P, et al., A Randomized Controlled Pilot Study of MDMA-Assisted Psychotherapy for Treatment of Resistant, chronic Post-Traumatic Stress Disorder (PTSD). Journal of Psychopharmacology. 2013:40-52.
Okamoto et al. The role of peripheral 5HT2A and 5HT1A receptors on the orofacial formalin test in rats with persistent temporomandibular joint inflammation. Neuroscience. 2005;130(2):465-474.
PCT/US2022/044771. International Search Report. Jan. 25, 2023.
PCT/US2022/044771. Search Strategy. Dec. 28, 2022.
PCT/US2022/044771. Written Opinion of the International Searching Authority. Jan. 25, 2023.
Adams CE, et al. Contingency Management for Patients with Cooccurring Disorders: Evaluation of a Case Study and Recommendations for Practitioners, Case Reports in Psychiatry, 2012, Article ID 731638.
Adler P, et al. Fluorination of carbonyls with nucleophilic fluorine. Nat. Chem. 2019;11:329-34.
Ahern E, Semkovska M. Cognitive functioning in the first-episode of major depressive disorder: A systematic review and meta-analysis. Neuropsychology. 2017;31(1):52-72.
Azra et al. AAPA PharmaSciTech., 2009;10(1):220-6.
Barry et al. Comparable efficacy of contingency management for cocaine dependence among African American, Hispanic, and White methadone maintenance clients. Psychol Addict Behav. 2009;23(1):168-174.
Berge et al., Pharmaceutical Salts. J.Pharm. Sci., 1977;66:1-19.
Boettger, et al. "Delirium in advanced age and dementia: A prolonged refractory course of delirium and lower functional status." Palliative & supportive care vol. 13,4 (2015): 1113-21.
Boyer & Shannon. "The serotonin syndrome." The New England journal of medicine vol. 352, 11 (2005): 1112-20.
Brown, et al. "Pharmacokinetics of Escalating Doses of Oral Psilocybin in Healthy Adults." Clinical pharmacokinetics 2017;56(12): 1543-1554.
Buysse Dj et al., The Pittsburgh Sleep Quality Index: a new instrument for psychiatric practice and research. Psychiatry Research. 1989;28(2):193-213.
Carter et al. "Drug-Induced Delirium" Drug Safety. 1996;15:291-301.
Casper, et al. Metabolism of the tryptamine-derived new psychoactive substances 5-MeO-2-Me-DALT, 5-MeO-2-Me-ALCHT, and 5-MeO-2-Me-DIPT and their detectability in urine studied by GC-MS, LC-MSn, and LC-HR-MS/MS. Drug Testing and Analysis. 2018;10(1):184-195.
Castellanos et al. Chronic pain and psychedelics: a review and proposed mechanism of action. Reg Anesth Pain Med. 2020;45(7):486-494.
Chan et al. Validation of the social functioning scale: Comparison and evaluation in early psychosis, autism spectrum disorder and social anxiety disorder. Psychiatry Res. 2019;276:45-55.
Chan FK, et al., Programmed Necrosis in the Cross Talk of Cell Death and Inflammation, Annu Rev Immunol. 2015;33:79-10.
Chavda VP & Shah D, Micro and Nano Technologies, Nanostructures for Cancer Therapy. Elsivier. 2017:643-718.
Chefer VI, et al., Curr Protoc Neurosci. 2009; Chapter: Unit 7.1.
Chi et al. Neuronal cell death mechanisms in major neurodegenerative diseases, Int J Mol Sci. 2018;19(10):3082.
Cozzi et al. Dimethyltryptamine and other hallucinogenic tryptamines exhibit substrate behavior at the serotonin uptake transporter and the vesicle monoamine transporter. J Neural Transm (Vienna). 2009; 116(12):1591-1599.
Crits-Cristoph P, et al., Psychosocial treatments for cocaine dependence: National Institute on Drug Abuse collaborative cocaine.
Darvesh AS, et al., In vivo brain microdialysis: advances in neuropsychopharmacology and drug discovery. Expert Opin Drug Discov. 2011; 6(2): 109-27.
Davis MH. Interpersonal Reactivity Index. 1980.
Dean et al. 2C or not 2C: phenethylamine designer drug review. J Med Toxicol. 2013;9(2):172-178.
Dos Santos et al. Hallucinogenic/psychedelic 5HT2A receptor agonists as rapid antidepressant therapeutics: Evidence and mechanisms of action. J Psychopharmacol. 2021;35(4):453-458.
Dugger BN & Dickson DW, Pathology of Neurodegenerative Diseases. Cold Spring Harb Perspect Biol. 2017;9(7):a028035.
Fabbri et al. Measuring Subjective Sleep Quality: A Review. Int J Environ Res Public Health. 2021;18(3):1082.
Flanagan & Nichols. Psychedelics as anti-inflammatory agents. Int Rev Psychiatry. 2018;30(4):363-375.
Flanagan et al. Activation of 5-HT2 Receptors Reduces Inflammation in Vascular Tissue and Cholesterol Levels in High-Fat Diet-Fed Apolipoprotein E Knockout Mice. Sci Rep. 2019;9(1):13444.
Flanagan et al. Structure-Activity Relationship Analysis of Psychedelics in a Rat Model of Asthma Reveals the Anti-Inflammatory Pharmacophore. ACS Pharmacol Transl Sci. 2020;4(2):488-502.
Foster A, et al., Deuterium isotope effects in the metabolism of drugs and xenobiotics: implications for drug design, Adv. Drug Res., 1985;14:1-36.
Frau L, et al., Effect of crowding, temperature and age on glia activation and dopaminergic neurotoxicity induced by MDMA in the mouse brain, Neurotoxicology. 2016;56:127-38.
Frau L, et al., Microglial and astroglial activation by 3,4-methylenedioxymethamphetamine (MDMA) in mice depends on S(+) enantiomer and is associated with an increase in body temperature and motility. J. Neurochem., 2013;124(1):69-78.
Gajula et al. Drug metabolic stability in early drug discovery to develop potential lead compounds. Drug Metab Rev. 2021;53(3):459-477.
Germolec et al. Markers of Inflammation. Methods Mol Biol. 2018;1803:57-79.
Gillis EP, et al., Applications of fluorine in medicinal chemistry. J Med Chem. 2015;58(21):8315-59.
Glennon R, Arylalkylamine Drugs of Abuse: An Overview of Drug Discrimination Studies, Pharmacology Biochemistry and Behavior, 1999; 64, 251-56.
Glennon R, et al., 5-HT1 and 5-HT2 binding characteristics of 1-(2,5-dimethoxy-4-bromophenyl)-2-aminopropane analogs. J Med Chem 1986;29(2):194-9.
Green BL, Trauma History Questionaire. Measurement of stress, self-report trauma, and adaptation. 1996.
Greene TA & Wuts PGM, "Protective Groups in Organic Chemistry," (Wiley, 2nd ed. 1991).
Grob CS & Grigsby J, Handbook of Medical Hallucinogens, 2021.
Gwaltney et al. Self-efficacy and smoking cessation: a meta-analysis. Psychol Addict Behav. 2009;23(1):56-66.

(56) References Cited

OTHER PUBLICATIONS

Halberstadt & Geyer. Characterization of the head-twitch response induced by hallucinogens in mice: detection of the behavior based on the dynamics of head movement. Psychopharmacology (Berl). 2013;227(4):727-739.
Halberstadt & Geyer. Effects of the hallucinogen 2,5-dimethoxy-4-iodophenethylamine (2C-I) and superpotent N-benzyl derivatives on the head twitch response. Neuropharmacology. 2014;77:200-207.
Halberstadt et al. Differential contributions of serotonin receptors to the behavioral effects of indoleamine hallucinogens in mice. J Psychopharmacol. 2011;25(11):1548-1561.
Halberstadt et al. Pharmacological characterization of the LSD analog N-ethyl-N-cyclopropyl lysergamide (ECPLA) [published correction appears in Psychopharmacology (Berl). Nov. 1, 20185;: ]. Psychopharmacology (Berl). 2019;236(2):799-808.
Harris DS, et al. "Subjective and hormonal effects of 3, 4-methylenedioxymethamphetamine (MDMA) in humans." Psychopharmacology 2002;162:396-405.
Harrison IT & Harrison S, et al., "Compendium of Synthetic Organic Methods," 1971-1996 vols. 1-8 John Wiley and Sons.
Hawker et al. Measures of adult pain: Visual Analog Scale for Pain (VAS Pain), Numeric Rating Scale for Pain (NRS Pain), McGill Pain Questionnaire (MPQ), Short-Form McGill Pain Questionnaire (SF-MPQ), Chronic Pain Grade Scale (CPGS), Short Form-36 Bodily Pain Scale (SF-36 Bps), and Measure of Intermittent and Constant Osteoarthritis Pain (ICOAP). Arthritis Care Res (Hoboken). 2011;63 Suppl 11:S240-S252.
Herndon JM, et al., Glial Cell Response to 3,4-(±)-Methylenedioxymethamphetamine and Its Metabolites, Toxicological Sciences, 2014;138(1):130-8.
Holland J, et al., Ecstasy: The Complete Guide; A Comprehensive Look at The Risks and Benefits of MDMA, 2001;82 n.2.
Pedersen AJ, Petersen Th & Linnet K, In vitro metabolism and pharmacokinetic studies on methylone, Drug Metab Dispos, 2013;41:1247-55.
Pelletier & Siegel. Wishing away inflammation? New links between serotonin and TNF signaling. Mol Interv. 2009;9(6):299-301.
Perez Silanes S, et al., J Heterocyclic Chem, 2001; 38(5):1025-30.
Perona et al. Animal models of depression in dopamine, serotonin, and norepinephrine transporter knockout mice: prominent effects of dopamine transporter deletions. Behav Pharmacol. 2008; 19(5-6):566-574.
Petry et al. "Prize reinforcement contingency management for cocaine dependence: integration with group therapy in a methadone clinic." Journal of consulting and clinical psychology. 2005;73(2):354.
Polderman. Acute renal failure and rhabdomyolysis. Int J Artif Organs. 2004;27(12):1030-1033.
Reckweg et al. A Phase 1, Dose-Ranging Study to Assess Safety and Psychoactive Effects of a Vaporized 5-Methoxy-N, N-Dimethyltryptamine Formulation (GH001) in Healthy Volunteers. Front Pharmacol. 2021;12:760671.
Redfern et al. Relationships between preclinical cardiac electrophysiology, clinical QT interval prolongation and torsade de pointes for a broad range of drugs: evidence for a provisional safety margin in drug development. Cardiovasc Res. 2003;58(1):32-45.
Revel et al. TAAR1 activation modulates monoaminergic neurotransmission, preventing hyperdopaminergic and hypoglutamatergic activity. Proc Natl Acad Sci U S A. 2011;108(20):8485-8490.
Rickli et al. Receptor interaction profiles of novel N-2-methoxybenzyl (NBOMe) derivatives of 2,5-dimethoxy-substituted phenethylamines (2C drugs). Neuropharmacology. 2015;99:546-553.
Rickli et al. Receptor interaction profiles of novel psychoactive tryptamines compared with classic hallucinogens. Eur Neuropsychopharmacol. 2016;26(8):1327-1337.
Rogers G, et al., The Harmful Effects of Recreational Ecstacy: A Systematic Review of Observational Evidence. Health Technology Assessment, 2009; 13(6): iii-iv, ix-xii, 1-315.
Salaffi et al. How to measure chronic pain: New concepts. Best Pract Res Clin Rheumatol. 2015;29(1):164-186.
Schenberg EE, Psychedelic-Assisted Psychotherapy: A Paradigm Shift in Psychiatric Research and Development. Neuropharmacology, 2018;9:733.
Segonzac et al. Tryptamine, a substrate for the serotonin transporter in human platelets, modifies the dissociation kinetics of [3H]imipramine binding: possible allosteric interaction. J Neurochem. 1985;44(2):349-356.
Sheehan DV, et al., The Mini-International Neuropsychiatric Interview (MINI): the development and validation of a structured diagnostic psychiatric interview for DSM-IV and ICD-10. 1998.
Shulgin & Shulgin. PiHKAL: A Chemical Love Story, 1992 Transform Press, Berkeley CA.
Shulgin & Shulgin. TiHKAL: The Continuation, 1997 Transform Press.
Simmler et al. In Vitro Characterization of Psychoactive Substances at Rat, Mouse, and Human Trace Amine-Associated Receptor 1. J Pharmacol Exp Ther. 2016;357(1):134-144.
Simmler et al. Pharmacological characterization of designer cathinones in vitro. Br J Pharmacol. 2013;168(2):458-470.
Simplício et al. Prodrugs for Amines, Molecules, 2008;13(3):519-47.
Spitzer RL et al., A Breif Measure for Assessing Generalized Anxiety Disorder: The GAD-7 Archives of Internal Medicine. 2006;166(10):1092-7.
Stotts AL, et al., Motivational Interviewing with Cocaine-Dependent Patients: A Pilot Study, J. Consul. Clin. Psychol. 2001;69(5):858-62.
Szabo & Slavish. Measuring salivary markers of inflammation in health research: A review of methodological considerations and best practices. Psychoneuroendocrinology. 2021;124:105069.
Tadano et al. Potentiation of para-hydroxyamphetamine-induced head-twitch response by inhibition of monoamine oxidase type A in the brain. J Pharmacol Exp Ther. 1989;250(1):254-260.
Taghizadeh G, et al., Protective effects of physical exercise on MDMA-induced cognitive and mitochondrial impairment. Free Radic. Biol. Med. 2016;99:11-9.
Takano H, Cognitive Function and Monoamine Neurotransmission in Schizophrenia: Evidence From Positron Emission Tomography Studies. Front Psychiatry, 2018;9:228.
Tarawneh R, et al., Cerebrospinal Fluid Markers of Neurodegeneration and Rates of Brain Atrophy in Early Alzheimer Disease, Neurol. 2015; 72(6):656-65.
Thiehoff C, Rey YP & Gilmour R. The flourine gauche effect: a brief history. Isreal. J. Chem. 2016;57(1-2):92-10.
Toh EA, et al., Comparison of cognitive and UHDRS measures in monitoring disease progression in Huntington's disease: a 12-month longitudinal study, Transl Neurodegener. 2014;3:15.
Toro-Sazo et al. 5-HT2 receptor binding, functional activity and selectivity in N-benzyltryptamines. PLoS One. 2019;14(1):e0209804.
Traschel D, Flourine in psychedelic phenethylamines. Drug Testing and Analysis. 2012;4(7-8):577-90.
Tsujikawa K, et al., Urinary excretion profiles of N-hydroxy-3,4-methylenedioxymethamphetamine in rats, Xenobiotica 2011;41(7):578-84.
Uebelhack R & Schewe FH., Inhibition of platelet MAO-B by kava pyrone-enriched extract from Piper methysticum Forster (kava-kava), Pharmacopsychiatry, 1998;31(5):187-92.
Vig BS, et al., Amino Acids as Promoieties in Prodrug Design and Development. Advanced Drug Delivery Reviews, 2013;65(10):1370-85.
Wang et al. Serotonin syndrome: Preventing, recognizing, and treating it. Cleve Clin J Med. 2016;83(11):810-817.
West et al. Serotonin 2B Receptor Antagonism Prevents Heritable Pulmonary Arterial Hypertension. PLoS One. 201611(2):e0148657.
Weyler W & Salach Ji, Purification and Properties of Mitochondrial Monoamine Oxidase Type A from Human Placenta, J Biol Chem, 1985; 260(24):13199-207.
Wojcikowsci J, et al., In vitro inhibition of human cytochrome P450 enzymes by the novel atypical antipsychotic drug asenapine: A prediction of possible drug-drug interactions. Pharmacol Rep. 2020;72(3)612-21.

(56) References Cited

OTHER PUBLICATIONS

Wong DF & Gjedde A, Monoamines: Human brain imaging, Encyclopedia of Neuroscience, 2009; 939-52.
Woods et al. 5-HT(6) receptor agonists and antagonists enhance learning and memory in a conditioned emotion response paradigm by modulation of cholinergic and glutamatergic mechanisms. Br J Pharmacol. 2012;167(2):436-449.
Yamamoto et al. Metabolism of methamphetamine, amphetamine and p-hydroxymethamphetamine by rat-liver microsomal preparations in vitro. Xenobiotica, 1984;14(11)867-75.
Yamashiro T, et al., pH-dependent pyridoxine transport by SLC19A2 and SLC19A3: Implications for absorption in acidic microclimates, J Biol Chem. 2020;295(50):16998-17008.
European Search Report for Applicant's co-pending counterpart EP application EP 22873724.3 with Supplementary Partial European Search Report and Provisional Opinion Accompanying the Partial Search Result.
Gallardo-Godoy et al. Sulfur-substituted alpha-alkyl phenethylamines as selective and reversible MAO-A inhibitors: biological activities, CoMFA analysis, and active site modeling. J Med Chem. 2005;48(7):2407-2419.
Harbeson et al. Deuterium in Drug Discovery and Development. Annual Reports in Medicinal Chemistry. 2011;46:403-417.
Timmins. Deuterated drugs: where are we now? Expert Opinion on Therapeutic Patients. 2014;24(10):29.

* cited by examiner

SUBSTITUTED ALPHA-ETHYL PHENYLALKYLAMINES

CROSS-REFERENCE

This application is a U.S. national stage entry under 35 U.S.C. § 371 of International Application No. PCT/US2022/044771, filed Sep. 26, 2022, which claims priority under PCT Article 8(1) and Rule 4.10 to U.S. Provisional Application No. 63/248,450, filed Sep. 25, 2021, both of which are incorporated by reference for all purposes as if fully set forth herein.

FIELD OF THE INVENTION

The present disclosure relates in some aspects to substituted phenylalkylamine compounds, such as 2,5-disubstituted phenylalkylamine compounds and 2,4,5-trisubstituted phenylalkylamine compounds. In some aspects, the disclosure further relates to methods of synthesizing the compounds, compositions containing the compounds, and methods of using such compounds, including their administration to subjects. In some aspects, features of the compounds include neuromodulatory activity, for example, activation of serotonin receptors.

BACKGROUND OF THE INVENTION

The enormous public health burden of mental health disorders, combined with the shortcomings of currently available treatments, reveal the necessity of developing improved treatments, for example, highly efficacious treatments with minimal side effects that are optimized for clinical use. In one example of an alternative treatment, psilocybin has shown efficacy for treating mental health disorders, such as depression. This psychedelic tryptamine has received FDA Breakthrough Therapy designation and is on track for approval as a medicine, to be provided together with psychotherapy. Other psychedelics have been explored in therapeutic applications, including tryptamines, phenethylamines, and ergolines. However, many known psychedelics have numerous drawbacks, including, for example, a variable duration of action that may limit clinical use and undermine treatment accessibility.

Novel compounds that can harness the therapeutic benefits of known compounds while reducing or eliminating one or more of their negative physiological and/or psychological side effects, and additionally optimizing their time course and duration of action, will be highly prized. Such changes will both increase the value of a compound for therapeutic use, and broaden the population of individuals who will be able to benefit. For these and other reasons, there remains a continuing need for the development of novel psychedelic compounds for therapeutic applications. Provided herein are therapeutic phenylalkylamine compounds as well as compositions, kits, and methods of use thereof that meet this need, and that have such other benefits and advantages as will become apparent in view of the disclosure below.

INCORPORATION BY REFERENCE

Each patent, publication, and non-patent literature cited in the application is hereby incorporated by reference in its entirety as if each was incorporated by reference individually. Unless specifically stated otherwise, reference to any document herein is not to be construed as an admission that the document referred to or any underlying information in the document is prior art in any jurisdiction, or forms part of the common general knowledge in the art.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In one aspect, provided herein is a compound of Formula (I):

(I)

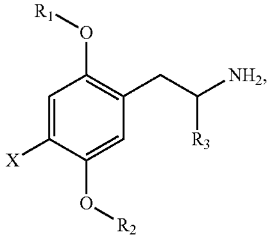

wherein: $R_1$ is —$CH_3$, —$CD_3$, or —$CF_3$; $R_2$ is —$CH_3$, —$CD_3$, or —$CF_3$; $R_3$ is H, —$CH_3$, or —$CH_2CH_3$; and X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I; or a pharmaceutically acceptable salt, prodrug, hydrate, or solvate thereof.

In some embodiments, wherein the compound, or a pharmaceutically acceptable salt, prodrug, hydrate, or solvate thereof, has the structure of Formula (I), one of $R_1$ and $R_2$ is —$CD_3$; and the other of $R_1$ and $R_2$ is —$CH_3$.

In some embodiments, the compound has the structure of Formula (I-A):

(I-A)

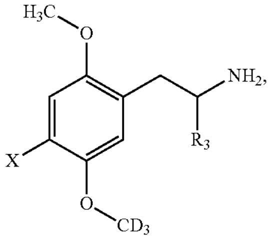

or a pharmaceutically acceptable salt, prodrug, hydrate, or solvate thereof.

In some embodiments, the compound has the structure of Formula (I-B):

(I-B)

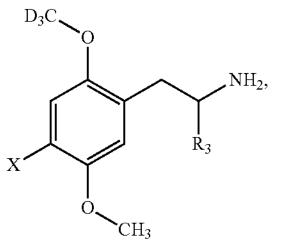

or a pharmaceutically acceptable salt, prodrug, hydrate, or solvate thereof.

In some embodiments, wherein the compound, or a pharmaceutically acceptable salt, prodrug, hydrate, or solvate thereof, has the structure of Formula (I-A) or Formula (I-B), $R_3$ is H. In some embodiments, $R_3$ is $-CH_3$ or $-CH_2CH_3$. In some embodiments, wherein the compound, or a pharmaceutically acceptable salt, prodrug, hydrate, or solvate thereof, has the structure of Formula (I-A) or Formula (I-B), X is F, Cl, Br, or I. In some embodiments, X is Br. In some embodiments, wherein the compound, or a pharmaceutically acceptable salt, prodrug, hydrate, or solvate thereof, has the structure of Formula (I), one of $R_1$ and $R_2$ is $-CF_3$; and the other of $R_1$ and $R_2$ is $-CH_3$.

In some embodiments, the compound has the structure of Formula (I-C):

(I-C)

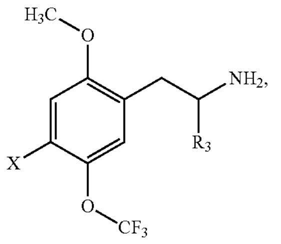

or a pharmaceutically acceptable salt, prodrug, hydrate, or solvate thereof.

In some embodiments, the compound has the structure of Formula (I-D):

(I-D)

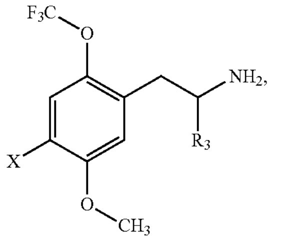

or a pharmaceutically acceptable salt, prodrug, hydrate, or solvate thereof.

In some embodiments, wherein the compound, or a pharmaceutically acceptable salt, prodrug, hydrate, or solvate thereof, has the structure of Formula (I-C) or Formula (I-D), X is $-CH_3$, $-CD_3$, $-CH_2CH_3$, $-CH_2CD_3$, $-CH_2CH_2CH_3$, $-CH_2CH_2CD_3$, $-CF_3$, $-CH_2CF_3$, $-CH_2CH_2CF_3$, $-OCH_3$, $-OCD_3$, $-OCF_3$, $-OCH_2CH_3$, $-OCH_2CD_3$, $-OCH_2CF_3$, $-OCH_2CH_2CH_3$, $-OCH_2CH_2CD_3$, $-OCH_2CH_2CF_3$, $-SCH_3$, $-SCD_3$, $-SCF_3$, $-SCH_2CH_3$, $-SCH_2CD_3$, $-SCH_2CF_3$, $-SCH_2CH_2CH_3$, $-SCH_2CH_2CD_3$, $-SCH_2CH_2CF_3$, F, Cl, Br, or I. In some embodiments, X is F, Cl, Br, or I. In some embodiments, X is Br. In some embodiments, wherein the compound, or a pharmaceutically acceptable salt, prodrug, hydrate, or solvate thereof, has the structure of Formula (I-C) or Formula (I-D), $R_3$ is H. In some embodiments, $R_3$ is $-CH_3$ or $-CH_2CH_3$. In some embodiments, wherein the compound, or a pharmaceutically acceptable salt, prodrug, hydrate, or solvate thereof, has the structure of Formula (I), one of $R_1$ and $R_2$ is $-CF_3$; and the other of $R_1$ and $R_2$ is $-CD_3$.

In some embodiments, the compound has the structure of Formula (I-E):

(I-E)

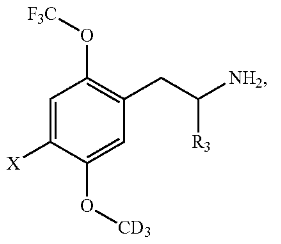

or a pharmaceutically acceptable salt, prodrug, hydrate, or solvate thereof.

In some embodiments, the compound has the structure of Formula (I-F):

(I-F)

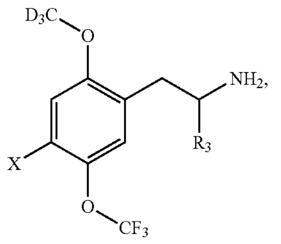

or a pharmaceutically acceptable salt, prodrug, hydrate, or solvate thereof.

In some embodiments, wherein the compound, or a pharmaceutically acceptable salt, prodrug, hydrate, or solvate thereof, has the structure of Formula (I-E) or Formula (I-F), $R_3$ is H. In some embodiments, $R_3$ is $-CH_3$ or $-CH_2CH_3$. In some embodiments, wherein the compound, or a pharmaceutically acceptable salt, prodrug, hydrate, or solvate thereof, has the structure of Formula (I-E) or Formula (I-F), X is F, Cl, Br, or I. In some embodiments, X is Br.

In another aspect, provided is a compound selected from Table I-A, Table I-B, Table I-C, Table I-D, Table I-E, Table I-F, Table I-G, Table I-H, or Table I-I, or a pharmaceutically acceptable salt, prodrug, hydrate, or solvate thereof. In yet another aspect, provided is a compound selected from Table I-A, Table I-B, Table I-C, Table I-D, Table I-E, Table I-F, or a pharmaceutically acceptable salt, prodrug, hydrate, or solvate thereof.

In some embodiments, the compound is selected from the group consisting of:

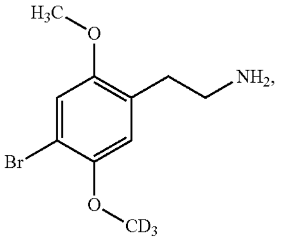

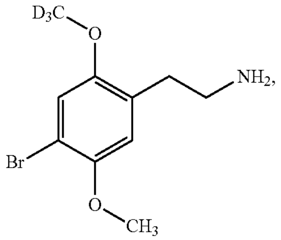

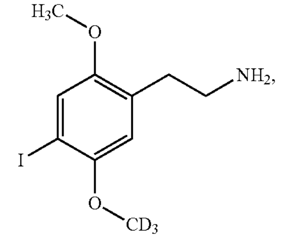

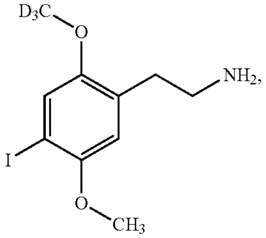

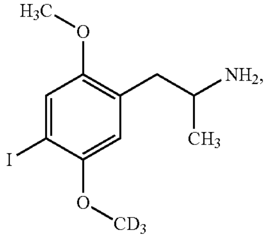

and

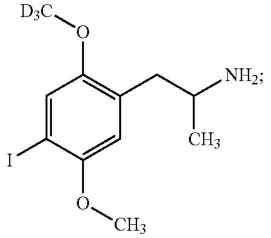

or a pharmaceutically acceptable salt, prodrug, hydrate, or solvate thereof.

In some embodiments, the compound is

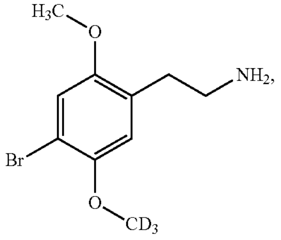

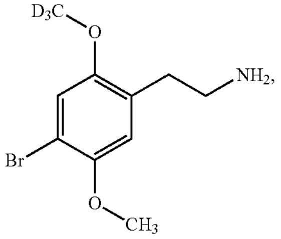

or

-continued

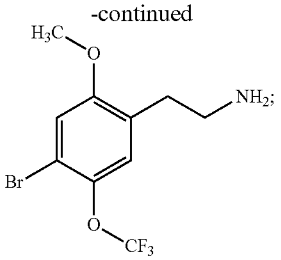

or a pharmaceutically acceptable salt, prodrug, hydrate, or solvate thereof.

In some embodiments, the compound, or a pharmaceutically acceptable salt, prodrug, hydrate, or solvate thereof, modulates the activity of a monoamine neurotransmitter receptor and/or the uptake activity of a monoamine transporter. In some embodiments, the compound, or a pharmaceutically acceptable salt, prodrug, hydrate, or solvate thereof, modulates the activity of a monoamine neurotransmitter receptor and/or the uptake activity of a monoamine transporter. In some embodiments, the monoamine neurotransmitter receptor is any of a serotonin receptor (HTR), a dopamine receptor, and a norepinephrine receptor; and the monoamine transporter is any of a serotonin transporter (SERT), a dopamine transporter (DAT), and a norepinephrine transporter (NET). In some embodiments, the HTR is any one or more of $HTR_{1A}$, $HTR_{1B}$, $HTR_{2A}$, $HTR_{2B}$, and $HTR_6$. In some embodiments, the compound, or a pharmaceutically acceptable salt, prodrug, hydrate, or solvate thereof, agonizes $HTR_{2A}$. In some embodiments, the compound, or a pharmaceutically acceptable salt, prodrug, hydrate, or solvate thereof, has an in vitro $EC_{50}$ for $HTR_{2A}$ of less than 1 μM, less than 0.5 μM, less than 0.1 μM, less than 0.05 μM, or less than 0.01 μM. In some embodiments, the compound, or a pharmaceutically acceptable salt, prodrug, hydrate, or solvate thereof, does not inhibit DAT uptake activity. In some embodiments, the compound, or a pharmaceutically acceptable salt, prodrug, hydrate, or solvate thereof, has an in vitro $IC_{50}$ for DAT of greater than 10 μM. In some embodiments, the compound, or a pharmaceutically acceptable salt, prodrug, hydrate, or solvate thereof, agonizes $HTR_{2A}$ and does not inhibit the uptake activity of DAT. In some embodiments, the compound, or a pharmaceutically acceptable salt, prodrug, hydrate, or solvate thereof, does not inhibit the activity of a monoamine oxidase enzyme. In embodiments, the compound, or a pharmaceutically acceptable salt, prodrug, hydrate, or solvate thereof, has an in vitro $IC_{50}$ of greater than 10 μM for the monoamine oxidase enzyme MAO-A. In embodiments, the compound, or a pharmaceutically acceptable salt, prodrug, hydrate, or solvate thereof, is orally bioavailable.

In a further aspect, provided is a pharmaceutical composition comprising a therapeutically effective amount of the compound of any of the foregoing embodiments, or a pharmaceutically acceptable salt, prodrug, hydrate, or solvate thereof, and a pharmaceutically acceptable carrier, diluent, or excipient.

In some embodiments, the compound, or a pharmaceutically acceptable salt, prodrug, hydrate, or solvate thereof, is a pure or substantially pure individual enantiomer, or an enantiomerically enriched mixture having an optical purity of between 0-25%, between 25-50%, between 50-75%, between 75-90%, between 90-95%, or at least 95% enantiomeric excess.

In yet another embodiment, provided is a pharmaceutical composition comprising a therapeutically effective amount of the compound of any of the foregoing embodiments, or a pharmaceutically acceptable salt, prodrug, hydrate, or solvate thereof, and its non-substituted analog, in a mixture by mole ratio or mass ratio of greater than 10:1, between 10:1 and 5:1, between 5:1 and 1:1, about 1:1, between 1:1 and 5:1, between 5:1 and 10:1, or greater than 10:1.

In yet another embodiment, provided is a pharmaceutical composition comprising a therapeutically effective amount of the compound of any one of any of the foregoing embodiments, or a pharmaceutically acceptable salt, prodrug, hydrate, or solvate thereof, wherein said compound is a fluorine-substituted or deuterium-substituted compound, and its corresponding deuterium-substituted or fluorine-substituted analog, in a mixture by mole ratio or mass ratio of greater than 10:1, between 10:1 and 5:1, between 5:1 and 1:1, about 1:1, between 1:1 and 5:1, between 5:1 and 10:1, or greater than 10:1.

In some embodiments, the composition is suitable for oral, buccal, sublingual, intranasal, injectable, subcutaneous, intravenous, or transdermal administration. In some embodiments, the composition is in unit dosage form. In some embodiments, the composition comprises the compound, or a pharmaceutically acceptable salt, prodrug, hydrate, or solvate thereof, in a total amount of between about 1 and about 500 mg, between about 2.5 and about 250 mg, between about 5 and about 125 mg, between about 7.5 and about 62.5 mg, or between about 10 and about 31.25 mg. In some embodiments, the composition is an immediate release, controlled release, sustained release, extended release, or modified release formulation.

In embodiments, the pharmaceutical composition further comprises a therapeutically effective amount of an additional active compound, or a pharmaceutically acceptable salt, prodrug, hydrate, or solvate thereof. In embodiments, the additional active compound is selected from the group consisting of amino acids, antioxidants, anti-inflammatory agents, analgesics, antineuropathic and antinociceptive agents, antimigraine agents, anxiolytics, antidepressants, antipsychotics, anti-PTSD agents, dissociatives, cannabinoids, immunostimulants, anti-cancer agents, antiemetics, orexigenics, antiulcer agents, antihistamines, antihypertensives, anticonvulsants, antiepileptics, bronchodilators, neuroprotectants, nootropics, empathogens, psychedelics, monoamine oxidase inhibitors, tryptamines, terpenes, phenethylamines, sedatives, stimulants, and vitamins; or a pharmaceutically acceptable salt, prodrug, hydrate, or solvate thereof. In some embodiments, the additional active compound, or a pharmaceutically acceptable salt, prodrug, hydrate, or solvate thereof, acts to increase a therapeutic effect, provide an additional therapeutic effect, decrease an unwanted effect, increase stability or shelf-life, improve bioavailability, induce synergy, or alter pharmacokinetics or pharmacodynamics. In embodiments, the additional therapeutic effect is an antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, nootropic, empathogenic, psychedelic, sedative, or stimulant effect.

In another aspect, provided herein is a compound of any one of the foregoing embodiments, or a pharmaceutically acceptable salt, prodrug, hydrate, or solvate thereof, for use in the treatment of a medical condition. In another aspect, provided is the use of the compound of any of the foregoing embodiments, or a pharmaceutically acceptable salt, prodrug, hydrate, or solvate thereof, for the manufacture of a medicament for the treatment of a medical condition.

In another aspect, provided is a method for modulating neurotransmission in a mammal, comprising administering to the mammal a therapeutically effective amount of the compound of any one of the foregoing embodiments, or a pharmaceutically acceptable salt, prodrug, hydrate, or solvate thereof, or the composition of any of the foregoing embodiments.

In yet another aspect, provided is a method of treating a medical condition in a mammal in need of such treatment, the method comprising administering the compound of any one of the foregoing embodiments, or a pharmaceutically acceptable salt, prodrug, hydrate, or solvate thereof, or the composition of any of the foregoing embodiments. In some embodiments, the medical condition is a disorder linked to dysregulation or inadequate functioning of neurotransmission. In some embodiments, the disorder linked to dysregulation or inadequate functioning of neurotransmission is that of monoaminergic neurotransmission. In some embodiments, the disorder linked to dysregulation or inadequate functioning of neurotransmission is that of serotonergic, dopaminergic, or noradrenergic neurotransmission.

In some embodiments, the medical condition is a mental health disorder. In some embodiments, the mental health disorder is any of post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, a substance use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders.

In some embodiments, the mental health disorder is a disorder related to rigid modes of thinking. In some embodiments, the disorder related to rigid modes of thinking is anxiety, depression, addiction, an eating disorder, an alcohol or drug abuse or dependence disorder, OCD, or PTSD. In some embodiments, depression is major depressive disorder (MDD) or treatment-resistant depression (TRD). In some embodiments, anxiety is generalized anxiety disorder (GAD). In some embodiments, the substance use disorder is any of alcohol use disorder, nicotine dependency, opioid use disorder, sedative, hypnotic, or anxiolytic use disorder, stimulant use disorder, or tobacco use disorder.

In some embodiments, the medical condition is a neurodegenerative disorder. In some embodiments, the neurodegenerative disorder is any of Alzheimer's disease (AD), corticobasal degeneration (CBD), a form of dementia, Huntington's disease, Lytico-Bodig disease, mild cognitive impairment (MCI), a motor neuron disease, progressive supranuclear palsy (PSP), multiple sclerosis, Parkinson's disease, and traumatic brain injury (TBI).

In some embodiments, the medical condition is pain and/or a pain disorder. In some embodiments, the pain disorder is any of arthritis, allodynia, atypical trigeminal neuralgia, trigeminal neuralgia, somatoform disorder, hypoesthesia, hyperalgesia, neuralgia, neuritis, neurogenic pain, phantom limb pain, analgesia, anesthesia dolorosa, causalgia, sciatic nerve pain disorder, degenerative joint disorder, fibromyalgia, visceral disease, chronic pain disorders, headache disorders, migraine headaches, chronic cluster headaches, concussion headache, short-lasting unilateral neuralgiform headache attacks, chronic fatigue syndrome, complex regional pain syndrome, neurodystrophy, plantar fasciitis, or pain associated with cancer.

In some embodiments, the medical condition is inflammation and/or an inflammatory disorder. In some embodiments, the inflammatory disorder is characterized by any one or more of skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, gastric inflammation, intestinal inflammation, neuroinflammation, and brain inflammation.

In some embodiments, the mammal of any of the foregoing embodiments has a genetic variation associated with drug metabolism, such as a variation relating to CYP2B6, CYP1A2, CYP2C19, CYP2D6, or CYP3A4 enzymes; or associated with a mental health disorder, trauma or stressor related disorder, depression, or anxiety, and including a genetic variation in mGluR5 or FKBP5; or relating to a membrane transporter, such as SERT, DAT, NET, or VMAT.

In some embodiments, the mammal of any of the foregoing embodiments has altered epigenetic regulation of a gene the expression of which is associated with a mental health condition or susceptibility to a mental health treatment, such as the SIGMAR1 gene for the non-opioid sigma-1 receptor.

In some embodiments, the mammal in any of the foregoing embodiments is a human.

In another aspect, provided herein is a method of improving mental health or functioning in a human, the method comprising identifying a human in need of said improving, and administering to the human the compound of any of the foregoing embodiments, or a pharmaceutically acceptable salt, prodrug, hydrate, or solvate thereof, or the composition of any of the foregoing embodiments. In some embodiments, the improvement in mental health or functioning is a reduction of neuroticism or psychological defensiveness, an increase in creativity or openness to experience, an increase in decision-making ability, an increase in feelings of wellness or satisfaction, or an increase in ability to fall or stay asleep.

In another aspect, provided is a method of reducing the symptoms of a mental health disorder in a human, the method comprising identifying a human in need of said reducing, and administering to the human the compound of any of the foregoing embodiments, or a pharmaceutically acceptable salt, prodrug, hydrate, or solvate thereof, or the composition of any of the foregoing embodiments.

In some embodiments, the compound of any of the foregoing embodiments, or a pharmaceutically acceptable salt, prodrug, hydrate, or solvate thereof, or the composition of any of the foregoing embodiments, is administered together with one or more sessions of psychotherapy, which may be sessions of drug-assisted and/or non-drug-assisted psychotherapy.

The foregoing has outlined broadly some pertinent features of certain exemplary embodiments of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be also realized that such equivalent structures do not depart from the spirit and scope of the invention as set forth in the appended claims. Hence, this summary has been made with the understanding that it is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled.

BRIEF SUMMARY OF THE DRAWINGS

To further clarify various aspects of the invention, a more particular description thereof will be rendered by reference to certain exemplary embodiments thereof which are illustrated in the figures. It will be understood and appreciated that the figures depict only illustrated embodiments of the invention and are not to be considered limiting of its scope. They are simply provided as exemplary illustrations of some embodiments of the invention. Certain aspects of the invention are therefore further described and explained with additional specificity and detail, but still by way of example only, with reference to the accompanying figures in which.

DETAILED DESCRIPTION

Figure 1:
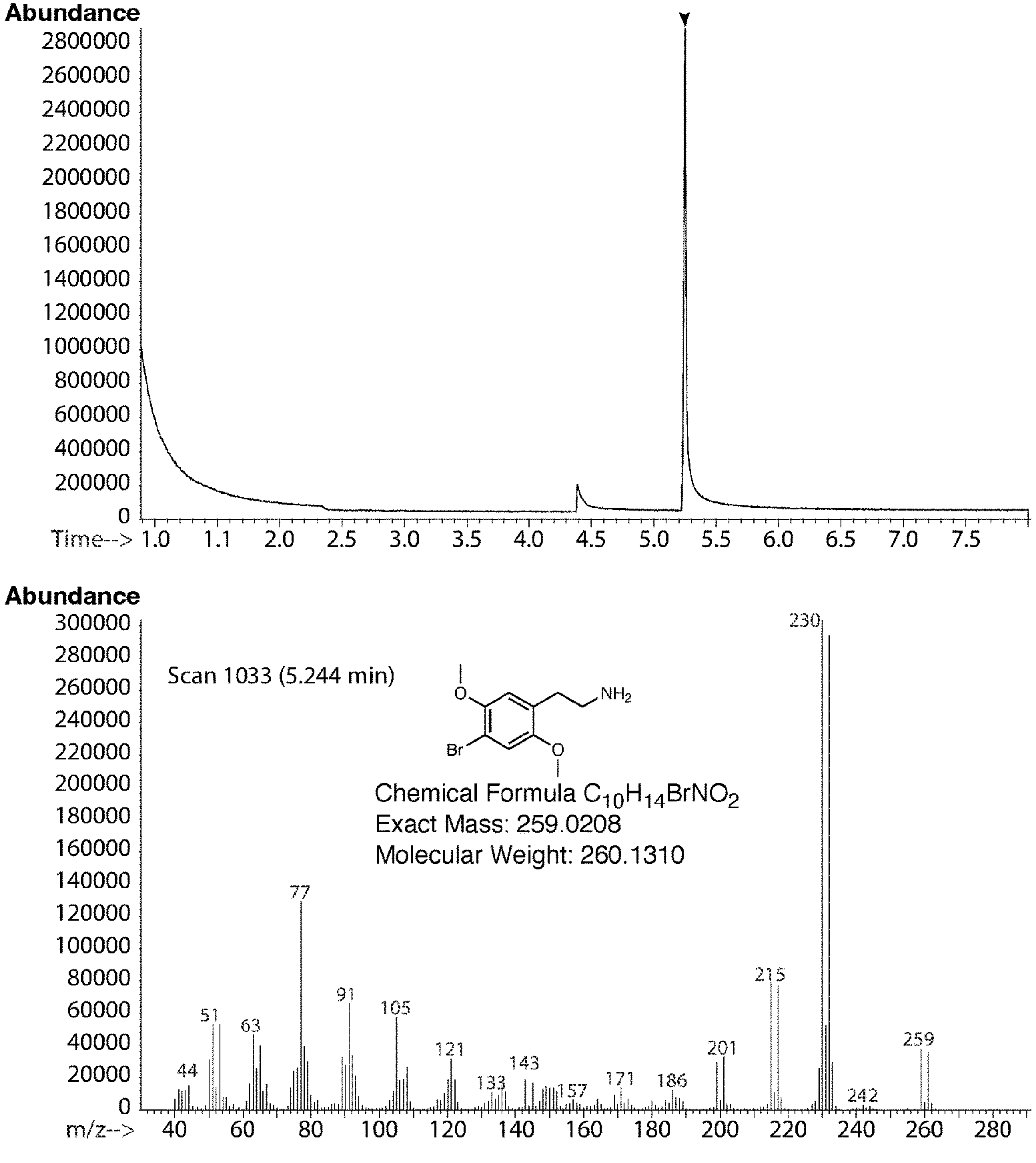
FIG. 1 shows the experimental MS data for 2C-B (2-(4-bromo-2,5-dimethoxyphenyl)ethanamine).

While various aspects and features of certain embodiments have been summarized above, the following detailed description illustrates several exemplary embodiments in further detail to enable one of skill in the art to practice such embodiments, and to make and use the full scope of the invention claimed. The described examples are provided for illustrative purposes and are not intended to limit the scope of the invention or its applications. It will be understood that many modifications, substitutions, changes, and variations in the described examples, embodiments, applications, and details of the invention illustrated herein can be made by those skilled in the art without departing from the spirit of the invention, or the scope of the invention as described in the appended claims, and the general principles defined herein may be applied to a wide range of aspects. Thus, the invention is not intended to be limited to the aspects presented, but is to be accorded the widest scope consistent with the principles and novel features disclosed. The description below is designed to make such embodiments apparent to a person of ordinary skill, in that the embodiments shall be both readily cognizable and readily creatable without undue experimentation, solely using the teachings herein together with general knowledge of the art.

Among the various aspects of the present invention are therapeutic phenylalkylamine compounds of Formula (I) (including all such subformulae as herein disclosed). Also provided are pharmaceutical compositions of the compounds of Formula (I). Further provided are kits containing such compositions together with instructions for use. Yet further provided are uses of any of the compounds or compositions described herein for treating a disease, preventing a disease, treating a condition, preventing a condition, and/or causing an effect. In embodiments, the methods of use are for treatment of a mental health disorder, or for the improvement of mental health and functioning.

A. General Definitions and Terms

As used in this specification and the appended claims, the singular forms "a," "an," and "the" include plural referents unless the context clearly dictates otherwise. Thus, for example, reference to "an active agent" includes reference to a combination of two or more active agents, and reference to "an excipient" includes reference to a combination of two or more excipients. While the term "one or more" may be used, its absence (or its replacement by the singular) does not signify the singular only, but simply underscores the possibility of multiple agents or ingredients in particular embodiments.

The terms "comprising," "including," "such as," and "having" are intended to be inclusive and not exclusive (i.e., there may be other elements in addition to the recited elements). Thus, the term "including" as used herein means, and is used interchangeably with, the phrase "including but not limited to." The term "or" is used herein to mean, and is used interchangeably with, the term "and/or," unless context clearly indicates otherwise.

Unless otherwise indicated, all numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless defined otherwise, all technical and scientific terms herein have the meaning as commonly understood by one of ordinary skill in the art to which this invention belongs ("one of skill"). Further definitions that may assist the reader to understand the disclosed embodiments are as follows; however, it will be appreciated that such definitions are not intended to limit the scope of the invention, which shall be properly interpreted and understood by reference to the full specification (as well as any plain meaning known to one of skill in the relevant art) in view of the language used in the appended claims. The terminology used herein is for the purpose of describing particular embodiments only and is not intended to be limiting.

"Alkyl" will be understood to include straight or branched radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" can also be used. Preferably, an alkyl group comprises from 1 to 10 carbon atoms, more preferably from 1 to 6 carbon atoms, more preferably from 1 to 4 carbon atoms, and most preferably from 1 to 3 carbon atoms. For any alkyl, the alkyl may be optionally substituted at one or more positions by deuterium, halogen, alkyl, alkyl ester, hydroxy, alkoxy, carboxy, formyl, aryl, cycloalkyl, heterocycloalkyl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, $—OP(O)(OH)_2$, —OC(O)H, $—OSO_2OH$, $—OC(O)NH_2$, and $—SONH_2$.

"Alkanyl" refers to saturated branched, straight-chain, or cyclic alkyl radicals derived by the removal of one hydrogen atom from a single carbon atom of a parent alkane. Typical alkanyl groups include methanyl; ethanyl; propanyls such as propan-1-yl, propan-2-yl (isopropyl), and cyclopropan-1-yl; butanyls such as butan-1-yl, butan-2-yl (sec-butyl), 2-methyl-propan-1-yl (isobutyl), 2-methyl-propan-2-yl (t-butyl), and cyclobutan-1-yl; etc.

"Alkenyl" refers to an unsaturated branched, straight-chain, or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include ethenyl; propenyls such as prop-1-en-1-yl, prop-1-en-2-yl, prop-2-en-1-yl (allyl), prop-2-en-2-yl, cycloprop-1-en-1-yl, and cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2yl, buta-1,3-dien-1-yl, buta-1,3-dien-2-yl, cyclobut-1-en-1-yl, cyclobut-1-en-3-yl, and cyclobuta-1,3-dien-1-yl; and the like.

"Alkynyl" refers to an unsaturated branched, straight-chain, or cyclic alkyl radical having at least one carbon-carbon triple bond derived by the removal of one hydrogen atom from a single carbon atom of a parent alkyne. Typical alkynyl groups include ethynyl; propynyls such as prop-1-yn-1-yl, and prop-2-yn-1-yl; butynyls such as but-1-yn-1-yl, but-1-yn-3-yl, and but-3-yn-1-yl; and the like.

"Aryl" refers to a monovalent aromatic hydrocarbon radical derived by the removal of one hydrogen atom from a single carbon atom of a parent aromatic ring system. Typical aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. Preferably, an aryl group comprises from 6 to 20 carbon atoms, and more preferably, from 6 to 12 carbon atoms, inclusive.

"Cycloalkyl" refers to a saturated monocyclic, bicyclic, fused bicyclic or bridged polycyclic ring assembly containing from 3 to 12 ring atoms, or the number of atoms indicated. Cycloalkyl can include any number of carbons, such as 3 to 6 carbon atoms, 4 to 6 carbon atoms, 5 to 6 carbon atoms, 3 to 8 carbon atoms, 4 to 8 carbon atoms, 5 to 8 carbon atoms, 6 to 8 carbon atoms, 7 to 8 carbon atoms, 3 to 9 carbon atoms, 4 to 9 carbon atoms, 5 to 9 carbon atoms, 6 to 9 carbon atoms, 7 to 9 carbon atoms, 8 to 9 carbon atoms, 3 to 10 carbon atoms, 4 to 10 carbon atoms, 5 to 10 carbon atoms, 6 to 10 carbon atoms, 7 to 10 carbon atoms, 8 to 10 carbon atoms, 9 to 10 carbon atoms, 3 to 11 carbon atoms, 4 to 11 carbon atoms, 5 to 11 carbon atoms, 6 to 11 carbon atoms, 7 to 11 carbon atoms, 8 to 11 carbon atoms, 9 to 11 carbon atoms, 10 to 11 carbon atoms, 3 to 12 carbon atoms, 4 to 12 carbon atoms, 5 to 12 carbon atoms, 6 to 12 carbon atoms, 7 to 12 carbon atoms, 8 to 12 carbon atoms, 9 to 12 carbon atoms, 10 to 12 carbon atoms, and 11 to 12 carbon atoms. Monocyclic cycloalkyl rings include, for example, cyclopropyl, cyclobutyl, cyclopentyl, cyclohexyl, and cyclooctyl. Bicyclic compounds include spirocyclic compounds, fused bicyclic compounds and bridged bicyclic compounds. Bicyclic and polycyclic cycloalkyl rings include, for example, norbornane, bicyclooctane, decahydronaphthalene and adamantane. When cycloalkyl is a monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a monocyclic $C_{3-6}$ cycloalkyl, exemplary groups include cyclopropyl, cyclobutyl, cyclopentyl, and cyclohexyl. Cycloalkyl groups can be substituted or unsubstituted.

"Cycloalkenyl" refers to a mono- or multi-cyclic hydrocarbon ring system that contains one or more double bonds in at least one ring. However, if there is more than one double bond, the double bonds cannot form a fully delocalized pi-electron system throughout all the rings (otherwise the group would be "aryl," as defined herein). When composed of two or more rings, the rings may be connected together in a fused fashion. Cycloalkenyl can include any number of carbons, such as 3 to 6 carbon atoms, 4 to 6 carbon atoms, 5 to 6 carbon atoms, 3 to 8 carbon atoms, 4 to 8 carbon atoms, 5 to 8 carbon atoms, 6 to 8 carbon atoms, 7 to 8 carbon atoms, 3 to 9 carbon atoms, 4 to 9 carbon atoms, 5 to 9 carbon atoms, 6 to 9 carbon atoms, 7 to 9 carbon atoms, 8 to 9 carbon atoms, 3 to 10 carbon atoms, 4 to 10 carbon atoms, 5 to 10 carbon atoms, 6 to 10 carbon atoms, 7 to 10 carbon atoms, 8 to 10 carbon atoms, 9 to 10 carbon atoms, 3 to 11 carbon atoms, 4 to 11 carbon atoms, 5 to 11 carbon atoms, 6 to 11 carbon atoms, 7 to 11 carbon atoms, 8 to 11 carbon atoms, 9 to 11 carbon atoms, 10 to 11 carbon atoms, 3 to 12 carbon atoms, 4 to 12 carbon atoms, 5 to 12 carbon atoms, 6 to 12 carbon atoms, 7 to 12 carbon atoms, 8 to 12 carbon atoms, 9 to 12 carbon atoms, 10 to 12 carbon atoms, and 11 to 12 carbon atoms. Representative Cycloalkenyl groups include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. A cycloalkenyl group may be unsubstituted or substituted.

"Halogen" refers to fluorine, chlorine, bromine, and iodine.

"Heterocycloalkyl" and "heterocyclyl" both refer to a cycloalkyl as defined above, having from 3 to 12 ring members and from 1 to 4 heteroatoms of N, O and S. Heterocycloalkyl and heterocyclyl include bicyclic compounds which include a heteroatom. Bicyclic compounds includes spirocyclic compounds, fused bicyclic compounds, and bridged bicyclic compounds The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

"Alkoxy" refers to the formula —OR, wherein R is an alkyl, an alkenyl, an alkynyl, a cycloalkyl, a cycloalkenyl, aryl, or heterocyclyl, as defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

"Acyl" refers to a hydrogen, an alkyl, an alkenyl, an alkynyl, a cycloalkyl, a cycloalkenyl, aryl, or heterocyclyl, connected via a carbonyl group as a substituent. Examples include formyl, acetyl, propanoyl, benzoyl, and acryl. An acyl may be substituted or unsubstituted.

"Haloalkyl" will be understood to include any alkyl group as defined above, wherein one or more hydrogen atoms are replaced by a halogen (e.g., a fluorine, a chlorine, a bromine, or an iodine). Where an alkyl radical is substituted by more than one halogen, it may be referred to using a prefix corresponding to the number of halogen substitutions. For example, dihaloalkyl refers to an alkyl substituted by two halo groups, which may be, but are not necessarily, the same halogen. Examples of haloalkyl groups include difluoromethyl (—$CHF_2$), bromofluoromethyl (—CHBrF), trifluoromethyl (—$CF_3$), and 2-fluoroethyl (—$CH_2CH_2F$). Additional examples of haloalkyl groups include —$CHF_2$, —$CH_2F$, —$CH_2CF_3$, —$CH_2CHF_2$, —$CH_2CH_2F$, —CH($CH_3$)($CF_3$), —CH($CH_3$)($CHF_2$), and —CH($CH_3$)($CH_2F$).

"Hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

"Haloalkoxy" refers to an —O-alkyl group in which one or more of the hydrogen atoms are replaced by a halogen (e.g., mono-haloalkoxy, di-haloalkoxy and tri-haloalkoxy). The halogens may be the same or different in each instance. Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

"Sulfenyl" refers to an —SR group in which R can be hydrogen, alkyl, alkenyl, alkynyl, cycloalkyl, cycloalkenyl, aryl, or heterocyclyl, as defined herein. A sulfenyl may be substituted or unsubstituted.

"Sulfinyl" refers to an —S(═O)—R group in which R can be the same as defined with respect to sulfenyl. A sulfinyl may be substituted or unsubstituted.

"Sulfonyl" refers to an —$SO_2$R group in which R can be the same as defined with respect to sulfenyl. A sulfonyl may be substituted or unsubstituted.

"O-carboxy" refers to a —RC(═O)O group in which R can be hydrogen, alkyl, alkenyl, alkynyl, cycloalkyl, cycloalkenyl, aryl, or heterocyclyl, as defined herein. An O-carboxy may be substituted or unsubstituted.

"Ester" and "C-carboxy" refer to a —C(═O)OR group in which R can be the same as defined with respect to O-carboxy. Ester and C-carboxy groups may be substituted or unsubstituted.

"Thiocarbonyl" refers to a —C(═S)R group in which R can be the same as defined with respect to O-carboxy. A thiocarbonyl may be substituted or unsubstituted.

"Trihalomethanesulfonyl" refers to an $X_3CSO_2$— group wherein each X is a halogen.

"Trihalomethanesulfonamido" refers to an $X_3CS(O)_2N(R_A)$— group wherein each X is a halogen, and $R_A$ is hydrogen, alkyl, alkenyl, alkynyl, cycloalkyl, cycloalkenyl, aryl, or heterocyclyl, as defined herein.

"S-sulfonamido" refers to a —$SO_2N(R_AR_B)$ group in which $R_A$ and $R_B$ can be independently hydrogen, alkyl, alkenyl, alkynyl, cycloalkyl, cycloalkenyl, aryl, or heterocyclyl, as defined herein. An S-sulfonamido may be substituted or unsubstituted.

"N-sulfonamido" refers to a —$RSO_2N(R_A)$ group in which R and $R_A$ can be independently hydrogen, alkyl, alkenyl, alkynyl, cycloalkyl, cycloalkenyl, aryl, or heterocyclyl, as defined herein. An N-sulfonamido may be substituted or unsubstituted.

"O-carbamyl" refers to a —OC(═O)$N(R_AR_B)$ group in which $R_A$ and $R_B$ can be independently hydrogen, alkyl, alkenyl, alkynyl, cycloalkyl, cycloalkenyl, aryl, or heterocyclyl, as defined herein. An O-carbamyl may be substituted or unsubstituted.

"N-carbamyl" refers to an —ROC(═O)$N(R_A)$ group in which R and $R_A$ can be independently hydrogen, alkyl, alkenyl, alkynyl, cycloalkyl, cycloalkenyl, aryl, or heterocyclyl, as defined herein. An N-carbamyl may be substituted or unsubstituted.

"O-thiocarbamyl" refers to a —OC(═S)—$N(R_AR_B)$ group in which $R_A$ and $R_B$ can be independently hydrogen, alkyl, alkenyl, alkynyl, cycloalkyl, cycloalkenyl, aryl, or heterocyclyl, as defined herein. An O-thiocarbamyl may be substituted or unsubstituted.

"N-thiocarbamyl" refers to an —ROC(═S)$N(R_A)$ group in which R and $R_A$ can be independently hydrogen, alkyl, alkenyl, alkynyl, cycloalkyl, cycloalkenyl, aryl, or heterocyclyl, as defined herein. An N-thiocarbamyl may be substituted or unsubstituted.

"C-amido" group refers to a —C(═O)$N(R_AR_B)$ group in which $R_A$ and $R_B$ can be independently hydrogen, alkyl, alkenyl, alkynyl, cycloalkyl, cycloalkenyl, aryl, or heterocyclyl, as defined herein. A C-amido may be substituted or unsubstituted.

"N-amido" refers to a —RC(═O)$N(R_A)$ group in which R and $R_A$ can be independently hydrogen, alkyl, alkenyl, alkynyl, cycloalkyl, cycloalkenyl, aryl, or heterocyclyl, as defined herein. An N-amido may be substituted or unsubstituted.

"Optionally substituted" unless otherwise specified means that a group may be unsubstituted, or substituted by one or more of the substituents listed for that group. Likewise, when a group is described as being "unsubstituted or substituted" if substituted, the substituent(s) may be selected from one or more of the indicated substituents. When there are more than one substituents, the substituents may be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. If no substituents are indicated for an "optionally substituted" or "substituted" group, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group, a di-substituted amino group, and a tri-substituted amino group.

A comprehensive list of the abbreviations utilized by organic chemists of ordinary skill in the art appears in the first issue of each volume of the Journal of Organic Chemistry; this list is typically presented in a table entitled Standard List of Abbreviations; the current list as of the date of this filing is hereby incorporated by reference as if fully set forth herein, and may be utilized to supplement or lend additional support to any definitions provided above and herein.

Herein, "a single compound of" will mean that the specified compound (e.g., by structural formula or description) is the only disclosed compound claimed in the embodiment, i.e., that a compound, composition, or method consists of, consists essentially of, or comprises no further disclosed compound(s) (i.e., compound(s) having a different structural formula or description), as the compound, composition, or method is claimed. It does not mean that the embodiment has only a single molecule or single instance of the specified compound. For instance, embodiments "consisting of a single compound of Formula (I)" will include claims to "a compound of Formula (I)," or the use of "a compound of Formula (I)," and such embodiments, as well as claims to a composition "consisting essentially of a single compound of Formula (I)," each may comprise for example 10 mg, 50 mg, 100 mg, 125 mg, 150 mg, and other disclosed or known mass amounts or molar amounts of the compound of Formula (I).

Accordingly, and for example, in some embodiments (or sometimes for shorthand and meant equivalently, "in embodiments") one or more compounds may be excluded from a claim to a group of compounds, such as a Markush group of compounds, such as "a compound of Formula (I)." In embodiments, one or more compounds also may be excluded from a claim to a composition consisting essentially of a group of compounds. In embodiments, one or more compounds also may be excluded from a claim to a composition comprising a group of compounds. In embodiments, one or more compounds also may be excluded from a claim to a use of a group of compounds. In embodiments, one or more compounds also may be excluded from a claim to a use of a composition consisting essentially of a group of compounds. In embodiments, one or more compounds also may be excluded from a claim to a use of a composition comprising a group of compounds. In embodiments, one or more compounds may be excluded from all claims to a group of compounds. In some embodiments, one or more compounds may be excluded from a claim to a group of compounds, and also may be excluded from a claim to a composition consisting essentially of a group of compounds, but are not excluded from a claim to a use of a group of compounds or compositions thereof. In embodiments, one or more compounds may be excluded from a claim to a group of compounds, and also may be excluded from a claim to a composition comprising a group of compounds, but are not excluded from a claim to a use of a group of compounds or compositions thereof. In embodiments, one or more compounds may be excluded from a claim to a group of compounds, and also may be excluded from a claim to a composition consisting essentially of a group of compounds, but are not excluded from a composition comprising the one or more compounds together with one or more additional disclosed compounds and/or additional active compounds. In embodiments, one or more compounds may be excluded from a claim to a group of compounds, and also may be excluded from a claim to a composition consisting essentially of a group of compounds, and also may be excluded from a claim to a use of a group of compounds or compositions consisting essentially thereof, but are not excluded from a composition comprising the one or more compounds together with one or more additional disclosed compounds and/or additional active compounds, or a use of a composition comprising the one or more compounds together with one or more additional disclosed compounds and/or additional active compounds. In embodiments, one or more compounds may be excluded from a claim to a group of compounds, and also may be excluded from a claim to a composition consisting essentially of a group of compounds, and also may be excluded from a claim to a use of a group of compounds or compositions consisting essentially thereof, and further may be excluded from a composition comprising the one or more compounds together with one or more additional disclosed compounds and/or additional active compounds, but are not excluded from a claim to a use of a composition comprising the one or more compounds together with one or more additional disclosed compounds and/or additional active compounds.

Generally, the nomenclature and terminology used and the procedures performed herein are those known in fields relating to that of one or more aspects of the invention, such as those of biology, pharmacology, neuroscience, organic chemistry, synthetic chemistry, medicinal chemistry, and/or pharmaceutical sciences, and are those that will be well-known and commonly employed in one or more of such fields. Standard techniques and procedures will be those generally performed according to conventional methods in the art. Although any materials and methods similar or equivalent to those described herein can be used in the practice of the invention, certain preferred materials and methods are described herein.

B. Substituted Phenylalkylamine Compounds

In human clinical studies currently underway, accumulating evidence demonstrates that the empathogen 3,4-methylenedioxymethamphetamine (MDMA) has promise in rapidly and effectively treating mental health disorders when taken in combination with psychotherapy. The term "empathogen" (meaning "generating a state of empathy") was independently suggested in 1983-84 by the psychologist and psychopharmacologist Ralph Metzner and the Purdue University professor of pharmacology and medicinal chemistry David Nichols. Nichols subsequently coined the term "entactogen" in 1986 (meaning "to touch within") (Holland et al., Park Street Press, 2001 at 182 n.2.). Findings from a randomized, double-blind, placebo-controlled, multi-site phase 3 clinical trial demonstrated that, compared to therapy with inactive placebo, MDMA-assisted therapy is highly efficacious in individuals with severe PTSD, and treatment is safe and well-tolerated, even in those with comorbidities (Mitchell et al., Nat. Med., 2021; 27, 1025-1033). Studies have demonstrated potential for MDMA to address other difficult-to-treat mental health conditions, including substance abuse, obsessive compulsive disorder (OCD), phobias, eating disorders, depression, end-of-life anxiety, and social anxiety.

Although MDMA generally produces no long-lasting or serious adverse events, it is known to cause transient adverse events that are mild to moderate in severity, including increased anxiety, cardiovascular effects such as increased blood pressure and heart rate, hyperthermia, hyperhidrosis, jaw tightness and bruxism, muscle tightness, unpleasant stimulation, reduced appetite, nausea, poor concentration, and impaired balance (see, e.g., Harris et al., Psychopharmacology (Berl), 2002; 162(4), 396-405; Lietchti 2001, Oehen et al., J. Psychopharmacol., 2013; 27(1), 40-52; Mas et al., J. Pharmacol. Exp. Ther., 1999; 290(1), 136-45; Mithoefer et al., Journal of Psychopharmacology, 2010; 25(4), 439-452; Rogers et al., Health Technol. Assess, 2009; 13(6), iii-iv, ix-xii, 1-315). Accordingly, compounds that can harness the therapeutic benefits of MDMA without its negative side effects have been highly sought after. Mitigating one or more of these side effects and improving the safety profile would both increase the value of the compound for therapeutic use, and broaden the population of patients who could benefit. Additionally, the duration of an administration session with MDMA is typically 6-8 hours, and usually requires two trained therapists or facilitators to be present throughout. To the extent the same therapeutic effects can be obtained in a shorter administration session, the number of patients who are able to access and benefit from drug-assisted therapy would increase. Indeed, some companies are currently working with the short-acting tryptamine N,N-dimethyltryptamine (DMT) in an attempt to achieve this goal. However, its duration of action of 15-20 minutes is so short as to limit its effectiveness in therapy.

One class of compounds, known as the "2C" or "2C-x" compounds, are ring-substituted phenethylamines containing methoxy groups on the 2 and 5 positions of the benzene ring, along with often lipophilic substituents at the 4 position (i.e., R" below).

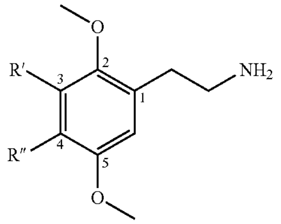

Certain 2C compounds may have effects that are similar to those of empathogens such as MDMA, as well as effects that are similar to those of psychedelics such as psilocybin. Certain 2C compounds may also share the stimulating effects of some substituted amphetamines.

Although some 2C compounds are generally well-tolerated within certain dose ranges, members of the class have been shown to result in adverse sympathomimetic effects including agitation, excited delirium, aggression, violence, dysphoria, hypertension, tachycardia, seizures, and hyperthermia, and many are known to be generally associated with heavy "body load" and gastrointestinal effects (see, e.g., Dean et al., J Med Toxicol, 2013; 9(2), 172-178).

In some aspects, provided are phenylalkylamine compounds, specifically substituted phenylalkylamines. In some embodiments, the substituted phenylalkylamine compounds are 2,5-disubstituted phenylalkylamine compounds or 2,4,5-trisubstituted phenylalkylamine compounds. Such compounds may be referred to interchangeably herein as "substituted phenylalkylamines," "therapeutic substituted phenylalkylamines," "disclosed compounds," "compounds described herein," or "compounds of the disclosure." The term "phenylalkylamine" refers to a compound containing a phenyl ring that is joined to an amino group via an alkyl chain. The term "substituted phenylalkylamine" describes a phenylalkylamine in which one or more hydrogen atoms has been replaced by a substituent, for example a deuterium atom, an alkyl group, a haloalkyl group, an alkoxy group, or a haloalkoxy group.

In one aspect, provided herein is a compound of Formula (I):

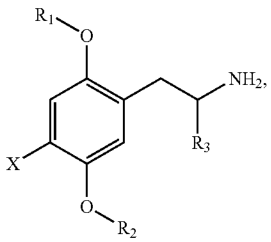

(I)

wherein $R_1$ is —$CH_3$, —$CD_3$, or —$CF_3$; $R_2$ is —$CH_3$, —$CD_3$, or —$CF_3$; $R_3$ is H, —$CH_3$, or —$CH_2CH_3$; and X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I; or a pharmaceutically acceptable salt, prodrug, hydrate, or solvate thereof.

In embodiments of Formula (I), $R_1$ is —$CH_3$, —$CD_3$, or —$CF_3$. In some embodiments, $R_1$ is —$CH_3$. In some embodiments, $R_1$ is —$CD_3$. In some embodiments, $R_1$ is —$CF_3$.

In embodiments of Formula (I), $R_2$ is —$CH_3$, —$CD_3$, or —$CF_3$. In some embodiments, $R_2$ is —$CH_3$. In some embodiments, $R_2$ is —$CD_3$. In some embodiments, $R_2$ is —$CF_3$.

In some preferred embodiments of Formula (I), one of $R_1$ and $R_2$ is —$CD_3$; and the other of $R_1$ and $R_2$ is —$CH_3$. In some embodiments, $R_1$ is —$CD_3$ and $R_2$ is —$CH_3$. In some embodiments, $R_1$ is —$CH_3$ and $R_2$ is —$CD_3$. In some embodiments of Formula (I), one of $R_1$ and $R_2$ is —$CF_3$; and the other of $R_1$ and $R_2$ is —$CH_3$. In some embodiments, $R_1$ is —$CF_3$ and $R_2$ is —$CH_3$. In some embodiments, $R_1$ is —$CH_3$ and $R_2$ is —$CF_3$. In some embodiments of Formula (I), one of $R_1$ and $R_2$ is —$CF_3$; and the other of $R_1$ and $R_2$ is —$CD_3$. In some embodiments, $R_1$ is —$CF_3$ and $R_2$ is —$CD_3$. In some embodiments, $R_1$ is —$CD_3$ and $R_2$ is —$CF_3$. In some embodiments, $R_1$ and $R_2$ are both —$CH_3$. In some embodiments, $R_1$ and $R_2$ are both —$CD_3$. In some embodiments, $R_1$ and $R_2$ are both —$CF_3$.

In some embodiments of Formula (I), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is $OCH_2CH_2CH_3$. In some embodiments, X is —$OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$.

In some embodiments, X is —$OCF_3$, —$OCH_2CF_3$, or —$OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I), $R_1$ is —$CD_3$, $R_2$ is —$CH_3$, and X is Br. In some embodiments, $R_1$ is —$CD_3$, $R_2$ is —$CH_3$, and X is I. In some embodiments, $R_1$ is —$CD_3$, $R_2$ is —$CH_3$, $R_3$ is H, and X is Br. In some embodiments, $R_1$ is —$CD_3$, $R_2$ is —$CH_3$, $R_3$ is H, and X is I. In some embodiments, $R_1$ is —$CD_3$, $R_2$ is —$CH_3$, $R_3$ is —$CH_3$, and X is Br. In some embodiments, $R_1$ is —$CD_3$, $R_2$ is —$CH_3$, $R_3$ is —$CH_3$, and X is I.

In some embodiments of Formula (I), $R_1$ is —$CH_3$, $R_2$ is —$CD_3$, and X is Br. In some embodiments, $R_1$ is —$CH_3$, $R_2$ is —$CD_3$, and X is I. In some embodiments, $R_1$ is —$CH_3$, $R_2$ is —$CD_3$, $R_3$ is H, and X is Br. In some embodiments, $R_1$ is —$CH_3$, $R_2$ is —$CD_3$, $R_3$ is H, and X is I. In some embodiments, $R_1$ is —$CH_3$, $R_2$ is —$CD_3$, $R_3$ is —$CH_3$, and X is Br. In some embodiments, $R_1$ is —$CH_3$, $R_2$ is —$CD_3$, $R_3$ is —$CH_3$, and X is I.

In some embodiments of Formula (I), $R_1$ is —$CF_3$, $R_2$ is —$CH_3$, and X is Br. In some embodiments, $R_1$ is —$CF_3$, $R_2$ is —$CH_3$, and X is I. In some embodiments, $R_1$ is —$CF_3$, $R_2$ is —$CH_3$, $R_3$ is H, and X is Br. In some embodiments, $R_1$ is —$CF_3$, $R_2$ is —$CH_3$, $R_3$ is H, and X is I. In some embodiments, $R_1$ is —$CF_3$, $R_2$ is —$CH_3$, $R_3$ is —$CH_3$, and X is Br. In some embodiments, $R_1$ is —$CF_3$, $R_2$ is —$CH_3$, $R_3$ is —$CH_3$, and X is I.

In some embodiments of Formula (I), $R_1$ is —$CH_3$, $R_2$ is —$CF_3$, and X is Br. In some embodiments, $R_1$ is —$CH_3$, $R_2$ is —$CF_3$, and X is I. In some embodiments, $R_1$ is —$CH_3$, $R_2$ is —$CF_3$, $R_3$ is H, and X is Br. In some embodiments, $R_1$ is —$CH_3$, $R_2$ is —$CF_3$, $R_3$ is H, and X is I. In some embodiments, $R_1$ is —$CH_3$, $R_2$ is —$CF_3$, $R_3$ is —$CH_3$, and X is Br. In some embodiments, $R_1$ is —$CH_3$, $R_2$ is —$CF_3$, $R_3$ is —$CH_3$, and X is I.

In some embodiments, the compound of Formula (I), or a pharmaceutically acceptable salt, prodrug, hydrate, or solvate thereof, has the structure of Formula (I-A):

(I-A)

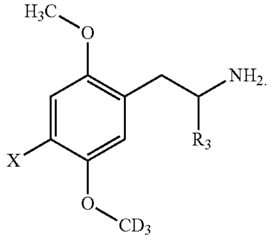

In some embodiments of Formula (I-A), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-A), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is $OCH_2CH_2CH_3$. In some embodiments, X is —$OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or —$OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I-A), $R_3$ is H and X is Br. In embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-B):

(I-B)

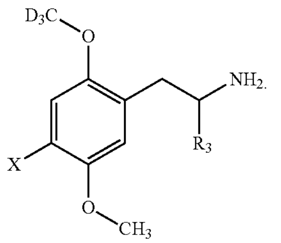

In some embodiments of Formula (I-B), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-B), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is $OCH_2CH_2CH_3$. In some embodiments, X is —$OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or —$OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In embodiments, X is Cl. In embodiments, X is Br. In embodiments, X is I.

In some embodiments of Formula (I-B), $R_3$ is H and X is Br. In some embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-C):

(I-C)

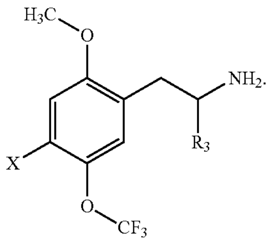

In some embodiments of Formula (I-C), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-C), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I.

In some embodiments of Formula (I-C), X is H. In some embodiments of Formula (I-C), X is not H. In some embodiments of Formula (I-C), X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I.

In some embodiments of Formula (I-C), X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is —$OCH_2CH_2CH_3$. In some embodiments, X is $OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or $OCH_2CH_2CF_3$. In some embodiments, X is $OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or $SCH_2CH_2CF_3$. In some embodiments, X is $SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I-C), $R_3$ is H and X is Br. In some embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-D):

(I-D)

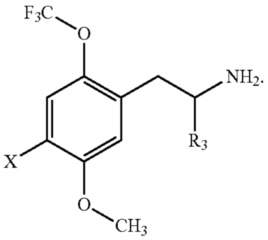

In some embodiments of Formula (I-D), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-D), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I.

In some embodiments of Formula (I-D), X is H. In some embodiments of Formula (I-C), X is not H. In some embodiments of Formula (I-C), X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I.

In some embodiments of Formula (I-D), X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is —$OCH_2CH_2CH_3$. In some embodiments, X is $OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or $OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or $SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I-D), $R_3$ is H and X is Br. In some embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-E):

(I-E)

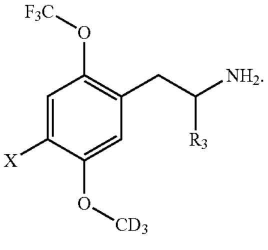

In some embodiments of Formula (I-E), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-E), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is $OCH_2CH_2CH_3$. In some embodiments, X is —$OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or —$OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I-E), $R_3$ is H and X is Br. In some embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-F):

(I-F)

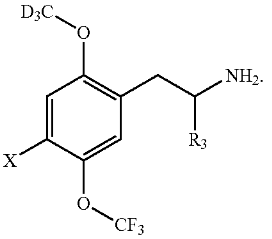

In some embodiments of Formula (I-F), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-F), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is $OCH_2CH_2CH_3$. In some embodiments, X is —$OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or —$OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I-F), $R_3$ is H and X is Br. In some embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-G):

(I-G)

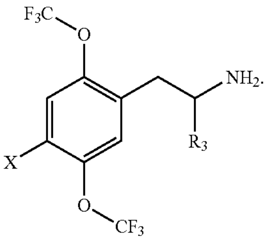

In some embodiments of Formula (I-G), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-G), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is $OCH_2CH_2CH_3$. In some embodiments, X is —$OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or —$OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I-G), $R_3$ is H and X is Br. In some embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-H):

(I-H)

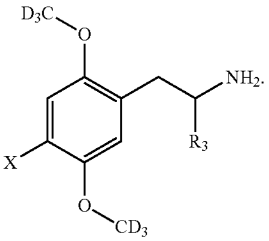

In some embodiments of Formula (I-H), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-H), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is —$CD_3$, —$CH_2CH_3$, —$CH_2CD_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$SCD_3$, —$SCH_2CD_3$, —$SCH_2CF_3$, or $SCH_2CH_2CD_3$. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is —$CH_2CH_2CH_3$. In some embodiments, X is —$CD_3$, —$CH_2CD_3$, or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is $OCH_2CH_2CH_3$. In some embodiments, X is —$OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or —$OCH_2CH_2CF_3$. In some embodiments, X is —$OCF_3$. In some embodiments, X is —$OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In some embodiments of Formula (I-H), $R_3$ is H and X is Br. In some embodiments, $R_3$ is H and X is I. In embodiments, $R_3$ is —$CH_3$ and X is Br. In embodiments, $R_3$ is —$CH_3$ and X is I.

In some embodiments, the compound of Formula (I), or a pharmaceutically acceptable salt, prodrug, hydrate, or solvate thereof, has the structure of Formula (I-I):

(I-I)

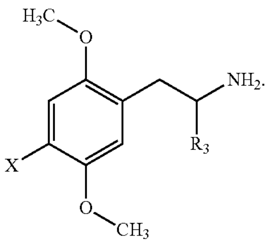

In some embodiments of Formula (I-I), $R_3$ is H, —$CH_3$, or —$CH_2CH_3$. In some embodiments, $R_3$ is H. In some embodiments, $R_3$ is —$CH_3$ or —$CH_2CH_3$. In some embodiments, $R_3$ is —$CH_3$. In some embodiments, $R_3$ is —$CH_2CH_3$.

In some embodiments of Formula (I-I), X is H, —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$, —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$, F, Cl, Br, or I. In some embodiments, X is —$CH_2CD_3$, —$CH_2CH_2CD_3$, —$OCD_3$, —$OCF_3$, —$OCH_2CD_3$, —$OCH_2CF_3$, —$OCH_2CH_2CD_3$, —$SCD_3$, —$SCH_2CD_3$, or $SCH_2CH_2CD_3$. In some embodiments, X is H. In some embodiments, X is —$CH_3$, —$CD_3$, —$CH_2CH_3$, —$CH_2CD_3$, —$CH_2CH_2CH_3$, —$CH_2CH_2CD_3$, —$CF_3$, —$CH_2CF_3$, —$CH_2CH_2CF_3$. In some embodiments, X is —$CH_3$, —$CH_2CH_3$, or —$CH_2CH_2CH_3$. In some embodiments, X is —$CH_3$. In some embodiments, X is —$CH_2CH_3$. In some embodiments, X is $CH_2CH_2CH_3$. In some embodiments, X is —$CD_3$, —$CH_2CD_3$, or —$CH_2CH_2CD_3$. In some embodiments, X is —$CH_2CD_3$ or —$CH_2CH_2CD_3$. In some embodiments, X is —$CD_3$. In some embodiments, X is —$CH_2CD_3$. In some embodiments, X is —$CH_2CH_2CD_3$. In some embodiments, X is —$CF_3$, —$CH_2CF_3$, or —$CH_2CH_2CF_3$. In some embodiments, X is —$CF_3$. In some embodiments, X is —$CH_2CF_3$. In some embodiments, X is —$CH_2CH_2CF_3$. In some embodiments, —$OCH_3$, —$OCD_3$, —$OCF_3$, —$OCH_2CH_3$, —$OCH_2CD_3$, —$OCH_2CF_3$, —$OCH_2CH_2CH_3$, —$OCH_2CH_2CD_3$, —$OCH_2CH_2CF_3$. In some embodiments, X is —$OCH_3$, —$OCH_2CH_3$, or $OCH_2CH_2CH_3$. In some embodiments, X is —$OCH_3$. In some embodiments, X is —$OCH_2CH_3$. In some embodiments, X is —$OCH_2CH_2CH_3$. In some embodiments, X is $OCD_3$, —$OCH_2CD_3$, or $OCH_2CH_2CD_3$. In some embodiments, X is —$OCD_3$. In some embodiments, X is —$OCH_2CD_3$. In some embodiments, X is —$OCH_2CH_2CD_3$. In some embodiments, X is —$OCF_3$, —$OCH_2CF_3$, or $OCH_2CH_2CF_3$. In some embodiments, X is $OCF_3$ or $OCH_2CF_3$. In some embodiments, X is —$OCF_3$. In some embodiments, X is $OCH_2CF_3$. In some embodiments, X is —$OCH_2CH_2CF_3$. In some embodiments, X is —$SCH_3$, —$SCD_3$, —$SCF_3$, —$SCH_2CH_3$, —$SCH_2CD_3$, —$SCH_2CF_3$, —$SCH_2CH_2CH_3$, —$SCH_2CH_2CD_3$, —$SCH_2CH_2CF_3$. In some embodiments, X is —$SCH_3$, —$SCH_2CH_3$, or $SCH_2CH_2CH_3$. In some embodiments, X is —$SCH_3$. In some embodiments, X is —$SCH_2CH_3$. In some embodiments, X is —$SCH_2CH_2CH_3$. In some embodiments, X is —$SCD_3$, —$SCH_2CD_3$, or $SCH_2CH_2CD_3$. In some embodiments, X is —$SCD_3$. In some embodiments, X is —$SCH_2CD_3$. In some embodiments, X is —$SCH_2CH_2CD_3$. In some embodiments, X is —$SCF_3$, —$SCH_2CF_3$, or —$SCH_2CH_2CF_3$. In some embodiments, X is —$SCF_3$. In some embodiments, X is —$SCH_2CF_3$. In some embodiments, X is —$SCH_2CH_2CF_3$. In some embodiments, X is F, Cl, Br, or I. In some embodiments, X is F. In some embodiments, X is Cl. In some embodiments, X is Br. In some embodiments, X is I.

In one aspect, the compound of Formula (I) is a compound of Formula (I1) (i.e., where X is hydrogen as depicted below, and similarly where X may be as depicted in any of the structural formulae that follow, as will be readily appreciated by those of skill):

(I1)

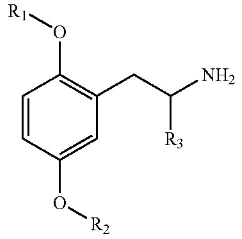

or a pharmaceutically acceptable salt, prodrug, hydrate, or solvate thereof (which will be understood to include all amorphous and polymorphic forms); wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I1), or a composition consisting essentially of a single compound of Formula (I1), the compound of Formula (I1) will be as described above, except where the resulting compound is 1-(2-methoxy-5-(trifluoromethoxy)phenyl)ethan-2-amine. In some embodiments, when both $R_1$ and $R_3$ are —$CH_3$, $R_2$ will not be —$CF_3$. In some embodiments, when both $R_1$ and $R_2$ are —$CH_3$, $R_3$ will not be H.

In another aspect, the compound of Formula (I) is a compound of Formula (I2):

(I2)

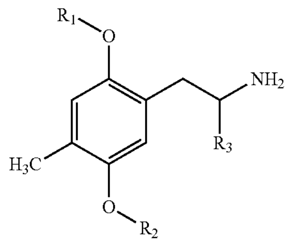

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (12), or a composition consisting essentially of a single compound of Formula (12), the compound of Formula (12) will be as described above, except when both $R_1$ and $R_2$ are —$CH_3$, $R_3$ will not be H, —$CH_3$, or —$CH_2CH_3$, or Br. In some embodiments, when both $R_1$ and $R_2$ are —$OCD_3$, $R_3$ will not be H, or —$CH_3$.

In a further aspect, the compound of Formula (I) is a compound of Formula (I3):

(I3)

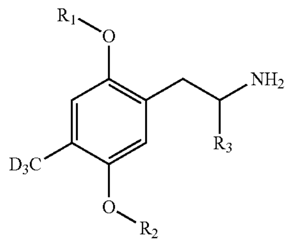

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I3), or a composition consisting essentially of a single compound of Formula (I3), the compound of Formula (I3) will be as described above, except when both $R_1$ and $R_2$ are —$CH_3$, $R_3$ will not be —$CH_3$.

In another aspect, the compound of Formula (I) is a compound of Formula (I4):

(I4)

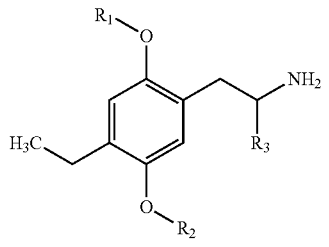

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I4), or a composition consisting essentially of a single compound of Formula (I4), the compound of Formula (I4) will be as described above, except when both $R_1$ and $R_2$ are —$CH_3$, $R_3$ will not be H, —$CH_3$, or —$CH_2CH_3$.

In another aspect, the compound of Formula (I) is a compound of Formula (I5):

(I5)

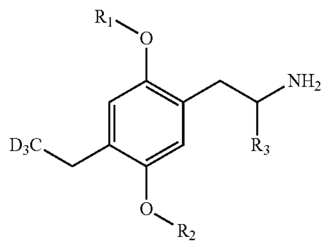

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I6):

(I6)

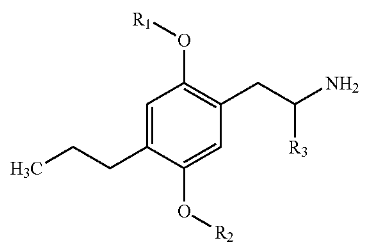

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I6), or a composition consisting essentially of a single compound of Formula (I6), the compound of Formula (I6) will be as described above, except when both $R_1$ and $R_2$ are —$CH_3$, $R_3$ will not be H, —$CH_3$, or —$CH_2CH_3$.

In a further aspect, the compound of Formula (I) is a compound of Formula (I7):

(I7)

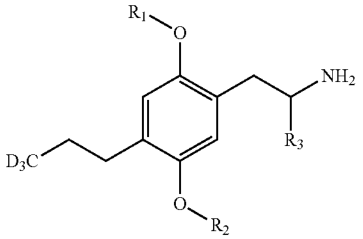

or a pharmaceutically acceptable salt, prodrug, hydrate, or solvate thereof; wherein $R_1$ is —$CH_3$, —$CD_3$ or $CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I8):

(I8)

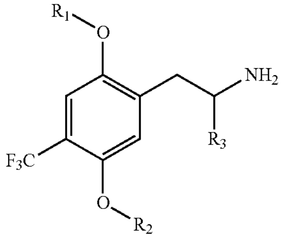

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I8), or a composition consisting essentially of a single compound of Formula (I8), the compound of Formula (I8) will be as described above, except where the resulting compound is 2-(2,5-dimethoxy-4-(trifluoromethyl)phenyl)ethan-1-amine or 1-(2,5-dimethoxy-4-(trifluoro-methyl)phenyl)propan-2-amine. In some embodiments, when both $R_1$ and $R_2$ are —$CH_3$, $R_3$ will be neither H nor —$CH_3$.

In a further aspect, the compound of Formula (I) is a compound of Formula (I9):

(I9)

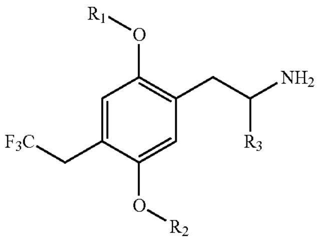

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I9), or a composition consisting essentially of a single compound of Formula (I9), the compound of Formula (I9) will be as described above, except where the resulting compound is 2-(2,5-dimethoxy-4-(2,2,2-trifluoroethyl)phenyl)ethan-1-amine or 1-(2,5-dimethoxy-4-(2,2,2-trifluoroethyl)phenyl)propan-2-amine. In some embodiments, when both $R_1$ and $R_2$ are —$CH_3$, $R_3$ will be neither H nor —$CH_3$.

In a further aspect, the compound of Formula (I) is a compound of Formula (I10):

(I10)

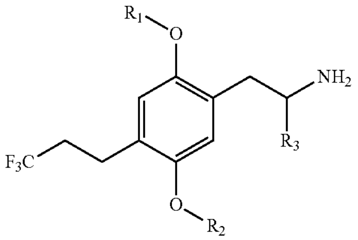

or a pharmaceutically acceptable salt, prodrug, hydrate, or solvate thereof; wherein $R_1$ is —$CH_3$, —$CD_3$ or $CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I10), or a composition consisting essentially of a single compound of Formula (I10), the compound of Formula (I10) will be as described above, except when both $R_1$ and $R_2$ are —$CH_3$, $R_3$ will not be —$CH_3$.

In a further aspect, the compound of Formula (I) is a compound of Formula (I11):

(I11)

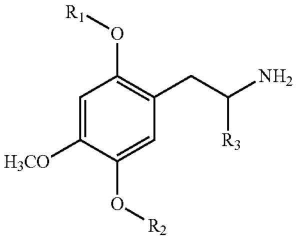

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I11), or a composition consisting essentially of a single compound of Formula (I11), the compound of Formula (I11) will be as described above, except when both $R_1$ and $R_2$ are $CH_3$, $R_3$ will not be H, —$CH_3$, or —$CH_2CH_3$.

In a further aspect, the compound of Formula (I) is a compound of Formula (I12):

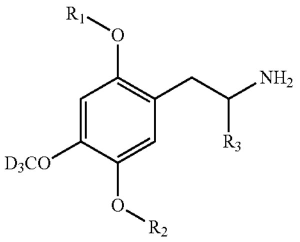

(I12)

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I13):

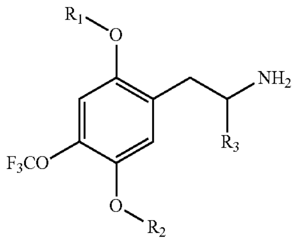

(I13)

or a pharmaceutically acceptable salt, prodrug, hydrate, or solvate thereof; wherein $R_1$ is —$CH_3$, —$CD_3$ or $CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I14):

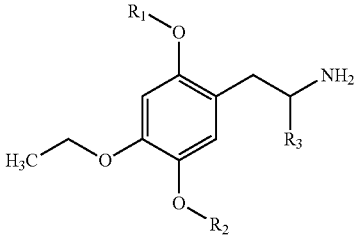

(I14)

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I14), or a composition consisting essentially of a single compound of Formula (I14), the compound of Formula (I14) will be as described above, except when both $R_1$ and $R_2$ are —$CH_3$, $R_3$ will not be —$CH_3$, or —$CH_2CH_3$.

In a further aspect, the compound of Formula (I) is a compound of Formula (I15):

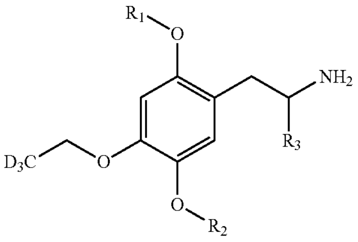

(I15)

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I16):

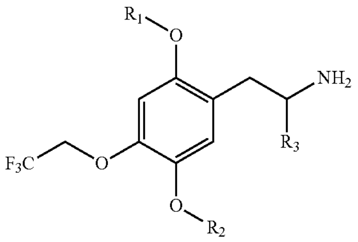

(I16)

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I16), or a composition consisting essentially of a single compound of Formula (I16), the compound of Formula (I16) will be as described above, except where the resulting compound is 2-(2,5-dimethoxy-4-(2,2,2-trifluoroethoxy)phenyl)ethan-1-amine or 1-(2,5-dimethoxy-4-(2,2,2-trifluoroethoxy)phenyl)propan-2-amine. In some embodiments, when both $R_1$ and $R_2$ are —$CH_3$, $R_3$ will be neither H nor —$CH_3$.

In a further aspect, the compound of Formula (I) is a compound of Formula (I17):

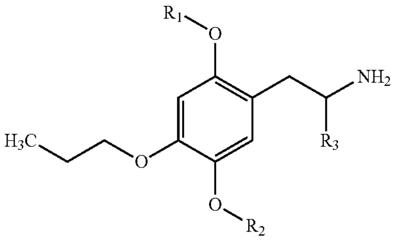

(I17)

or a pharmaceutically acceptable salt, prodrug, hydrate, or solvate thereof; wherein $R_1$ is —$CH_3$, —$CD_3$ or $CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I17), or a composition consisting essentially of a single compound of Formula (I17), the compound of Formula (I17) will be as described above, except when both $R_1$ and $R_2$ are —$CH_3$, $R_3$ will not be —$CH_3$, or —$CH_2CH_3$.

In a further aspect, the compound of Formula (I) is a compound of Formula (I18):

(I18)

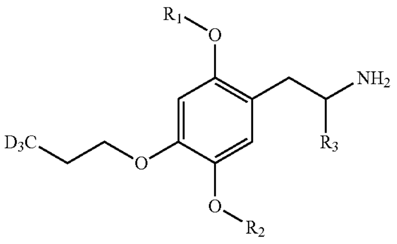

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I19):

(I19)

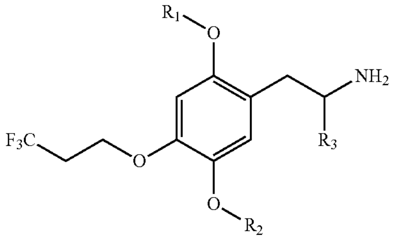

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I20):

(I20)

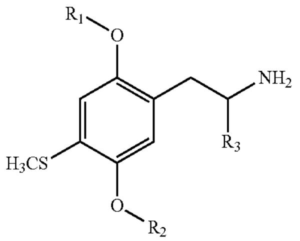

or a pharmaceutically acceptable salt, prodrug, hydrate, or solvate thereof; wherein $R_1$ is —$CH_3$, —$CD_3$ or $CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I20), or a composition consisting essentially of a single compound of Formula (I20), the compound of Formula (I20) will be as described above, except when both $R_1$ and $R_2$ are —$CH_3$, $R_3$ will not be H, —$CH_3$, or —$CH_2CH_3$.

In a further aspect, the compound of Formula (I) is a compound of Formula (I21):

(I21)

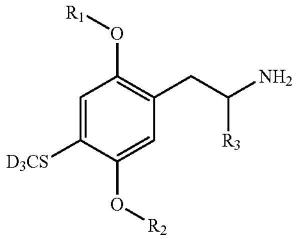

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I22):

(I22)

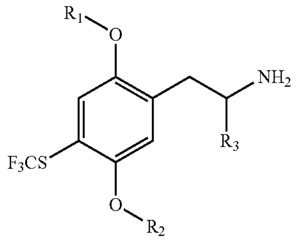

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I23):

(I23)

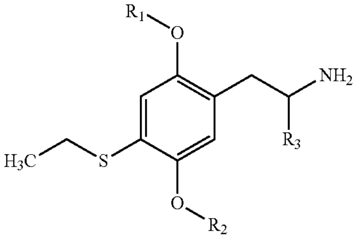

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I23), or a composition consisting essentially of a single compound of Formula (I23), the compound of Formula (I23) will be as described above, except where the resulting compound is 1-(4-(ethylthio)-2,5-bis(methoxy-d3)phenyl)propan-2-amine. In some embodiments, when both $R_1$ and $R_2$ are —$CD_3$, $R_3$ will be neither H nor —$CH_3$. In some embodiments, for instance embodiments consisting of a single compound of Formula (I23), or a composition consisting essentially of a single compound of Formula (I23), the compound of Formula (I23) will be as described above, except when both $R_1$ and $R_2$ are —$CH_3$, $R_3$ will not be H, —$CH_3$, or —$CH_2CH_3$.

In a further aspect, the compound of Formula (I) is a compound of Formula (I24):

(I24)

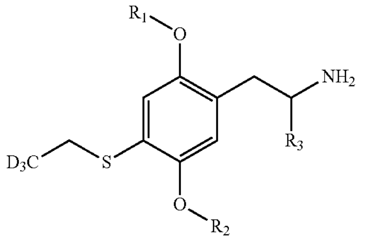

or a pharmaceutically acceptable salt, prodrug, hydrate, or solvate thereof; wherein $R_1$ is —$CH_3$, —$CD_3$ or $CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I25):

(I25)

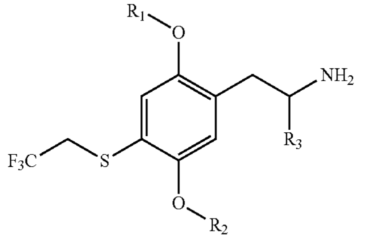

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I25), or a composition consisting essentially of a single compound of Formula (I25), the compound of Formula (I25) will be as described above, except where the resulting compound is 2-(2,5-dimethoxy-4-((2,2,2-trifluoroethyl)thio)phenyl)ethan-1-amine. In some embodiments, when both $R_1$ and $R_2$ are —$CH_3$, $R_3$ will not be H.

In a further aspect, the compound of Formula (I) is a compound of Formula (I26):

(I26)

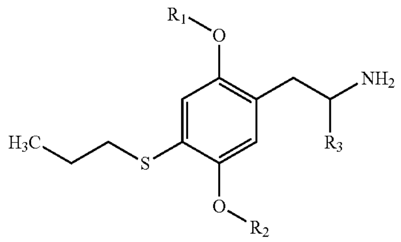

or a pharmaceutically acceptable salt, prodrug, hydrate, or solvate thereof; wherein $R_1$ is —$CH_3$, —$CD_3$ or $CF_3$, $R_2$ is —$CH_3$, —$CD_3$ or —$CF_3$, and $R_3$ is H, —$CH_3$, or —$CH_2CH_3$.

In some embodiments, for instance embodiments consisting of a single compound of Formula (I26), or a composition consisting essentially of a single compound of Formula (I26), the compound of Formula (I26) will be as described above, except where the resulting compound is 1-(2,5-bis(methoxy-d3)-4-(propylthio)phenyl)propan-2-amine. In some embodiments, when both $R_1$ and $R_2$ are —$CD_3$, $R_3$ will not be H. In some embodiments, for instance embodiments consisting of a single compound of Formula (I26), or a composition consisting essentially of a single compound of Formula (I26), the compound of Formula (I26) will be as described above, except when both $R_1$ and $R_2$ are —$CH_3$, $R_3$ will not be H, —$CH_3$, or —$CH_2CH_3$.

In a further aspect, the compound of Formula (I) is a compound of Formula (I27):

(I27)

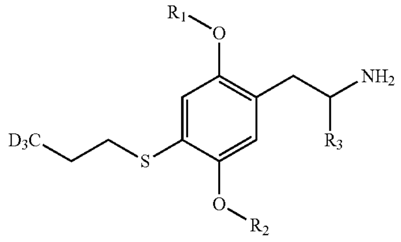

or a pharmaceutically acceptable salt, prodrug, hydrate, or solvate thereof; wherein $R_1$ is —$CH_3$, —$CD_3$ or —$CF_3$, $R_2$ is —$CH_3$, —$CD_3$ or —$CF_3$, and $R_3$ is H, —$CH_3$, or —$CH_2CH_3$.

In a further aspect, the compound of Formula (I) is a compound of Formula (I28):

(I28)

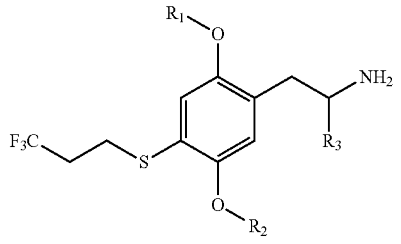

or a pharmaceutically acceptable salt, prodrug, hydrate, or solvate thereof; wherein $R_1$ is $—CH_3$, $—CD_3$ or $—CF_3$, $R_2$ is $—CH_3$, $—CD_3$ or $—CF_3$, and $R_3$ is H, $—CH_3$, or $—CH_2CH_3$.

In a further aspect, the compound of Formula (I) is a compound of Formula (I29):

(I29)

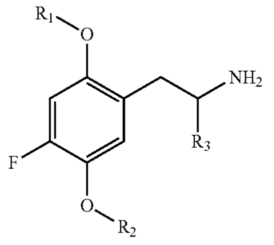

or a pharmaceutically acceptable salt, prodrug, hydrate, or solvate thereof; wherein $R_1$ is $—CH_3$, $—CD_3$ or $—CF_3$, $R_2$ is $—CH_3$, $—CD_3$ or $—CF_3$, and $R_3$ is H, $—CH_3$, or $—CH_2CH_3$.

In some embodiments, for instance embodiments consisting of a single compound of Formula (I29), or a composition consisting essentially of a single compound of Formula (I29), the compound of Formula (I29) will be as described above, except where the resulting compound is 2-(4-fluoro-2,5-dimethoxyphenyl)ethan-1-amine or 1-(4-fluoro-2,5-dimethoxyphenyl)propan-2-amine. In embodiments, when both $R_1$ and $R_2$ are $—CH_3$, $R_3$ will be neither H nor $—CH_3$.

In a further aspect, the compound of Formula (I) is a compound of Formula (I30):

(I30)

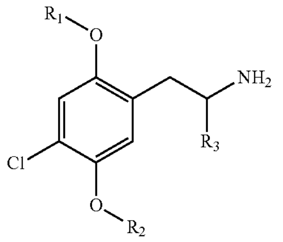

or a pharmaceutically acceptable salt, prodrug, hydrate, or solvate thereof; wherein $R_1$ is $—CH_3$, $—CD_3$ or $CF_3$, $R_2$ is $—CH_3$, $—CD_3$ or $—CF_3$, and $R_3$ is H, $—CH_3$, or $—CH_2CH_3$.

In some embodiments, for instance embodiments consisting of a single compound of Formula (I30), or a composition consisting essentially of a single compound of Formula (I30), the compound of Formula (I30) will be as described above, except where the resulting compound is 1-(4-chloro-2,5-bis(methoxy-d3)phenyl)propan-2-amine. In some embodiments, when both $R_1$ and $R_2$ are $—CD_3$, $R_3$ will be neither H nor $—CH_3$. In some embodiments, for instance embodiments consisting of a single compound of Formula (I30), or a composition consisting essentially of a single compound of Formula (I30), the compound of Formula (I30) will be as described above, except when both $R_1$ and $R_2$ are $—CH_3$, $R_3$ will not be H, $—CH_3$, or $—CH_2CH_3$.

In a further aspect, the compound of Formula (I) is a compound of Formula (I31):

(I31)

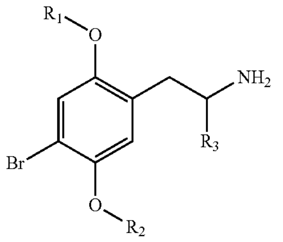

or a pharmaceutically acceptable salt, prodrug, hydrate, or solvate thereof; wherein $R_1$ is $—CH_3$, $—CD_3$ or $—CF_3$, $R_2$ is $—CH_3$, $—CD_3$ or $—CF_3$, and $R_3$ is H, $—CH_3$, or $—CH_2CH_3$.

In some embodiments, for instance embodiments consisting of a single compound of Formula (I31), or a composition consisting essentially of a single compound of Formula (I31), the compound of Formula (I31) will be as described above, except where the resulting compound is 1-(4-bromo-2,5-bis(methoxy-d3)phenyl)propan-2-amine. In some embodiments, when both $R_1$ and $R_2$ are $—CD_3$, $R_3$ will be neither H nor $—CH_3$.

In some embodiments, for instance embodiments consisting of a single compound of Formula (I31), or a composition consisting essentially of a single compound of Formula (I31), the compound of Formula (I31) will be as described above, except when both $R_1$ and $R_2$ are $—CH_3$, $R_3$ will not be H, $—CH_3$, or $—CH_2CH_3$.

In a further aspect, the compound of Formula (I) is a compound of Formula (I32):

(I32)

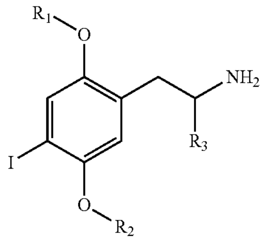

or a pharmaceutically acceptable salt, prodrug, hydrate, or solvate thereof; wherein $R_1$ is $—CH_3$, $—CD_3$ or $CF_3$, $R_2$ is $—CH_3$, $—CD_3$ or $—CF_3$, and $R_3$ is H, $—CH_3$, or $—CH_2CH_3$.

In some embodiments, for instance embodiments consisting of a single compound of Formula (I32), or a composition consisting essentially of a single compound of Formula (I32), the compound of Formula (I32) will be as described above, except where the resulting compound is 1-(4-iodo-2,5-bis(methoxy-d3)phenyl)propan-2-amine. In some embodiments, when both $R_1$ and $R_2$ are $—CD_3$, $R_3$ will be neither H nor $—CH_3$. In some embodiments, for instance embodiments consisting of a single compound of Formula (I32), or a composition consisting essentially of a single compound of Formula (I32), the compound of Formula (I32) will be as described above, except when both $R_1$ and $R_2$ are $—CH_3$, $R_3$ will not be H, $—CH_3$, or $—CH_2CH_3$.

In some preferred embodiments of any of Formula (I1)-(I32), one of $R_1$ and $R_2$ is —$CD_3$; and the other of $R_1$ and $R_2$ is —$CH_3$. In some embodiments, $R_1$ is —$CD_3$ and $R_2$ is —$CH_3$. In some embodiments, $R_1$ is —$CH_3$ and $R_2$ is —$CD_3$. In some embodiments of any of Formula (I1)-(I32), one of $R_1$ and $R_2$ is —$CF_3$; and the other of $R_1$ and $R_2$ is —$CH_3$. In some embodiments, $R_1$ is —$CF_3$ and $R_2$ is —$CH_3$. In some embodiments, $R_1$ is —$CH_3$ and $R_2$ is —$CF_3$. In some embodiments of any of Formula (I1)-(I32), one of $R_1$ and $R_2$ is —$CF_3$; and the other of $R_1$ and $R_2$ is —$CD_3$. In some embodiments, $R_1$ is —$CF_3$ and $R_2$ is —$CD_3$. In some embodiments, $R_1$ is —$CD_3$ and $R_2$ is —$CF_3$. In some embodiments, $R_1$ and $R_2$ are both —$CH_3$. In some embodiments, $R_1$ and $R_2$ are both —$CD_3$. In some embodiments, $R_1$ and $R_2$ are both —$CF_3$.

Non-limiting exemplary compounds of the disclosure of Formula (I) are below, which may according to embodiments herein be claimed, for example, as individual compounds, as part of compositions comprising an individual compound, as part of compositions comprising mixtures of two (or more) compounds, and as such compounds and/or compositions for use in preparing medicaments for treatment, or for use (as such compounds and/or compositions) in methods for modulating neurotransmission, methods of treating a medical condition or improving the symptoms thereof, and/or methods of improving mental health or functioning.

In embodiments, the compound of Formula (I) is a compound of Formula (I-A) selected from Table I-A, or a pharmaceutically acceptable salt, prodrug, hydrate, or solvate thereof:

(I-A)

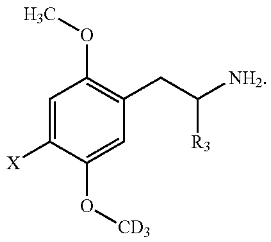

TABLE I-A

| Representative compounds of Formula (I-A) | | |
|---|---|---|
| Compound No. | $R_3$ | X |
| I-A-1 | H | H |
| I-A-2 | H | —$CH_3$ |
| I-A-3 | H | —$CD_3$ |
| I-A-4 | H | —$CH_2CH_3$ |
| I-A-5 | H | —$CH_2CD_3$ |
| I-A-6 | H | —$CH_2CH_2CH_3$ |
| I-A-7 | H | —$CH_2CH_2CD_3$ |
| I-A-8 | H | —$CF_3$ |
| I-A-9 | H | —$CH_2CF_3$ |
| I-A-10 | H | —$CH_2CH_2CF_3$ |
| I-A-11 | H | —$OCH_3$ |
| I-A-12 | H | —$OCD_3$ |
| I-A-13 | H | —$OCF_3$ |
| I-A-14 | H | —$OCH_2CH_3$ |
| I-A-15 | H | —$OCH_2CD_3$ |
| I-A-16 | H | —$OCH_2CF_3$ |
| I-A-17 | H | —$OCH_2CH_2CH_3$ |
| I-A-18 | H | —$OCH_2CH_2CD_3$ |
| I-A-19 | H | —$OCH_2CH_2CF_3$ |

TABLE I-A-continued

| Representative compounds of Formula (I-A) | | |
|---|---|---|
| Compound No. | $R_3$ | X |
| I-A-20 | H | —$SCH_3$ |
| I-A-21 | H | —$SCD_3$ |
| I-A-22 | H | —$SCF_3$ |
| I-A-23 | H | —$SCH_2CH_3$ |
| I-A-24 | H | —$SCH_2CD_3$ |
| I-A-25 | H | —$SCH_2CF_3$ |
| I-A-26 | H | —$SCH_2CH_2CH_3$ |
| I-A-27 | H | —$SCH_2CH_2CD_3$ |
| I-A-28 | H | —$SCH_2CH_2CF_3$ |
| I-A-29 | H | F |
| I-A-30 | H | Cl |
| I-A-31 | H | Br |
| I-A-32 | H | I |
| I-A-33 | H | H |
| I-A-34 | —$CH_3$ | —$CH_3$ |
| I-A-35 | —$CH_3$ | —$CD_3$ |
| I-A-36 | —$CH_3$ | —$CH_2CH_3$ |
| I-A-37 | —$CH_3$ | —$CH_2CD_3$ |
| I-A-38 | —$CH_3$ | —$CH_2CH_2CH_3$ |
| I-A-39 | —$CH_3$ | —$CH_2CH_2CD_3$ |
| I-A-40 | —$CH_3$ | —$CF_3$ |
| I-A-41 | —$CH_3$ | —$CH_2CF_3$ |
| I-A-42 | —$CH_3$ | —$CH_2CH_2CF_3$ |
| I-A-43 | —$CH_3$ | —$OCH_3$ |
| I-A-44 | —$CH_3$ | —$OCD_3$ |
| I-A-45 | —$CH_3$ | —$OCF_3$ |
| I-A-46 | —$CH_3$ | —$OCH_2CH_3$ |
| I-A-47 | —$CH_3$ | —$OCH_2CD_3$ |
| I-A-48 | —$CH_3$ | —$OCH_2CF_3$ |
| I-A-49 | —$CH_3$ | —$OCH_2CH_2CH_3$ |
| I-A-50 | —$CH_3$ | —$OCH_2CH_2CD_3$ |
| I-A-51 | —$CH_3$ | —$OCH_2CH_2CF_3$ |
| I-A-52 | —$CH_3$ | —$SCH_3$ |
| I-A-53 | —$CH_3$ | —$SCD_3$ |
| I-A-54 | —$CH_3$ | —$SCF_3$ |
| I-A-55 | —$CH_3$ | —$SCH_2CH_3$ |
| I-A-56 | —$CH_3$ | —$SCH_2CD_3$ |
| I-A-57 | —$CH_3$ | —$SCH_2CF_3$ |
| I-A-58 | —$CH_3$ | —$SCH_2CH_2CH_3$ |
| I-A-59 | —$CH_3$ | —$SCH_2CH_2CD_3$ |
| I-A-60 | —$CH_3$ | —$SCH_2CH_2CF_3$ |
| I-A-61 | —$CH_3$ | F |
| I-A-62 | —$CH_3$ | Cl |
| I-A-63 | —$CH_3$ | Br |
| I-A-64 | —$CH_3$ | I |
| I-A-65 | —$CH_2CH_3$ | —$CH_3$ |
| I-A-66 | —$CH_2CH_3$ | —$CD_3$ |
| I-A-67 | —$CH_2CH_3$ | —$CH_2CH_3$ |
| I-A-68 | —$CH_2CH_3$ | —$CH_2CD_3$ |
| I-A-69 | —$CH_2CH_3$ | —$CH_2CH_2CH_3$ |
| I-A-70 | —$CH_2CH_3$ | —$CH_2CH_2CD_3$ |
| I-A-71 | —$CH_2CH_3$ | —$CF_3$ |
| I-A-72 | —$CH_2CH_3$ | —$CH_2CF_3$ |
| I-A-73 | —$CH_2CH_3$ | —$CH_2CH_2CF_3$ |
| I-A-74 | —$CH_2CH_3$ | —$OCH_3$ |
| I-A-75 | —$CH_2CH_3$ | —$OCD_3$ |
| I-A-76 | —$CH_2CH_3$ | —$OCF_3$ |
| I-A-77 | —$CH_2CH_3$ | —$OCH_2CH_3$ |
| I-A-78 | —$CH_2CH_3$ | —$OCH_2CD_3$ |
| I-A-79 | —$CH_2CH_3$ | —$OCH_2CF_3$ |
| I-A-80 | —$CH_2CH_3$ | —$OCH_2CH_2CH_3$ |
| I-A-81 | —$CH_2CH_3$ | —$OCH_2CH_2CD_3$ |
| I-A-82 | —$CH_2CH_3$ | —$OCH_2CH_2CF_3$ |
| I-A-83 | —$CH_2CH_3$ | —$SCH_3$ |
| I-A-84 | —$CH_2CH_3$ | —$SCD_3$ |
| I-A-85 | —$CH_2CH_3$ | —$SCF_3$ |
| I-A-86 | —$CH_2CH_3$ | —$SCH_2CH_3$ |
| I-A-87 | —$CH_2CH_3$ | —$SCH_2CD_3$ |
| I-A-88 | —$CH_2CH_3$ | —$SCH_2CF_3$ |
| I-A-89 | —$CH_2CH_3$ | —$SCH_2CH_2CH_3$ |
| I-A-90 | —$CH_2CH_3$ | —$SCH_2CH_2CD_3$ |
| I-A-91 | —$CH_2CH_3$ | —$SCH_2CH_2CF_3$ |
| I-A-92 | —$CH_2CH_3$ | F |
| I-A-93 | —$CH_2CH_3$ | Cl |

TABLE I-A-continued

| Representative compounds of Formula (I-A) | | |
|---|---|---|
| Compound No. | $R_3$ | X |
| I-A-94 | —$CH_2CH_3$ | Br |
| I-A-95 | —$CH_2CH_3$ | I |

In embodiments, the compound of Formula (I) is a compound of Formula (I-B) selected from Table I-B, or a pharmaceutically acceptable salt, prodrug, hydrate, or solvate thereof:

(I-B)

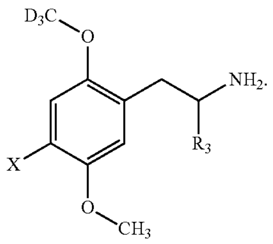

TABLE I-B

| Representative compounds of Formula (I-B) | | |
|---|---|---|
| Compound No. | $R_3$ | X |
| I-B-1 | H | H |
| I-B-2 | H | —$CH_3$ |
| I-B-3 | H | —$CD_3$ |
| I-B-4 | H | —$CH_2CH_3$ |
| I-B-5 | H | —$CH_2CD_3$ |
| I-B-6 | H | —$CH_2CH_2CH_3$ |
| I-B-7 | H | —$CH_2CH_2CD_3$ |
| I-B-8 | H | —$CF_3$ |
| I-B-9 | H | —$CH_2CF_3$ |
| I-B-10 | H | —$CH_2CH_2CF_3$ |
| I-B-11 | H | —$OCH_3$ |
| I-B-12 | H | —$OCD_3$ |
| I-B-13 | H | —$OCF_3$ |
| I-B-14 | H | —$OCH_2CH_3$ |
| I-B-15 | H | —$OCH_2CD_3$ |
| I-B-16 | H | —$OCH_2CF_3$ |
| I-B-17 | H | —$OCH_2CH_2CH_3$ |
| I-B-18 | H | —$OCH_2CH_2CD_3$ |
| I-B-19 | H | —$OCH_2CH_2CF_3$ |
| I-B-20 | H | —$SCH_3$ |
| I-B-21 | H | —$SCD_3$ |
| I-B-22 | H | —$SCF_3$ |
| I-B-23 | H | —$SCH_2CH_3$ |
| I-B-24 | H | —$SCH_2CD_3$ |
| I-B-25 | H | —$SCH_2CF_3$ |
| I-B-26 | H | —$SCH_2CH_2CH_3$ |
| I-B-27 | H | —$SCH_2CH_2CD_3$ |
| I-B-28 | H | —$SCH_2CH_2CF_3$ |
| I-B-29 | H | F |
| I-B-30 | H | Cl |
| I-B-31 | H | Br |
| I-B-32 | H | I |
| I-B-33 | H | H |
| I-B-34 | —$CH_3$ | —$CH_3$ |
| I-B-35 | —$CH_3$ | —$CD_3$ |
| I-B-36 | —$CH_3$ | —$CH_2CH_3$ |
| I-B-37 | —$CH_3$ | —$CH_2CD_3$ |
| I-B-38 | —$CH_3$ | —$CH_2CH_2CH_3$ |
| I-B-39 | —$CH_3$ | —$CH_2CH_2CD_3$ |
| I-B-40 | —$CH_3$ | —$CF_3$ |
| I-B-41 | —$CH_3$ | —$CH_2CF_3$ |
| I-B-42 | —$CH_3$ | —$CH_2CH_2CF_3$ |
| I-B-43 | —$CH_3$ | —$OCH_3$ |
| I-B-44 | —$CH_3$ | —$OCD_3$ |
| I-B-45 | —$CH_3$ | —$OCF_3$ |
| I-B-46 | —$CH_3$ | —$OCH_2CH_3$ |
| I-B-47 | —$CH_3$ | —$OCH_2CD_3$ |
| I-B-48 | —$CH_3$ | —$OCH_2CF_3$ |
| I-B-49 | —$CH_3$ | —$OCH_2CH_2CH_3$ |
| I-B-50 | —$CH_3$ | —$OCH_2CH_2CD_3$ |
| I-B-51 | —$CH_3$ | —$OCH_2CH_2CF_3$ |
| I-B-52 | —$CH_3$ | —$SCH_3$ |
| I-B-53 | —$CH_3$ | —$SCD_3$ |
| I-B-54 | —$CH_3$ | —$SCF_3$ |
| I-B-55 | —$CH_3$ | —$SCH_2CH_3$ |
| I-B-56 | —$CH_3$ | —$SCH_2CD_3$ |
| I-B-57 | —$CH_3$ | —$SCH_2CF_3$ |
| I-B-58 | —$CH_3$ | —$SCH_2CH_2CH_3$ |
| I-B-59 | —$CH_3$ | —$SCH_2CH_2CD_3$ |
| I-B-60 | —$CH_3$ | —$SCH_2CH_2CF_3$ |
| I-B-61 | —$CH_3$ | F |
| I-B-62 | —$CH_3$ | Cl |
| I-B-63 | —$CH_3$ | Br |
| I-B-64 | —$CH_3$ | I |
| I-B-65 | —$CH_2CH_3$ | —$CH_3$ |
| I-B-66 | —$CH_2CH_3$ | —$CD_3$ |
| I-B-67 | —$CH_2CH_3$ | —$CH_2CH_3$ |
| I-B-68 | —$CH_2CH_3$ | —$CH_2CD_3$ |
| I-B-69 | —$CH_2CH_3$ | —$CH_2CH_2CH_3$ |
| I-B-70 | —$CH_2CH_3$ | —$CH_2CH_2CD_3$ |
| I-B-71 | —$CH_2CH_3$ | —$CF_3$ |
| I-B-72 | —$CH_2CH_3$ | —$CH_2CF_3$ |
| I-B-73 | —$CH_2CH_3$ | —$CH_2CH_2CF_3$ |
| I-B-74 | —$CH_2CH_3$ | —$OCH_3$ |
| I-B-75 | —$CH_2CH_3$ | —$OCD_3$ |
| I-B-76 | —$CH_2CH_3$ | —$OCF_3$ |
| I-B-77 | —$CH_2CH_3$ | —$OCH_2CH_3$ |
| I-B-78 | —$CH_2CH_3$ | —$OCH_2CD_3$ |
| I-B-79 | —$CH_2CH_3$ | —$OCH_2CF_3$ |
| I-B-80 | —$CH_2CH_3$ | —$OCH_2CH_2CH_3$ |
| I-B-81 | —$CH_2CH_3$ | —$OCH_2CH_2CD_3$ |
| I-B-82 | —$CH_2CH_3$ | —$OCH_2CH_2CF_3$ |
| I-B-83 | —$CH_2CH_3$ | —$SCH_3$ |
| I-B-84 | —$CH_2CH_3$ | —$SCD_3$ |
| I-B-85 | —$CH_2CH_3$ | —$SCF_3$ |
| I-B-86 | —$CH_2CH_3$ | —$SCH_2CH_3$ |
| I-B-87 | —$CH_2CH_3$ | —$SCH_2CD_3$ |
| I-B-88 | —$CH_2CH_3$ | —$SCH_2CF_3$ |
| I-B-89 | —$CH_2CH_3$ | —$SCH_2CH_2CH_3$ |
| I-B-90 | —$CH_2CH_3$ | —$SCH_2CH_2CD_3$ |
| I-B-91 | —$CH_2CH_3$ | —$SCH_2CH_2CF_3$ |
| I-B-92 | —$CH_2CH_3$ | F |
| I-B-93 | —$CH_2CH_3$ | Cl |
| I-B-94 | —$CH_2CH_3$ | Br |
| I-B-95 | —$CH_2CH_3$ | I |

In embodiments, the compound of Formula (I) is a compound of Formula (I-C) selected from Table I-C, or a pharmaceutically acceptable salt, prodrug, hydrate, or solvate thereof:

(I-C)

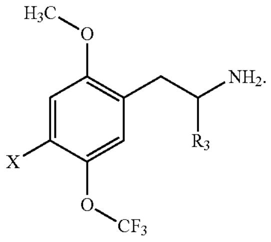

TABLE I-C

| Representative compounds of Formula (I-C) | | |
|---|---|---|
| Compound No. | $R_3$ | X |
| I-C-1 | H | $—CH_3$ |
| I-C-2 | H | $—CD_3$ |
| I-C-3 | H | $—CH_2CH_3$ |
| I-C-4 | H | $—CH_2CD_3$ |
| I-C-5 | H | $—CH_2CH_2CH_3$ |
| I-C-6 | H | $—CH_2CH_2CD_3$ |
| I-C-7 | H | $—CF_3$ |
| I-C-8 | H | $—CH_2CF_3$ |
| I-C-9 | H | $—CH_2CH_2CF_3$ |
| I-C-10 | H | $—OCH_3$ |
| I-C-11 | H | $—OCD_3$ |
| I-C-12 | H | $—OCF_3$ |
| I-C-13 | H | $—OCH_2CH_3$ |
| I-C-14 | H | $—OCH_2CD_3$ |
| I-C-15 | H | $—OCH_2CF_3$ |
| I-C-16 | H | $—OCH_2CH_2CH_3$ |
| I-C-17 | H | $—OCH_2CH_2CD_3$ |
| I-C-18 | H | $—OCH_2CH_2CF_3$ |
| I-C-19 | H | $—SCH_3$ |
| I-C-20 | H | $—SCD_3$ |
| I-C-21 | H | $—SCF_3$ |
| I-C-22 | H | $—SCH_2CH_3$ |
| I-C-23 | H | $—SCH_2CD_3$ |
| I-C-24 | H | $—SCH_2CF_3$ |
| I-C-25 | H | $—SCH_2CH_2CH_3$ |
| I-C-26 | H | $—SCH_2CH_2CD_3$ |
| I-C-27 | H | $—SCH_2CH_2CF_3$ |
| I-C-28 | H | F |
| I-C-29 | H | Cl |
| I-C-30 | H | Br |
| I-C-31 | H | I |
| I-C-32 | H | H |
| I-C-33 | $—CH_3$ | $—CH_3$ |
| I-C-34 | $—CH_3$ | $—CD_3$ |
| I-C-35 | $—CH_3$ | $—CH_2CH_3$ |
| I-C-36 | $—CH_3$ | $—CH_2CD_3$ |
| I-C-37 | $—CH_3$ | $—CH_2CH_2CH_3$ |
| I-C-38 | $—CH_3$ | $—CH_2CH_2CD_3$ |
| I-C-39 | $—CH_3$ | $—CF_3$ |
| I-C-40 | $—CH_3$ | $—CH_2CF_3$ |
| I-C-41 | $—CH_3$ | $—CH_2CH_2CF_3$ |
| I-C-42 | $—CH_3$ | $—OCH_3$ |
| I-C-43 | $—CH_3$ | $—OCD_3$ |
| I-C-44 | $—CH_3$ | $—OCF_3$ |
| I-C-45 | $—CH_3$ | $—OCH_2CH_3$ |
| I-C-46 | $—CH_3$ | $—OCH_2CD_3$ |
| I-C-47 | $—CH_3$ | $—OCH_2CF_3$ |
| I-C-48 | $—CH_3$ | $—OCH_2CH_2CH_3$ |
| I-C-49 | $—CH_3$ | $—OCH_2CH_2CD_3$ |
| I-C-50 | $—CH_3$ | $—OCH_2CH_2CF_3$ |
| I-C-51 | $—CH_3$ | $—SCH_3$ |
| I-C-52 | $—CH_3$ | $—SCD_3$ |
| I-C-53 | $—CH_3$ | $—SCF_3$ |
| I-C-54 | $—CH_3$ | $—SCH_2CH_3$ |
| I-C-55 | $—CH_3$ | $—SCH_2CD_3$ |
| I-C-56 | $—CH_3$ | $—SCH_2CF_3$ |
| I-C-57 | $—CH_3$ | $—SCH_2CH_2CH_3$ |
| I-C-58 | $—CH_3$ | $—SCH_2CH_2CD_3$ |
| I-C-59 | $—CH_3$ | $—SCH_2CH_2CF_3$ |
| I-C-60 | $—CH_3$ | F |
| I-C-61 | $—CH_3$ | Cl |
| I-C-62 | $—CH_3$ | Br |
| I-C-63 | $—CH_3$ | I |
| I-C-64 | $—CH_2CH_3$ | $—CH_3$ |
| I-C-65 | $—CH_2CH_3$ | $—CD_3$ |
| I-C-66 | $—CH_2CH_3$ | $—CH_2CH_3$ |
| I-C-67 | $—CH_2CH_3$ | $—CH_2CD_3$ |
| I-C-68 | $—CH_2CH_3$ | $—CH_2CH_2CH_3$ |
| I-C-69 | $—CH_2CH_3$ | $—CH_2CH_2CD_3$ |
| I-C-70 | $—CH_2CH_3$ | $—CF_3$ |
| I-C-71 | $—CH_2CH_3$ | $—CH_2CF_3$ |
| I-C-72 | $—CH_2CH_3$ | $—CH_2CH_2CF_3$ |
| I-C-73 | $—CH_2CH_3$ | $—OCH_3$ |
| I-C-74 | $—CH_2CH_3$ | $—OCD_3$ |
| I-C-75 | $—CH_2CH_3$ | $—OCF_3$ |
| I-C-76 | $—CH_2CH_3$ | $—OCH_2CH_3$ |

TABLE I-C-continued

| Representative compounds of Formula (I-C) | | |
|---|---|---|
| Compound No. | $R_3$ | X |
| I-C-77 | $—CH_2CH_3$ | $—OCH_2CD_3$ |
| I-C-78 | $—CH_2CH_3$ | $—OCH_2CF_3$ |
| I-C-79 | $—CH_2CH_3$ | $—OCH_2CH_2CH_3$ |
| I-C-80 | $—CH_2CH_3$ | $—OCH_2CH_2CD_3$ |
| I-C-81 | $—CH_2CH_3$ | $—OCH_2CH_2CF_3$ |
| I-C-82 | $—CH_2CH_3$ | $—SCH_3$ |
| I-C-83 | $—CH_2CH_3$ | $—SCD_3$ |
| I-C-84 | $—CH_2CH_3$ | $—SCF_3$ |
| I-C-85 | $—CH_2CH_3$ | $—SCH_2CH_3$ |
| I-C-86 | $—CH_2CH_3$ | $—SCH_2CD_3$ |
| I-C-87 | $—CH_2CH_3$ | $—SCH_2CF_3$ |
| I-C-88 | $—CH_2CH_3$ | $—SCH_2CH_2CH_3$ |
| I-C-89 | $—CH_2CH_3$ | $—SCH_2CH_2CD_3$ |
| I-C-90 | $—CH_2CH_3$ | $—SCH_2CH_2CF_3$ |
| I-C-91 | $—CH_2CH_3$ | F |
| I-C-92 | $—CH_2CH_3$ | Cl |
| I-C-93 | $—CH_2CH_3$ | Br |
| I-C-94 | $—CH_2CH_3$ | I |

In embodiments, the compound of Formula (I) is a compound of Formula (I-D) selected from Table I-D, or a pharmaceutically acceptable salt, prodrug, hydrate, or solvate thereof:

(I-D)

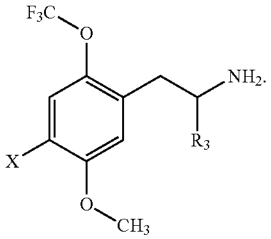

TABLE I-D

| Representative compounds of Formula (I-D) | | |
|---|---|---|
| Compound No. | $R_3$ | X |
| I-D-1 | H | $—CH_3$ |
| I-D-2 | H | $—CD_3$ |
| I-D-3 | H | $—CH_2CH_3$ |
| I-D-4 | H | $—CH_2CD_3$ |
| I-D-5 | H | $—CH_2CH_2CH_3$ |
| I-D-6 | H | $—CH_2CH_2CD_3$ |
| I-D-7 | H | $—CF_3$ |
| I-D-8 | H | $—CH_2CF_3$ |
| I-D-9 | H | $—CH_2CH_2CF_3$ |
| I-D-10 | H | $—OCH_3$ |
| I-D-11 | H | $—OCD_3$ |
| I-D-12 | H | $—OCF_3$ |
| I-D-13 | H | $—OCH_2CH_3$ |
| I-D-14 | H | $—OCH_2CD_3$ |
| I-D-15 | H | $—OCH_2CF_3$ |
| I-D-16 | H | $—OCH_2CH_2CH_3$ |
| I-D-17 | H | $—OCH_2CH_2CD_3$ |
| I-D-18 | H | $—OCH_2CH_2CF_3$ |
| I-D-19 | H | $—SCH_3$ |
| I-D-20 | H | $—SCD_3$ |
| I-D-21 | H | $—SCF_3$ |
| I-D-22 | H | $—SCH_2CH_3$ |
| I-D-23 | H | $—SCH_2CD_3$ |
| I-D-24 | H | $—SCH_2CF_3$ |
| I-D-25 | H | $—SCH_2CH_2CH_3$ |
| I-D-26 | H | $—SCH_2CH_2CD_3$ |
| I-D-27 | H | $—SCH_2CH_2CF_3$ |

TABLE I-D-continued

| Representative compounds of Formula (I-D) | | |
|---|---|---|
| Compound No. | $R_3$ | X |
| I-D-28 | H | F |
| I-D-29 | H | Cl |
| I-D-30 | H | Br |
| I-D-31 | H | I |
| I-D-32 | H | H |
| I-D-33 | —$CH_3$ | —$CH_3$ |
| I-D-34 | —$CH_3$ | —$CD_3$ |
| I-D-35 | —$CH_3$ | —$CH_2CH_3$ |
| I-D-36 | —$CH_3$ | —$CH_2CD_3$ |
| I-D-37 | —$CH_3$ | —$CH_2CH_2CH_3$ |
| I-D-38 | —$CH_3$ | —$CH_2CH_2CD_3$ |
| I-D-39 | —$CH_3$ | —$CF_3$ |
| I-D-40 | —$CH_3$ | —$CH_2CF_3$ |
| I-D-41 | —$CH_3$ | —$CH_2CH_2CF_3$ |
| I-D-42 | —$CH_3$ | —$OCH_3$ |
| I-D-43 | —$CH_3$ | —$OCD_3$ |
| I-D-44 | —$CH_3$ | —$OCF_3$ |
| I-D-45 | —$CH_3$ | —$OCH_2CH_3$ |
| I-D-46 | —$CH_3$ | —$OCH_2CD_3$ |
| I-D-47 | —$CH_3$ | —$OCH_2CF_3$ |
| I-D-48 | —$CH_3$ | —$OCH_2CH_2CH_3$ |
| I-D-49 | —$CH_3$ | —$OCH_2CH_2CD_3$ |
| I-D-50 | —$CH_3$ | —$OCH_2CH_2CF_3$ |
| I-D-51 | —$CH_3$ | —$SCH_3$ |
| I-D-52 | —$CH_3$ | —$SCD_3$ |
| I-D-53 | —$CH_3$ | —$SCF_3$ |
| I-D-54 | —$CH_3$ | —$SCH_2CH_3$ |
| I-D-55 | —$CH_3$ | —$SCH_2CD_3$ |
| I-D-56 | —$CH_3$ | —$SCH_2CF_3$ |
| I-D-57 | —$CH_3$ | —$SCH_2CH_2CH_3$ |
| I-D-58 | —$CH_3$ | —$SCH_2CH_2CD_3$ |
| I-D-59 | —$CH_3$ | —$SCH_2CH_2CF_3$ |
| I-D-60 | —$CH_3$ | F |
| I-D-61 | —$CH_3$ | Cl |
| I-D-62 | —$CH_3$ | Br |
| I-D-63 | —$CH_3$ | I |
| I-D-64 | —$CH_2CH_3$ | —$CH_3$ |
| I-D-65 | —$CH_2CH_3$ | —$CD_3$ |
| I-D-66 | —$CH_2CH_3$ | —$CH_2CH_3$ |
| I-D-67 | —$CH_2CH_3$ | —$CH_2CD_3$ |
| I-D-68 | —$CH_2CH_3$ | —$CH_2CH_2CH_3$ |
| I-D-69 | —$CH_2CH_3$ | —$CH_2CH_2CD_3$ |
| I-D-70 | —$CH_2CH_3$ | —$CF_3$ |
| I-D-71 | —$CH_2CH_3$ | —$CH_2CF_3$ |
| I-D-72 | —$CH_2CH_3$ | —$CH_2CH_2CF_3$ |
| I-D-73 | —$CH_2CH_3$ | —$OCH_3$ |
| I-D-74 | —$CH_2CH_3$ | —$OCD_3$ |
| I-D-75 | —$CH_2CH_3$ | —$OCF_3$ |
| I-D-76 | —$CH_2CH_3$ | —$OCH_2CH_3$ |
| I-D-77 | —$CH_2CH_3$ | —$OCH_2CD_3$ |
| I-D-78 | —$CH_2CH_3$ | —$OCH_2CF_3$ |
| I-D-79 | —$CH_2CH_3$ | —$OCH_2CH_2CH_3$ |
| I-D-80 | —$CH_2CH_3$ | —$OCH_2CH_2CD_3$ |
| I-D-81 | —$CH_2CH_3$ | —$OCH_2CH_2CF_3$ |
| I-D-82 | —$CH_2CH_3$ | —$SCH_3$ |
| I-D-83 | —$CH_2CH_3$ | —$SCD_3$ |
| I-D-84 | —$CH_2CH_3$ | —$SCF_3$ |
| I-D-85 | —$CH_2CH_3$ | —$SCH_2CH_3$ |
| I-D-86 | —$CH_2CH_3$ | —$SCH_2CD_3$ |
| I-D-87 | —$CH_2CH_3$ | —$SCH_2CF_3$ |
| I-D-88 | —$CH_2CH_3$ | —$SCH_2CH_2CH_3$ |
| I-D-89 | —$CH_2CH_3$ | —$SCH_2CH_2CD_3$ |
| I-D-90 | —$CH_2CH_3$ | —$SCH_2CH_2CF_3$ |
| I-D-91 | —$CH_2CH_3$ | F |
| I-D-92 | —$CH_2CH_3$ | Cl |
| I-D-93 | —$CH_2CH_3$ | Br |
| I-D-94 | —$CH_2CH_3$ | I |

In embodiments, the compound of Formula (I) is a compound of Formula (I-E) selected from Table I-E, or a pharmaceutically acceptable salt, prodrug, hydrate, or solvate thereof:

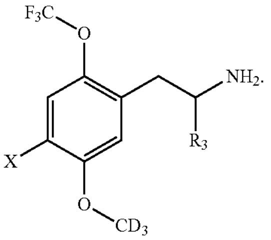

(I-E)

TABLE I-E

| Representative compounds of Formula (I-E) | | |
|---|---|---|
| Compound No. | $R_3$ | X |
| I-E-1 | H | H |
| I-E-2 | H | —$CH_3$ |
| I-E-3 | H | —$CD_3$ |
| I-E-4 | H | —$CH_2CH_3$ |
| I-E-5 | H | —$CH_2CD_3$ |
| I-E-6 | H | —$CH_2CH_2CH_3$ |
| I-E-7 | H | —$CH_2CH_2CD_3$ |
| I-E-8 | H | —$CF_3$ |
| I-E-9 | H | —$CH_2CF_3$ |
| I-E-10 | H | —$CH_2CH_2CF_3$ |
| I-E-11 | H | —$OCH_3$ |
| I-E-12 | H | —$OCD_3$ |
| I-E-13 | H | —$OCF_3$ |
| I-E-14 | H | —$OCH_2CH_3$ |
| I-E-15 | H | —$OCH_2CD_3$ |
| I-E-16 | H | —$OCH_2CF_3$ |
| I-E-17 | H | —$OCH_2CH_2CH_3$ |
| I-E-18 | H | —$OCH_2CH_2CD_3$ |
| I-E-19 | H | —$OCH_2CH_2CF_3$ |
| I-E-20 | H | —$SCH_3$ |
| I-E-21 | H | —$SCD_3$ |
| I-E-22 | H | —$SCF_3$ |
| I-E-23 | H | —$SCH_2CH_3$ |
| I-E-24 | H | —$SCH_2CD_3$ |
| I-E-25 | H | —$SCH_2CF_3$ |
| I-E-26 | H | —$SCH_2CH_2CH_3$ |
| I-E-27 | H | —$SCH_2CH_2CD_3$ |
| I-E-28 | H | —$SCH_2CH_2CF_3$ |
| I-E-29 | H | F |
| I-E-30 | H | Cl |
| I-E-31 | H | Br |
| I-E-32 | H | I |
| I-E-33 | H | H |
| I-E-34 | —$CH_3$ | —$CH_3$ |
| I-E-35 | —$CH_3$ | —$CD_3$ |
| I-E-36 | —$CH_3$ | —$CH_2CH_3$ |
| I-E-37 | —$CH_3$ | —$CH_2CD_3$ |
| I-E-38 | —$CH_3$ | —$CH_2CH_2CH_3$ |
| I-E-39 | —$CH_3$ | —$CH_2CH_2CD_3$ |
| I-E-40 | —$CH_3$ | —$CF_3$ |
| I-E-41 | —$CH_3$ | —$CH_2CF_3$ |
| I-E-42 | —$CH_3$ | —$CH_2CH_2CF_3$ |
| I-E-43 | —$CH_3$ | —$OCH_3$ |
| I-E-44 | —$CH_3$ | —$OCD_3$ |
| I-E-45 | —$CH_3$ | —$OCF_3$ |
| I-E-46 | —$CH_3$ | —$OCH_2CH_3$ |
| I-E-47 | —$CH_3$ | —$OCH_2CD_3$ |
| I-E-48 | —$CH_3$ | —$OCH_2CF_3$ |
| I-E-49 | —$CH_3$ | —$OCH_2CH_2CH_3$ |
| I-E-50 | —$CH_3$ | —$OCH_2CH_2CD_3$ |
| I-E-51 | —$CH_3$ | —$OCH_2CH_2CF_3$ |
| I-E-52 | —$CH_3$ | —$SCH_3$ |
| I-E-53 | —$CH_3$ | —$SCD_3$ |
| I-E-54 | —$CH_3$ | —$SCF_3$ |
| I-E-55 | —$CH_3$ | —$SCH_2CH_3$ |
| I-E-56 | —$CH_3$ | —$SCH_2CD_3$ |
| I-E-57 | —$CH_3$ | —$SCH_2CF_3$ |
| I-E-58 | —$CH_3$ | —$SCH_2CH_2CH_3$ |
| I-E-59 | —$CH_3$ | —$SCH_2CH_2CD_3$ |

TABLE I-E-continued

| Representative compounds of Formula (I-E) | | |
|---|---|---|
| Compound No. | $R_3$ | X |
| I-E-60 | —$CH_3$ | —$SCH_2CH_2CF_3$ |
| I-E-61 | —$CH_3$ | F |
| I-E-62 | —$CH_3$ | Cl |
| I-E-63 | —$CH_3$ | Br |
| I-E-64 | —$CH_3$ | I |
| I-E-65 | —$CH_2CH_3$ | —$CH_3$ |
| I-E-66 | —$CH_2CH_3$ | —$CD_3$ |
| I-E-67 | —$CH_2CH_3$ | —$CH_2CH_3$ |
| I-E-68 | —$CH_2CH_3$ | —$CH_2CD_3$ |
| I-E-69 | —$CH_2CH_3$ | —$CH_2CH_2CH_3$ |
| I-E-70 | —$CH_2CH_3$ | —$CH_2CH_2CD_3$ |
| I-E-71 | —$CH_2CH_3$ | —$CF_3$ |
| I-E-72 | —$CH_2CH_3$ | —$CH_2CF_3$ |
| I-E-73 | —$CH_2CH_3$ | —$CH_2CH_2CF_3$ |
| I-E-74 | —$CH_2CH_3$ | —$OCH_3$ |
| I-E-75 | —$CH_2CH_3$ | —$OCD_3$ |
| I-E-76 | —$CH_2CH_3$ | —$OCF_3$ |
| I-E-77 | —$CH_2CH_3$ | —$OCH_2CH_3$ |
| I-E-78 | —$CH_2CH_3$ | —$OCH_2CD_3$ |
| I-E-79 | —$CH_2CH_3$ | —$OCH_2CF_3$ |
| I-E-80 | —$CH_2CH_3$ | —$OCH_2CH_2CH_3$ |
| I-E-81 | —$CH_2CH_3$ | —$OCH_2CH_2CD_3$ |
| I-E-82 | —$CH_2CH_3$ | —$OCH_2CH_2CF_3$ |
| I-E-83 | —$CH_2CH_3$ | —$SCH_3$ |
| I-E-84 | —$CH_2CH_3$ | —$SCD_3$ |
| I-E-85 | —$CH_2CH_3$ | —$SCF_3$ |
| I-E-86 | —$CH_2CH_3$ | —$SCH_2CH_3$ |
| I-E-87 | —$CH_2CH_3$ | —$SCH_2CD_3$ |
| I-E-88 | —$CH_2CH_3$ | —$SCH_2CF_3$ |
| I-E-89 | —$CH_2CH_3$ | —$SCH_2CH_2CH_3$ |
| I-E-90 | —$CH_2CH_3$ | —$SCH_2CH_2CD_3$ |
| I-E-91 | —$CH_2CH_3$ | —$SCH_2CH_2CF_3$ |
| I-E-92 | —$CH_2CH_3$ | F |
| I-E-93 | —$CH_2CH_3$ | Cl |
| I-E-94 | —$CH_2CH_3$ | Br |
| I-E-95 | —$CH_2CH_3$ | I |

In embodiments, the compound of Formula (I) is a compound of Formula (I-F) selected from Table I-F, or a pharmaceutically acceptable salt, prodrug, hydrate, or solvate thereof:

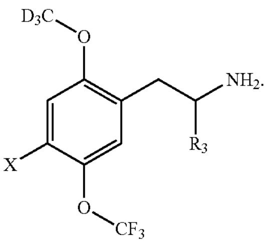

(I-F)

TABLE I-F

| Representative compounds of Formula (I-F) | | |
|---|---|---|
| Compound No. | $R_3$ | X |
| I-F-1 | H | H |
| I-F-2 | H | —$CH_3$ |
| I-F-3 | H | —$CD_3$ |
| I-F-4 | H | —$CH_2CH_3$ |
| I-F-5 | H | —$CH_2CD_3$ |
| I-F-6 | H | —$CH_2CH_2CH_3$ |
| I-F-7 | H | —$CH_2CH_2CD_3$ |
| I-F-8 | H | —$CF_3$ |
| I-F-9 | H | —$CH_2CF_3$ |
| I-F-10 | H | —$CH_2CH_2CF_3$ |
| I-F-11 | H | —$OCH_3$ |
| I-F-12 | H | —$OCD_3$ |
| I-F-13 | H | —$OCF_3$ |
| I-F-14 | H | —$OCH_2CH_3$ |
| I-F-15 | H | —$OCH_2CD_3$ |
| I-F-16 | H | —$OCH_2CF_3$ |
| I-F-17 | H | —$OCH_2CH_2CH_3$ |
| I-F-18 | H | —$OCH_2CH_2CD_3$ |
| I-F-19 | H | —$OCH_2CH_2CF_3$ |
| I-F-20 | H | —$SCH_3$ |
| I-F-21 | H | —$SCD_3$ |
| I-F-22 | H | —$SCF_3$ |
| I-F-23 | H | —$SCH_2CH_3$ |
| I-F-24 | H | —$SCH_2CD_3$ |
| I-F-25 | H | —$SCH_2CF_3$ |
| I-F-26 | H | —$SCH_2CH_2CH_3$ |
| I-F-27 | H | —$SCH_2CH_2CD_3$ |
| I-F-28 | H | —$SCH_2CH_2CF_3$ |
| I-F-29 | H | F |
| I-F-30 | H | Cl |
| I-F-31 | H | Br |
| I-F-32 | H | I |
| I-F-33 | H | H |
| I-F-34 | —$CH_3$ | —$CH_3$ |
| I-F-35 | —$CH_3$ | —$CD_3$ |
| I-F-36 | —$CH_3$ | —$CH_2CH_3$ |
| I-F-37 | —$CH_3$ | —$CH_2CD_3$ |
| I-F-38 | —$CH_3$ | —$CH_2CH_2CH_3$ |
| I-F-39 | —$CH_3$ | —$CH_2CH_2CD_3$ |
| I-F-40 | —$CH_3$ | —$CF_3$ |
| I-F-41 | —$CH_3$ | —$CH_2CF_3$ |
| I-F-42 | —$CH_3$ | —$CH_2CH_2CF_3$ |
| I-F-43 | —$CH_3$ | —$OCH_3$ |
| I-F-44 | —$CH_3$ | —$OCD_3$ |
| I-F-45 | —$CH_3$ | —$OCF_3$ |
| I-F-46 | —$CH_3$ | —$OCH_2CH_3$ |
| I-F-47 | —$CH_3$ | —$OCH_2CD_3$ |
| I-F-48 | —$CH_3$ | —$OCH_2CF_3$ |
| I-F-49 | —$CH_3$ | —$OCH_2CH_2CH_3$ |
| I-F-50 | —$CH_3$ | —$OCH_2CH_2CD_3$ |
| I-F-51 | —$CH_3$ | —$OCH_2CH_2CF_3$ |
| I-F-52 | —$CH_3$ | —$SCH_3$ |
| I-F-53 | —$CH_3$ | —$SCD_3$ |
| I-F-54 | —$CH_3$ | —$SCF_3$ |
| I-F-55 | —$CH_3$ | —$SCH_2CH_3$ |
| I-F-56 | —$CH_3$ | —$SCH_2CD_3$ |
| I-F-57 | —$CH_3$ | —$SCH_2CF_3$ |
| I-F-58 | —$CH_3$ | —$SCH_2CH_2CH_3$ |
| I-F-59 | —$CH_3$ | —$SCH_2CH_2CD_3$ |
| I-F-60 | —$CH_3$ | —$SCH_2CH_2CF_3$ |
| I-F-61 | —$CH_3$ | F |
| I-F-62 | —$CH_3$ | Cl |
| I-F-63 | —$CH_3$ | Br |
| I-F-64 | —$CH_3$ | I |
| I-F-65 | —$CH_2CH_3$ | —$CH_3$ |
| I-F-66 | —$CH_2CH_3$ | —$CD_3$ |
| I-F-67 | —$CH_2CH_3$ | —$CH_2CH_3$ |
| I-F-68 | —$CH_2CH_3$ | —$CH_2CD_3$ |
| I-F-69 | —$CH_2CH_3$ | —$CH_2CH_2CH_3$ |
| I-F-70 | —$CH_2CH_3$ | —$CH_2CH_2CD_3$ |
| I-F-71 | —$CH_2CH_3$ | —$CF_3$ |
| I-F-72 | —$CH_2CH_3$ | —$CH_2CF_3$ |
| I-F-73 | —$CH_2CH_3$ | —$CH_2CH_2CF_3$ |
| I-F-74 | —$CH_2CH_3$ | —$OCH_3$ |
| I-F-75 | —$CH_2CH_3$ | —$OCD_3$ |
| I-F-76 | —$CH_2CH_3$ | —$OCF_3$ |
| I-F-77 | —$CH_2CH_3$ | —$OCH_2CH_3$ |
| I-F-78 | —$CH_2CH_3$ | —$OCH_2CD_3$ |
| I-F-79 | —$CH_2CH_3$ | —$OCH_2CF_3$ |
| I-F-80 | —$CH_2CH_3$ | —$OCH_2CH_2CH_3$ |
| I-F-81 | —$CH_2CH_3$ | —$OCH_2CH_2CD_3$ |
| I-F-82 | —$CH_2CH_3$ | —$OCH_2CH_2CF_3$ |
| I-F-83 | —$CH_2CH_3$ | —$SCH_3$ |
| I-F-84 | —$CH_2CH_3$ | —$SCD_3$ |
| I-F-85 | —$CH_2CH_3$ | —$SCF_3$ |

TABLE I-F-continued

| Representative compounds of Formula (I-F) | | |
|---|---|---|
| Compound No. | $R_3$ | X |
| I-F-86 | —$CH_2CH_3$ | —$SCH_2CH_3$ |
| I-F-87 | —$CH_2CH_3$ | —$SCH_2CD_3$ |
| I-F-88 | —$CH_2CH_3$ | —$SCH_2CF_3$ |
| I-F-89 | —$CH_2CH_3$ | —$SCH_2CH_2CH_3$ |
| I-F-90 | —$CH_2CH_3$ | —$SCH_2CH_2CD_3$ |
| I-F-91 | —$CH_2CH_3$ | —$SCH_2CH_2CF_3$ |
| I-F-92 | —$CH_2CH_3$ | F |
| I-F-93 | —$CH_2CH_3$ | Cl |
| I-F-94 | —$CH_2CH_3$ | Br |
| I-F-95 | —$CH_2CH_3$ | I |

In embodiments, the compound of Formula (I) is a compound of Formula (I-G) selected from Table I-G, or a pharmaceutically acceptable salt, prodrug, hydrate, or solvate thereof:

(I-G)

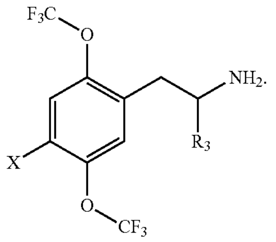

TABLE I-G

| Representative compounds of Formula (I-G) | | |
|---|---|---|
| Compound No. | $R_3$ | X |
| I-G-1 | H | H |
| I-G-2 | H | —$CH_3$ |
| I-G-3 | H | —$CD_3$ |
| I-G-4 | H | —$CH_2CH_3$ |
| I-G-5 | H | —$CH_2CD_3$ |
| I-G-6 | H | —$CH_2CH_2CH_3$ |
| I-G-7 | H | —$CH_2CH_2CD_3$ |
| I-G-8 | H | —$CF_3$ |
| I-G-9 | H | —$CH_2CF_3$ |
| I-G-10 | H | —$CH_2CH_2CF_3$ |
| I-G-11 | H | —$OCH_3$ |
| I-G-12 | H | —$OCD_3$ |
| I-G-13 | H | —$OCF_3$ |
| I-G-14 | H | —$OCH_2CH_3$ |
| I-G-15 | H | —$OCH_2CD_3$ |
| I-G-16 | H | —$OCH_2CF_3$ |
| I-G-17 | H | —$OCH_2CH_2CH_3$ |
| I-G-18 | H | —$OCH_2CH_2CD_3$ |
| I-G-19 | H | —$OCH_2CH_2CF_3$ |
| I-G-20 | H | —$SCH_3$ |
| I-G-21 | H | —$SCD_3$ |
| I-G-22 | H | —$SCF_3$ |
| I-G-23 | H | —$SCH_2CH_3$ |
| I-G-24 | H | —$SCH_2CD_3$ |
| I-G-25 | H | —$SCH_2CF_3$ |
| I-G-26 | H | —$SCH_2CH_2CH_3$ |
| I-G-27 | H | —$SCH_2CH_2CD_3$ |
| I-G-28 | H | —$SCH_2CH_2CF_3$ |
| I-G-29 | H | F |
| I-G-30 | H | Cl |
| I-G-31 | H | Br |
| I-G-32 | H | I |
| I-G-33 | H | H |
| I-G-34 | —$CH_3$ | —$CH_3$ |
| I-G-35 | —$CH_3$ | —$CD_3$ |

TABLE I-G-continued

| Representative compounds of Formula (I-G) | | |
|---|---|---|
| Compound No. | $R_3$ | X |
| I-G-36 | —$CH_3$ | —$CH_2CH_3$ |
| I-G-37 | —$CH_3$ | —$CH_2CD_3$ |
| I-G-38 | —$CH_3$ | —$CH_2CH_2CH_3$ |
| I-G-39 | —$CH_3$ | —$CH_2CH_2CD_3$ |
| I-G-40 | —$CH_3$ | —$CF_3$ |
| I-G-41 | —$CH_3$ | —$CH_2CF_3$ |
| I-G-42 | —$CH_3$ | —$CH_2CH_2CF_3$ |
| I-G-43 | —$CH_3$ | —$OCH_3$ |
| I-G-44 | —$CH_3$ | —$OCD_3$ |
| I-G-45 | —$CH_3$ | —$OCF_3$ |
| I-G-46 | —$CH_3$ | —$OCH_2CH_3$ |
| I-G-47 | —$CH_3$ | —$OCH_2CD_3$ |
| I-G-48 | —$CH_3$ | —$OCH_2CF_3$ |
| I-G-49 | —$CH_3$ | —$OCH_2CH_2CH_3$ |
| I-G-50 | —$CH_3$ | —$OCH_2CH_2CD_3$ |
| I-G-51 | —$CH_3$ | —$OCH_2CH_2CF_3$ |
| I-G-52 | —$CH_3$ | —$SCH_3$ |
| I-G-53 | —$CH_3$ | —$SCD_3$ |
| I-G-54 | —$CH_3$ | —$SCF_3$ |
| I-G-55 | —$CH_3$ | —$SCH_2CH_3$ |
| I-G-56 | —$CH_3$ | —$SCH_2CD_3$ |
| I-G-57 | —$CH_3$ | —$SCH_2CF_3$ |
| I-G-58 | —$CH_3$ | —$SCH_2CH_2CH_3$ |
| I-G-59 | —$CH_3$ | —$SCH_2CH_2CD_3$ |
| I-G-60 | —$CH_3$ | —$SCH_2CH_2CF_3$ |
| I-G-61 | —$CH_3$ | F |
| I-G-62 | —$CH_3$ | Cl |
| I-G-63 | —$CH_3$ | Br |
| I-G-64 | —$CH_3$ | I |
| I-G-65 | —$CH_2CH_3$ | —$CH_3$ |
| I-G-66 | —$CH_2CH_3$ | —$CD_3$ |
| I-G-67 | —$CH_2CH_3$ | —$CH_2CH_3$ |
| I-G-68 | —$CH_2CH_3$ | —$CH_2CD_3$ |
| I-G-69 | —$CH_2CH_3$ | —$CH_2CH_2CH_3$ |
| I-G-70 | —$CH_2CH_3$ | —$CH_2CH_2CD_3$ |
| I-G-71 | —$CH_2CH_3$ | —$CF_3$ |
| I-G-72 | —$CH_2CH_3$ | —$CH_2CF_3$ |
| I-G-73 | —$CH_2CH_3$ | —$CH_2CH_2CF_3$ |
| I-G-74 | —$CH_2CH_3$ | —$OCH_3$ |
| I-G-75 | —$CH_2CH_3$ | —$OCD_3$ |
| I-G-76 | —$CH_2CH_3$ | —$OCF_3$ |
| I-G-77 | —$CH_2CH_3$ | —$OCH_2CH_3$ |
| I-G-78 | —$CH_2CH_3$ | —$OCH_2CD_3$ |
| I-G-79 | —$CH_2CH_3$ | —$OCH_2CF_3$ |
| I-G-80 | —$CH_2CH_3$ | —$OCH_2CH_2CH_3$ |
| I-G-81 | —$CH_2CH_3$ | —$OCH_2CH_2CD_3$ |
| I-G-82 | —$CH_2CH_3$ | —$OCH_2CH_2CF_3$ |
| I-G-83 | —$CH_2CH_3$ | —$SCH_3$ |
| I-G-84 | —$CH_2CH_3$ | —$SCD_3$ |
| I-G-85 | —$CH_2CH_3$ | —$SCF_3$ |
| I-G-86 | —$CH_2CH_3$ | —$SCH_2CH_3$ |
| I-G-87 | —$CH_2CH_3$ | —$SCH_2CD_3$ |
| I-G-88 | —$CH_2CH_3$ | —$SCH_2CF_3$ |
| I-G-89 | —$CH_2CH_3$ | —$SCH_2CH_2CH_3$ |
| I-G-90 | —$CH_2CH_3$ | —$SCH_2CH_2CD_3$ |
| I-G-91 | —$CH_2CH_3$ | —$SCH_2CH_2CF_3$ |
| I-G-92 | —$CH_2CH_3$ | F |
| I-G-93 | —$CH_2CH_3$ | Cl |
| I-G-94 | —$CH_2CH_3$ | Br |
| I-G-95 | —$CH_2CH_3$ | I |

In embodiments, the compound of Formula (I) is a compound of Formula (I-H) selected from Table I-H, or a pharmaceutically acceptable salt, prodrug, hydrate, or solvate thereof:

(I-H)

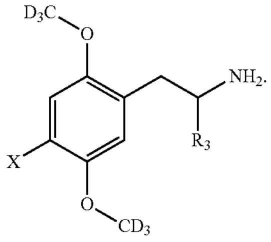

TABLE I-H

| Representative compounds of Formula (I-H) | | |
|---|---|---|
| Compound No. | $R_3$ | X |
| I-H-3 | H | $—CD_3$ |
| I-H-4 | H | $—CH_2CH_3$ |
| I-H-5 | H | $—CH_2CD_3$ |
| I-H-7 | H | $—CH_2CH_2CD_3$ |
| I-H-8 | H | $—CF_3$ |
| I-H-9 | H | $—CH_2CF_3$ |
| I-H-10 | H | $—CH_2CH_2CF_3$ |
| I-H-11 | H | $—OCH_3$ |
| I-H-12 | H | $—OCD_3$ |
| I-H-13 | H | $—OCF_3$ |
| I-H-14 | H | $—OCH_2CH_3$ |
| I-H-15 | H | $—OCH_2CD_3$ |
| I-H-16 | H | $—OCH_2CF_3$ |
| I-H-17 | H | $—OCH_2CH_2CH_3$ |
| I-H-18 | H | $—OCH_2CH_2CD_3$ |
| I-H-21 | H | $—SCD_3$ |
| I-H-24 | H | $—SCH_2CD_3$ |
| I-H-25 | H | $—SCH_2CF_3$ |
| I-H-27 | H | $—SCH_2CH_2CD_3$ |
| I-H-33 | H | $—CD_3$ |
| I-H-34 | $—CH_3$ | $—CH_2CH_3$ |
| I-H-35 | $—CH_3$ | $—CH_2CD_3$ |
| I-H-36 | $—CH_3$ | $—CH_2CH_2CD_3$ |
| I-H-37 | $—CH_3$ | $—CF_3$ |
| I-H-38 | $—CH_3$ | $—CH_2CF_3$ |
| I-H-39 | $—CH_3$ | $—CH_2CH_2CF_3$ |
| I-H-40 | $—CH_3$ | $—OCH_3$ |
| I-H-41 | $—CH_3$ | $—OCD_3$ |
| I-H-42 | $—CH_3$ | $—OCF_3$ |
| I-H-43 | $—CH_3$ | $—OCH_2CH_3$ |
| I-H-44 | $—CH_3$ | $—OCH_2CD_3$ |
| I-H-45 | $—CH_3$ | $—OCH_2CF_3$ |
| I-H-46 | $—CH_3$ | $—OCH_2CH_2CH_3$ |
| I-H-47 | $—CH_3$ | $—OCH_2CH_2CD_3$ |
| I-H-48 | $—CH_3$ | $—SCD_3$ |
| I-H-49 | $—CH_3$ | $—SCH_2CD_3$ |
| I-H-50 | $—CH_3$ | $—SCH_2CF_3$ |
| I-H-51 | $—CH_3$ | $—SCH_2CH_2CD_3$ |
| I-H-65 | $—CH_2CH_3$ | $—CD_3$ |
| I-H-66 | $—CH_2CH_3$ | $—CH_2CH_3$ |
| I-H-67 | $—CH_2CH_3$ | $—CH_2CD_3$ |
| I-H-68 | $—CH_2CH_3$ | $—CH_2CH_2CD_3$ |
| I-H-69 | $—CH_2CH_3$ | $—CF_3$ |
| I-H-70 | $—CH_2CH_3$ | $—CH_2CF_3$ |
| I-H-71 | $—CH_2CH_3$ | $—CH_2CH_2CF_3$ |
| I-H-72 | $—CH_2CH_3$ | $—OCH_3$ |
| I-H-73 | $—CH_2CH_3$ | $—OCD_3$ |
| I-H-74 | $—CH_2CH_3$ | $—OCF_3$ |
| I-H-75 | $—CH_2CH_3$ | $—OCH_2CH_3$ |
| I-H-76 | $—CH_2CH_3$ | $—OCH_2CD_3$ |
| I-H-77 | $—CH_2CH_3$ | $—OCH_2CF_3$ |
| I-H-78 | $—CH_2CH_3$ | $—OCH_2CH_2CH_3$ |
| I-H-79 | $—CH_2CH_3$ | $—OCH_2CH_2CD_3$ |
| I-H-80 | $—CH_2CH_3$ | $—SCD_3$ |
| I-H-81 | $—CH_2CH_3$ | $—SCH_2CD_3$ |
| I-H-82 | $—CH_2CH_3$ | $—SCH_2CF_3$ |

In embodiments, the compound of Formula (I) is a compound of Formula (I-I) selected from Table I-I, or a pharmaceutically acceptable salt, prodrug, hydrate, or solvate thereof:

(I-I)

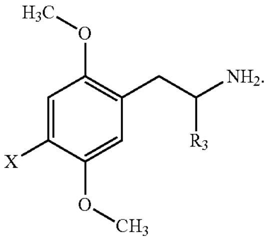

TABLE I-I

| Representative compounds of Formula (I-I) | | |
|---|---|---|
| Compound No. | $R_3$ | X |
| I-I-1 | H | $—CH_2CD_3$ |
| I-I-2 | H | $—CH_2CH_2CD_3$ |
| I-I-3 | H | $—OCD_3$ |
| I-I-4 | H | $—OCF_3$ |
| I-I-5 | H | $—OCH_2CD_3$ |
| I-I-6 | H | $—OCH_2CF_3$ |
| I-I-7 | H | $—OCH_2CH_2CD_3$ |
| I-I-8 | H | $—SCD_3$ |
| I-I-9 | H | $—SCH_2CD_3$ |
| I-I-10 | H | $—SCH_2CH_2CD_3$ |
| I-I-11 | $—CH_3$ | $—CH_2CD_3$ |
| I-I-12 | $—CH_3$ | $—CH_2CH_2CD_3$ |
| I-I-13 | $—CH_3$ | $—OCD_3$ |
| I-I-14 | $—CH_3$ | $—OCF_3$ |
| I-I-15 | $—CH_3$ | $—OCH_2CD_3$ |
| I-I-16 | $—CH_3$ | $—OCH_2CF_3$ |
| I-I-17 | $—CH_3$ | $—OCH_2CH_2CD_3$ |
| I-I-18 | $—CH_3$ | $—SCD_3$ |
| I-I-19 | $—CH_3$ | $—SCH_2CD_3$ |
| I-I-20 | $—CH_3$ | $—SCH_2CH_2CD_3$ |
| I-I-21 | $—CH_2CH_3$ | $—CH_2CD_3$ |
| I-I-22 | $—CH_2CH_3$ | $—CH_2CH_2CD_3$ |
| I-I-23 | $—CH_2CH_3$ | $—OCD_3$ |
| I-I-24 | $—CH_2CH_3$ | $—OCF_3$ |
| I-I-25 | $—CH_2CH_3$ | $—OCH_2CD_3$ |
| I-I-26 | $—CH_2CH_3$ | $—OCH_2CF_3$ |
| I-I-27 | $—CH_2CH_3$ | $—OCH_2CH_2CD_3$ |
| I-I-28 | $—CH_2CH_3$ | $—SCD_3$ |
| I-I-29 | $—CH_2CH_3$ | $—SCH_2CD_3$ |
| I-I-30 | $—CH_2CH_3$ | $—SCH_2CH_2CD_3$ |

In some embodiments, the compound of Formula (I) is a compound selected from Table I-A, or a pharmaceutically acceptable salt, prodrug, hydrate, or solvate thereof. In some embodiments, the compound of Formula (I) is a compound selected from Table I-A or Table I-B, or a pharmaceutically acceptable salt, prodrug, hydrate, or solvate thereof. In some embodiments, the compound of Formula (I) is a compound selected from Table I-C, or a pharmaceutically acceptable salt, prodrug, hydrate, or solvate thereof. In some embodiments, the compound of Formula (I) is a compound selected from Table I-C or Table I-D, or a pharmaceutically acceptable salt, prodrug, hydrate, or solvate thereof. In some embodiments, the compound of Formula (I) is a compound selected from Table I-E, or a pharmaceutically acceptable salt, prodrug, hydrate, or solvate thereof. In some embodiments, the compound of Formula (I) is a compound selected from Table I-E or Table I-F, or a pharmaceutically acceptable salt, prodrug, hydrate, or solvate thereof. In some embodiments, the compound of Formula (I) is a compound selected from Table I-A, Table I-B, Table I-C, or Table I-D, or a pharmaceutically acceptable salt, prodrug, hydrate, or solvate thereof. In some embodiments, the compound of Formula (I) is a compound selected from Table I-A, Table I-B, Table I-E, or Table I-F, or a pharmaceutically acceptable salt, prodrug, hydrate, or solvate thereof. In some embodiments, the compound of Formula (I) is a compound selected from Table I-C, Table I-D, Table I-E, or Table I-F, or a pharmaceutically acceptable salt, prodrug, hydrate, or solvate thereof. In some embodiments, the compound of Formula (I) is a compound selected from Table I-A, Table I-B, Table I-C, Table I-D, Table I-E, or Table I-F, or a pharmaceutically acceptable salt, prodrug, hydrate, or solvate thereof. In some embodiments, the compound of Formula (I) is a compound selected from Table I-G, Table I-H, or Table I-I, or a pharmaceutically acceptable salt, prodrug, hydrate, or solvate thereof. In some embodiments, the compound of Formula (I) is a compound selected from Table I-A, Table I-B, Table I-C, Table I-D, Table I-E, Table I-F, Table I-G, Table I-H, or Table I-I, or a pharmaceutically acceptable salt, prodrug, hydrate, or solvate thereof.

In embodiments, the compound of Formula (I) is selected from the group consisting of:

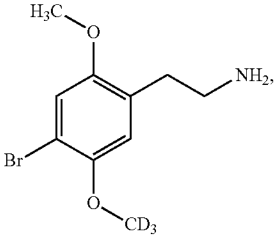
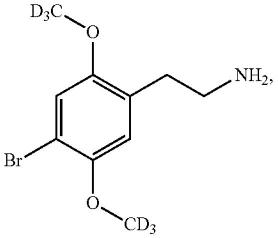
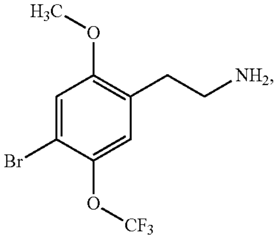
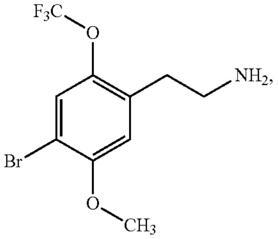
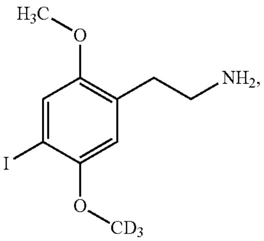
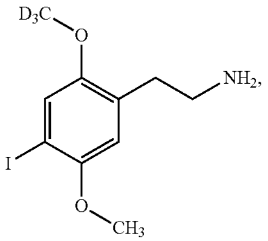
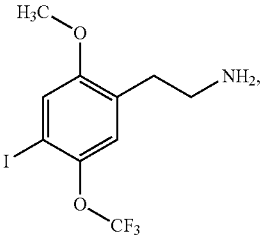
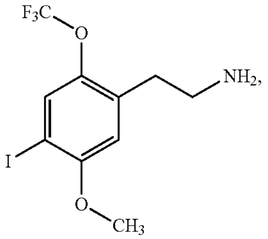

-continued

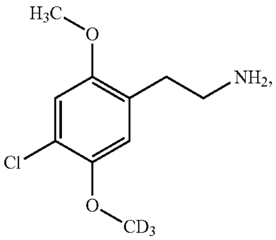
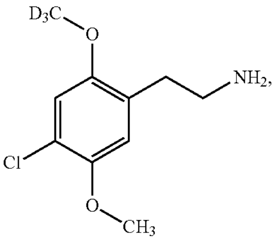
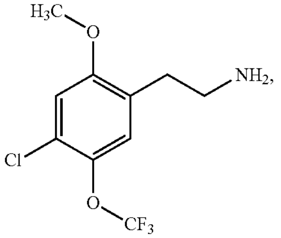
and
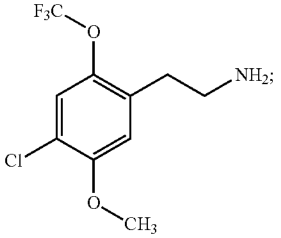

or a pharmaceutically acceptable salt, prodrug, hydrate, or solvate thereof.

In embodiments, the compound of Formula (I) is selected from the group consisting of:

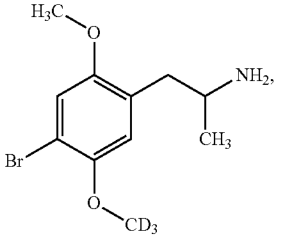
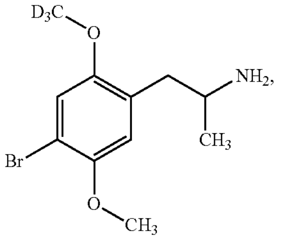
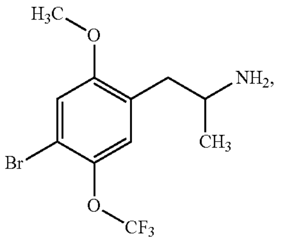

-continued
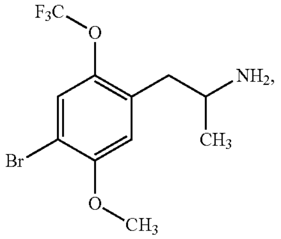
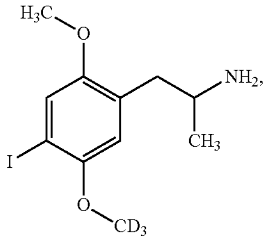
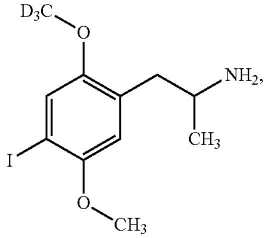
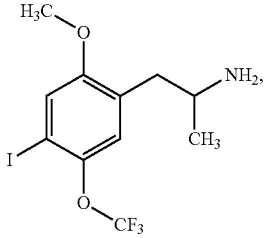
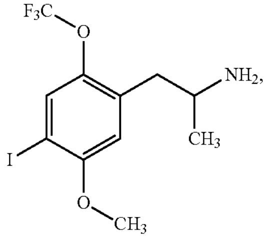
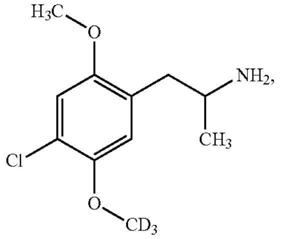
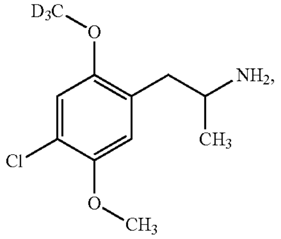
-continued
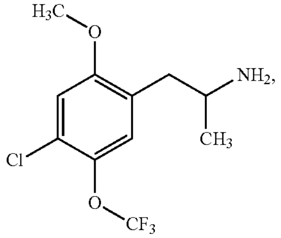
and
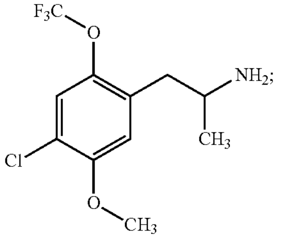
or a pharmaceutically acceptable salt, prodrug, hydrate, or solvate thereof.
In embodiments, the compound of Formula (I) is selected from the group consisting of:
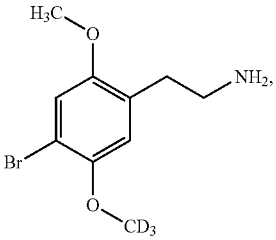
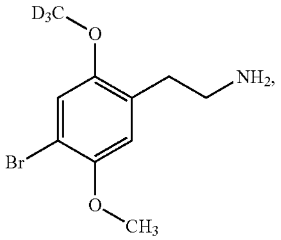
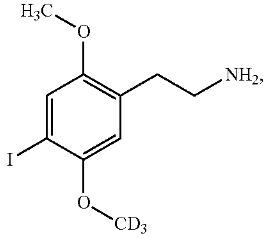
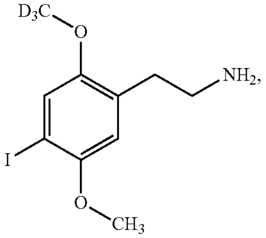
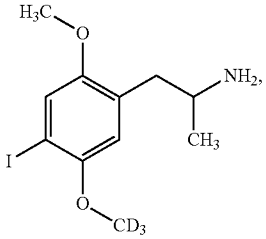
and
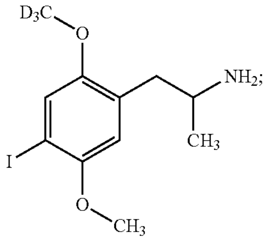
or a pharmaceutically acceptable salt, prodrug, hydrate, or solvate thereof.

In embodiments, disclosed compounds are more resistant to metabolism, and may have reduced dosage requirements and/or optimized durations of action relative to known compounds. Moreover, by reducing the rate of the creation of certain metabolites, such compounds, including the disclosed fluorinated and/or deuterated compounds, may produce fewer species or lower concentrations of metabolites responsible for adverse effects, resulting in improved side-effect profiles, as well as other advantages compared to corresponding non-substituted compounds.

Disclosed fluorine-substituted compounds may provide benefits over their hydrogen counterparts due to the larger steric requirement of covalently bound fluorine over hydrogen. Additionally, the one or more fluorine atoms in a disclosed compound may increase metabolic stability, modulating properties such as pKa and lipophilicity, and/or exerting conformational control (e.g., by the fluorine gauche effect, see Thiehoff, Rey & Gilmour, Israel. J. Chem., 2016; 57(1-2), 92-100). Disclosed fluorinated compounds thus may be more stable towards metabolic degradation and last longer in the organism. Disclosed deuterated compounds also may be more stable towards degradation and last longer in the organism. Incorporating fluorine and/or deuterium in place of one or more hydrogens may improve the bioavailability of a disclosed compound by modifying its electronic properties and/or metabolic fate, while having minimal effect on the structure and retaining the pharmacologic activity and selectivity (see, e.g., Adler et al., Nat. Chem., 2019; 11, 329-334). For example, substituted compounds herein may affect the metabolic rates of oxidative O-dealkylation, resulting in reduced dosage requirements and longer duration of action. In some circumstances, certain disclosed fluorinated and/or deuterated compounds may therefore positively impact safety, efficacy and/or tolerability.

In some embodiments herein, disclosed compounds will have relatively high selectivity at specific receptors (e.g., 5-$HT_{2A}$ and/or 5-$HT_{2C}$ receptors) compared to known compounds, or compared to other receptors (e.g., other 5-HT2 receptors or other serotonin receptor subfamilies [5-$HT_1$, 5-$HT_3$, 5-$HT_5$, 5-$HT_6$, and 5-$HT_7$], other monoaminergic receptors such as norepinephrine receptors [$\alpha$1A, $\alpha$1B, $\alpha$1C, $\alpha$2A, $\alpha$2B, $\alpha$2C] and/or dopamine receptors [$D_1$, $D_2$, $D_3$, $D_4$, $D_5$]). In some embodiments, disclosed compounds have fewer off-target effects (including adverse effects).

In embodiments, the disclosed compounds will allow the optimization of empathogenic, psychedelic, and/or stimulating effects, relative to known compounds (using measures such as discussed in, e.g., González et al., BioMed Research International, 2015; 6443878).

Certain compounds disclosed herein also have the advantage of producing similar effects to related enantiopure compounds (e.g., in some embodiments, an achiral phenethylamine to a single enantiomer such as the (S)-enantiomer of its alpha-methylated or alpha-ethylated analog), while not requiring stereospecific synthetic or separation conditions to obtain.

The individual compounds of the disclosed compositions will be understood to also encompass pharmaceutically acceptable salts of such compounds. "Pharmaceutically acceptable salt" refers to salts prepared from pharmaceutically acceptable non-toxic acids or bases, and which may be synthesized by conventional chemical methods. Generally, such salts are prepared by reacting the free acid or base forms of these agents with a stoichiometric amount of the appropriate base or acid in water or in an organic solvent, or in a mixture of the two; generally, nonaqueous media (e.g., ether, ethyl acetate, ethanol, isopropanol, or acetonitrile) are preferred. For therapeutic use, salts of the disclosed compounds are those wherein the counter-ion is pharmaceutically acceptable.

Exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. (See Berge et al. (1977) "Pharmaceutical Salts," J. Pharm. Sci. 66:1-19.) In some embodiments, preferred pharmaceutically acceptable salts are those employing a hydrochloride anion.

In some aspects, also provided herein are prodrugs of the disclosed compounds. "Prodrug" refers to a precursor of a biologically active pharmaceutical agent, which may undergo a chemical or a metabolic conversion to become the biologically active agent. A prodrug can be converted ex vivo to the biologically active pharmaceutical agent by chemical transformative processes. In vivo, a prodrug is converted to the biologically active pharmaceutical agent by the action of a metabolic process, an enzymatic process or a degradative process that removes the prodrug moiety, such as a glycoside or acetyl group, to form the biologically active pharmaceutical agent. Other examples include addition of hydroxyl groups (Tsujikawa et al. 2011. Xenobiotica, 41(7), 578-584; Yamamoto et al. 1984. Xenobiotica, 14(11), 867-875), acyloxyalkoxycarbonyl derivatives, amino acids, vitamins, or peptides (Vig et al. 2013. Advanced Drug Delivery Reviews, 65(10), 1370-1385), which are generally added to the amine, and can be removed within the body by chemical reactions or enzymes, but other prodrugs and precursors, at the amine and other sites, should be understood to be within the scope of the invention (Simplicio, Clancy, & Gilmer. 2008. Molecules, 13(3), 519-547; Shah, Chauhan, Chauhan, & Mishra (Eds.). 2020. Recent Advancement in Prodrugs. CRC Press).

Types of prodrugs of the disclosed compounds that are contemplated herein include those that are transformed in various organs or locations in the body (e.g., liver, kidney, G.I., lung, tissue) to release the active compound. For example, liver prodrugs will include active compounds conjugated with a polymer or chemical moiety that is not released until acted upon by liver cytochrome enzymes; CYP metabolism includes dealkylation, dehydrogenation, reduction, hydrolysis, oxidation, and the breakdown of aromatic rings. Kidney prodrugs will include active compounds conjugated to L-gamma-glutamyl or N-acetyl-L-gamma glutamic moieties so that they are metabolized by gamma-glutamyl transpeptidase before they are bioactive; alternatively, they may be conjugated to alkylglucoside moieties to create glycosylation-based prodrugs. Digestive or G.I. prodrugs will include those where an active compound is, e.g., formulated into microspheres or nanospheres that do not degrade until the spheres are subjected to an acidic pH; formulated with an amide that will resist biochemical degradation until colonic pH is achieved; or conjugated with a linear polysaccharide such as pectin that will delay activation until the combination reaches the bacteria in the colon. Besides these exemplary prodrug forms, many others will be known to those of ordinary skill.

Examples of certain preferred prodrugs are those having a biologically labile or cleavable (protecting) group on a functional moiety of a disclosed compound. Prodrugs further include those that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce a disclosed compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a disclosed compound. Conventional procedures for the selection and preparation of suitable prodrugs of disclosed compounds are described, e.g., in “Design of Prodrugs” Ed. H. Bundgaard, Elsevier, 1985.

In embodiments, a prodrug of a disclosed compound is an amino acid prodrug. Amino acid refers to molecules comprising an amine group, a carboxylic acid group and a side-chain that varies among different amino acids. In some embodiments, one or more amino acids are directly conjugated to a disclosed compound to prepare a prodrug thereof. In some embodiments, a linker is used to conjugate a disclosed compound to the one or more amino acids to prepare a prodrug thereof. In some embodiments, amino acid prodrugs improve poor solubility, poor permeability, sustained release, intravenous delivery, drug targeting, and metabolic stability of the parent drug. See, e.g., Vig et al., Advanced Drug Delivery Reviews, 2013; 65(10):1370-1385.

In some embodiments, a disclosed compound is attached to a single amino acid which is either a naturally occurring amino acid or a synthetic amino acid. In some embodiments, a disclosed compound is attached to a dipeptide or tripeptide, which could be any combination of naturally occurring amino acids and/or synthetic amino acids. In some embodiments, the amino acids are selected from L-amino acids for digestion by proteases. In some embodiments a carrier peptide is attached to a disclosed compound through the carrier peptide’s N-terminus, C-terminus, or side chain of an amino acid which may be either a single amino acid or part of a longer chain sequence (i.e., a dipeptide, tripeptide, oligopeptide, or polypeptide). The carrier peptide may also be (i) a homopolymer of a naturally occurring amino acid, (ii) a heteropolymer of two or more naturally occurring amino acids, (iii) a homopolymer of a synthetic amino acid, (iv) a heteropolymer of two or more synthetic amino acids, or (v) a heteropolymer of one or more naturally occurring amino acids and one or more synthetic amino acids. For example, carrier peptides may be homopolymers or heteropolymers of glutamic acid, aspartic acid, serine, lysine, cysteine, threonine, asparagine, arginine, tyrosine, and glutamine. Examples of peptides include, Lys, Ser, Phe, Gly-Gly-Gly, Leu-Ser, Leu-Glu, homopolymers of Glu and Leu, and heteropolymers of (Glu)n-Leu-Ser.

In some embodiments, a prodrug of a disclosed compound is a vitamin prodrug. In some embodiments, the vitamin is pyridoxine. Pyridoxine is the 4-methanol form of vitamin B6. Transporters, such as SLC19A2 and SLC19A3, also known as thiamine transporters (THTR) 1 and 2, have been shown to transport pyridoxine. Such transport may be exploited using pyridoxine as a prodrug component. See, e.g., Yamashiro et al., J Biol Chem. 2020; 295(50):16998-17008.

Generally, the individual compounds of the disclosure shall be administered as part of a pharmaceutical composition or formulation, but will be prepared for inclusion in such composition or formulations as isolated or purified compounds. The terms “isolated,” “purified,” or “substantially pure,” as used herein, refer to material that is substantially or essentially free from components that normally accompany the material when the material is synthesized, manufactured, or otherwise produced. An “isolated,” “purified,” or “substantially pure” preparation of a compound is accordingly defined as a preparation having a chromatographic purity (of the desired compound) of greater than 90%, more preferably greater than 95%, more preferably greater than 96%, more preferably greater than 97%, more preferably greater than 98%, more preferably greater than 99%, more preferably greater than 99.5%, and most preferably greater than 99.9%, as determined by area normalization of an HPLC profile or other similar detection method.

Preferably the substantially pure compound used in the invention is substantially free of any other active compounds which are not intended to be administered to a subject. In this context “substantially free” can be taken to mean that no active compound(s) other than the active compound intended to be administered to a subject are detectable by HPLC or other similar detection method, or are below a desired threshold of detection such as defined above.

It should be understood that any reference to a disclosed compound or a pharmaceutically acceptable salt, prodrug, hydrate, or solvate thereof, will include all amorphous and polymorphic forms. In the case of solid compositions, in particular, it is understood that the compounds used in the disclosed compositions and methods may exist in different forms. For example, the compounds may exist in stable and metastable crystalline forms, isotropic and amorphous forms, milled forms and nano-particulate forms, all of which are intended to be within the scope of the invention. In addition, disclosed compounds may include crystalline forms, known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The disclosed compounds now generally described will be more readily understood by reference to the following description and examples, which are included for the purposes of illustration of certain aspects of the embodiments of the present invention. The following is not intended to limit the invention, as one of skill in the art would recognize from the teachings and examples herein that other techniques and methods can satisfy the claims and be employed without departing from the scope of the invention. Indeed, while this invention has been particularly shown and described with reference to certain exemplary embodiments, it will be understood by those skilled in the art that various changes in form and details may be made without departing from the scope or spirit of the invention encompassed by the appended claims.

a. Mixtures of Halogen-Substituted and Non-Halogenated Compounds

In some aspects, provided herein are mixtures comprising halogen-substituted and non-halogenated compounds, such as disclosed compounds. In some embodiments, the mixtures are mixtures comprising fluorine-substituted and non-fluorinated compounds, such as disclosed compounds. In some embodiments, the mixtures are mixtures comprising halogen-substituted and non-halogenated compounds, wherein at least one of the halogen-substituted atoms is not a fluorine atom. In some embodiments, the mixtures are mixtures comprising halogen-substituted and non-halogenated compounds, wherein none of the halogen-substituted atoms is a fluorine atom. In some embodiments, the mixtures are mixtures comprising halogen-substituted and non-halogenated compounds, wherein all of the halogen-substituted atoms are fluorine atoms. In some embodiments, the mixtures are mixtures comprising halogen-substituted and non-halogenated compounds, wherein the halogen-substituted atoms are different halogen atoms.

In some embodiments, a disclosed composition comprises a mixture of one or more halogen-substituted compounds of the disclosure and corresponding non-substituted compounds in a fixed ratio, and will contain a ratio of halogen-substituted to non-substituted compounds (as mole ratio or mass ratio), including a pharmaceutically acceptable salt, hydrate, solvate or prodrug thereof, of 1:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including the exact above-listed ratios themselves. In some embodiments, the disclosed mixture of one or more halogen-substituted compounds and corresponding non-substituted compounds in a fixed ratio is a mixture in said ratio of fluorine-substituted to non-fluorine-substituted compounds.

In some embodiments, a disclosed composition comprises a mixture of one or more halogen-substituted compounds of the disclosure and corresponding non-substituted compounds in a fixed ratio, and will contain a ratio of non-substituted to halogen-substituted compounds (as mole ratio or mass ratio), including a pharmaceutically acceptable salt, hydrate, solvate or prodrug thereof, of 1:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including the exact above-listed ratios themselves. In some embodiments, the disclosed mixture of one or more halogen-substituted compounds and corresponding non-substituted compounds in a fixed ratio is a mixture in said ratio of fluorine-substituted to non-fluorine-substituted compounds.

In some embodiments, a compound of Formula (I), or a pharmaceutically acceptable salt, hydrate, solvate or prodrug thereof, will be a mixture of (a) the compound of Formula (I) of the invention having at least one halogen (i.e., a "halogenated compound," a "halogen-substituted" compound, or a "haloalkyl" compound), and (b) a corresponding "non-substituted compound" (i.e., the corresponding compound having a hydrogen in place of each halogen), or a pharmaceutically acceptable salt, hydrate, solvate or prodrug thereof. In such mixtures, at least 1%, 2%, 3%, 4%, 5%, 10%, 20%, 30%, 40%, 50%, 55%, 60%, 65%, 70%, 75%, 80%, 85%, 90%, 91%, 92%, 93%, 94%, 95%, 96%, 97%, 98%, 99%, 99.5%, 99.0%, 99.7%, 99.8%, 99.9% or 100% are halogenated compounds of Formula (I) (i.e., halogen-substituted), or a pharmaceutically acceptable salt, hydrate, solvate or prodrug thereof (wherein the other compounds in such mixtures are the corresponding non-substituted compounds). In an embodiment, at least 1% of the compounds of Formula (I), or a pharmaceutically acceptable salt, hydrate, solvate or prodrug thereof, are halogen-substituted. In an embodiment, at least 2% of the compounds of Formula (I), or a pharmaceutically acceptable salt, hydrate, solvate or prodrug thereof, are halogen-substituted. In an embodiment, at least 3% of the compounds of Formula (I), or a pharmaceutically acceptable salt, hydrate, solvate or prodrug thereof, are halogen-substituted. In an embodiment, at least 4% of the compounds of Formula (I), or a pharmaceutically acceptable salt, hydrate, solvate or prodrug thereof, are halogen-substituted. In an embodiment, at least 5% of the compounds of Formula (I), or a pharmaceutically acceptable salt, hydrate, solvate or prodrug thereof, are halogen-substituted. In an embodiment, at least 10% of the compounds of Formula (I), or a pharmaceutically acceptable salt, hydrate, solvate or prodrug thereof, are halogen-substituted. In an embodiment, at least 20% of the compounds of Formula (I), or a pharmaceutically acceptable salt, hydrate, solvate or prodrug thereof, are halogen-substituted. In an embodiment, at least 30% of the compounds of Formula (I), or a pharmaceutically acceptable salt, hydrate, solvate or prodrug thereof, are halogen-substituted. In an embodiment, at least 40% of the compounds of Formula (I), or a pharmaceutically acceptable salt, hydrate, solvate or prodrug thereof, are halogen-substituted. In an embodiment, at least 50% of the compounds of Formula (I), or a pharmaceutically acceptable salt, hydrate, solvate or prodrug thereof, are halogen-substituted. In an embodiment, the compound of Formula (I), or a pharmaceutically acceptable salt, hydrate, solvate or prodrug thereof, at least 55% are halogen-substituted. In another embodiment, the compound of Formula (I), or a pharmaceutically acceptable salt, hydrate, solvate or prodrug thereof, at least 60% are halogen-substituted. In yet another embodiment, the compound of Formula (I), or a pharmaceutically acceptable salt, hydrate, solvate or prodrug thereof, at least 65% are halogen-substituted. In another embodiment, the compound of Formula (I), or a pharmaceutically acceptable salt, hydrate, solvate or prodrug thereof, at least 70% are halogen-substituted. In another embodiment, the compound of Formula (I), or a pharmaceutically acceptable salt, hydrate, solvate or prodrug thereof, at least 75% are halogen-substituted. In another embodiment, the compound of Formula (I), or a pharmaceutically acceptable salt, hydrate, solvate or prodrug thereof, at least 80% are halogen-substituted. In another embodiment, the compound of Formula (I), or a pharmaceutically acceptable salt, hydrate, solvate or prodrug thereof, at least 85% are halogen-substituted. In another embodiment, the compound of Formula (I), or a pharmaceutically acceptable salt, hydrate, solvate or prodrug thereof, at least 90% are halogen-substituted. In another embodiment, the compound of Formula (I), or a pharmaceutically acceptable salt, hydrate, solvate or prodrug thereof, at least 91% are halogen-substituted. In another embodiment, the compound of Formula (I), or a pharmaceutically acceptable salt, hydrate, solvate or prodrug thereof, at least 92% are halogen-substituted. In another embodiment, the compound of Formula (I), or a pharmaceutically acceptable salt, hydrate, solvate or prodrug thereof, at least 93% are halogen-substituted. In another embodiment, the compound of Formula (I), or a pharmaceutically acceptable salt, hydrate, solvate or prodrug thereof, at least 94% are halogen-substituted. In another embodiment, the compound of Formula (I), or a pharmaceutically acceptable salt, hydrate, solvate or prodrug thereof, at least 95% are halogen-substituted. In another embodiment, the compound of Formula (I), or a pharmaceutically acceptable salt, hydrate, solvate or prodrug thereof, at least 96% are halogen-substituted. In another embodiment, the compound of Formula (I), or a pharmaceutically acceptable salt, hydrate, solvate or prodrug thereof, at least 97% are halogen-substituted. In another embodiment, the compound of Formula (I), or a pharmaceutically acceptable salt, hydrate, solvate or prodrug thereof, at least 98% are halogen-substituted. In another embodiment, the compound of Formula (I), or a pharmaceutically acceptable salt, hydrate, solvate or prodrug thereof, at least 99% are halogen-substituted. In another embodiment, the compound of Formula (I), or a pharmaceutically acceptable salt, hydrate, solvate or prodrug thereof, at least 99.5% are halogen-substituted. In another embodiment, the compound of Formula (I), or a pharmaceutically acceptable salt, hydrate, solvate or prodrug thereof, at least 99.6% are halogen-substituted. In another embodiment, the compound of Formula (I), or a pharmaceutically acceptable salt, hydrate, solvate or prodrug thereof, at least 99.7% are halogen-substituted. In another embodiment, the compound of Formula (I), or a pharmaceutically acceptable salt, hydrate, solvate or prodrug thereof, at least 99.8% are halogen-substituted. In another embodiment, the compound of Formula (I), or a pharmaceutically acceptable salt, hydrate, solvate or prodrug thereof, at least 99.9% are halogen-substituted. In any of the embodiments described above, a non-substituted compound may be described as a compound of Formula (I), or a pharmaceutically acceptable salt, hydrate, solvate or prodrug thereof, wherein all of the halogen atoms are replaced with hydrogen atoms.

In some embodiments, a compound of Formula (I), or a pharmaceutically acceptable salt, hydrate, solvate or prodrug thereof, will be a mixture of (a) the compound of Formula (I) of the invention having at least one fluorine (i.e., a "fluorinated compound," or a "fluorine-substituted" compound), and (b) a corresponding "non-substituted compound" (i.e., the corresponding compound having a hydrogen in place of each fluorine), or a pharmaceutically acceptable salt, hydrate, solvate or prodrug thereof. In such mixtures, at least 1%, 2%, 3%, 4%, 5%, 10%, 20%, 30%, 40%, 50%, 55%, 60%, 65%, 70%, 75%, 80%, 85%, 90%, 91%, 92%, 93%, 94%, 95%, 96%, 97%, 98%, 99%, 99.5%, 99.0%, 99.7%, 99.8%, 99.9%, or 100% are fluorinated compounds of Formula (I) (i.e., fluorine-substituted), or a pharmaceutically acceptable salt, hydrate, solvate or prodrug thereof (wherein the other compounds in such mixtures are the corresponding non-substituted compounds). In an embodiment, at least 1% of the compounds of Formula (I), or a pharmaceutically acceptable salt, hydrate, solvate or prodrug thereof, are fluorine-substituted. In an embodiment, at least 2% of the compounds of Formula (I), or a pharmaceutically acceptable salt, hydrate, solvate or prodrug thereof, are fluorine-substituted. In an embodiment, at least 3% of the compounds of Formula (I), or a pharmaceutically acceptable salt, hydrate, solvate or prodrug thereof, are fluorine-substituted. In an embodiment, at least 4% of the compounds of Formula (I), or a pharmaceutically acceptable salt, hydrate, solvate or prodrug thereof, are fluorine-substituted. In an embodiment, at least 5% of the compounds of Formula (I), or a pharmaceutically acceptable salt, hydrate, solvate or prodrug thereof, are fluorine-substituted. In an embodiment, at least 10% of the compounds of Formula (I), or a pharmaceutically acceptable salt, hydrate, solvate or prodrug thereof, are fluorine-substituted. In an embodiment, at least 20% of the compounds of Formula (I), or a pharmaceutically acceptable salt, hydrate, solvate or prodrug thereof, are fluorine-substituted. In an embodiment, at least 30% of the compounds of Formula (I), or a pharmaceutically acceptable salt, hydrate, solvate or prodrug thereof, are fluorine-substituted. In an embodiment, at least 40% of the compounds of Formula (I), or a pharmaceutically acceptable salt, hydrate, solvate or prodrug thereof, are fluorine-substituted. In an embodiment, at least 50% of the compounds of Formula (I), or a pharmaceutically acceptable salt, hydrate, solvate or prodrug thereof, are fluorine-substituted. In an embodiment, the compound of Formula (I), or a pharmaceutically acceptable salt, hydrate, solvate or prodrug thereof, at least 55% are fluorine-substituted. In another embodiment, the compound of Formula (I), or a pharmaceutically acceptable salt, hydrate, solvate or prodrug thereof, at least 60% are fluorine-substituted. In yet another embodiment, the compound of Formula (I), or a pharmaceutically acceptable salt, hydrate, solvate or prodrug thereof, at least 65% are fluorine-substituted. In another embodiment, the compound of Formula (I), or a pharmaceutically acceptable salt, hydrate, solvate or prodrug thereof, at least 70% are fluorine-substituted. In another embodiment, the compound of Formula (I), or a pharmaceutically acceptable salt, hydrate, solvate or prodrug thereof, at least 75% are fluorine-substituted. In another embodiment, the compound of Formula (I), or a pharmaceutically acceptable salt, hydrate, solvate or prodrug thereof, at least 80% are fluorine-substituted. In another embodiment, the compound of Formula (I), or a pharmaceutically acceptable salt, hydrate, solvate or prodrug thereof, at least 85% are fluorine-substituted. In another embodiment, the compound of Formula (I), or a pharmaceutically acceptable salt, hydrate, solvate or prodrug thereof, at least 90% are fluorine-substituted. In another embodiment, the compound of Formula (I), or a pharmaceutically acceptable salt, hydrate, solvate or prodrug thereof, at least 91% are fluorine-substituted. In another embodiment, the compound of Formula (I), or a pharmaceutically acceptable salt, hydrate, solvate or prodrug thereof, at least 92% are fluorine-substituted. In another embodiment, the compound of Formula (I), or a pharmaceutically acceptable salt, hydrate, solvate or prodrug thereof, at least 93% are fluorine-substituted. In another embodiment, the compound of Formula (I), or a pharmaceutically acceptable salt, hydrate, solvate or prodrug thereof, at least 94% are fluorine-substituted. In another embodiment, the compound of Formula (I), or a pharmaceutically acceptable salt, hydrate, solvate or prodrug thereof, at least 95% are fluorine-substituted. In another embodiment, the compound of Formula (I), or a pharmaceutically acceptable salt, hydrate, solvate or prodrug thereof, at least 96% are fluorine-substituted. In another embodiment, the compound of Formula (I), or a pharmaceutically acceptable salt, hydrate, solvate or prodrug thereof, at least 97% are fluorine-substituted. In another embodiment, the compound of Formula (I), or a pharmaceutically acceptable salt, hydrate, solvate or prodrug thereof, at least 98% are fluorine-substituted. In another embodiment, the compound of Formula (I), or a pharmaceutically acceptable salt, hydrate, solvate or prodrug thereof, at least 99% are fluorine-substituted. In another embodiment, the compound of Formula (I), or a pharmaceutically acceptable salt, hydrate, solvate or prodrug thereof, at least 99.5% are fluorine-substituted. In another embodiment, the compound of Formula (I), or a pharmaceutically acceptable salt, hydrate, solvate or prodrug thereof, at least 99.6% are fluorine-substituted. In another embodiment, the compound of Formula (I), or a pharmaceutically acceptable salt, hydrate, solvate or prodrug thereof, at least 99.7% are fluorine-substituted. In another embodiment, the compound of Formula (I), or a pharmaceutically acceptable salt, hydrate, solvate or prodrug thereof, at least 99.8% are fluorine-substituted. In another embodiment, the compound of Formula (I), or a pharmaceutically acceptable salt, hydrate, solvate or prodrug thereof, at least 99.9% are fluorine-substituted. In any of the embodiments described above, a non-substituted compound may be described as a compound of Formula (I), or a pharmaceutically acceptable salt, hydrate, solvate or prodrug thereof, wherein all of the fluorine atoms are replaced with hydrogen atoms.

b. Mixtures of Deuterated and Undeuterated Compounds

In some embodiments, a disclosed compound will comprise a hydrogen isotope, such as protium, deuterium, or tritium. Such a compound may be referred to as an isotope-labeled compound. In some embodiments, each hydrogen (H) will be protium ($^1$H), in other embodiments, one or more protium ($^1$H) atoms(s) may be replaced by one or more deuterium atoms(s) ($^2$H or D) resulting in a compound or composition in which the abundance of deuterium at each position of the compound is higher than the natural abundance of the deuterium isotope, which is approximately one atom per 6,500 of hydrogen (~154 ppm), i.e., approximately 0.0154% (alternately, on a mass basis, 0.0308%). In some embodiments, any one or more hydrogens will be replaced by tritium ($^3$H or T).

In some embodiments, deuterated compounds and compositions thereof are deuterium enriched. "Deuterium enriched," which may include compounds that are "deuterium substituted," refers to a compound or composition where the abundance of deuterium at at least one position is higher than the natural abundance of deuterium, which is about 0.0154%, i.e., the amount of deuteration in a "naturally occurring" non-deuterated compound. In deuterium enriched compounds and compositions, the abundance of deuterium at each deuterated position may be higher than 10%, 20%, 30%, 40%, 50%, 60%, 70% or 80%, preferably higher than 90%, 95%, 96% or 97%, even more preferably higher than 98%, 99% or 99.5% at said position(s). It is understood that the abundance of deuterium at each deuterated position is independent of the abundance of deuterium at other deuterated position(s). "Non-substituted," "non-deuterated," and "undeuterated" may refer to compounds having no greater than the amount of deuterium expected as a percentage of naturally occurring hydrogen in a compound.

The use of an alternate isotope may change the kinetics of a chemical reaction. This phenomenon is known as the kinetic isotope effect ("KIE"). For example, substituting a deuterium for a hydrogen may affect the reaction rate; this phenomenon is known as the "deuterium kinetic isotope effect" (DKIE). The DKIE can range from about 1 (no effect) to 50 or more, meaning that a reaction can be fifty or more times slower when deuterium is substituted for hydrogen (see, e.g., Foster et al., Adv. Drug Res., 14:1-36 (1985); Kushner et al., Can. J. Physiol. Pharmacol. 77:79-88 (1999)). In some embodiments, the experimental or computed DKIE is at least 1.1, at least 1.2, at least 1.3, at least 1.4, at least 1.5, at least 1.6, at least 1.7, at least 1.8, at least 1.9, at least 2.0, at least 2.5, at least 3.0, at least 3.5, at least 4.0, at least 4.5, at least 5.0, at least 5.5, at least 6.0, at least 6.5, at least 7.0, at least 7.5, at least 8.0, at least 8.5, at least 9.0, at least 9.5, at least 10.0, at least 11.0, at least 12.0, at least 13.0, at least 14.0, at least 15.0, at least 20.0, at least 25.0, at least 30.0, at least 40.0, at least 45.0, or at least 50.

In some embodiments, incorporating deuterium in place of hydrogen will improve the pharmacodynamic and pharmacokinetic profiles of the disclosed compounds by modifying the metabolic fate while retaining the pharmacologic activity and selectivity of the compounds.

In some embodiments, the disclosed deuterated compounds will positively impact safety, efficacy, and/or tolerability, compared to undeuterated compounds.

In some embodiments, a composition of the invention will be a mixture of one or more deuterium-substituted compounds and corresponding non-substituted compounds in a fixed ratio, and will contain a ratio of deuterium-substituted to non-substituted compounds (as mole ratio or mass ratio), including a pharmaceutically acceptable salt, hydrate, solvate or prodrug thereof, of 1:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, and at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including the exact above-listed ratios themselves.

In some embodiments, a composition of the invention will be a mixture of one or more deuterium-substituted compounds and corresponding non-substituted compounds in a fixed ratio, and will contain a ratio of non-substituted to deuterium-substituted compounds (as mole ratio or mass ratio), including a pharmaceutically acceptable salt, hydrate, solvate or prodrug thereof, of 1:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, and at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including the exact above-listed ratios themselves.

In some embodiments, the disclosed compounds are both halogen-substituted and deuterium-substituted, and may be deuterium-substituted at one or more positions, 2 or more positions, 3 or more positions, 4 or more positions, 5 or more positions, or more than 6 positions, in addition to one or more halogen-substitutions as taught herein. In some embodiments, the disclosed compounds are both fluorine-substituted and deuterium-substituted, and may be deuterium-substituted at one or more positions, 2 or more positions, 3 or more positions, 4 or more positions, 5 or more positions, or more than 6 positions, in addition to one or more fluorine-substitutions as taught herein.

In some embodiments, a halogen-substituted compound or a composition comprising a mixture of halogen-substituted and non-halogen-substituted compounds will have an improved pharmacokinetic profile compared to the corresponding non-halogen-substituted compound or a composition thereof. In some embodiments, a fluorine-substituted compound or a composition comprising a mixture of fluorine-substituted and non-fluorine-substituted compounds will have an improved pharmacokinetic profile compared to the corresponding non-fluorine-substituted compound or a composition thereof. In some embodiments, a halogen-substituted or a fluorine-substituted compound or a composition having a mixture of halogen- or fluorine-substituted and non-substituted compounds will also be deuterium-substituted, and will have an improved pharmacokinetic profile compared to the corresponding non-halogen- or non-fluorine-substituted compound, the corresponding non-deuterium-substituted compound, and/or the fully non-substituted compound, or a composition comprising any of the foregoing. In some embodiments, a deuterium-substituted compound or a composition having a mixture of deuterium-substituted and non-substituted compounds will have an improved pharmacokinetic profile compared to the corresponding non-deuterium-substituted compound or a composition thereof. It therefore will be understood that the substituted and non-substituted compounds may be compared as administered alone, and also may be compared as administered as part of a pharmaceutical composition further comprising one or more pharmaceutically-acceptable carriers, diluents, and/or excipients, and also may be compared as administered in a composition further comprising one or more additional active compounds, and that a comparison will be between a composition comprising the substituted compound and a composition comprising the non-substituted compound, all other aspects of the compositions being the same.

In embodiments, a halogen will be replaced by a radiohalogen.

In some embodiments, the improved pharmacokinetics of the disclosed compounds when used in a composition having a mixture of substituted (i.e., halogenated, fluorinated, and/or deuterated) and non-substituted compounds will reduce or eliminate the need for re-dosing. In embodiments, reducing or eliminating re-dosing will reduce or eliminate one or more adverse events or unwanted side effects. In some embodiments, reducing or eliminating re-dosing will provide benefits relating to ease of administration and patient compliance. In embodiments, a composition having a mixture of substituted and non-substituted compounds will have other benefits relating to an improved pharmacokinetic profile compared to the substituted compound, such as earlier onset, shorter time to peak effect, longer peak effects, or longer half-life.

In some embodiments, the disclosed compounds are used as research tools, such as tools for scientific research. In some embodiments, the disclosed compounds are used as analytical reagents. In some embodiments, the disclosed compounds are used for spectroscopy, quality control, and forensic applications. In some embodiments, disclosed compounds are useful in an imaging context, such as medical imaging. In some embodiments, disclosed compounds may be used for tissue imaging.

One example of use as a research tool is in the determination of the structure and function of a receptor in vitro, in vivo, or in silico. In some embodiments, disclosed compounds may be used in receptor, ion channel, enzyme, and transporter binding studies. In some embodiments, disclosed compounds may be used in mapping, and functional studies. In some embodiments, disclosed compounds may be used to identify binding sites. In some embodiments, disclosed compounds for such uses are radiolabeled. In some embodiments, disclosed compounds for such uses comprise an isotope of hydrogen and/or a radiohalogen. In some embodiments, the isotope of hydrogen is protium, deuterium, or tritium. In some embodiments, the radiohalogen is radioactive fluorine, chlorine, bromine, iodine, or astatine.

In some embodiments, disclosed compounds may be used as research tools, such as receptor probes, for serotonin receptors, for example, $HTR_1$, $HTR_2$, and $HTR_6$ receptors, including subtypes thereof. In some embodiments, disclosed compounds may be used as research tools for 5-$HT_{2A}$ receptors. In some embodiments, the research tool is a receptor probe, which may be used for determining downstream events of receptor-ligand interaction, e.g., calcium regulation, kinase, phosphatase and phospholipase activation, and lipid trafficking. In some embodiments, the receptor is a recombinant receptor. In some embodiments, the receptor is a wild-type receptor. In some embodiments, the receptors are of mammalian origin. In some embodiments, the receptors are of human origin.

c. Stereoisomers and Enantiomeric Mixtures

The disclosed compounds may contain one or more asymmetric centers and give rise to enantiomers, diastereomers, and other stereoisomeric forms. Each chiral center may be defined, in terms of absolute stereochemistry, as (R)- or (S)-. The invention is meant to include all such possible isomers, as well as mixtures thereof, including racemic and optically pure forms.

Optically active (R)- and (S)-, (−)- and (+)-, or (D)- and (L)-isomers may be prepared using chiral synthons or chiral reagents, or resolved using conventional techniques. Various methods are known in the art for preparing optically active forms and determining activity. Such methods include standard tests described herein and other similar tests which are well known in the art. Examples of methods that can be used to obtain optical isomers of the compounds according to the present disclosure include the following: i) physical separation of crystals whereby macroscopic crystals of the individual enantiomers are manually separated. This technique may particularly be used if crystals of the separate enantiomers exist (i.e., the material is a conglomerate), and the crystals are visually distinct; ii) simultaneous crystallization whereby the individual enantiomers are separately crystallized from a solution of the racemate, possible only if the latter is a conglomerate in the solid state; iii) enzymatic resolutions whereby partial or complete separation of a racemate by virtue of differing rates of reaction for the enantiomers with an enzyme; iv) enzymatic asymmetric synthesis, a synthetic technique whereby at least one step of the synthesis uses an enzymatic reaction to obtain an enantiomerically pure or enriched synthetic precursor of the desired enantiomer; v) chemical asymmetric synthesis whereby the desired enantiomer is synthesized from an achiral precursor under conditions that produce asymmetry (i.e., chirality) in the product, which may be achieved using chiral catalysts or chiral auxiliaries; vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers; viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions; ix) enantiospecific synthesis from non-racemic precursors whereby the desired enantiomer is obtained from non-chiral starting materials and where the stereochemical integrity is not or is only minimally compromised over the course of the synthesis; x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions; xi) chiral gas chromatography whereby the racemate is volatilized and enantiomers are separated by virtue of their differing interactions in the gaseous mobile phase with a column containing a fixed non-racemic chiral adsorbent phase; xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane, which allows only one enantiomer of the racemate to pass through.

The disclosed compounds may be provided in a composition that is enantiomerically enriched, such as a mixture of enantiomers in which one enantiomer is present in excess, in particular to the extent of at least 50%, at least 55%, at least 60%, at least 65%, at least 70%, at least 75%, at least 80%, at least 85%, at least 90%, at least 95%, at least 98%, at least 99%, at least 99.5%, or at least 99.9%, and up to (and including) 100%.

When the compounds described herein contain olefinic double bonds or other centers of geometric asymmetry, and unless specified otherwise, it is intended that the compounds include both E and Z geometric isomers. Likewise, tautomeric forms are included.

d. Exemplary Features of Disclosed Phenylalkylamines

In some aspects, features of disclosed compounds provide various advantages. Such advantages may be related to modulation of neurotransmission, pharmacokinetics, such as properties related to absorption, distribution, metabolism, and excretion of a disclosed compound, and subjective effects, such as upon administration to a subject. In some embodiments, such advantages are determined relative to a comparator. In some embodiments, the comparator is a known phenylalkylamine psychedelic. For example, in some embodiments, the comparator is 2C-B, or analogs thereof. In some embodiments, the comparator is an analog of a known phenylalkylamine psychedelic with 2,5-di(trideuteromethoxy) substitution. For example, in some embodiments, the comparator is 2-(4-bromo-2,5-di(trideutero-methoxy) phenyl)ethanamine (i.e., 4-bromo-2,5-di(trideuteromethoxy)phenethylamine).

In some embodiments, disclosed compounds modulate the activity of one or more monoamine receptors and/or one or more monoamine transporters. In some embodiments, disclosed compounds potently agonize serotonin receptors. In some embodiments, disclosed compounds potently agonize the 5-$HT_{2A}$ receptor ($HTR_{2A}$). Activation of $HTR_{2A}$, which may provide therapeutic value through a variety of mechanisms, is implicated in producing subjective hallucinogenic or psychedelic effects. See, e.g., López-Gimenez & Gonzilez-Maeso, Curr Top Behav Neurosci. 2018; 36:45-73.

In some embodiments, disclosed compounds potently antagonize serotonin receptors. In some embodiments, disclosed compounds potently agonize the 5-$HT_{2B}$ receptor ($HTR_{2B}$). Antagonism of $HTR_{2B}$ is associated with various effects, including a reduction in fibrotic response, collagen deposition, and headache pain, such as migraines. Reduced fibrosis and collagen deposition are implicated in the prevention of pulmonary and cardiac liabilities, for example, pulmonary and ventricular fibrosis. See, e.g., Löfdahl et al., Physiol Rep. 2016; 4(15):e12873, Janssen et al., Biomed Res Int. 2015; 2015:438403, and West et al., PLoS One. 2016 Feb. 10; 11(2):e0148657.

In some embodiments, disclosed compounds selectively inhibit the update activity of the serotonin transporter (SERT). Blocking the uptake activity of monoamine transporters, such as SERT, DAT, or NET, may result in an increase of circulating monoamines and neurotransmission modulated by the same. In some embodiments, the receptors and transporters are of mammalian origin. In some embodiments, the receptors and transporters are of human origin.

In some embodiments, a disclosed compound has medium permeability. In some embodiments, a disclosed compound has high permeability. In some embodiments, a disclosed compound has increased permeability relative to its corresponding non-fluorinated compound. In some embodiments, a disclosed compound has increased permeability relative to a comparator. In some embodiments, permeability of a disclosed compound is increased by about or at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to a comparator.

The permeability, such as apparent permeability, of a compound describes how effectively it can pass through a membrane. A medium permeability compound may have an in vitro apparent permeability of 50-150 nm/s, wherein the range is inclusive. A high permeability compound may have an in vitro apparent permeability in excess of 150 nm/s, wherein the range is inclusive. Measures of permeability, such as in vitro methods, are available to one of skill in the art and include, e.g., a Madin-Darby canine kidney cell line (MDCK) permeability assay and a parallel artificial membrane permeation assay (PAMPA). For example, PAMPA is an in vitro model of passive diffusion, which has shown a high degree of correlation with permeation across a variety of barriers, including Caco-2 cultures, the gastrointestinal tract, blood-brain barrier, and skin. See, e.g., Chavda & Shah, Chapter 25—Self-emulsifying delivery systems: one step ahead in improving solubility of poorly soluble drugs, In Micro and Nano Technologies, Nanostructures for Cancer Therapy, Elsevier, 2017, pages 653-718.

In some embodiments, a disclosed compound has increased clearance relative to a comparator. In some embodiments, a disclosed compound has reduced clearance relative to a comparator. In some embodiments, clearance is increased by about or at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to the comparator. In embodiments, the half-life of a disclosed compound is decreased by about or at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to the comparator.

In some embodiments, clearance refers to intrinsic clearance. In some embodiments, pharmacokinetic parameters, including intrinsic clearance and half-life, are determined using an in vitro metabolic stability study comprising human liver microsomes. Methods for assessing metabolic stability, such as in vitro clearance and half-life, are described in, e.g., Gajula et al., Drug Metab Rev. 2021; 53(3):459-477 and Knights et al., Curr Protoc Pharmacol. 2016; 74:7.8.1-7.8.24. Pharmacokinetic parameters may also be determined in vivo, such as in a human, e.g., according to the paradigm described by Brown et al., Clin Pharmacokinet. 2017; 56(12):1543-1554. Additionally, identification of metabolites and interactions with CYP enzymes may be performed as described in, e.g., Caspar et al., Drug Test Anal. 2018; 10(1):184-195.

In some embodiments, administration of a disclosed compound to a subject produces psychoactive effects in said subject. Herein, "psychoactive" effects may be used interchangeably with "psychedelic" and "hallucinogenic" effects. In some embodiments, the subject administered a disclosed compound experiences psychoactive effects for less than 8 hours, less than 7 hours, less than 6 hours, less than 5 hours, less than 4 hours, less than 3 hours, less than 2 hours, less than 1 hour, or less than 0.5 hours. In some embodiments, the subject experiences the onset of such effects at about or at less than 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, or 130 minutes post-administration of a disclosed compound.

In some embodiments, psychoactive effects are assessed using one or more of a Peak Experience Scale (PES), e.g., as described in Reckweg et al., Front Pharmacol. 2021; 12:760671, the Mystical Experience Questionnaire (MEQ), the Ego Dissolution Inventory (EDI), the Challenging Experience Questionnaire (CEQ), and the 5-Dimensional Altered States of Consciousness Questionnaire (5D-ASC). In some embodiments, onset and duration of psychoactive effects may be determined by observing and/or interviewing the subject, such as by using a self-report symptom questionnaire, or by asking the subject to document subjective psychoactive effects, i.e., the subject's experience. In some embodiments, the self-report symptom questionnaire is the Subjective Drug Effects Questionnaire (SDEQ), a 272-item questionnaire measuring perceptual, mood, and somatic changes caused by psychedelics (Katz et al. J Abnorm Psych, 1968; 73:1-14). In some embodiments, the self-report symptom questionnaire is the List of Complaints (LC), a 66-item questionnaire that reliably measures physical and general discomfort (see, e.g., Holze et al. 2022. Psychopharmacol, 239:1893-1905). Psychoactive effects and onset and duration of such effects may additionally be determined according to methods known to one of skill in the art.

In some embodiments, disclosed compounds are not substrates for monoamine oxidase enzymes. In some embodiments, disclosed compounds do not inhibit the activity of monoamine oxidase enzymes. In some embodiments, disclosed compounds do not irreversibly inhibit the activity of monoamine oxidase enzymes. In some embodiments, disclosed compounds do not reversibly inhibit the activity of monoamine oxidase enzymes. Monoamine oxidase enzymes include isoenzymes MAO-A and MAO-B. In some embodiments, disclosed compounds are not substrates for monoamine oxidase A (MAO-A). In some embodiments, disclosed compounds do not inhibit the activity of MAO-A. In some embodiments, disclosed compounds do not irreversibly inhibit the activity of MAO-A. In some embodiments, disclosed compounds do not reversibly inhibit the activity of MAO-A. In some embodiments, disclosed compounds are not reversible inhibitors of MAO-A (RIMAs). In some embodiments, the $IC_{50}$ of disclosed compounds at MAO-A is greater than 10 μM. Herein, a threshold of greater than or equal to 10 μM ($EC_{50}$ or $IC_{50}$) may be used to determine an absence of activity. In embodiments, the MAO enzymes are of mammalian origin. In embodiments, the MAO enzymes are of human origin.

In some embodiments, disclosed compounds are orally bioavailable. In some embodiments, disclosed compounds have an oral bioavailability (% F) of about or at least 50%, 60%, 70%, 80%, or 90%. Bioavailability studies, both in vitro measures and in vivo determinations, are described in, e.g., Kim et al., Pharm Res. 2014; 31(4): 1002-1014, EP2007397B1, EP3565550B1, and US20200009067A1.

In some embodiments, a halogenated compound of the disclosure will have altered conformation, pKa, intrinsic potency, membrane permeability, metabolic pathways, and/or pharmacokinetic properties relative to its corresponding non-halogenated compound. In some embodiments, a fluorinated compound of the disclosure will have altered conformation, pKa, intrinsic potency, membrane permeability, metabolic pathways, and/or pharmacokinetic properties relative to its corresponding non-fluorinated compound. See, e.g., Gillis et al., J Med Chem, 2015; 58(21):8315-8359; Trachsel, Drug Test Anal 2012; 4:577-590. In some embodiments, an advantage of a disclosed fluorine-substituted compound over its corresponding non-fluorinated compound can be attributed to the larger steric requirement of covalently bound fluorine over hydrogen (C—F bond length is 138 pm whereas C—H bond length is 109 pm). In some embodiments, the introduction of a fluorine in a disclosed compound increases metabolic stability, modulating properties such as pKa and lipophilicity, and/or exerting conformational control (e.g., by the fluorine gauche effect, see Thiehoff, Rey & Gilmour, Israel. J. Chem., 2016; 57(1-2): 92-100), relative to the corresponding non-fluorinated compound.

In some embodiments, the introduction of one or more fluorine atoms in a disclosed compound forms stronger bonds with one or more carbon atoms (485 KJ/mol) compared to hydrogen in a corresponding non-fluorinated compound (416 KJ/mol). In some embodiments, the fluorinated compounds of the disclosure therefore may be more stable towards metabolic degradation and last longer in a subject. In some embodiments, a disclosed fluorinated compound has improved bioavailability compared with a corresponding non-fluorinated compound because of the modification of the electronic properties of the compound while there is minimal effect on the structure (see, e.g., Adler et al., Nat. Chem., 2019; 11, 329-334). In some embodiments, disclosed fluorinated compounds have high membrane permeability, such as increased permeability relative to a non-fluorinated compound.

In some embodiments, incorporating a halogen in place of hydrogen will improve the pharmacodynamic and pharmacokinetic profiles of the disclosed compounds by modifying the metabolic fate while retaining the pharmacologic activity and selectivity of the compounds. In some embodiments, disclosed halogenated compounds will positively impact safety, efficacy and/or tolerability. In some embodiments, incorporating fluorine in place of hydrogen will improve the pharmacodynamic and pharmacokinetic profiles of the disclosed compounds by modifying the metabolic fate while retaining the pharmacologic activity and selectivity of the compounds. In some embodiments, disclosed fluorinated compounds will positively impact safety, efficacy and/or tolerability.

In some embodiments, a halogen-substituted, fluorine-substituted, and/or deuterium-substituted disclosed phenylalkylamine has a reduced rate of metabolism, for example by N-demethylation or N-dealkylation, relative to a corresponding non-substituted compound, in an amount of at least a 5% reduction, at least a 10% reduction, at least a 15% reduction, at least a 25% reduction, at least a 50% reduction, at least a 75% reduction, at least a 90% reduction, at least a 95% reduction, or at least a 99% reduction.

In some embodiments, a disclosed compound has reduced adverse events relative to a comparator. Examples of adverse events include those related to neurotoxicity, cardiotoxicity, and renal toxicity, among others. In some embodiments, the reduction for at least one adverse event is at least a 5% reduction, at least a 10% reduction, at least a 15% reduction, at least a 25% reduction, at least a 50% reduction, at least a 75% reduction, at least a 90% reduction, at least a 95% reduction, at least a 99% reduction, or a reduction beyond the threshold of measurement, whether determined within-patient or across patients or patient groups, or in a rodent or other suitable animal model, or determined in vitro, in silico, or otherwise measured using a standard such as one known to those of ordinary skill for the determination or quantification of the adverse event(s) in question, such as relating to anxiety, cardiovascular effects such as blood pressure and heart rate, hyperthermia, hyperhidrosis, jaw tightness and bruxism, muscle tightness, psychostimulation, appetite, nausea, concentration, and balance, as well as markers for or correlated with potential neurotoxicity, and including such exemplary tests and procedures that are in silico (e.g., computer analysis or simulation, including by AI, machine learning, or deep learning), in vitro (e.g., biochemical assays, tissue culture), and in vivo (e.g., behavioral assessment; functional observational batteries; tests of motor activity, schedule-controlled operant behavior, neurological function, neurophysiological function, nerve-conduction, evoked-potential; neurochemical, neuroendocrine, or neuropathological measures; EEG; imaging), as well as the use of physiological biomarkers (body temperature; heart rate; respiratory rate; blood oxygenation; systolic blood pressure (SBP); diastolic blood pressure (DBP); mean arterial pressure (MAP); pulse pressure (PP); Continuous Beat-by-Beat Blood Pressure (CNIBP); heart rate variability (HRV); hemodynamic response (HR); glucose; cortisol; serotonin; dopamine; and brain derived neurotrophic factor (BDNF)), and patient assessments.

In some embodiments, a disclosed compound or composition thereof does not cause a neurotoxic effect, such as in an in vitro assay or upon administration to a subject. In some embodiments, a disclosed compound or composition thereof causes a reduced neurotoxic effect, such as in an in vitro assay or upon administration to a subject. In some embodiments, the reduction of a neurotoxic effect is at least a 5% reduction, at least a 10% reduction, at least a 15% reduction, at least a 25% reduction, at least a 50% reduction, at least a 75% reduction, at least a 90% reduction, or at least a 95% reduction, or at least a 99% reduction, relative to a comparator. In some embodiments, the comparator is the disclosed compound's corresponding non-fluorinated compound.

In some embodiments, the neurotoxic effect is determined by measuring one or more of: a) oxidative stress and dopamine-based quinones; b) mitochondrial dysfunction; and c) activation of glial cells. In some embodiments, neurotoxicity or a reduction thereof is determined by evaluating mitochondrial dysfunction. Mitochondrial dysfunction may be evaluated by measuring one or more of mitochondrial membrane potential (MMP), mitochondrial swelling, mitochondrial outer membrane damage, the mitochondrial cytochrome c release, and ADP/ATP ratio. See, e.g., Taghizadeh et al., Free Radic. Biol. Med. 2016; 99: 11-19, in which markers of mitochondrial dysfunction include a significant increase in ROS formation, collapse of MMP, mitochondrial swelling, outer membrane damage, cytochrome c release from the mitochondria, and increased ADP/ATP ratio.

In some embodiments, neurotoxicity or a reduction thereof is determined by assessing the activation of glial cells. Activation of quiescent glial cells has been described, e.g., by Herndon et al., Toxicological Sciences, 2014; 138 (1):130-138. Reactive astrogliosis can be measured with glial fibrillary acidic protein (GFAP) staining, and microglia reactivity can be visualized by immunostaining complement type 3 receptor (CD11b). See, e.g., Frau et al., J Neurochem. 2013; 124(1):69-78 and Frau et al., Neurotoxicology. 2016; 56:127-138. In embodiments, neurotoxicity or a reduction thereof is determined in vitro. In embodiments, neurotoxicity or a reduction thereof is determined in vivo.

In some embodiments, a subject administered a disclosed compound does not experience serotonin syndrome. In embodiments, a subject administered a disclosed compound experiences reduced incidence and/or severity of serotonin syndrome, e.g., relative to administration of a comparator compound. Co-administration of agents that increase serotonin levels, such as SERT inhibitors and MAOIs have been shown to potentiate serotonin neuromodulation, a potential complication of which is serotonin syndrome. See, e.g., Izumi et al., Eur J Pharmacol. 2006; 532(3):258-64, Nakagawasai et al., Neurotoxicol. 2004; 25(1-2):223-32, and Tadano et al., J Pharmacol Exp Ther. 1989; 250(1):254-60. Serotonin syndrome ranges in severity from mild to fatal, and clinical presentations include autonomic dysfunction, neuromuscular excitation, and altered mental status, as described in, e.g., Boyer & Shannon, N Engl J Med. 2005; 352(11):1112-20 and Wang et al., Cleve Clin J Med. 2016 November; 83(11):810-817.

In some embodiments, a subject administered a disclosed compound does not experience delirium. In embodiments, a subject administered a disclosed compound experiences reduced incidence and/or severity of delirium, e.g., relative to administration of a comparator compound. Signs of delirium, such as drug-induced delirium, include disturbances of consciousness, attention, cognition, and perception. The severity of delirium may be assessed using available tools, e.g., the Memorial Delirium Assessment Scale (MDAS) subitems and Karnofsky Performance Status scale (KPS). See, e.g., Boettger et al., Journal of Geriatrics. 2014:247042; Carter et al. Drug Saf. 1996; 15(4):291-301; Karlsson, Dement Geriatr Cogn Disord. 1999; 10(5):412-5. Delirium has been described following ingestion of some psychedelics, such as the tryptamine 5-MeO-DALT, e.g., in Jovel et al., J Forensic Sciences, 59(3), 844-846.

In some embodiments, disclosed compounds do not cause cardiotoxicity following administration to a subject. In some embodiments, reduced severity and/or incidence of cardiotoxicity is observed following administration of a disclosed compound to a subject, e.g., relative to administration of a comparator compound. In some embodiments, disclosed compounds do not cause irregular heartbeat, e.g., tachycardia. In some embodiments, disclosed compounds show reduced inhibition of a cardiac ion channel, such as by at least 5%, 10%, 25%, 50%, 75%, 100%, 150%, or 200% relative to a comparator. In some embodiments, disclosed compounds do not inhibit the function of, such as block, cardiac ion channels. In some embodiments, disclosed compounds do not block calcium channel CAV1.2. In some embodiments, disclosed compounds do not block potassium channel hERG. In some embodiments, disclosed compounds do not block sodium channel NAV1.5. In embodiments, a disclosed compound has an $IC_{50}$ of greater than 10 μM for any one or more of CAV1.2, hERG, and NAV1.5. In some embodiments, CAV1.2, hERG, and NAV1.5 are of human origin.

In some embodiments, disclosed compounds do not cause rhabdomyolysis following administration to a subject. In some embodiments, reduced severity and/or incidence of rhabdomyolysis is observed following administration of a disclosed compound to a subject, e.g., relative to administration of a comparator compound. In some embodiments, disclosed compounds do not cause kidney injury, such as acute kidney injury, following administration to a subject. In some embodiments, reduced severity and/or incidence of kidney injury is observed following administration of a disclosed compound to a subject, e.g., relative to administration of a comparator compound. In embodiments, disclosed compounds do not elevate serum levels of rhabdomyolysis markers and/or kidney injury markers, e.g., muscular enzymes and creatinine phosphokinase. In embodiments, administration of a disclosed compound results in reduced markers of rhabdomyolysis and/or kidney injury, such as reductions by at least 5%, 10%, 25%, 50%, 75%, 100%, 150%, or 200%, relative to a comparator. In embodiments administration of disclosed compounds to a subject does not result in or results in a reduction of any one or more of renal vasoconstriction, intraluminal cast formation, and direct myoglobin toxicity.

Adverse effects of certain psychedelics, such as the tryptamine 5-MeO-DALT, have been described and include, e.g., cardiac abnormalities, acute kidney injury and rhabdomyolysis. See, e.g., Dailey et al., Toxicol. Clin. Toxicol. 2003; 41:742-743 and Jovel et al., Journal of Forensic Sciences, 59(3), 844-846. Rhabdomyolysis is a breakdown of skeletal muscle due to direct or indirect muscle injury that may lead to kidney injury, such as renal failure. See, e.g., Polderman, Int J Artif Organs. 2004; 27(12):1030-3 and Lima et al., Saudi J Kidney Dis Transpl. 2008; 19(5):721-9. Signs of rhabdomyolysis and kidney injury may be determined according to known methods, including, e.g., measuring an elevation of muscular enzymes and creatinine phosphokinase, and identifying renal vasoconstriction, intraluminal cast formation, and direct myoglobin toxicity. Measurements and comparisons of toxicity can be made according to ordinary methods known to those in the art.

C. Methods of Preparing Substituted Phenylalkylamines

Phenylalkylamine compounds of Formula (I) of the present disclosure can be synthesized following the reaction scheme provided below, wherein $R_1$, $R_2$, $R_3$, and X are as defined for Formula (I):

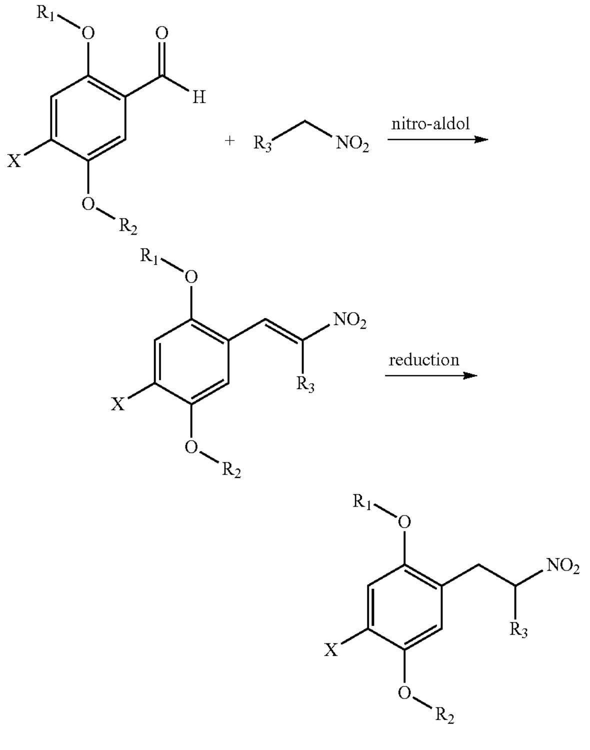

In an embodiment, alkylated, alkoxylated, and thioalkylated analogs of Formula (I) are synthesized by nitro-aldol reaction of an aldehyde with a nitro alkane, followed by reduction.

In another embodiment, halogenated and trifluoromethylated analogs of Formula (I) are synthesized by nitro-aldol reaction of an aldehyde with a nitro alkane, followed by reduction. In such an embodiment, phenylalkylamine compounds of Formula (I) of the present disclosure can be synthesized following the reaction scheme provided below, wherein $R_1$, $R_2$, $R_3$, are as defined for Formula (I); and X is F, Cl, Br, I, or $CF_3$.

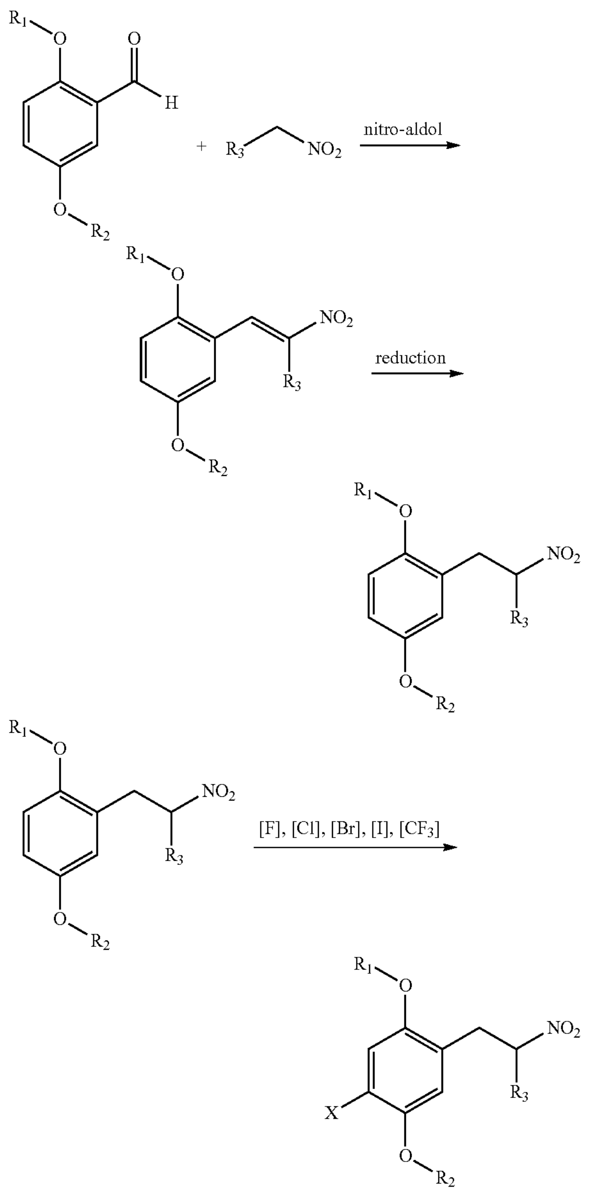

In such embodiments, in a first reaction sequence, phenylalkylamines wherein X is H are synthesized as described above. In a second reaction sequence, the F, Cl, Br, I, or $CF_3$ group is introduced by direct substitution of the phenylalkylamine phenyl ring. In the reaction scheme above, [F], [Cl], [Br], [I], and [$CF_3$] each represent a suitable chemical precursor for the introduction of a F, Cl, Br, I, or $CF_3$ group, respectively, to the phenylalkylamine phenyl ring.

In yet another embodiment, fluorinated analogs of Formula (I) are synthesized by amination of alkyl halides, wherein alkyl halides are treated with primary amines.

Additional synthetic methods that may be useful for the synthesis of certain phenylalkylamines and any necessary starting materials may be found in general references well-known in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the disclosed compounds. In general, the approaches used for similar compounds may be used (e.g., PiHKAL; Glennon et al., J. Med. Chem., 1986; 29(2), 194-199; Nichols et al. 1991. J. Med. Chem., 34(1), 276-281; Kedrowski et al. 2007. Organic Letters, 9(17), 3205-3207; Heravi & Zadsirjan. 2016. Current Organic Synthesis, 13(6), 780-833; Keri et al. 2017. European J. Med. Chem., 138, 1002-1033; Perez-Silanes et al. 2001. J. Heterocyclic Chem, 38(5), 1025-1030; and references therein), such adaptation being that known and understood to those of ordinary skill; see also Brandt et al. (2011). Drug Test Anal, 4: 24-32; Gambarotti, et al., Current Organic Chemistry, 2013, 17 (10), 1108-1113; Leth-Peterson, et al., Chem. Res. Toxicol. 2016, 29, 96-100; Katritzky, et al., ARKIVOC, 2000 (vi), 868-875; and U.S. Pat. No. 4,933,504.

C. Pharmaceutical Compositions

In some aspects, provided herein are compositions, such as pharmaceutical compositions, comprising the disclosed compounds, such as compounds of Formula (I). While it is possible to administer a compound employed in the disclosed methods directly without any formulation, the compounds are usually administered in the form of pharmaceutical compositions.

"Pharmaceutical compositions" are compositions that include the disclosed compound(s) together in an amount (for example, in a unit dosage form) with a pharmaceutically acceptable carrier, diluent, or excipient. Some embodiments will not have a single carrier, diluent, or excipient alone, but will include multiple carriers, diluents, and/or excipients. Compositions can be prepared by standard pharmaceutical formulation techniques such as disclosed in, e.g., Remington: The Science & Practice of Pharmacy (2020) 23th ed., Academic Press, Cambridge, Mass.; The Merck Index (1996) 12th ed., Merck Pub. Group, Whitehouse, N.J.; Pharm. Principles of Solid Dosage Forms (1993), Technomic Pub. Co., Inc., Lancaster, Pa.; and Ansel & Stoklosa, Pharm. Calculations (2001) 11th ed., Lippincott Williams & Wilkins, Baltimore, Md.; & Poznansky et al. Drug Delivery Systems (1980), R. L. Juliano, ed., Oxford, N.Y., pp. 253-315).

"Pharmaceutically acceptable" used in connection with an excipient, carrier, diluent, or other ingredient means the ingredient is generally safe and, within the scope of sound medical judgment, suitable for use in contact with cells of humans and animals without undue toxicity, irritation, allergic response, or complication, commensurate with a reasonable risk/benefit ratio.

In some embodiments, pharmaceutical compositions comprising a disclosed compound can be administered by a variety of routes including oral, mucosal (e.g., buccal, sublingual), rectal, transdermal, subcutaneous, intravenous, intramuscular, inhaled, and intranasal. In some embodiments, the compounds employed in the methods of this invention are effective as oral, mucosal (e.g., buccal, sublingual), rectal, transdermal, subcutaneous, intravenous, intramuscular, inhaled, and intranasal compositions. Such compositions are prepared in a manner well known in the pharmaceutical art and comprise at least one active compound. (See, e.g., Remington, 2020.)

In making the compositions employed in the invention the active ingredient is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets (including orally disintegrating, swallowable, sublingual, buccal, and chewable tablets), pills, powders, lozenges, troches, oral films, thin strips, sachets, cachets, elixirs, suspensions, emulsions, microemulsions, liposomal dispersions, aqueous and non-aqueous solutions, slurries, syrups, aerosols (as a solid or in a liquid medium), ointments containing for example up to 10% by weight of the active compound, soft and hard gelatin capsules, suppositories, topical preparations, transdermal patches, sterile injectable solutions, and sterile packaged powders. Compositions may be formulated as immediate release, controlled release, sustained (extended) release or modified release formulations. In some embodiments, the composition is prepared as a dry powder for inhalation or a liquid preparation for vaporization and inhalation, and is administered, e.g., using an electronic cigarette or other vaping device, a nebulizer, a pressurized metered dose inhaler (pMDI), a dry powder inhaler (DPI), or the like.

Different embodiments of the invention include the following examples: Pharmaceutically acceptable complex derivatives of each drug in each group, including solvates, salts, esters, enantiomers, isomers (stereoisomers and/or constitutional, including ones based on substituting fluorine for hydrogen), derivatives or prodrugs of the disclosed compounds. Among derivatives of a compound are included its "physiologically functional derivatives," which refers to physiologically tolerated chemical derivatives of the compound having the same physiological function thereof, for example, by being convertible in the body thereto, and which on administration to a mammal such as a human is able to form (directly or indirectly) the compound or an active metabolite thereof (acting therefore, like a prodrug), or by otherwise having the same physiological function, despite one or more structural differences. According to the present invention, examples of physiologically functional derivatives include esters, amides, carbamates, ureas, and heterocycles.

In other embodiments are disclosed multiple variations in the pharmaceutical dosages of each drug in the combination as further outlined below. Another embodiment of the invention includes various forms of preparations including using solids, liquids, immediate or delayed or extended-release forms. Many types of variations are possible as known to those of skill.

In other embodiments are disclosed multiple routes of administration, which may differ in different patients according to their preference, comorbidities, side effect profile, pharmacokinetic and pharmacodynamic considerations, and other factors (IV, PO, transdermal, etc.). In other embodiments are disclosed the presence of other substances with the active drugs, known to those of skill, such as fillers, carriers, gels, skin patches, lozenges, or other modifications in the preparation to facilitate absorption through various routes (such as gastrointestinal, transdermal, etc.) and/or to extend the effect of the drugs, and/or to attain higher or more stable serum levels or to enhance the therapeutic effect of the drugs in the combination.

In preparing a formulation, it may be necessary to mill a disclosed compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. Formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The disclosed compositions can be formulated so as to provide quick, sustained or delayed release of the active ingredient after administration to the patient by employing procedures known in the art.

The disclosed compositions are preferably formulated in a unit dosage form, each dosage containing a therapeutically effective amount of the active ingredients, for example in the dosage amounts disclosed below. The term "unit dosage form" refers to a physically discrete unit suited as unitary dosages for the subject to be treated, each unit containing a predetermined quantity of active material calculated to produce the desired therapeutic effect(s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof (e.g., one half a "full" dose for a "booster" dose as described below), of the pharmaceutical composition administered.

Unit dosage forms include capsules, troches, cachets, lozenges, tablets, ampules and vials, which may include a composition in a freeze-dried or lyophilized state; a sterile liquid carrier, for example, can be added prior to administration or delivery in vivo. Unit dosage forms also include ampules and vials with liquid compositions disposed therein. Unit dosage forms further include compounds for transdermal administration, such as "patches" that contact the epidermis (including the mucosa) of a subject for an extended or brief period of time.

In some embodiments, the disclosed compositions are formulated in a pharmaceutically acceptable oral dosage form. Oral dosage forms include oral liquid dosage forms (such as tinctures, drops, emulsions, syrups, elixirs, suspensions, and solutions, and the like) and oral solid dosage forms. The disclosed pharmaceutical compositions also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

a. Oral Solid Dosage Forms

Oral solid dosage forms may include but are not limited to, lozenges, troches, tablets, capsules, caplets, powders, pellets, multiparticulates, beads, spheres, and/or any combinations thereof. Oral solid dosage forms may be formulated as immediate release, controlled release, sustained release, extended release, or modified release formulations. Accordingly, in some embodiments, the disclosed oral solid dosage forms may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. Additionally, pharmaceutical formulations may be administered as a single capsule or in multiple capsule dosage form. In some embodiments, the pharmaceutical formulation is administered in two, three, four, or more capsules or tablets.

Oral solid dosage forms may contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. Oral solid dosage forms also can comprise one or more pharmaceutically acceptable additives such as a compatible carrier, complexing agent, ionic dispersion modulator, disintegrating agent, surfactant, lubricant, colorant, moistening agent, plasticizer, stabilizer, penetration enhancer, wetting agent, anti-foaming agent, alone or in combination, as well as supplementary active compound(s).

Supplementary active compounds include preservatives, antioxidants, antimicrobial agents including biocides and biostats such as antibacterial, antiviral and antifungal agents. Preservatives can be used to inhibit microbial growth or increase stability of the active ingredient thereby prolonging the shelf life of the formulation. Suitable preservatives are known in the art and include EDTA, EGTA, benzalkonium chloride or benzoic acid or benzoates, such as sodium benzoate. Antioxidants include vitamin A, vitamin C (ascorbic acid), vitamin E, tocopherols, other vitamins or provitamins, and compounds such as alpha lipoic acid.

Using standard coating procedures, a film coating may be provided around the disclosed compounds (see Remington, supra). In one embodiment, some or all of the disclosed compounds are coated. In another embodiment, some or all of the disclosed compounds are microencapsulated. In yet another embodiment, some or all of the disclosed compounds are amorphous material coated and/or microencapsulated with inert excipients. In still another embodiment, the disclosed compounds are not microencapsulated and are uncoated.

Suitable carriers for use in oral solid dosage forms include acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose (HPMC), hydroxypropylmethylcellulose acetate stearate (HPMCAS), sucrose, microcrystalline cellulose, lactose, and mannitol.

Suitable filling agents for use in oral solid dosage forms include lactose, calcium carbonate, calcium phosphate, dibasic calcium phosphate, calcium sulfate, microcrystalline cellulose, cellulose powder, dextrose, dextrates, dextrose, dextran, starches, pregelatinized starch, HPMC, HPMCAS, hydroxypropylmethylcellulose phthalate, sucrose, xylitol, lactitol, mannitol, sorbitol, sodium chloride, and PEG.

Suitable disintegrants for use in oral solid dosage forms include those disclosed below for oral liquid aqueous suspensions and dispersions.

Suitable binders impart cohesiveness to solid oral dosage form formulations. For powder-filled capsules, they aid in plug formation that can be filled into soft or hard shell capsules. For tablets, they ensure that the tablet remains intact after compression and help assure blend uniformity prior to a compression or fill step. Materials suitable for use as binders in the solid dosage forms described herein include celluloses, microcrystalline dextrose, amylose, magnesium aluminum silicate, polysaccharide acids, bentonites, gelatin, polyvinylpyrrolidone/vinyl acetate copolymer, cross-povidone, povidone, starch, pregelatinized starch, tragacanth, dextrin, a sugar (e.g., sucrose, glucose, dextrose, molasses, mannitol, sorbitol, xylitol, lactose), a natural or synthetic gum (e.g., acacia, tragacanth, gum ghatti, mucilage of isabgol husks), starch, PVP, larch arabinogalactan, Veegum®, PEG, waxes, and sodium alginate.

In general, binder levels of 20-70% are used in powder-filled gelatin capsule formulations. Binder usage level in tablet formulations is a function of whether direct compression, wet granulation, roller compaction, or usage of other excipients such as fillers which itself can act as moderate binders are used. Formulators skilled in the art can determine binder level for formulations, but binder usage of up to 70% in tablet formulations is common.

Suitable lubricants or glidants for use in oral solid dosage forms include stearic acid, calcium hydroxide, talc, corn starch, sodium stearyl fumarate, alkali-metal and alkaline earth metal salts, stearic acid, sodium stearates, magnesium stearate, zinc stearate, waxes, Stearowet®, boric acid, sodium benzoate, sodium acetate, sodium chloride, leucine, PEG, methoxy-polyethylene glycol, propylene glycol, sodium oleate, glyceryl behenate, glyceryl palmitostearate, glyceryl benzoate, and magnesium or sodium lauryl sulfate.

Suitable diluents for use in oral solid dosage forms include sugars (including lactose, sucrose, and dextrose), polysaccharides (including dextrates and maltodextrin), polyols (including mannitol, xylitol, and sorbitol), and cyclodextrins. Non-water-soluble diluents are compounds typically used in the formulation of pharmaceuticals, such as calcium phosphate, calcium sulfate, starches, modified starches and microcrystalline cellulose, and micro cellulose (e.g., having a density of about 0.45 g/cm3, e.g., Avicel, powdered cellulose), and talc.

Suitable wetting agents for use in oral solid dosage forms include oleic acid, triethanolamine oleate, glyceryl monostearate, sorbitan monooleate, sorbitan monolaurate, polyoxyethylene sorbitan monooleate, polyoxyethylene sorbitan monolaurate, quaternary ammonium compounds (e.g., Polyquat 10@), sodium oleate, sodium lauryl sulfate, magnesium stearate, sodium docusate, triacetin, and vitamin E TPGS. Wetting agents include surfactants. Suitable surfactants for use in the solid dosage forms described herein include docusate and its pharmaceutically acceptable salts, sodium lauryl sulfate, sorbitan monooleate, poly-oxyethylene sorbitan monooleate, polysorbates, poloxamers, bile salts, glyceryl monostearate, copolymers of ethylene oxide and propylene oxide, e.g., Pluronic® (BASF), and the like.

Suitable suspending agents for use in oral solid dosage forms include polyvinylpyrrolidone, PEG (having a molecular weight of about 300 to about 6000, or about 3350 to about 4000, or about 7000 to about 18000), vinylpyrrolidone/vinyl acetate copolymer (S630), sodium alginate, gums (e.g., gum tragacanth and gum acacia, guar gum, xanthans, including xanthan gum), sugars, celluloses, polysorbate-80, polyethoxylated sorbitan monolaurate, polyethoxylated sorbitan monolaurate, and povidone.

Suitable antioxidants for use in oral solid dosage forms include butylated hydroxytoluene (BHT), butyl hydroxyanisole (BHA), sodium ascorbate, Vitamin E TPGS, ascorbic acid, sorbic acid, and tocopherol.

Immediate-release formulations may be prepared by combining a superdisintegrant such as croscarmellose sodium and different grades of microcrystalline cellulose in different ratios. To aid disintegration, sodium starch glycolate may be added.

In cases where different agents included in the disclosed fixed-dose combinations are incompatible, cross-contamination can be avoided by incorporation of the agents in different layers in the oral dosage form with the inclusion of barrier layer(s) between the different layers, wherein the barrier layer(s) comprise inert and non-functional material(s).

The above-listed additives should be taken as merely exemplary types of additives that can be included in the disclosed solid dosage forms. The amounts of such additives can be readily determined by one skilled in the art, according to the particular properties desired.

Tablets of the invention can be prepared by methods well known in the art. Various methods for the preparation of the immediate release, modified release, controlled release, and extended-release dosage forms (e.g., as matrix tablets having one or more modified, controlled, or extended-release layers) and the vehicles therein are well known in the art. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein. Generally recognized compendia of methods include: Remington (2020); Sheth et al. (1980), Compressed tablets, in Pharm. dosage forms, Vol. 1, Lieberman & Lachtman, eds., Dekker, NY.

In certain embodiments, solid dosage forms are prepared by mixing the disclosed compounds with one or more pharmaceutical excipients to form a "bulk blend" composition. The bulk blend composition is homogeneous, i.e., the active agents are dispersed evenly throughout so that the bulk blend may be readily subdivided into equally effective unit dosage forms, such as tablets, pills, and capsules. The individual unit dosages may also comprise film coatings, which disintegrate upon oral ingestion or upon contact with diluents. These formulations can be manufactured by conventional pharmaceutical techniques.

Conventional pharmaceutical techniques for preparation of solid dosage forms include the following methods, which may be used alone or in combination: (1) dry mixing, (2) direct compression, (3) milling, (4) dry or non-aqueous granulation, (5) wet granulation, or (6) fusion. See Lachman et al., Theory and Practice of Industrial Pharmacy (1986). Other methods include spray drying, pan coating, melt granulation, granulation, fluidized bed spray drying or coating (e.g., Wurster coating), tangential coating, top spraying, tableting, and extruding.

Compressed tablets are solid dosage forms prepared by compacting the bulk blend. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the disclosed compounds. In other embodiments, the film coating aids in patient compliance (e.g., flavor or sweetener coatings).

A capsule may be prepared by placing the bulk blend inside of a capsule, such as a soft gelatin capsule, a standard gelatin capsule, or a non-gelatin capsule such as a capsule comprising HPMC. The bulk blend also may be placed in a sprinkle capsule, wherein the capsule may be swallowed whole or the capsule may be opened and the contents sprinkled on food prior to eating. In some embodiments, the therapeutic dose is split into multiple capsules. In some embodiments, the entire dose of the disclosed compounds is delivered in a capsule form. In some embodiments the capsule is a size 000, size 00, or size 0 soft gelatin capsule. In other embodiments, the capsule is a size 1, size 2, size 3, or size 4 soft gelatin capsule. In other embodiments, the capsule is a hard gelatin capsule of equivalent size.

Capsules can be capped and packaged using a manual capsule filling machine as follows: (1) Open empty capsules and place lower halves (the 'bodies') in the holes of the bottom plate of the filling machine. Often machines have spacers that are inserted between the base plate and the plate with holes into which capsules are fitted. These need to be set so that the lower body of each capsule is flush with the top of the plate that holds the capsule bodies. (2) Place powder into the body of each capsule, ensuring an even distribution of powder using a spreader plate. (3) Take out the spacers and gently tap the plate with holes downwards so that each of the capsule bodies protrudes from the top of the plate. (4) Place the top half ('cap') of each capsule onto the lower half but do not press down firmly until all are in place. Once all the tops are in place, they can be pressed down gently (often a click is heard when they are all completely fitted). (5) If the machine has an upper plate into which caps can be loaded, fit these into the upper plate, and then flip the plate over and align it with the bottom plate, ensuring that all capsules halves are perfectly aligned. (6) Press the top plate firmly to secure the top of each capsule with the corresponding lower half. The above process also can be automated.

In certain embodiments, the formulations are fixed-dose pharmaceutical compositions comprising at least one other pharmacological agent, such as an additional active compound as described herein. Fixed-dose combination formulations may contain therapeutically efficacious fixed-dose combinations of formulations of the disclosed compounds and other pharmacological agents in the form of a single-layer monolithic tablet or multi-layered monolithic tablet or in the form of a core tablet-in-tablet or multi-layered multi-disk tablet or beads inside a capsule or tablets inside a capsule.

Depending on the desired release profile, oral solid dosage forms may be prepared as immediate release formulations, or as modified release formulations, such as controlled release, extended release, sustained release, or delayed release.

In some embodiments, oral solid dosage forms are formulated as a delayed release dosage form by utilizing an enteric coating to affect release in the small intestine of the gastrointestinal tract. An enteric-coated oral dosage form may be a compressed or molded or extruded tablet/mold (coated or uncoated) containing granules, powder, pellets, beads or particles of the active ingredient and/or other composition components, which are themselves coated or uncoated. The enteric-coated oral dosage form may also be a capsule (coated or uncoated) containing pellets, beads or granules of the solid carrier or the composition, which are themselves coated or uncoated.

Enteric coatings may also be used to prepare other controlled release dosage forms including extended release and pulsatile release dosage forms. Pulsatile release dosage forms may be formulated using techniques known in the art, such as those described in U.S. Pat. Nos. 5,011,692, 5,017,381, 5,229,135, and 5,840,329. Other suitable dosage forms are described in U.S. Pat. Nos. 4,871,549, 5,260,068, 5,260,069, 5,508,040, 5,567,441 and 5,837,284.

In one embodiment, the controlled release dosage form is a pulsatile release solid oral dosage form comprising at least two groups of particles, each containing disclosed compounds described herein. The first group of particles provides a substantially immediate dose of the disclosed compounds upon ingestion by a subject. The first group of particles can be either uncoated or comprise a coating and/or sealant. The second group of particles comprises coated particles, which may comprise from about 2% to about 75%, preferably from about 2.5% to about 70%, or from about 40% to about 70%, by weight of the total dose of the disclosed compounds, in admixture with one or more binders. Using such means, a single unit dosage form can provide both a first and a second dosage amount in the single form (i.e., the first dosage amount in an immediate release form, and the second dosage amount in a delayed release form).

In another embodiment, gastroretentive sustained release tablets are formulated by using a combination of hydrophilic polymer (e.g., hydroxypropyl methylcellulose), together with swelling agents (e.g., crospovidone, sodium starch glycolate, and croscarmellose sodium), and an effervescent substance (e.g., sodium bicarbonate). Using known methods, gastroretentive tablets can be formulated so as to prolong the gastric emptying time and extend the mean residence time (MRT) in the stomach for optimal drug release and absorption (see, e.g., Arza et al. Formulation and evaluation of swellable and floating gastroretentive ciprofloxacin hydrochloride tablets, AAPS PharmSciTech., 10(1): 220-226 (2009)).

Coatings for providing a controlled, delayed, or extended release may be applied to the disclosed pharmaceutical compositions or to a core containing the compositions. The coating may comprise a pharmaceutically acceptable ingredient in an amount sufficient, e.g., to provide an extended release from e.g., about 1 hours to about 7 hours following ingestion before release of the compositions. Suitable coatings include one or more differentially degradable coatings including pH-sensitive coatings (enteric coatings), or non-enteric coatings having variable thickness to provide differential release of the active agents.

Many other types of modified release systems are known to those of ordinary skill in the art and are suitable for the formulations described herein. Examples of such delivery systems include both polymer- and non polymer-based systems, silastic systems, peptide-based systems, wax coatings, bioerodible dosage forms, and compressed tablets using conventional binders. (See, e.g., Liberman et al. Pharmaceutical Dosage Forms, 2 Ed., Vol. 1, pp. 209-214 (1990); Singh et al. Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.)

b. Oral Liquid Dosage Forms

Oral liquid dosage forms include tinctures, drops, emulsions, syrups, elixirs, suspensions, and solutions, and the like. These oral liquid dosage forms may be formulated with any pharmaceutically acceptable excipient known to those of skill in the art for the preparation of liquid dosage forms, and with solvents, diluents, carriers, excipients, and the like chosen as appropriate to the solubility and other properties of the active agents and other ingredients. Solvents may be, for example, water, glycerin, simple syrup, alcohol, medium chain triglycerides (MCT), and combinations thereof.

Liquid dosage forms for oral administration may be in the form of pharmaceutically acceptable emulsions, syrups, elixirs, suspensions, and solutions, which may contain an inactive diluent, such as water. Pharmaceutical formulations may be prepared as liquid suspensions or solutions using a sterile liquid, such as but not limited to, an oil, water, an alcohol, and combinations of these pharmaceutically suitable surfactants, suspending agents, emulsifying agents, may be added for oral or parenteral administration. Liquid formulations also may be prepared as single dose or multidose beverages. Suspensions may include oils. Such oils include peanut oil, sesame oil, cottonseed oil, corn oil, and olive oil. Suitable oils also include carrier oils such as MCT and long chain triglyceride (LCT) oils. Suspension preparation may also contain esters of fatty acids such as ethyl oleate, isopropyl myristate, fatty acid glycerides, and acetylated fatty acid glycerides. Suspension formulations may include alcohols, (such as ethanol, isopropyl alcohol, hexadecyl alcohol), glycerol, and propylene glycol. Ethers, such as poly(ethylene glycol), petroleum hydrocarbons such as mineral oil and petrolatum, and water may also be used in suspension formulations. Suspension can thus include an aqueous liquid or a non-aqueous liquid, an oil-in-water liquid emulsion, or a water-in-oil emulsion.

In some embodiments, formulations are provided comprising the disclosed compositions and at least one dispersing agent or suspending agent for oral administration to a subject. The formulation may be a powder and/or granules for suspension, and upon admixture with water, a substantially uniform suspension is obtained. The aqueous dispersion can comprise amorphous and non-amorphous particles consisting of multiple effective particle sizes such that a drug is absorbed in a controlled manner over time.

Dosage forms for oral administration can be aqueous suspensions selected from the group including pharmaceutically acceptable aqueous oral dispersions, emulsions, solutions, and syrups. See, e.g., Singh et al., Encyclopedia of Pharm. Tech., 2nd Ed., 754-757 (2002). In addition to the disclosed compounds, the liquid dosage forms may comprise additives, such as one or more (a) disintegrating agents, (b) dispersing agents, (c) wetting agents, (d) preservatives, (e) viscosity enhancing agents, (f) sweetening agents, or (g) flavoring agents.

Examples of disintegrating agents for use in the aqueous suspensions and dispersions include a starch, e.g., a natural starch such as corn starch or potato starch, a pregelatinized starch, or sodium starch glycolate; a cellulose such as a wood product, microcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay; a gum such as agar, guar, locust bean, Karaya, pectin, or tragacanth; sodium starch glycolate; bentonite; a natural sponge; a surfactant; a resin such as a cation-exchange resin; citrus pulp; and sodium lauryl sulfate.

Examples of dispersing agents suitable for the aqueous suspensions and dispersions include hydrophilic polymers, electrolytes, Tween® 60 or 80, polyethylene glycol (PEG), polyvinylpyrrolidone (PVP), carbohydrate-based dispersing agents, noncrystalline cellulose, magnesium aluminum silicate, triethanolamine, polyvinyl alcohol (PVA), polyvinylpyrrolidone/vinyl acetate copolymer, poloxamers, and poloxamines.

Examples of wetting agents (including surfactants) suitable for the aqueous suspensions and dispersions include acetyl alcohol, glycerol monostearate, polyoxyethylene sorbitan fatty acid esters, PEG, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, and phosphatidylcholine.

Examples of preservatives suitable for aqueous suspensions or dispersions include potassium sorbate, parabens (e.g., methylparaben and propylparaben) and their salts, benzoic acid and its salts, other esters of para hydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Examples of viscosity enhancing agents suitable for aqueous suspensions or dispersions include methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans, and combinations thereof. The concentration of the viscosity-enhancing agent will depend upon the agent selected and the viscosity desired.

In addition to the additives listed above, the disclosed liquid formulations can also comprise inert diluents commonly used in the art, such as water or other solvents, solubilizing agents, emulsifiers, flavoring agents and/or sweeteners. Co-solvents and adjuvants also may be added to a formulation. Non-limiting examples of co-solvents contain hydroxyl groups or other polar groups, for example, alcohols, glycols, glycerol, polyoxyethylene alcohols, and polyoxyethylene fatty acid esters. Adjuvants include surfactants such as soy lecithin and oleic acid, sorbitan esters such as sorbitan trioleate, and PVP.

c. Additional Dosage Forms

Disclosed compositions also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

Examples of suitable aqueous and non-aqueous carriers, diluents, solvents, or vehicles include water, ethanol, polyols, suitable mixtures thereof, vegetable oils, and injectable organic esters such as ethyl oleate. Additionally, the disclosed compositions can be dissolved at concentrations of >1 mg/ml using water-soluble beta cyclodextrins (e.g., beta-sulfobutyl-cyclodextrin and 2-hydroxypropyl-betacyclodextrin. Proper fluidity can be maintained, for example, by the use of a coating such as a lecithin, by the maintenance of the required particle size in the case of dispersions, and by the use of surfactants.

Formulations suitable for subcutaneous injection also may contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, and sorbic acid. Isotonic agents, such as sugars and sodium chloride may be used. Prolonged drug absorption of an injectable form can be brought about by use of agents delaying absorption, e.g., aluminum monostearate or gelatin.

Disclosed compositions also may be prepared as suspension formulations designed for extended-release via subcutaneous or intramuscular injection. Such formulations avoid first-pass metabolism, and lower dosages of the active agents will be necessary to maintain equivalent plasma levels when compared to oral formulations. In such formulations, the mean particle size of the active agents and the range of total particle sizes can be used to control the release of those agents by controlling the rate of dissolution in fat or muscle. The compositions also may be prepared for micro-injection or injection cannula.

In still other embodiments, effervescent powders containing the disclosed compositions may be prepared. Effervescent salts are used to disperse medicines in water for oral administration. Effervescent salts also may be packaged as single dose or multi-dose drink mixes, alone or in combination with other ingredients, such as vitamins or electrolytes. Effervescent salts are granules or coarse powders containing a medicinal agent in a dry mixture, usually composed of sodium bicarbonate and sodium carbonate, citric acid, and/or tartaric acid. When salts are added to water, the acids and the base react to liberate carbon dioxide gas, thereby causing "effervescence." Any acid-base combination that results in the liberation of carbon dioxide can be used, as long as the ingredients are suitable for pharmaceutical use and result in a pH of about 6.0 or higher.

In yet other embodiments, the pharmaceutical compositions disclosed herein are prepared for administration as a nanostructured formulation such as a nanoemulsion, a nanocapsule, a nanoparticle conjugate, or a nano-encapsulated oral or nasal spray. Preparations of the disclosed compositions as certain nanostructured formulations may be done by reference to the general knowledge of the art. (See, e.g., Jaiswal et al., Nanoemulsion: an advanced mode of drug delivery system, Biotech 3(5):123-27 (2015).)

The prefix "nano" as used in the terms describing various embodiments of a nanostructured formulation denotes a size range in the nanometer ("nm") scale. Accordingly, sizes of such nanoparticle delivery vehicles include those in the about 1 to about 100 nm, about 100 to about 200 nm, about 200 to about 400 nm, about 400 to about 600 nm, about 600 to about 800 nm, and about 800 to about 1000 nm, as well as "microparticles" in the about 1000 to about 2000 nm (1-2 micrometer ("m") scale). Particles of certain sizes may be particularly advantageous depending on the method of administration (e.g., for oral liquid emulsion versus for transdermal or topical application). Regardless of method of administration, one will appreciate that smaller particles provide for increased surface area over larger particles such that a higher concentration of agent may be applied per volume of particles. A nanoparticle may be metal, lipid, polymer or other materials, or a combination of materials, and nanoparticles may be functionalized such that another moiety also may be attached thereto. Surface functionalization may involve the use of a moiety comprising an anchor group, a spacer and/or a functional group.

Lipid-based nanoparticles (LBNPs) such as liposomes, solid lipid nanoparticles (SLN), and nanostructured lipid carriers (NLC) can be used to transport both hydrophobic and hydrophilic molecules, and can be formulated to display very low or no toxicity, and increase the time of drug action by means of prolonged half-life and controlled release of active agents. Lipid nanosystems also can include chemical modifications to avoid immune system detection (e.g., gangliosides or PEG) or to improve solubility of active agents. In addition, nanosystems can be prepared in formulations sensitive to pH so as to promote drug release in an acid environment.

The primary components of nanoparticles are phospholipids, which are organized in a bilayer structure due to their amphipathic properties. In presence of water, they form vesicles, improving the solubility and stability of the active agents once they are loaded into their structure. Besides phospholipids, other compounds can be added to the formulations, such as cholesterol, which decreases the fluidity of the nanoparticle and increases the permeability of hydrophobic drugs through the bilayer membrane, improving stability of nanoparticles in blood. Cholesterol-modified liposomes may present a multiple bilayer with sizes from 0.5-10 nm, as multilaminar vesicles (MLVs); a single bilayer with sizes above 100 nm, as large unilamellar vesicles (LUVs); and intermediate sizes (10-100 nm), as small unilamellar vesicles (SUVs).

In other embodiments, disclosed pharmaceutical compositions may be formulated into a topical dosage form. Topical dosage forms include transmucosal and transdermal formulations, such as aerosols, emulsions, sprays, ointments, salves, gels, pastes, lotions, liniments, oils, and creams. For such formulations, penetrants and carriers can be included in the pharmaceutical composition. Penetrants are known in the art, and include, for transmucosal administration, detergents, bile salts, and fusidic acid derivatives. For transdermal administration, carriers which may be used include Vaseline®, lanolin, PEG, alcohols, transdermal enhancers, and combinations thereof.

An exemplary topical delivery system is a transdermal delivery device ("patch") containing the active agents. Such transdermal patches may be used to provide continuous or discontinuous infusion of the disclosed compounds in controlled amounts. Such patches may be constructed for continuous, gradual, pulsatile, or on demand delivery of pharmaceutical agents. A "patch" within the meaning of the invention may be simply a medicated adhesive patch, i.e., a patch impregnated with a disclosed composition for application onto the skin. Thus, a patch may be a single-layer or multi-layer drug-in-adhesive patch, wherein the one or more adhesive layers also contain the active agents.

A patch may also be a "matrix" (or "monolithic") patch, wherein the adhesive layer surrounds and overlays the drug layer (wherein a solution or suspension of the active agents is in a semisolid matrix). A "reservoir" patch may also be used, comprising a drug layer, typically as a solution or suspension of the active agents in a liquid compartment (i.e., the reservoir), separate from an adhesive layer. For example, the reservoir may be totally encapsulated in a shallow compartment molded from a drug-impermeable metallic plastic laminate, with a rate-controlling membrane made of vinyl acetate or a like polymer on one surface. A patch also may be part of a delivery system, for instance used with an electronic device communicatively coupled to the mobile device of a user, and coupled with a mobile application (e.g., to control the delivery rate from the reservoir, and optionally to provide information about delivery back to the application or user). Various transdermal patch technologies may be accordingly utilized.

One such transdermal patch technology as herein contemplated comprises a self-contained module including a built-in battery that produces a low-level electric current to heat the skin and deliver a prescribed dose of a composition of the invention, wherein a therapeutically effective amount of the composition crosses the skin and enters the underlying tissue, so as to produce a therapeutic effect. Such a transdermal delivery device may, for example, comprise an adhesive layer, a protective film, a drug-containing reservoir (for the disclosed pharmaceutical compositions), a heating coil, a battery, a hardware board, optionally all within a device holder, and optionally, functionally coupled to a device which is able to control drug delivery (e.g., a mobile device such as a smartphone) using a downloadable application. Such devices may, for instance, additionally shut off drug delivery automatically when a prescribed dose has been administered, or may shut off automatically upon reaching a certain temperature or defined time. Such transdermal devices may be reusable or disposable.

By way of non-limiting examples, the following formulations may be prepared, and may be used in disclosed methods, wherein "substituted phenylalkylamine" refers to one or more of the disclosed compounds. Thus, where the composition comprises more than one disclosed compound, the "substituted phenylalkylamine" is the combined weight of those compounds (e.g., the substituted and non-substituted compounds, or the one or more non-substituted, halogenated, fluorinated and/or deuterated compounds). Accordingly, it will be appreciated that in some embodiments, a disclosed pharmaceutical composition comprises an substituted phenylalkylamine, where "substituted phenylalkylamine" may refer to one or more disclosed compounds, such as a compound of Formula (I), Formula (I-A), Formula (I-B), Formula (I-C), Formula (I-D), Formula (I-E), Formula (I-F), Formula (I-G), Formula (I-H), Formula (I-I), or another disclosed Formula, one or more pharmaceutically acceptable carriers, diluents, or excipients, and optionally one or more additional active compounds, such as disclosed herein.

Example 1: Formulation of Tablets

Exemplary tablets are prepared as follows:

| Ingredient | Quantity (mg/tablet) |
|---|---|
| Substituted phenylalkylamine | 25.0 |
| Cellulose, microcrystalline | 170.0 |
| Colloidal silicon dioxide | 10.0 |
| Stearic acid | 7.5 |

The substituted phenylalkylamine and inactive ingredients are blended and compressed to form tablets.

Example 2: Alternate Formulation of Tablets

| Exemplary scorable tablets are prepared as follows: | |
|---|---|
| Ingredient | Quantity (mg/tablet) |
| Substituted phenylalkylamine | 50.0 |
| Starch | 45.0 |
| Microcrystalline cellulose | 35.0 |
| PVP (as 10% solution in water) | 4.0 |
| Sodium carboxymethyl starch | 4.5 |
| Magnesium stearate | 0.5 |
| Talc | 1.0 |

The substituted phenylalkylamine, starch and cellulose are passed through a No. 20 mesh U.S. sieve and mixed thoroughly. The solution of polyvinylpyrrolidone (PVP) is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets. Tablets are scored to provide the ability to create equal half doses.

Example 3: Formulation of Capsules

| Exemplary capsules are made as follows: | |
|---|---|
| Ingredient | Quantity (mg/capsule) |
| Substituted phenylalkylamine | 15.0 |
| Starch | 119.0 |
| Magnesium stearate | 1.0 |

The substituted phenylalkylamine, cellulose, starch, and magnesium stearate are blended, passed through a No. 20 mesh U.S. sieve, and filled into hard or soft gelatin capsules.

Example 4: Formulation of Capsules with Additional Active Agent(s)

| Exemplary capsules are made as follows: | |
|---|---|
| Ingredient | Quantity (mg/capsule) |
| Substituted phenylalkylamine | 50.0 |
| Serotonergic agent | 50.0 |
| Starch | 100.0 |
| Magnesium stearate | 1.0 |

The substituted phenylalkylamine, cellulose, starch, and magnesium stearate are blended, passed through a No. 20 mesh U.S. sieve, and filled into hard or soft gelatin capsules. The serotonergic agent may be an antidepressant or anxiolytic, such as a pharmaceutical agent known to one of ordinary skill in the art or as described herein.

Example 5: Formulation of Suspension

| Exemplary suspensions are made as follows: | |
|---|---|
| Ingredient | Amount |
| Substituted phenylalkylamine | 30.0 mg |
| Xanthan gum | 4.0 mg |
| Sodium carboxymethyl cellulose (11%) | 50.0 mg |
| Microcrystalline cellulose (89%) | 50.0 mg |
| Sucrose | 1.75 g |
| Sodium benzoate | 10.0 mg |
| Flavor and color (optional) | q.v. |
| Purified water | To 5.0 ml |

The substituted phenylalkylamine, sucrose and xanthan gum are blended, passed through a No. 10 mesh U.S. sieve, and then mixed with a previously made solution of the microcrystalline cellulose and sodium carboxymethyl cellulose in water. The sodium benzoate and optional flavor and color are diluted with some of the water and added with stirring. Sufficient water is then added to produce the required volume.

Example 6: Formulation of Intravenous Solution

| An exemplary intravenous formulation is prepared as follows: | |
|---|---|
| Ingredient | Amount |
| Substituted phenylalkylamine | 500 mg |
| Isotonic saline | 1000 mL |

The substituted phenylalkylamine is dissolved in appropriate solvent as will understood by those of skill; isotonic saline is used in this Example, but it will be appreciated that other solvents may be used, and additional active or inactive ingredients such as preservatives may be added, as otherwise described above, and within the general knowledge of the art. It will be understood that the amount of substituted phenylalkylamine can be adjusted accordingly to reach desired mg/mL.

Example 7: Formulations of Injectable Solution

| An exemplary injectable formulation is prepared as follows: | |
|---|---|
| Ingredient | Amount |
| Substituted phenylalkylamine | 125 mg |
| Isotonic saline | 5 mL |

The substituted phenylalkylamine is dissolved in appropriate solvent as will be understood by those of ordinary skill; isotonic saline is used in this Example, but it will be appreciated that other solvents may be used, and additional active or inactive ingredients such as preservatives may be added, as otherwise described above, and within the general knowledge of the art.

Example 8: Formulation of Topical for Transdermal Administration

An exemplary topical formulation is prepared as follows:

| Ingredient | Amount (g) |
|---|---|
| Substituted phenylalkylamine | 1.0 |
| Emulsifying Wax | 30.0 |
| Liquid Paraffin | 20.0 |
| White Soft Paraffin | To 100 |

The white soft paraffin is heated until molten. The liquid paraffin and emulsifying wax are incorporated and stirred until dissolved. The substituted phenylalkylamine is added and stirring is continued until dispersed. The mixture is then cooled until solid.

Example 9: Formulation of Cut Matrix Sublingual or Buccal Tablets

Exemplary sublingual or buccal tablets are made as a single matrix and then cut to size:

| Ingredient | Amount (mg/tablet) |
|---|---|
| Substituted phenylalkylamine | 15.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

Example 10: Formulation of Individually Formed Sublingual or Buccal Lozenges

Exemplary sublingual or buccal lozenges are made from individual forms or molds:

| Ingredient | Amount (mg/each lozenge) |
|---|---|
| Substituted phenylalkylamine | 20.0 |
| Silica gel powder | 350.0 |
| Citric acid powder | 400.0 |
| Acacia powder | 600.0 |
| Flavor (optional) | 100.0 |
| Polyethylene glycol | 1,000 |

The inactive ingredients are admixed by continuous stirring and maintaining the temperature at about 90° C. When the PEG has melted and the other ingredients have gone into solution, the solution is cooled to about 50-55° C. and the substituted phenylalkylamine is slowly admixed. The homogenous mixture is poured into separate molds and allowed to cool. Reference is made to U.S. Ser. No. 10/034,832B2 and Examples therein, the entirety of which is incorporated herein.

Example 11: Formulation of Intranasal Delivery Form

An exemplary nasal spray formulation for intranasal delivery is prepared as follows:

| Ingredient | Quantity (units) |
|---|---|
| Substituted phenylalkylamine | 800 mg |
| DMSO | 50 μL |
| MCT | 5 mL |
| Saline (1% cremophor) | To 10 mL |

The solution at 10 mg/mL of active ingredients in 49.5% MCT, 49.5% saline, 0.5% DMSO, and 0.5% cremophor is prepared, as above (but with MCT in place of TEG), for use in nasal spray device. In other embodiments, a nasal formulation can be prepared as a dry powder for inhalation, e.g., by combining the active agents with lactose and mixing for use with a dry powder inhaling appliance, or as in U.S. Pub. No. US2015/0367091A1 and references cited.

It should be readily appreciated that the above formulation examples are illustrative only. An "active agent" or "active ingredient" in the above examples will be understood to include the one or more disclosed substituted phenylalkylamine compounds, e.g., any of Formula (I), that comprise the formulation. Accordingly, any of the compounds may be substituted with the same compound in a different dosage amount. It will be understood that reference to particular compounds is merely illustrative, and both active and inactive compounds in any Example may be substituted by other disclosed compounds.

Moreover, for any of the compounds, active or inactive, and including the disclosed substituted phenylalkylamine compounds, substitution of the compound by its ion, free base, salt form, polymorph, hydrate or solvate form, co-crystal, or an isomer or enantiomerically enriched mixture, shall be understood to provide merely an alternative embodiment still within the scope of the invention (with modifications to the formulation and dosage amounts made according to the teachings herein and ordinary skill, if necessary or desired). Further, compositions within the scope of the invention will be understood to be open-ended and may include additional active or inactive compounds and ingredients, such as an additional active compound as described herein.

d. Dose, Additional Agents, and Kits

In some embodiments, pharmaceutical compositions comprise a therapeutically effective amount or an effective amount of a disclosed compound, such as for administration to a subject. Administration of pharmaceutical compositions in a "therapeutically effective amount," or an "effective amount" to a subject means administration of an amount of composition sufficient to achieve the desired effect. When an "effective amount" means an amount effective in treating the stated disorder or symptoms in a subject, "therapeutic effect" would be understood to mean the responses(s) in a mammal after treatment that are judged to be desirable and beneficial. Hence, depending on the mental health disorder to be treated, or improvement in mental health or functioning sought, and depending on the particular constituent(s) in the disclosed compositions under consideration, those responses shall differ, but would be readily understood by those of ordinary skill, through an understanding of the disclosure herein and the general knowledge of the art (e.g., by reference to the symptoms listed in the Diagnostic and Statistical Manual of Mental Disorders, 5th Edition (DSM-5) for the stated disorder).

In embodiments, the pharmaceutical compositions disclosed herein comprise therapeutic amounts of substituted phenylalkylamines and in some embodiments other active or inactive ingredients. Dosage amounts will be understood by reference to all of the teachings herein as well as the general knowledge in the art, but certain exemplary dosage amounts, known to be useful in the practice of the invention, are listed below for ease of reference.

In some embodiments, where a pharmaceutical composition includes a disclosed substituted phenylalkylamine compound, it may be present in an amount so that a single dose is (in a milligram dosage amount calculated based on the kilogram weight of the patient), e.g., 0.25 mg/kg or less (including a dose of 0.10 mg/kg or less, 0.05 mg/kg or less, 0.01 mg/kg or less, and 0.005 mg/kg or less), at least 0.50 mg/kg, at least 0.55 mg/kg, at least 0.60 mg/kg, at least 0.65 mg/kg, at least 0.70 mg/kg, at least 0.75 mg/kg, at least 0.80 mg/kg, at least 0.85 mg/kg, at least 0.90 mg/kg, at least 0.95 mg/kg, at least 1.0 mg/kg, at least 1.1 mg/kg, at least 1.2 mg/kg, at least 1.3 mg/kg, or at least 1.4 mg/kg, at least 1.5 mg/kg, at least 1.6 mg/kg, at least 1.7 mg/kg, at least 1.8 mg/kg, at least 1.9 mg/kg, at least 2.0 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, or at least 3.0 mg/kg, as well as amounts within these ranges.

In some embodiments, where a pharmaceutical composition includes a disclosed substituted phenylalkylamine compound, it may be present in an amount so that a single dose is (whether or not such dose is present in a unit dosage form), e.g., 25 mg or less (including a dose of 10 mg or less, 5 mg or less, 1 mg or less, and 0.5 mg or less), at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, or at least 250 mg, as well as amounts within these ranges.

In some embodiments, where a pharmaceutical composition includes an additional active compound, for instance where the additional active compound is a phenethylamine or another substituted phenylalkylamine, it may be present in an amount so that a single dose is (in a milligram dosage amount calculated based on the kilogram weight of the patient), e.g., 0.25 mg/kg or less (including a dose of 0.10 mg/kg or less, 0.05 mg/kg or less, 0.01 mg/kg or less, and 0.005 mg/kg or less), at least 0.50 mg/kg, at least 0.55 mg/kg, at least 0.60 mg/kg, at least 0.65 mg/kg, at least 0.70 mg/kg, at least 0.75 mg/kg, at least 0.80 mg/kg, at least 0.85 mg/kg, at least 0.90 mg/kg, at least 0.95 mg/kg, at least 1.0 mg/kg, at least 1.1 mg/kg, at least 1.2 mg/kg, at least 1.3 mg/kg, or at least 1.4 mg/kg, at least 1.5 mg/kg, at least 1.6 mg/kg, at least 1.7 mg/kg, at least 1.8 mg/kg, at least 1.9 mg/kg, at least 2.0 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, or at least 3.0 mg/kg, as well as amounts within these ranges.

In some embodiments, where a pharmaceutical composition includes an additional active compound, for instance where the additional active compound is a phenethylamine or another substituted phenylalkylamine, it may be present in an amount so that a single dose is (whether or not such dose is present in a unit dosage form), e.g., 25 mg or less (including a dose of 10 mg or less, 5 mg or less, 1 mg or less, and 0.5 mg or less), at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, or at least 250 mg, as well as amounts within these ranges.

It will be readily appreciated that dosages may vary depending upon whether the treatment is therapeutic or prophylactic, the onset, progression, severity, frequency, duration, probability of or susceptibility of the symptom to which treatment is directed, clinical endpoint desired, previous, simultaneous or subsequent treatments, general health, age, gender, and race of the subject, bioavailability, potential adverse systemic, regional or local side effects, the presence of other disorders or diseases in the subject, and other factors that will be appreciated by the skilled artisan (e.g., medical or familial history).

Dose amount, frequency or duration may be increased or reduced, as indicated by the clinical outcome desired, status of the pathology or symptom, any adverse side effects of the treatment or therapy, or concomitant medications. The skilled artisan with the teaching of this disclosure in hand will appreciate the factors that may influence the dosage, frequency, and timing required to provide an amount sufficient or effective for providing a therapeutic effect or benefit, and to do so depending on the type of therapeutic effect desired, as well as to avoid or minimize adverse effects.

It will be understood that, in some embodiments, the dose actually administered will be determined by a physician, in light of the relevant circumstances, including the disorder to be treated, the chosen route of administration, the actual composition or formulation administered, the age, weight, and response of the individual patient, and the severity of the patient's symptoms, and therefore any dosage ranges disclosed herein are not intended to limit the scope of the invention. In some instances, dosage levels below the lower limit of a disclosed range may be more than adequate, while in other cases doses above a range may be employed without causing any harmful side effects, provided for instance that such larger doses also may be divided into several smaller doses for administration, either taken together or separately.

In these embodiments, the disclosed pharmaceutical compositions will be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Starting and maintenance dosage levels thus may differ from patient to patient, for individual patients across time, and for different pharmaceutical compositions and formulations, but shall be able to be determined with ordinary skill.

It should be appreciated that in other embodiments, e.g., when the disclosed compositions are taken without the direct intervention or guidance of a medical professional, appropriate dosages to achieve a therapeutic effect, including the upper and lower bounds of any dose ranges, can be determined by an individual by reference to available public information and knowledge, and reference to subjective considerations regarding desired outcomes and effects.

Determination of appropriate dosing shall include not only the determination of single dosage amounts, but also the determination of the number and timing of doses, e.g., administration of a particular dosage amount once per day, twice per day, or more than twice per day, and the time(s) of day or time(s) during a therapy session preferable for their administration.

In some embodiments, especially where a formulation is prepared in single unit dosage form, such as a capsule, tablet, or lozenge, suggested dosage amounts shall be known by reference to the format of the preparation itself. In other embodiments, where a formulation is prepared in multiple dosage form, for instance liquid suspensions and topical preparations, suggested dosage amounts may be known by reference to the means of administration or by reference to the packaging and labeling, package insert(s), marketing materials, training materials, or other information and knowledge available to those of skill or the public.

Accordingly, another aspect of this disclosure provides pharmaceutical kits containing a pharmaceutical composition or formulation of the invention, suggested administration guidelines or prescribing information therefor, and a suitable container. Individual unit dosage forms can be included in multi-dose kits or containers. pharmaceutical formulations also can be packaged in single or multiple unit dosage forms for uniformity of dosage and ease of administration.

In an exemplary pharmaceutical kit, capsules, tablets, caplets, or other unit dosage forms are packaged in blister packs. "Blister pack" refers to any of several types of pre-formed container, especially plastic packaging, that contains separate receptacles (e.g., cavities or pockets) for single unit doses, where such separate receptacles are individually sealed and can be opened individually. Blister packs thus include such pharmaceutical blister packs known to those of ordinary skill, including Aclar® Rx160, Rx20e, SupRx, and UltRx 2000, 3000, 4000, and 6000 (Honeywell). Within the definition of multi-dose containers, and also often referred to as blister packs, are blister trays, blister cards, strip packs, push-through packs, and the like.

Preferably, information pertaining to dosing and proper administration (if needed) will be printed onto a multi-dose kit directly (e.g., on a blister pack or other interior packaging holding the compositions or formulations of the invention); however, kits of the invention can further contain package inserts and other printed instructions (e.g., on exterior packaging) for administering the disclosed compositions and for their appropriate therapeutic use.

In some embodiments, a patient will have the option of using online software such as a website, or downloadable software such as a mobile application, to assist with compliance or to provide data relating to treatment. Such software can be used to, e.g., keep track of last dose taken and total doses taken, provide reminders and alerts for upcoming doses, provide feedback to discourage taking doses outside of set schedules, and allow for recording of specific subjective effects, or provide means for unstructured journaling. Such data collection can assist with individual patient compliance, can be used to improve or tailor individual patient care plans, and can be anonymized, aggregated, and analyzed (including by AI or natural language processing means) to allow research into the effects of various methods of treatment.

It should be readily appreciated that the disclosed compositions are not limited to combinations of a single compound, or (when formulated as a pharmaceutical composition) limited to a single carrier, diluent, and/or excipient alone, but may also include combinations of multiple compounds (including additional active compounds), and/or multiple carriers, diluents, and excipients. Pharmaceutical compositions of this invention thus may comprise a compound of Formula (I) together with one or more other active agents (or their derivatives and analogs) in combination, together with one or more pharmaceutically-acceptable carriers, diluents, and/or excipients, and additionally with one or more other active compounds.

In some embodiments, a formulation of the invention will be prepared so as to increase an existing therapeutic effect, provide an additional therapeutic effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

"Therapeutic effects" that may be increased or added in embodiments of the invention include, but are not limited to, antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, empathogenic, psychedelic, sedative, and stimulant effects.

"Synergistic effects" should be understood to include increases in potency, bioactivity, bioaccessibility, bioavailability, or therapeutic effect, that are greater than the additive contributions of the components acting alone. Numerous methods known to those of skill in the art exist to determine whether there is synergy as to a particular effect, i.e., whether, when two or more components are mixed together, the effect is greater than the sum of the effects of the individual components when applied alone, thereby producing "1+1>2." One such method is the isobologram analysis (or contour method) (see Huang, Front Pharmacol., 2019; 10:1222).

The goal of increasing an existing therapeutic effect, providing an additional therapeutic effect, increasing a desired property such as stability or shelf-life, decreasing an unwanted effect or property, altering a property in a desirable way (such as pharmacokinetics or pharmacodynamics), modulating a desired system or pathway (e.g, a neurotransmitter system), or otherwise inducing synergy, in some embodiments is achieved by the inclusion of an additional active compound.

Such additional active compounds may be selected from the group including amino acids, antioxidants, anti-inflammatory agents, analgesics, antineuropathic and antinociceptive agents, antimigraine agents, anxiolytics, antidepressants, antipsychotics, anti-PTSD agents, cannabinoids, dissociatives, immunostimulants, anti-cancer agents, antiemetics, orexigenics, antiulcer agents, antihistamines, antihypertensives, anticonvulsants, antiepileptics, bronchodilators, neuroprotectants, nootropics, empathogens, psychedelics, monoamine oxidase inhibitors, tryptamines, terpenes, phenethylamines, sedatives, stimulants, serotonergic agents, and vitamins. These active compounds may be in ion, freebase, or salt form, and may be isomers, prodrugs, derivatives (preferably physiologically functional derivatives), or analogs.

In some embodiments, an additional active compound is a tryptamine. "Tryptamines" are as readily understood by those in the art, and non-limiting examples of other tryptamines useful in the practice of the invention include 6-allyl-N,N-diethyl-norlysergamide (AL-LAD), N,N-dibutyltryptamine (DBT), N,N-diethyltryptamine (DET), N,N-diisopropyltryptamine (DiPT), 5-methoxy-α-methyl-tryptamine (α,O-DMS), N,N-dimethyl-tryptamine (DMT), 2,α-dimethyltryptamine (2,α-DMT), α,N-dimethyltryptamine (α,N-DMT), N,N-dipropyltryptamine (DPT), N-ethyl-N-isopropyltryptamine (EiPT), α-ethyltryptamine (AET), 6,N,N-triethylnorlysergamide (ETH-LAD), 3,4-dihydro-7-methoxy-1-methylcarboline (Harmaline), 7-methoxy-1-methylcarboline (Harmine), N,N-dibutyl-4-hydroxytryptamine (4-HO-DBT), N,N-diethyl-4-hydroxytryptamine (4-HO-DET), N,N-diisopropyl-4-hydroxytryptamine (4-HO-DiPT), N,N-dimethyl-4-hydroxytryptamine (4-HO-DMT), N,N-dimethyl-5-hydroxytryptamine (5-HO-DMT, bufotenine), N,N-dipropyl-4-hydroxytryptamine (4-HO-DPT), N-ethyl-4-hydroxy-N-methyltryptamine (4-HO-MET), 4-hydroxy-N-isopropyl-N-methyltryptamine (4-HO-MiPT), 4-hydroxy-N-methyl-N-propyl-tryptamine (4-HO-MPT), 4-hydroxy-N,N-tetramethylenetryptamine (4-HO-pyr-T), 12-methoxyibogamine (Ibogaine), N-butyl-N-methyltryptamine (MBT), N,N-diisopropyl-4,5-methylenedioxytryptamine (4,5-MDO-DiPT), N,N-diisopropyl-5,6-methylenedioxytryptamine (5,6-MDO-DiPT), N,N-dimethyl-4,5-methylenedioxytryptamine (4,5-MDO-DMT), N,N-dimethyl-5,6-methylenedioxytryptamine (5,6-MDO-DMT), N-isopropyl-N-methyl-5,6-methylenedioxytryptamine (5,6-MDO-MiPT), N,N-diethyl-2-methyl-tryptamine (2-Me-DET), 2,N,N-trimethyltryptamine (2-Me-DMT), N-acetyl-5-methoxytryptamine (melatonin), N,N-diethyl-5-methoxytryptamine (5-MeO-DET), N,N-diisopropyl-5-methoxytryptamine (5-MeO-DiPT), 5-methoxy-N,N-dimethyltryptamine (5-MeO-DMT), N-isopropyl-4-methoxy-N-methyltryptamine (4-MeO-MiPT), N-isopropyl-5-methoxy-N-methyltryptamine (5-MeO-MiPT), 5,6-dimethoxy-N-isopropyl-N-methyltryptamine (5,6-MeO-MiPT), 5-methoxy-N-methyltryptamine (5-MeO-NMT), 5-methoxy-N,N-tetramethylenetryptamine (5-MeO-pyr-T), 6-methoxy-1-methyl-1,2,3,4-tetrahydrocarboline (6-MeO-THH), 5-methoxy-2,N,N-trimethyltryptamine (5-MeO-TMT), N,N-dimethyl-5-methylthiotryptamine (5-MeS-DMT), N-isopropyl-N-methyltryptamine (MiPT), α-methyltryptamine (α-MT), N-ethyltryptamine (NET), N-methyltryptamine (NMT), 6-propylnorlysergamide (PRO-LAD), N,N-tetramethylenetryptamine (pyr-T), Tryptamine (T), 7-methoxy-1-methyl-1,2,3,4-tetrahydrocarboline (Tetrahydroharmine), or α,N-dimethyl-5-methoxytryptamine (α,N,O-TMS), or a pharmaceutically acceptable salt, hydrate, solvate, prodrug, stereoisomer, or tautomer thereof, or a combination thereof. See Shulgin and Shulgin, TiHKAL: The Continuation, Transform Press (1997) ("TiHKAL"), which is incorporated by reference as if fully set forth herein.

In embodiments, a tryptamine useful as an additional active compound will be a substituted tryptamine having the structure below, wherein $R^{N1}$, $R^{N2}$, $R^{\alpha}$, $R^{\beta}$, $R^2$, $R^4$, $R^5$, $R^6$, and $R^7$ will be as taught herein and as generally understood in the art:

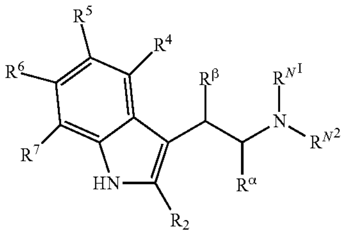

For example, in some embodiments, $R^{N1}$, $R^{N2}$, $R^{\alpha}$, $R^{\beta}$, $R^2$, $R^4$, $R^5$, $R^6$, and $R^7$ are independently hydrogen, deuterium, halogen, hydroxy, methoxy, phosphoryloxy, $C_1$-$C_5$ alkyl, $C_2$-$C_8$ alkenyl, $C_2$-$C_8$ alkynyl, $C_3$-$C_8$ cycloalkyl (independently or ring closed with the nitrogen), $C_3$-$C_8$ cycloalkenyl (independently or ring closed with the nitrogen), aryl, or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —$OP(O)(OH)_2$, —OC(O)H, —$OSO_2OH$, —$OC(O)NH_2$, and —SONH. In some embodiments, the tryptamine comprises a quaternary ammonium cation wherein each of $R^{N1}$, $R^{N2}$, and an additional $R^{N3}$ are independently an alkyl group or an aryl group, and with all other substituents as above.

In some embodiments, a tryptamine will be a "complex tryptamine" or other indolamine and including such examples as ergolines, ergot alkaloids, lysergamides, iboga alkaloids such as ibogaine, and their analogs, metabolites, and derivatives, and beta-carbolines.

In some embodiments, the additional active compound is a phenethylamine. "Phenethylamines" are as readily understood by those in the art, and non-limiting examples of phenethylamines useful in the practice of the invention include α-ethyl-3,4,5-trimethoxyphenethylamine (AEM), 4-allyloxy-3,5-dimethoxyphenethylamine (AL), 2,5-dimethoxy-4-methylthioamphetamine (ALEPH), 2,5-dimethoxy-4-ethylthioamphetamine (ALEPH-2), 2,5-dimethoxy-4-isopropylthioamphetamine (ALEPH-4), 2,5-dimethoxy-4-phenylthio-amphetamine (ALEPH-6), 2,5-dimethoxy-4-propylthioamphetamine (ALEPH-7), 2,5-dimethoxy-α-ethyl-4-methylphenethylamine (ARIADNE), 3,4-diethoxy-5-methoxyphenethylamine (ASB), 4-butoxy-3,5-dimethoxyphenethylamine (B), 2,5-dimethoxy-4,N-dimethylamphetamine (BEATRICE), 2,5-bismethylthio-4-methylamphetamine (BIS-TOM), 4-bromo-2,5,β-trimethoxyphenethylamine (BOB), 2,5,13-trimethoxy-4-methylphenethylamine (BOD), β-methoxy-3,4-methylenedioxyphenethylamine (BOH), 2,5-dimethoxy-3-hydroxy-4-methylphenethylamine (BOHD), 3,4,5,13-tetramethoxyphenethylamine (BOM), 4-bromo-3,5-dimethoxyamphetamine (4-Br-3,5-DMA), 2-bromo-4,5-methylenedioxyamphetamine (2-Br-4,5-MDA), 4-bromo-2,5-dimethoxyphenethylamine (2C-B), 4-benzyloxy-3,5-dimethoxyamphetamine (3C-BZ), 4-chloro-2,5-dimethoxyphenethylamine (2C-C), 2,5-dimethoxy-4-methyl-phenethylamine (2C-D), 2,5-dimethoxy-4-ethyl-phenethylamine (2C-E), 3,5-dimethoxy-4-ethoxyamphetamine (3C-E), 2,5-dimethoxy-4-fluorophenethylamine (2C-F), 2,5-dimethoxy-3,4-dimethylphenethylamine (2C-G), 2,5-dimethoxy-3,4-trimethylene-phenethylamine (2C-G-3), 2,5-dimethoxy-3,4-tetramethylenephenethylamine (2C-G-4), 3,4-norbornyl-2, 5-dimethoxyphenethylamine (2C-G-5), 1,4-dimethoxynaphthyl-2-ethylamine (2C-G-N), 2,5-dimethoxyphenethylamine (2C-H), 4-iodo-2,5-dimethoxyphenethylamine (2C-I), 2,5-dimethoxy-4-nitro-phenethylamine (2C-N), 2,5-dimethoxy-4-isopropoxyphenethylamine (2C-O-4), 2,5-dimethoxy-4-propylphenethylamine (2C-P), 4-cyclopropylmethoxy-3,5-dimethoxyphenethylamine (CPM), 2,5-dimethoxy-4-methylselenophenethylamine (2C-SE), 2,5-dimethoxy-4-methylthiophenethylamine (2C-T), 2,5-dimethoxy-4-ethylthiophenethylamine (2C-T-2), 2,5-dimethoxy-4-isopropylthiophenethylamine (2C-T-4), 2,6-dimethoxy-4-isopropylthiophenethylamine (psi-2C-T-4), 2,5-dimethoxy-4-propylthiophenethylamine (2C-T-7), 4-cyclopropylmethylthio-2,5-dimethoxyphenethylamine (2C-T-8), 4-(t)-butylthio-2,5-dimethoxy-phenethylamine (2C-T-9), 2,5-dimethoxy-4-(2-methoxyethylthio)phenethylamine (2C-T-13), 4-cyclopropylthio-2,5-dimethoxyphenethylamine (2C-T-15), 4-(s)-butylthio-2,5-dimethoxyphenethylamine (2C-T-17), 2,5-dimethoxy-4-(2-fluoroethylthio) phenethylamine (2C-T-21), 3,5-dimethoxy-4-trideuteromethylphenethylamine (4-D), β,β-dideutero-3,4,5-trimethoxyphenethylamine (β-D), 3,5-dimethoxy-4-methyl-phenethylamine (DESOXY), 2,4-dimethoxyamphetamine (2,4-DMA), 2,5-dimethoxyamphetamine (2,5-DMA), 3,4-dimethoxyamphetamine (3,4-DMA), 2-(2,5-dimethoxy-4-methylphenyl)cyclopropylamine (DMCPA), 3,4-dimethoxy-8-hydroxyphenethylamine (DME), 2,5-dimethoxy-3,4-methylenedioxyamphetamine (DMMDA), 2,3-dimethoxy-4,5-methylenedioxyamphetamine (DMMDA-2), 3,4-dimethoxyphenethylamine (DMPEA), 4-amyl-2,5-dimethoxyamphetamine (DOAM), 4-bromo-2,5-dimethoxyamphetamine (DOB), 4-butyl-2,5-dimethoxyamphetamine (DOBU), 4-chloro-2,5-dimethoxyamphetamine (DOC), 2,5-dimethoxy-4-(2-fluoroethyl) amphetamine (DOEF), 2,5-dimethoxy-4-ethylamphetamine (DOET), 4-iodo-2,5-dimethoxyamphetamine (DOI), 2,5-dimethoxy-4-methylamphetamine (DOM (STP)), 2,6-dimethoxy-4-methylamphetamine (psi-DOM), 2,5-dimethoxy-4-nitroamphetamine (DON), 2,5-dimethoxy-4-propylamphetamine (DOPR), 3,5-dimethoxy-4-ethoxyphenethylamine (E), 2,4,5-triethoxyamphetamine (EEE), 2,4-diethoxy-5-methoxyamphetamine (EEM), 2,5-diethoxy-4-methoxyamphetamine (EME), 4,5-dimethoxy-2-ethoxyamphetamine (EMM), 2-ethylamino-1-(3,4-methylenedioxyphenyl)butane (ETHYL-J), 2-ethylamino-1-(3,4-methylenedioxyphenyl)pentane (ETHYL-K), 6-(2-aminopropyl)-5-methoxy-2-methyl-2,3-dihydrobenzofuran (F-2), 6-(2-aminopropyl)-2,2-dimethyl-5-methoxy-2,3-dihydrobenzofuran (F-22), N-hydroxy-N-methyl-3,4-methylenedioxyamphetamine (FLEA), 2,5-dimethoxy-3,4-(trimethylene)amphetamine (G-3), 2,5-dimethoxy-3,4-(tetramethylene)amphetamine (G-4), 3,6-dimethoxy-4-(2-aminopropyl)benzonorbornane (G-5), 2,5-dimethoxy-3,4-dimethylamphetamine (GANESHA), 1,4-dimethoxynaphthyl-2-isopropylamine (G-N), 2,5-dimethoxy-4-ethylthio-N-hydroxyphenethylamine (HOT-2), 2,5-dimethoxy-N-hydroxy-4-(n)-propylthiophenethylamine (HOT-7), 4-(s)-butylthio-2,5-dimethoxy-N-hydroxyphenethylamine (HOT-17), 2,5-dimethoxy-N,N-dimethyl-4-iodoamphetamine (IDNNA), 2,3,4-trimethoxyphenethylamine (IM), 3,5-dimethoxy-4-isopropoxyphenethylamine (IP), 5-ethoxy-2-methoxy-4-methylamphetamine (IRIS), 2-amino-1-(3,4-methylenedioxyphenyl)butane(J, BDB), 3-methoxy-4,5-methylenedioxyphenethylamine (LOPHOPHINE), 3,4,5-trimethoxyphenethylamine (M), 4-methoxyamphetamine (4-MA, PMA), 2,N-dimethyl-4,5-methylenedioxyamphetamine (MADAM-6), 3,5-dimethoxy-4-methallyloxyphenethylamine (MAL), 3,4-methylenedioxyamphetamine (MDA), N-allyl-3,4-methylenedioxyamphetamine (MDAL), N-butyl-3,4-methylenedioxyamphetamine (MDBU), N-benzyl-3,4-methylenedioxyamphetamine (MDBZ), N-cyclopropylmethyl-3,4-methylenedioxyamphetamine (MDCPM), N,N-dimethyl-3,4-methylenedioxyamphetamine (MDDM), N-ethyl-3,4-methylenedioxyamphetamine (MDE), N-(2-hydroxyethyl)-3,4-methylenedioxyamphetamine (MDHOET), N-isopropyl-3,4-methylenedioxyamphetamine (MDIP), N-methyl-3,4-methylenedioxyamphetamine (MDMA), 3,4-ethylenedioxy-N-methylamphetamine (MDMC), N-methoxy-3,4-methylenedioxyamphetamine (MDMEO), N-(2-methoxyethyl)-3,4-methylenedioxyamphetamine (MDMEOET), 3,4-methylenedioxy-α,α,N-trimethylphenethylamine (MDMP), N-hydroxy-3,4-methylenedioxyamphetamine (MDOH), 3,4-methylenedioxyphenethylamine (MDPEA), α,α-dimethyl-3,4-methylenedioxyphenethylamine (MDPH), 3,4-methylenedioxy-N-propargyl-amphetamine (MDPL), 3,4-methylenedioxy-N-propyl-amphetamine (MDPR), 3,4-dimethoxy-5-ethoxyphenethylamine (ME), 4,5-ethylenedioxy-3-methoxyamphetamine (MEDA), 4,5-diethoxy-2-methoxyamphetamine (MEE), 2,5-dimethoxy-4-ethoxyamphetamine (MEM), 4-ethoxy-3-methoxyphenethylamine (MEPEA), 5-bromo-2,4-dimethoxyamphetamine (META-DOB), 2,4-dimethoxy-5-methylthioamphetamine (META-DOT), 2,5-dimethoxy-N-methylamphetamine (METHYL-DMA), 4-bromo-2,5-dimethoxy-N-methylamphetamine (METHYL-DOB), 2-methylamino-1-(3,4-methylenedioxyphenyl)butane (METHYL-J, MBDB), 2-methylamino-1-(3,4-methylenedioxyphenyl)pentane (METHYL-K), 4-methoxy-N-methylamphetamine (METHYL-MA, PMMA), 2-methoxy-N-methyl-4,5-methylenedioxyamphetamine (METHYL-MMDA-2), 3-methoxy-4,5-methylenedioxyamphetamine (MMDA), 2-methoxy-4,5-methylenedioxyamphetamine (MMDA-2), 2-methoxy-3,4-methylenedioxyamphetamine (MMDA-3a), 4-methoxy-2,3-methylenedioxyamphetamine (MMDA-3b), 2,4-dimethoxy-5-ethoxyamphetamine (MME), 3,4-dimethoxy-5-(n)-propoxyphenethylamine (MP), 2,5-dimethoxy-4-(n)-propoxyamphetamine (MPM), 4,5-dimethoxy-2-methylthioamphetamine (ORTHO-DOT), 3,5-dimethoxy-4-propoxyphenethylamine (P), 3,5-dimethoxy-4-phenethyloxyphenethylamine (PE), phenethylamine (PEA), 3,5-dimethoxy-4-(2-propynyloxy) phenethylamine (PROPYNYL), 3,5-diethoxy-4-methoxyphenethylamine (SB), 2,3,4,5-tetra-methoxyamphetamine (TA), 4-ethoxy-3-ethylthio-5-methoxyphenethylamine (3-TASB), 3-ethoxy-4-ethylthio-5-methoxyphenethylamine (4-TASB), 3,4-diethoxy-5-methylthiophenethylamine (5-TASB), 4-(n)-butylthio-3,5-dimethoxyphenethylamine (TB), 4-ethoxy-5-methoxy-3-methylthiophenethylamine (3-TE), 3,5-dimethoxy-4-ethylthiophenethylamine (TE, 4-TE), 3,4-dimethoxy-2-methylthiophenethylamine (2-TIM), 2,4-dimethoxy-3-methylthiophenethylamine (3-TIM), 2,3-dimethoxy-4-methylthiophenethylamine (4-TIM), 3,4-dimethoxy-5-methylthiophenethylamine (3-TM), 3,5-dimethoxy-4-methylthiophenethylamine (4-TM), 3,4,5-trimethoxyamphetamine (TMA), 2,4,5-trimethoxyamphetamine (TMA-2), 2,3,4-trimethoxyamphetamine (TMA-3), 2,3,5-trimethoxyamphetamine (TMA-4), 2,3,6-trimethoxyamphetamine (TMA-5), 2,4,6-trimethoxyamphetamine (TMA-6), 4,5-dimethoxy-3-ethylthiophenethylamine (3-TME), 3-ethoxy-5-methoxy-4-methylthiophenethylamine (4-TME), 3-ethoxy-4-methoxy-5-methylthiophenethylamine (5-TME), 3,4-methylenedioxy-2-methylthioamphetamine (2T-MMDA-3a), 2-methoxy-4,5-methylene-thiooxyamphetamine (4T-MMDA-2), 2,4,5-trimethoxyphenethylamine (TMPEA), 4-ethyl-5-methoxy-2-methylthioamphetamine (2-TOET), 4-ethyl-2-methoxy-5-methylthioamphetamine (5-TOET), 5-methoxy-4-methyl-2-methylthioamphetamine (2-TOM), 2-methoxy-4-methyl-5-methylthioamphetamine (5-TOM), 2-methoxy-4-methyl-5-methyl-sulfinylamphetamine (TOMSO), 3,5-dimethoxy-4-propylthiophenethylamine (TP), 3,4,5-triethoxyphenethylamine (TRIS), 3-ethoxy-5-ethylthio-4-methoxyphenethylamine (3-TSB), 3,5-diethoxy-4-methylthiophenethylamine (4-TSB), 3,4-diethoxy-5-ethylthiophenethylamine (3-T-TRIS), 3,5-diethoxy-4-ethylthiophenethylamine (4-T-TRIS), (R)-2,5-dimethoxy-4-iodoamphetamine (R-DOI), or a pharmaceutically acceptable salt, hydrate, solvate, prodrug, stereoisomer, or tautomer thereof, or a combination thereof. See Shulgin and Shulgin, PiHKAL: A Chemical Love Story, Transform Press (1991), which is incorporated by reference as if fully set forth herein.

In embodiments, a phenethylamine useful as an additional active compound will be a substituted phenethylamine having the structure below, wherein $R^{N1}$, $R^{N2}$, $R^{\alpha}$, $R^{\beta}$, and each of $R^2$-$R^6$ will be as taught herein and as generally understood in the art:

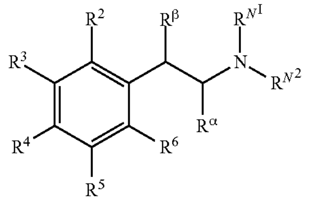

For example, in some embodiments, $R^{N1}$, $R^{N2}$, $R^{\alpha}$, $R^{\beta}$, and each of $R^{2-6}$ are independently hydrogen, deuterium, halogen, $C_1$-$C_5$ alkyl, $C_2$-$C_8$ alkenyl, $C_2$-$C_8$ alkynyl, $C_3$-$C_8$ cycloalkyl (independently or ring closed with the nitrogen, when $R^N$), $C_3$-$C_8$ cycloalkenyl (independently or ring closed with the nitrogen, when $R^N$), aryl, or heterocyclyl; including where $R^3$ and $R^4$ may be joined together to form a dioxole (as with MDMA), a furan, a tetrahydrofuran, a thiophene, a pyrrole, a pyridine, a pyrrolidine, an ethylene oxide, an ethylenimine, a trimethylene oxide, a pyran, a piperidine, an imidazole, a thiazole, a dioxane, a morpholine, a pyrimidine, or otherwise so as to create a benzene heterocycle; and any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —$OP(O)(OH)_2$, —OC(O)H, —$OSO_2OH$, —OC(O)$NH_2$, and —SONH. In some embodiments, the phenethylamine comprises a quaternary ammonium cation wherein each of $R^{N1}$, $R^{N2}$, and an additional $R^{N3}$ are independently an alkyl group or an aryl group, and with all other substituents as above.

Other tryptamines, phenylalkylamines, and phenethylamines useful as additional active compounds for purposes of the invention and thus contemplated for inclusion therein will be as generally known in the art (see, e.g., Grob & Grigsby, Handbook of Medical Hallucinogens, 2021; Luethi & Liechti, Arch. Toxicol., 2020; 94, 1085-1133; Nichols, Pharmacol Reviews, 2016; 68(2), 264-355; Glennon, Pharmacology Biochemistry and Behavior, 1999; 64, 251-256).

In some embodiments the additional active compound is a serotonergic agent. A "serotonergic agent" refers to a compound that binds to, blocks, or otherwise influences (e.g., via an allosteric reaction) activity at one or more serotonin receptors, including any one or more serotonin receptor subtypes. In some embodiments, a serotonergic agent binds to a serotonin receptor. In some embodiments, a serotonergic agent indirectly affects a serotonin receptor, e.g., via interactions affecting the reactivity of other molecules at the serotonin receptor. In some embodiments, a serotonergic agent is an agonist, e.g., a compound activating a serotonin receptor. In some embodiments, a serotonergic agent is an antagonist, e.g., a compound binding but not activating a serotonin receptor, e.g., blocking a receptor. In some embodiments, a serotonergic agent is an effector molecule, e.g., a compound binding to an enzyme for allosteric regulation. In embodiments, a serotonergic agent acts (either directly or indirectly) at more than one type of receptor, including receptors other than serotonergic or other monoaminergic receptors. In embodiments, a serotonergic agent blocks the serotonin transporter (SERT) and results in an elevation of the synaptic concentration of serotonin, and an increase of neurotransmission. In embodiments, a serotonergic agent acts as a reuptake modulator and inhibits the plasmalemmal transporter-mediated reuptake of serotonin from the synapse into the presynaptic neuron, leading to an increase in extracellular concentrations of serotonin and an increase in neurotransmission. In embodiments, a serotonergic agent inhibits the activity of one or both monoamine oxidase enzymes, resulting in an increase in concentrations of serotonin and an increase in neurotransmission. In embodiments, a serotonergic agent is an antidepressant or anxiolytic, such as an SSRI, serotonin-norepinephrine reuptake inhibitor (SNRI), tricyclic antidepressant (TCA), monoamine oxidase inhibitor (MAOI), or atypical antidepressant.

The type of formulation employed for the administration of the compounds employed in the disclosed methods generally may be dictated by the compound(s) employed, the type of pharmacokinetic profile desired from the route of administration and the compound(s), and the state of the patient. It will be readily appreciated that any of the above embodiments and classes of embodiments can be combined to form additional embodiments.

D. Methods of Use

In some aspects, provided herein are methods of using the disclosed compounds. In some embodiments, disclosed compounds are used to modulate neurotransmission. In some embodiments, disclosed compounds are used to treat a condition, such as a disease or a disorder. In some embodiments, disclosed compounds are used in the manufacture of a medicament for the therapeutic and/or the prophylactic treatment of a condition, such as a disease or a disorder. In some embodiments, disclosed compounds are administered as part of psychedelic-assisted therapy. In some embodiments, disclosed compounds are administered in a therapeutically effective amount to a subject having a condition, such as a disease or a disorder. In some embodiments, the condition is a mental health disorder. In some embodiments, the condition is a neurodegenerative disorder. In some embodiments, the condition is related to pain and/or inflammation, such as a pain disorder or an inflammatory disorder. In some embodiments, disclosed compounds are administered to a subject that is healthy.

As used herein, the terms "subject," "user," "patient," and "individual" are used interchangeably, and refer to any mammal, including murines, simians, mammalian farm animals, mammalian sport animals, and mammalian pets, such as canines and felines, although preferably humans. Such terms will be understood to include one who has an indication for which a compound, composition, or method described herein may be efficacious, or who otherwise may benefit by the invention. In general, all of the compounds, compositions, and disclosed methods will be appreciated to work for all individuals, although individual variation is to be expected, and will be understood. The disclosed methods of treatment also can be modified to treat multiple patients at once, including couples or families. Hence, these terms will be understood to also mean two or more individuals.

In some embodiments, disclosed compounds or compositions thereof are orally, mucosally, rectally, subcutaneously, intravenously, intramuscularly, intranasally, by inhalation or transdermally administered to a subject. In some embodiments, when administered through one or more such routes, the disclosed compounds and the disclosed compositions and formulations comprising them are useful in methods for treating a patient in need of such treatment.

a. Modulating Neurotransmission

In some embodiments, the disclosed compounds modulate neurotransmission in a subject, such as following administration of a pharmacologically effective amount to said subject. In some embodiments, modulating neurotransmission comprises regulating levels of monoamines in, for example, the CNS and peripheral tissues. In some embodiments, modulating neurotransmission comprises increasing levels of monoamines in, for example, the CNS and peripheral tissues of a subject to whom a disclosed compound has been administered. In some embodiments, modulating neurotransmission comprises decreasing levels of monoamines in, for example, the CNS and peripheral tissues of a subject to whom a disclosed compound has been administered. In some embodiments, modulating neurotransmission by administering a disclosed compound to a subject treats a medical condition, such as a disease or disorder in the subject.

In some embodiments, disclosed compounds, when administered in a pharmacologically effective amount, inhibit the reuptake of one or more neurotransmitters, such as any one or more of serotonin, dopamine, and norepinephrine. In some embodiments, disclosed compounds, when administered in a pharmacologically effective amount, inhibit the reuptake activity of one or more monoamine transporters, such as the dopamine transporter (DAT), norepinephrine transporter (NET), and serotonin transporter (SERT). In some embodiments, the disclosed compositions, when administered in a pharmacologically effective amount, increase the extracellular concentration of one or more neurotransmitters, including the amount of extracellular serotonin, dopamine, or norepinephrine.

In some embodiments, the disclosed compounds are used to modulate neurotransmission, such as neurotransmission in a subject. In some methods herein, the disclosed compositions, when administered in a pharmacologically effective amount, thus affect monoaminergic neurotransmission, including serotonergic, dopaminergic, and noradrenergic neurotransmission. Accordingly, in some embodiments, the disclosed compositions, when administered in a pharmacologically effective amount, are used to treat a medical condition linked to dysregulation or inadequate functioning of neurotransmission, and in specific embodiments, are used to treat a medical condition linked to monoaminergic neurotransmission.

In embodiments, disclosed compounds or compositions, when administered in a pharmacologically effective amount, act on or modulate one or more monoamine receptors, such as a serotonin receptor, a dopamine receptor, and a norepinephrine receptor. In embodiments, the compositions are agonists or partial agonists of a monoamine receptor, including any one or more of a serotonin receptor, a dopamine receptor, and a norepinephrine receptor.

In some embodiments, disclosed compounds are HTR agonists. In some embodiments, disclosed compounds activate one or more serotonin receptors (HTRs). In some embodiments, disclosed compounds agonize one or more HTRs. In some embodiments, disclosed compounds agonize and/or antagonize one or more HTRs. In some embodiments, disclosed compounds agonize one or more HTRs. In some embodiments, the one or more HTRs is any of an $HTR_1$ receptor, e.g., $HTR_{1A}$ and $HTR_{1B}$, an $HTR_2$ receptor, e.g., $HTR_{2A}$, $HTR_{2B}$, and $HTR_2c$, an $HTR_3$ receptor, e.g., $HTR_{3A}$, an $HTR_4$ receptor, an $HTR_5$ receptor, e.g, $HTR_{5A}$, an $HTR_6$ receptor, and an $HTR_7$ receptor, e.g., $HTR_{7D}$. In some embodiments, the HTR is not $HTR_{2B}$. In some embodiments, the HTRs is one or both of $HTR_{2A}$ and $HTR_{2C}$. In some embodiments, a disclosed compound has an in vitro $EC_{50}$ for one or more HTRs of less than 1 μM, less than 0.5 μM, less than 0.1 μM, less than 0.05 μM, or less than 0.01 μM.

In some embodiments, disclosed compounds will have relatively high selectivity at HTRs compared to known compounds, or compared to other receptors. In some embodiments, disclosed compounds will have relatively high selectivity at $HTR_{2A}$ and/or $HTR_2c$ receptors relative to any of other $HTR_2$ receptors or other HTR subfamilies, e.g., $HTR_1$, $HTR_3$, HTRs, $HTR_6$, and $HTR_7$, other monoaminergic receptors, such as norepinephrine receptors, e.g., α1A, α1B, α1C, α2A, α2B, α2C, and dopamine receptors, e.g., D1, D2, D3, D4, D5. In some embodiments, disclosed compounds have fewer off-target effects, including adverse effects. In some embodiments, fewer off-target effects comprises enhanced potency at $HTR_{2A}$ and/or $HTR_2c$ relative to other HTRs and other monoaminergic receptors, including dopamine and norepinephrine receptors.

In some embodiments, disclosed compounds are $HTR_{2A}$ agonists. In some embodiments, disclosed compounds activate, such as agonize, $HTR_{2A}$. In some embodiments, disclosed compounds are selective $HTR_{2A}$ agonists. In some embodiments, selectively activating $HTR_{2A}$ comprises having an $EC_{50}$ for $HTR_{2A}$ that is reduced by at least 10%, 25%, 50%, 75%, 100%, 150%, 200%, 250%, or 500% relative to the HTR at which the compound is next most potent. In one representative example, the HTR at which a compound is next most potent would be $HTR_{2B}$ in an exemplary scenario wherein the compound has an $EC_{50}$ of less than 10 μM at only $HTR_{2A}$ and $HTR_{2B}$, and the compound has the greatest potency (lowest $EC_{50}$) at $HTR_{2A}$.

In some embodiments, disclosed compounds are $HTR_2c$ agonists. In some embodiments, disclosed compounds activate, such as agonize, $HTR_2c$. In some embodiments, selectively activating $HTR_2c$ comprises having an $EC_{50}$ for $HTR_2c$ that is reduced by at least 10%, 25%, 50%, 75%, 100%, 150%, 200%, 250%, or 500% relative to the HTR at which the compound is next most potent. In some embodiments, disclosed compounds are $HTR_{2A}$ and $HTR_2c$ agonists.

In some embodiments, disclosed compounds modulate the activity of a dopamine receptor (DRD), such as any one or more of DRD1, DRD2, DRD3, DRD4, and DRD5. In some embodiments, disclosed compounds activate a DRD. In some embodiments, disclosed compounds agonize a DRD. In some embodiments, disclosed compounds antagonize a DRD. In some embodiments disclosed compounds agonize and/or antagonize a DRD. In some embodiments, disclosed compounds agonize a dopamine receptor. In some embodiments, disclosed compounds agonize DRD2. In some embodiments, disclosed compounds agonize or the DRD2 short isoform (DRD2S).

In some embodiments, disclosed compounds are HTR antagonists. In some embodiments, disclosed compounds inhibit the activity of one or more serotonin receptors (HTRs). In some embodiments, disclosed compounds antagonize one or more HTRs. In some embodiments, disclosed compounds are $HTR_2$ antagonists. In some embodiments, disclosed compounds are $HTR_{2B}$ antagonists. In some embodiments, disclosed compounds have an IC50 for $HTR_{2B}$ of less than 1 μM, less than 0.5 μM, or less than 0.1 μM.

Herein, the term "agonist" refers to a substance that activates a receptor, e.g., a serotonin receptor (HTR), and may describe either a partial or a full agonist and the activity thereof. Herein, the term "antagonist" refers to a substance that inhibits activation of a receptor. Determining agonism and antagonism, and measuring $EC_{50}$ and $IC_{50}$, respectively, may be determined according to methods available to one of skill in the art. In one example, measuring Gq-mediated calcium flux is a known method for assessing modulation, e.g., activation, of $HTR_{2A}$, a widely recognized target of psychedelic compounds. See, e.g., Klein et al., ACS Pharmacol Transl Sci. 2020 14; 4(2):533-542; Flanagan et al., ACS Pharmacol Transl Sci. 2020; 4(2):488-502; Toro-Sazo et al., PLoS One. 2019; 14(1):e0209804; Halberstadt et al., Psychopharmacology (Berl). 2019; 236(2):799-808. As would be recognized by one of skill, a partial agonist is one that shows reduced maximum efficacy ($E_{MAX}$) relative to a full agonist ($E_{MAX}$=100%), e.g., serotonin in the example of an HTR.

In some embodiments, disclosed compounds or compositions thereof, when administered in a pharmacologically effective amount, act on or modulate one or more membrane transporters, including any one or more of a serotonin membrane transporter (SERT), a dopamine membrane transporter (DAT), a norepinephrine membrane transporter (NET), and a vesicular monoamine transporter (VMAT). In some embodiments, disclosed compounds block the uptake activity of monoamine transporters. In some embodiments, disclosed compounds block the uptake activity of one or more of a serotonin transporter (SERT), dopamine transporter (DAT), and norepinephrine transporter (NET).

In some embodiments, disclosed compounds inhibit the uptake activity of any one or more of SERT, DAT, and NET. In some embodiments, disclosed compounds inhibit the uptake activity of SERT, DAT, and NET. In some embodiments, disclosed compounds have an in vitro $IC_{50}$ of less than 10 μM for any one or more of SERT, DAT, and NET.

In some embodiments, disclosed compounds do not inhibit the uptake activity of any one or more of SERT, DAT, and NET. In some embodiments, disclosed compounds do not inhibit the uptake activity of SERT, DAT, and NET. In some embodiments, disclosed compounds have an in vitro $IC_{50}$ of greater than 10 μM for any one or more of SERT, DAT, and NET.

Determining whether a disclosed compound inhibits the uptake activity of a monoamine transporter, or whether such activity is lacking, may be determined according to available methods, which may include live-cell fluorescent assays or radioactive assays. In some examples, inhibition of monoamine uptake may be determined in rat synaptosomes or human platelets. See, e.g., Segonzac et al., J Neurochem. 1985; 44(2):349-56; Cozzi et al., J Neural Transm (Vienna). 2009; 116(12):1591-9. In some examples, inhibitory activity may be compared to uptake inhibitors having low nm potency, e.g., DAT inhibitor GBR 12909, NET inhibitor desipramine, and SERT inhibitor clomipramine.

In some embodiments, administration of a composition of the present disclosure that comprises a disclosed fluorine-substituted phenylalkylamine, according to the methods described herein, will have an improved pharmacological profile, such as a relative increase in agonism of serotonin receptors compared to dopamine and/or norepinephrine receptors, compared to a corresponding non-substituted composition, which may be an increase of 5% or more, 10% or more, 25% or more, or 50% or more, and including amounts in between. Measurements of agonism of a receptor will be as understood by those in the art or by reference to the general knowledge in the art.

In some embodiments, an improved pharmacological profile of a composition of the present disclosure that comprises a disclosed fluorine-substituted phenylalkylamine will be a relative increase in extracellular concentration of serotonin compared to dopamine and/or norepinephrine, compared to a corresponding non-substituted composition, which may be an increase of 5% or more, 10% or more, 25% or more, or 50% or more, and including amounts in between. Measurements of extracellular concentration of a neurotransmitter will be as understood by those in the art or by reference to the general knowledge in the art.

In some embodiments, administration of a composition of the present disclosure that comprises a disclosed deuterium-substituted phenylalkylamine, according to the methods described herein, will have an improved pharmacological profile, such as a relative increase in agonism of serotonin receptors compared to dopamine and/or norepinephrine receptors, compared to a corresponding non-substituted composition, which may be an increase of 5% or more, 10% or more, 25% or more, or 50% or more, and including amounts in between. Measurements of agonism of a receptor will be as understood by those in the art or by reference to the general knowledge in the art.

In some embodiments, an improved pharmacological profile of a composition of the present disclosure that comprises a disclosed deuterium-substituted phenylalkylamine will be a relative increase in extracellular concentration of serotonin compared to dopamine and/or norepinephrine, compared to a corresponding non-substituted composition, which may be an increase of 5% or more, 10% or more, 25% or more, or 50% or more, and including amounts in between. Measurements of extracellular concentration of a neurotransmitter will be as understood by those in the art or by reference to the general knowledge in the art.

Detecting a change in monoamine levels in a subject, such as an increase or a decrease, can be achieved according to methods known to one of skill, for example, brain microdialysis (Chefer et al., Curr Protoc Neurosci. 2009; Chapter: Unit 7.1; Darvesh et al., Expert Opin Drug Discov. 2011; 6(2): 109-127) and brain imaging, for example, positron emission tomography (PET) and single photon emission computed tomography (SPECT) (see e.g., Wong & Gjedde, Encyclopedia of Neuroscience, 2009; 939-952 and Takano, Front Psychiatry., 2018; 9:228).

In some embodiments, disclosed compounds are not substrates for monoamine oxidase enzymes. In some embodiments, disclosed compounds do not inhibit the activity of monoamine oxidase enzymes. In some embodiments, disclosed compounds are not substrates for monoamine oxidase A (MAO-A). In some embodiments, disclosed compounds do not inhibit the activity of MAO-A. In some embodiments, the in vitro $IC_{50}$ of disclosed compounds at MAO-A is greater than 10 μM. In some embodiments, disclosed compounds are orally bioavailable. In some embodiments, the disclosed compositions, when administered in a pharmacologically effective amount, inhibit a monoamine oxidase enzyme, including MAO-A and MAO-B.

In some embodiments, administration of a disclosed fluorine-substituted composition according to the methods herein will affect a decreased inhibition of, and/or metabolism by, at least one cytochrome P450 enzyme or monoamine oxidase isoform (e.g., MAO-A or MAO-B) in a subject during treatment, as compared to a corresponding non-substituted composition, which may be a decrease of 5% or more, 10% or more, 25% or more, or 50% or more, and including amounts in between. Measurements of inhibition and metabolism will be as understood by those in the art or by reference to the general knowledge in the art (see, e.g., Ko et al., Br J Clin Pharmacol, 2000; 49(4), 343-351; Uebelhack, Franke & Schewe, Pharmacopsych, 1998; 31(5), 187-192; Weyler & Salach, J Biol Chem, 1985; 260(24), 13199-13207).

b. Treatment

In some aspects are provided methods for using therapeutically effective amounts of the disclosed compounds and pharmaceutical compositions thereof in a mammal, and preferably a human. Such methods include those for treating a mental health disorder and for improving mental health and functioning, including in a healthy individual. In some embodiments, the disclosed compounds are used to treat a condition, such as a disease or a disorder. In some embodiments, described herein are disclosed compounds for use in treating a condition, such as a disease or a disorder. In some embodiments, the disclosed compounds are used in the manufacture of a medicament to treat a condition, such as a disease or disorder. In some embodiments, described are methods of administering disclosed compounds to a subject having a condition, such as a disease or disorder, thereby treating said condition.

In some embodiments, disclosed compounds or pharmaceutical compositions comprising the disclosed compounds are administered to a subject by one or more routes of administration, including, e.g., oral, mucosal, rectal, subcutaneous, intravenous, intramuscular, intranasal, inhaled, and transdermal routes. When administered through one or more of such routes, the compound(s) of the invention and the disclosed compositions and formulations comprising them are useful in methods for treating a patient in need of such treatment.

As used herein, "an effective amount" or "a pharmacologically effective amount" refers to an amount of an active agent that is non-toxic and sufficient to provide the desired therapeutic effect with performance at a reasonable benefit/risk ratio attending any medical treatment. The effective amount will vary depending upon the subject and the disease condition being treated or health benefit sought, the weight and age of the subject, the severity of the disease condition or degree of health benefit sought, the manner of administration, and the like, all of which can readily be determined by one of ordinary skill in the art.

Herein, "therapeutic effect" or "therapeutic efficacy" means the responses(s) in a mammal, and preferably a human, after treatment that are judged to be desirable and beneficial. Depending on the disorder to be treated, or improvement in mental health or functioning sought, and depending on the particular constituent(s) in the disclosed compositions under consideration, those responses may therefore differ, but would be readily understood by those of ordinary skill.

Measures of therapeutic effect includes any outcome measure, endpoint, effect measure, or measure of effect within clinical or medical practice or research which is used to assess the effect, both positive and negative, of an intervention or treatment, whether patient-reported (e.g., questionnaires), based on other patient data (e.g., patient monitoring), gathered through laboratory tests such as blood work, urine samples, etc., through medical examination by a doctor or other medical professional, or by digital tools or means, e.g., electronic tools such as online tools, smartphones, wireless devices, biosensors, or health apps.

In some embodiments, measures of therapeutic effect will include an assessment. "Assessment" refers to any means or method used with a patient, whether before, during, after, or unrelated in time to a specific treatment protocol, to measure, estimate, or evaluate a nature, ability, symptom, disorder, or other characteristic of the patient, whether qualitatively or quantitatively, and whether performed by the therapist or other clinician (e.g., an interview), by the patient his or herself (e.g., a self-reported questionnaire), by a third-party or by a computer, including a medical device (e.g., as such as defined by the FDA or other regulatory body) or other device (e.g., a medical sensor or biosensor, a watch or fitness tracker, or a "wearable"), and whether graded by a human decision-maker or an artificial intelligence, machine learning, or computer algorithm. Non-limiting examples of assessments include those in Table 28 below.

TABLE 28

| | Exemplary Patient Assessments |
|---|---|
| 1 | The Mini International Neuropsychiatric Interview 5 (MINI 5) (Sheehan et al. 1998) to screen for comorbid psychiatric disorders. |
| 2 | The Columbia Suicide Severity Rating Scale (C-SSRS) (Mundt, JC et al. 2013), to screen for acute and recent suicide and self-harm thoughts and behaviors, taking approximately five minutes to complete. |
| 3 | The Patient Health Questionnaire (PHQ-9) (Kroenke et al. 2001). A brief self-administered screening questionnaire for depressive symptoms. |
| 4 | Generalized Anxiety Disorder 7 (GAD-7) (Spitzer et al. 2006) is a self-reported questionnaire for screening and severity measuring of generalized anxiety disorder. |
| 5 | Pittsburgh Sleep Quality Index (PSQI) (Buysse 1989) is used to assess the level of sleep disturbance. |

TABLE 28-continued

| Exemplary Patient Assessments | |
|---|---|
| 6 | Interpersonal reactivity Index (IRI) (Davis 1980) comprises 28 items answered on a 5 point scale. This scale measures different aspects of empathy and provides different subscales relating to these. |
| 7 | The Short Form (36) Health Survey (SF-36) is a gold standard patient-reported measure of quality of life. |
| 8 | The Self-Compassion Scale (SCS) (Neff 2003) Comprises 26 items answered on a 5 point scale. This scale measures core aspects of self-compassion including components of mindfulness. |
| 9 | The Trauma History Questionnaire (THQ) (Green 1996) is a self-report measure that examines experiences with potentially traumatic events using a yes/no format. For each event endorsed, respondents are asked to provide the frequency of the event as well as their age at the time of the event. |

An assessment may be computer-assisted, and other computer-assisted assessments may be performed besides the assessments above. The term “computer-assisted” in “computer-assisted assessment” means an assessment comprising the use of electronic tools such as online tools, smartphones, wireless devices, or health apps (in some such examples, also known as “digital phenotyping”). Computer-assisted assessment will include the use of an electronic psychiatric notes system, where relevant clinical information will be recorded for the duration of the therapy by a therapist interacting face-to-face with a patient, and will also include the use of computer systems where the therapist and patient interact virtually (either synchronously or asynchronously), as well as where a patient only interacts with a computer (“computer” broadly meaning any electronic tool suitable for such purposes, including desktop, laptop, and notebook computers; tablets, smartphones, and other mobile devices; watches, fitness trackers, and personal electronic devices; and the like). One or more other aspects of a psychosocial, behavioral, or drug-assisted therapy also may be “computer-assisted,” wherein one or more steps of such therapy involve the use of a computer in addition to or as a replacement for some work which would otherwise be performed by a therapist.

In embodiments, the invention provides methods of treating and/or preventing a condition in a mammal, the method comprising administering to the mammal a therapeutically effective and/or prophylactically effective amount of a formulation with one or more active agents. As used herein, “treating” or “treatment” covers any treatment of a disorder in a mammal, and preferably in a human, and includes causing a desired biological or pharmacological effect as above, as well as any one or more of: (a) preventing a disorder from occurring in a subject who may be predisposed to the disorder but has not yet been diagnosed with it; (b) inhibiting a disorder, i.e. arresting its development; (c) relieving a disorder, i.e., causing regression thereof, (d) protection from or relief of a symptom or pathology caused by or related to a disorder; (e) reduction, decrease, inhibition, amelioration, or prevention of onset, severity, duration, progression, frequency or probability of one or more symptoms or pathologies associated with a disorder; and (f) prevention or inhibition of a worsening or progression of symptoms or pathologies associated with a disorder or comorbid with a disorder. Other such measurements, benefits, and surrogate or clinical endpoints, alone or in combination, will be understood to one of ordinary skill based on the teachings herein and the knowledge in the art.

Herein, “an effective amount,” a “therapeutically effective amount,” or “a pharmacologically effective amount” refers to an amount of an active agent that is non-toxic and sufficient to provide the desired therapeutic effect with performance at a reasonable benefit/risk ratio attending any medical treatment. The effective amount will vary depending upon the subject and the disease condition being treated or health benefit sought, the weight and age of the subject, the severity of the disease condition or degree of health benefit sought, the manner of administration, and the like, all of which can readily be determined by one of skill.

Herein, “therapeutic effect” or “therapeutic efficacy” means the responses(s) in a mammal, and preferably a human, after treatment that are judged to be desirable and beneficial. Hence, depending on the disorder to be treated, or improvement in mental health or functioning sought, and depending on the particular constituent(s) in the formulations of the invention under consideration, those responses shall differ, but would be readily understood by those of skill.

i. Mental Health Disorders

In some embodiments, the disclosed compounds are used to treat mental health disorders. In some embodiments, disclosed compounds are administered, such as in a pharmacologically effective amount, to a subject having a mental health disorder, thereby treating said mental health disorder. In some methods herein, the disclosed compositions, when administered in a pharmacologically effective amount, provide beneficial therapeutic effects for the treatment of mental health disorders.

“Mental health disorder” refers to a disease condition in a mammal, and preferably in a human, that generally involves negative changes in emotion, mood, thinking, and/or behavior. In some embodiments, disclosed compounds are used to treat mental health disorders, including any of depression, major depressive disorder, treatment-resistant depression, dysthymia, anxiety and phobia disorders, generalized anxiety, social anxiety, panic, end-of-life anxiety, anxiety associated with a terminal illness, cancer-related anxiety, post-traumatic stress and adjustment disorders, feeding and eating disorders (including binge eating, bulimia, and anorexia nervosa), other binge behaviors, body dysmorphic syndromes, a substance use disorder, such as any of alcohol use disorder, *cannabis* use disorder, hallucinogen use disorder, inhalant use disorder, opioid use disorder, nicotine dependence and tobacco use disorder, sedative, hypnotic, and anxiolytic use disorder, and stimulant use disorder, drug abuse or dependence disorders, disruptive behavior disorders, impulse control disorders, gaming disorders, gambling disorders, memory loss, dementia of aging, attention deficit hyperactivity disorder, personality disorders (including antisocial, avoidant, borderline, histrionic, narcissistic, obsessive compulsive, paranoid, schizoid and schizotypal personality disorders), attachment disorders, autism, and dissociative disorders, and such other mental health disorders as will be known to one of skill.

For instance, other classifications and examples of mental health disorders include those disclosed in Merck Manual of Diagnosis and Therapy, 20th Ed. (2018), i.e., anxiety and stressor-related disorders, dissociative disorders, eating disorders, mood disorders, obsessive-compulsive and related disorders, personality disorders, schizophrenia and related disorders, sexuality, gender dysphoria, and paraphilias, somatic symptom and related disorders, suicidal behavior and self-injury, and substance-related disorders, which includes substance-induced and substance use disorders.

A mental health disorder, where otherwise undefined, will be understood to refer to the disorder as defined in the DSM-5. Although such terms generally shall refer to the criteria in the DSM-5, or a patient with a diagnosis based thereon, it will be appreciated that the compositions and disclosed methods are equally applicable to patients having the equivalent underlying disorder, whether that disorder is diagnosed based on the criteria in DSM-5 or in DSM-IV, whether the diagnosis is based on other clinically acceptable criteria, or whether the patient has not yet had a formal clinical diagnosis.

In some embodiments, disclosed compounds are used to treat "trauma- and stressor-related disorders," which include acute stress disorder, adjustment disorders, and post-traumatic stress disorder (Merck Manual, 20th Ed.), as well as reactive attachment disorder, disinhibited social engagement disorder, and others (DSM-5), including such stressor-related disorders as brief psychotic disorder with marked stressor(s), and other disorders associated with psychological trauma. In certain embodiments, the mental health disorder of the invention is specifically PTSD.

While the neurophysiology underlying mental health disorders may be distinct, an aspect in common of many is the presence of a deleterious, repetitive, and often "rigid" thought process that negatively impacts an individual's ability to function. For someone with PTSD, for instance, symptoms involve re-experiencing trauma and the feelings associated with it; for depression it can take the form of a recurrent internal editor that attaches negative connotations to normal life events; and for addiction it is the preoccupation with acquiring and using the substance of choice. Thus, in many embodiments, the method of treating a mental health disorder involves the treatment of a disorder related to rigid modes of thinking. In different embodiments, the disorder related to rigid modes of thinking can be anxiety, depression, addiction, an eating disorder, obsessive compulsive disorder, or PTSD.

In some embodiments, the pharmaceutical compositions and formulations of the invention are used to reduce the symptoms of a mental health disorder. The symptoms of the mental health disorder to be treated shall be able to be determined by one of skill in the art, by reference to the general understanding of the art regarding that disorder.

Symptoms of PTSD, for example, include transient waking dissociative states in which events are relived as if happening ("flashbacks"), nightmares, distressing and intense memories, other intrusive negative memories, distress or physical reactions after being exposed to triggers, blaming self or others for the trauma, decreased interest in things that were once enjoyable and other feelings of emotional numbness, negative feelings about self and the world, inability to remember the trauma clearly, difficulty feeling positive, feelings of isolation, negative affect, difficulty feeling positive, other negative alterations in cognition and mood, avoidance, aggression or irritability, hypervigilance and hyper-awareness, difficulty concentrating, difficulty sleeping, heightened startle response, engaging in self-destructive, or risky behavior, difficulty sleeping or staying asleep, and suicidal ideation. Accordingly, disclosed methods that reduce the symptoms of PTSD would be understood to reduce any such symptoms.

As would be apparent to one of skill, symptoms for each mental health condition will be different, however, through medical monitoring (such as monitoring of objective measurements, as described herein), patient reporting (such as, but not limited to through journaling), completion of questionnaires, etc., one will be able to objectively determine if a symptom has reduced in its frequency and/or magnitude.

In some embodiments, measures of therapeutic efficacy include reports by a subject or an observer. In some embodiments, measures of therapeutic efficacy include responses to a questionnaire. Non-limiting representative examples of applicable measures of symptom improvement include The Generalized Anxiety Disorder Scale-7 (GAD-7), the Montgomery-Asberg Depression Rating Scale (MADRS), Global Assessment of Functioning (GAF) Scale, Clinical Global Impression (CGI), The Substance Abuse Questionnaire (SAQ), and related subject- or observer-reported measures.

ii. Neurodegenerative Conditions

In some embodiments, disclosed compounds are used to treat a neurodegenerative disorder. In some embodiments, disclosed compounds are administered, such as in a pharmacologically effective amount, to a subject having a neurodegenerative disorder, thereby treating said neurodegenerative disorder. In some methods herein, the disclosed compositions, when administered in a pharmacologically effective amount, provide beneficial therapeutic effects for the treatment of said neurodegenerative disorder.

In some embodiments, the neurodegenerative disorder is any of Alzheimer's disease (AD), corticobasal degeneration (CBD), a form of dementia, Huntington's disease, Lytico-Bodig disease, mild cognitive impairment (MCI), a motor neuron disease, progressive supranuclear palsy (PSP), multiple sclerosis, Parkinson's disease, and traumatic brain injury (TBI). In some embodiments, the form of dementia is any of frontotemporal dementia (FTD), Lewy body dementia, tangle-predominant senile dementia, Pick's disease (PiD), argyrophilic grain disease, Guam parkinsonism-dementia complex, frontotemporal dementia with parkinsonism-17 (FTDP-17), and vascular dementia. In some embodiments, the motor neuron disease is any of amyotrophic lateral sclerosis (ALS), progressive bulbar palsy (PBP), pseudobulbar palsy, progressive muscular atrophy (PMA), primary lateral sclerosis (PLS), spinal muscular atrophy (SMA) and monomelic amyotrophy (MMA).

Neurodegenerative conditions can be classified according to primary clinical features, e.g., dementia, parkinsonism, or motor neuron disease, anatomic distribution of neurodegeneration, e.g., frontotemporal degenerations, extrapyramidal disorders, or spinocerebellar degenerations, or principal molecular abnormality (Dugger & Dickson, Cold Spring Harb Perspect Biol. 2017; 9(7):a028035.

A feature of neurodegenerative conditions is neuronal cell death, which, among other aspects, is implicated in the promotion of inflammation. See, e.g., Chan et al., Annu Rev Immunol. 2015; 33: 79-106 and Chi et al., Int J Mol Sci. 2018; 19(10):3082. Neurodegeneration may be assessed, e.g., by measuring markers of neuronal loss, such as cerebrospinal fluid markers, e.g., visinin-like protein 1 (VILIP-1), tau, and p-tau181 (Tarawneh et al., Neurol. 2015; 72(6): 656-665). In another example, Alzheimer's disease may be assessed using any of biomarket PET scans, blood tests, CSF tests, and neuropsychological assessments, e.g., to assess the presence of amyloid plaque and aggregated tau. Cognitive decline may also be used as a measure of neurodegeneration. Methods for assessing cognitive decline, e.g., comprehensive neuropsychological testing, are known to one of skill in the art. Exemplary cognitive evaluations include Mini-Mental State Examination (MMSE) and Montreal Cognitive Assessment (MoCA). See, e.g., Toh et al., Transl Neurodegener. 2014; 3:15. Cognitive decline and the progression of disease state may also be assessed using a condition-specific measure, e.g., the Unified Huntington's Disease Rating Scale (UHDRS).

iii. Pain and Inflammation

In some embodiments, the disclosed compounds are used to treat pain and/or inflammation, such as a pain disorder and/or an inflammatory disorder. In some embodiments, disclosed compounds are administered, such as in a pharmacologically effective amount, to a subject having pain and/or inflammation, thereby treating said pain and/or inflammation. In some methods, the disclosed compositions, when administered in a pharmacologically effective amount, provide beneficial therapeutic effects for the treatment of pain and/or inflammation.

In some embodiments, disclosed compounds are used to treat a pain disorder. In some embodiments, the pain disorder is any of arthritis, allodynia, atypical trigeminal neuralgia, trigeminal neuralgia, somatoform disorder, hypoesthesia, hyperalgesia, neuralgia, neuritis, neurogenic pain, phantom limb pain, analgesia, anesthesia dolorosa, causalgia, sciatic nerve pain disorder, degenerative joint disorder, fibromyalgia, visceral disease, chronic pain disorders, headache disorders, migraine headaches, chronic cluster headaches, concussion headache, short-lasting unilateral neuralgiform headache attacks, chronic fatigue syndrome, complex regional pain syndrome, neurodystrophy, plantar fasciitis, or pain associated with cancer.

In some embodiments, disclosed compounds are used to treat an inflammatory disorder. In some embodiments, the inflammatory disorder is characterized by inflammation of an organ or tissue. In some embodiments, the inflammatory disorder comprises any one or more of skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, gastric inflammation, intestinal inflammation, neuroinflammation, and brain inflammation. In some embodiments, the inflammatory disorder is a disorder that causes acute inflammation, or that exhibits chronic inflammation as a symptom. In some embodiments, the inflammatory disorder comprises chronic inflammation.

In some embodiments, the inflammatory disorder is any of acne vulgaris, oxalic acid/heartburn, age-related macular degeneration (AIMD), allergies, allergic rhinitis, Alzheimer's disease, amyotrophic lateral sclerosis, Anemia, appendicitis, arteritis, arthritis, including osteoarthritis, rheumatoid arthritis, juvenile idiopathic arthritis, spondyloarthropathy such as ankylosing spondylitis, reactive arthritis (Reiter syndrome), psoriatic arthritis, enteroarthritis associated with inflammatory bowel disease, Whipple and Behcet's disease, septic arthritis, gout (also known as gouty arthritis, crystalline synovitis, metabolic arthritis), pseudogout (calcium pyrophosphate deposition disease), and Still's disease. Arthritis can affect a single joint (monoarthritis), two to four joints (oligoarthritis), or five or more joints (polyarthritis).

In some embodiments, the inflammatory disorder is any of long COVID, a food allergy, post-treatment lyme disease syndrome, and an ulcer. In some embodiments, an inflammatory disorder is any of asthma, atherosclerosis, autoimmune disorder, balanitis, blepharitis, bronchiolitis, bronchitis, bullous pemphigoid, burns, bursitis, cancer, including NF-κB-induced inflammatory cancer; cardiovascular disease, including hypertension, endocarditis, myocarditis, heart valve dysfunction, congestive heart failure, myocardial infarction, diabetic heart abnormalities, vascular inflammation, including arteritis, phlebitis, and vasculitis; arterial occlusive disease, including arteriosclerosis and stenosis; inflammatory cardiac hypertrophy, peripheral arterial disease, aneurysm, embolism, incision, pseudoaneurysm, vascular malformation, vascular nevus, thrombosis, thrombophlebitis, varicose veins, stroke, cardiac arrest, and carditis; celiac disease, cellulitis, cervicitis, cholangitis, cholecystitis, chorioamnionitis, chronic obstructive pulmonary disease (COPD), cirrhosis, congestive heart failure, conjunctivitis, colitis, cyclophosphamide-induced cystitis, cystic fibrosis, cystitis, lacrimal inflammation, and dementia.

In some embodiments, the inflammtory disorder is any of dermatitis, including atopic dermatitis, chronic photosensitivity dermatitis, eczema, atopic eczema, contact eczema, dryness eczema, seborrheic eczema, sweating disorders, discoid eczema, venous eczema, herpetic dermatitis, neurodermatitis, and autosensitizing dermatitis, stasis dermatitis, purulent sweaty, lichen planus, psoriasis, including psoriasis vulgaris, nail psoriasis, prickly psoriasis, scalp psoriasis, inverse psoriasis, pustular psoriasis, erythrodermic psoriasis, and psoriatic arthritis; rosacea, and scleroderma, including morphea; pharmacologically induced inflammation, including from legal or illegal drugs, and chemicals; chronic neurogenic inflammation, including primary and secondary neural inflammation; dermatomyositis, diabetes, diabetic neuropathy, diabetic retinopathy, diabetic nephropathy, diabetic ulcer, digestive system disease, emphysema, encephalitis, endocarditis, endometritis, enterocolitis, epicondylitis, epididymis, fasciitis, fibromyalgia, fibrosis, connectitis, gastritis, gastroenteritis, gingivitis, glomerulonephritis, glossitis, heart disease, heart valvular dysfunction, hepatitis, purulent spondylitis, Huntington's disease, hyperlipidemic pancreatitis, hypertension, ileitis, infection, including lymphangitis, lymphadenitis, bacterial cystitis, bacterial encephalitis, pandemic influenza, viral encephalitis, and viral hepatitis (types A, B, and C); inflammatory bowel disease, including Crohn's disease; inflammatory heart enlargement, inflammatory neuropathy, insulin resistance, between interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), migraine, multiple sclerosis, myelitis, myocarditis, myositis, nephritis, non-alcoholic steatohepatitis, obesity, umbilitis, ovitis, testitis, osteochondritis, osteopenia, osteomyelitis, osteoporosis, osteomyelitis, otitis, pancreatitis, Parkinson's disease, parotitis, pelvic inflammatory disease, pemphigus vulgaris, pericarditis, peritonitis, pharyngitis, phlebitis, pleurisy, interstitial pneumonia, polycystic nephritis, polymyositis, proctitis, prostatitis, psoriasis, pulpitis, pyelonephritis, portal vein, renal failure, reperfusion injury, retinitis, rheumatic fever Rhinitis, fallopianitis, sarcoidosis, salivary glanditis, sepsis, including bacteremia and viremia; sinusitis, spastic colon, stenosis, stomatitis, stroke, inflammation associated with surgical complications, synovitis, tendonitis, tendonitis, tendonitis, thrombophlebitis, tonsillitis, trauma, traumatic brain injury, graft rejection, including graft versus host disease (GVHD);

a Thl-mediated inflammatory disease, trigonitis, tuberculosis, tumor, urethritis, bursitis, uveitis, vaginitis, vasculitis, including Buerger's disease, cerebral vasculitis, Churg-Strauss arteritis, cryoglobulinemia, essential cryoglobulin vasculitis, giant cells arteritis, golfer vasculitis, Henoch-Schonlein purpura, hypersensitivity vasculitis, Kawasaki disease, microscopic polyarteritis/polyvasculitis, nodular polyarteritis, rheumatoid polymuscular muscle pain (PMR), rheumatic vasculitis, Takayasu arteritis, Wegener's granulomatosis, systemic lupus erythematosus (SLE), relapsing polychondritis, Behcet's disease; ulcerative colitis such as ulcerative proctitis, left side colitis, total colitis, and fulminant colitis; and vulvitis.

In some embodiments, the disclosed compounds are used to reduce inflammation. In some embodiments, the disclosed compounds are used in the manufacture of a medicament to reduce inflammation. In some embodiments, the disclosed compounds, e.g., in a therapeutically effective amount, are administered to a subject to reduce inflammation.

The International Association for the Study of Pain (IASP) defines pain as "an unpleasant sensory and emotional experience associated with actual or potential tissue damage, or described in terms of such damage." Although the mechanism for serotonin modulators, such as 5-HT2A agonists and 5-HT2A antagonists, to ameliorate pain remains unclear, the synaptic plasticity associated with such compounds may alter pathologic changes in neural connections seen in chronic pain states, potentially resulting in a reduced pain intensity and duration (Castellanos et al., Reg Anesth Pain Med. 2020; 45(7):486-494). Additionally, 5-HT2AR activation has been shown to promote anti-inflammatory effects, e.g., a reduction of TNF-α-induced inflammation. See, e.g., Pelletier & Siegel, Mol Interv., 2009; 9(6):299-301, Flanagan et al., Sci Rep. 2019; 9(1):13444, Nichols et al., Clin Pharmacol Ther. 2017; 101(2):209-219; Int Rev Psychiatry. 2018; 30(4):363-375, Okamoto et al., Neuroscience. 2005; 130(2):465-74.

Pain, such as chronic pain, and improvements thereof, such as a reduction of symptoms, may be measured according to known methods, e.g., by subject reporting, pain diaries, pain scales, applicable questionnaires (assessments of chronic pain and its impact on physical, emotional and social functions), ecological momentary assessments and computerized versions thereof. See, e.g., Salaffi et al., Best Practice & Research Clinical Rheumatology, 2015; 29(1): 164-186 and Hawker et al., Arthritis Care Res (Hoboken). 2011; 63 Suppl 11:S240-52. Exemplary questionnaires include the Visual Analog Scale for Pain (VAS Pain), Numeric Rating Scale for Pain (NRS Pain), McGill Pain Questionnaire (MPQ), Short-Form McGill Pain Questionnaire (SF-MPQ), Chronic Pain Grade Scale (CPGS), Short Form-36 Bodily Pain Scale (SF-36 BPS), and Measure of Intermittent and Constant Osteoarthritis Pain (ICOAP), Migraine Diagnosis Questionnaire, the Migraine-Screen Questionnaire (MS-Q), the Fibromyalgia Survey Questionnaire (FSQ).

A reduction in inflammation, such as chronic systemic inflammation, may be measured according to various methods available to one of skill. Inflammatory biomarkers may be detected from biological specimens, for example, a subject's blood, such as plasma or serum, or saliva. In one example, inflammation may be detected by measuring high-sensitivity C-reactive protein (CRP) and white blood cell count from a blood test. CRP may also be detected in a saliva sample. Salivary CRP is not synthesized locally in the mouth and may reflect more systemic levels of inflammation compared to other inflammatory biomarkers, such as cytokines (Szabo & Slavish, Psychoneuroendocrinology. 202; 124: 105069). Additionally clinical pathology data, e.g., hematology data on erythrocyte parameters, platelet count, total number of leukocytes, and leukocyte differentials and morphology, coagulation data on clotting times and fibrinogen, and clinical chemistry data on total protein, albumin and globulin, liver enzymes, renal parameters, electrolytes, and bilirubin can provide an initial indication of the presence and potentially the location of inflammation, in the absence of specific data on immune tissues. See, e.g., Germolec et al., Methods Mol Biol. 2018; 1803:57-79 and Luo et al., Clin Lab. 2019 1; 65(3).

iv. Mental Functioning

In some embodiments, the invention provides methods of improving mental health and/or functioning, such as cognitive functioning. Improvements in mental health and functioning may include one or more of a reduction of neuroticism or psychological defensiveness, an increase in creativity or openness to experience, an increase in decision-making ability, an increase in feelings of wellness or satisfaction, or an increase in ability to fall or stay asleep. Additionally, improvements in mental health and functioning may include improvements in or a return to baseline in processing speed, learning and memory, autobiographical memory, shifting, and IQ. Measurements of such will be readily understood and appreciated according to ordinary skill. See, e.g., cognitive functioning aspects reviewed by Ahern & Semskova, Neuropsychology. 2017; 31(1):52-72. Exemplary measures of improvements of mental health and/or functioning include the Global Assessment of Functioning (GAF) scale, the Sleep Quality Scale (SQS) and other measures of sleep quality (see, e.g., Fabbri et al., Int J Environ Res Public Health. 2021; 18(3):1082, and the Social Functioning Scale (SFS) (see, e.g., Chan et al., Psychiatry Res. 2019; 276:45-55). In some embodiments, the invention provides methods of improving mental health and/or functioning, such as cognitive functioning, in healthy people, such as "healthy normals," and the invention will thus include in some embodiments the "betterment of the well."

v. Psychedelic-Assisted Psychotherapy

In some embodiments, a disclosed compound or composition is administered together with psychotherapy, such as psychosocial or behavioral therapy, including any of (or adapted from any of) cognitive behavioral therapy (e.g., as described in Arch. Gen. Psychiatry 1999; 56:493-502), interpersonal therapy (e.g., as described in Psychol Addict Behav 2009; 23(1): 168-174), contingency management based therapy (e.g., as described in Psychol Addict Behav 2009; 23(1): 168-174; in J. Consul. Clin. Psychol. 2005; 73(2): 354-59; or in Case Reports in Psychiatry, Vol. 2012, Article ID 731638), motivational interviewing based therapy (e.g., as described in J. Consul. Clin. Psychol. 2001; 69(5): 858-62), meditation based therapy, such as transcendental meditation based therapy (e.g., as described in J. Consul. Clin. Psychol. 2000; 68(3): 515-52), or the therapeutic approach used by MAPS to treat patients with PTSD (e.g., as described in Mithoefer, M (2017). A Manual for MDMA-Assisted Psychotherapy in the Treatment of Post-traumatic Stress Disorder).

In some embodiments, "psychotherapy" is specifically "psychedelic-assisted psychotherapy." Psychedelic-assisted psychotherapy, broadly, includes a range of related approaches that involve at least one session where the patient ingests a psychedelic and is monitored, supported, or otherwise engaged by one or more trained mental health professionals while under the effects of the psychedelic (see, e.g., Schenberg 2018). Protocols have been developed for the standardization of procedures which emphasize a high degree of care (see, e.g., Johnson 2008), such as the therapeutic approach used by MAPS to treat patients with PTSD using MDMA (e.g., as described in Mithoefer 2017).

In some embodiments, the psychotherapy conducted with a disclosed compound is conducted in widely spaced sessions. These sessions can be as frequently as weekly but are more often approximately monthly or less frequently. In most cases, a small number of sessions, on the order of one to three, is needed for a patient to experience significant clinical progress, as indicated, for example, by a reduction in the symptoms of the mental health disorder being treated. In some embodiments, psychotherapy comprises multiple sessions, during some of which a disclosed compound is administered ("drug-assisted psychotherapy"); in others, the patient participates in psychosocial or behavioral therapy without concomitant administration of a drug, or without administration of a disclosed compound.

In some embodiments, a disclosed compound or composition is administered together with standardized psychological treatment or support, which refers to any accepted modality of standard psychotherapy or counseling sessions, whether once a week, twice a week, or as needed; whether in person or virtual (e.g., over telemedicine or by means of a web program or mobile app); and whether with a human therapist or a virtual or AI "therapist." As used herein, "therapist" refers to a person who treats a patient using the disclosed compositions and methods, whether that person is a psychiatrist, clinical psychologist, clinical therapist, registered therapist, psychotherapist, or other trained clinician, counselor, facilitator, or guide, although it will be understood that certain requirements will be appropriate to certain aspects of the drug-assisted therapy (e.g., prescribing, dispensing, or administering a drug, offering psychotherapeutic support). In some embodiments, a "person" may also include an AI.

In some embodiments, a patient will participate in a treatment protocol or a disclosed method, or be administered a disclosed composition as part of such a method, if the patient meets certain specified inclusion criteria, does not meet certain specified exclusion criteria, does not meet any specified withdrawal criteria during the course of treatment, and otherwise satisfies the requirements of the embodiment of the invention as claimed.

Preferably, where the disclosed pharmaceutical compositions are administered, such administration occurs without or with reduced risk of side effects that would require physician supervision, and therefore allow for treatment at home or otherwise outside of a clinic and without the need for such supervision, and/or additionally without the requirement of adjunctive psychotherapy (although it also may be provided in certain embodiments herein).

In some embodiments, the disclosed compositions may be administered in conjunction with or as an adjunct to psychotherapy. In other embodiments, psychotherapy is neither necessitated nor desired, or no specific type of psychotherapy is necessitated or desired, however any of the disclosed methods can be used in combination with one or more psychotherapy sessions. The flexibility to participate in specific therapies, as well as to choose between any such therapies (or to decide to forgo any specific therapy), while still receiving clinically significant therapeutic effects, is among the advantages of the invention. Furthermore, a patient can participate in numerous other therapeutically beneficial activities, where such participation follows or is in conjunction with the administration of the composition, including breathing exercises, meditation and concentration practices, focusing on an object or mantra, listening to music, physical exercise, stretching or bodywork, journaling, grounding techniques, positive self-talk, or engaging with a pet or animal, and it should be understood that such participation can occur with or without the participation or guidance of a therapist.

In some instances, certain personalized approaches (i.e., "personalized" or "precision" medicine) may be utilized, based on individual characteristics, including drug metabolism (e.g., CYP2D6 or CYP3A4) or individual genetic variation. The term "genetic variation" refers to a change in a gene sequence relative to a reference sequence (e.g., a commonly-found and/or wild-type sequence). Genetic variation may be recombination events or mutations such as substitution/deletion/insertion events like point and splice site mutations.

In one embodiment, the genetic variation is a genetic variation in one or more cytochrome P450 (CYP or CYP450) enzymes that affects drug metabolism, including metabolism of a disclosed composition, and including CYP1A2, CYP2C9, CYP2D6, CYP2C19, CYP3A4 and CYP3A5. Other examples of CYP enzymes include CYP1A1, CYP1B1, CYP2A6, CYP2A13, CYP2B6, CYP2C8, CYP2C9, CYP2C18, CYP2E1, CYP2G1, CYP2J2, CYP2R1, CYP2S1, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

In some embodiments, a disclosed composition is taken together with a compound that is metabolized by the same CYP enzyme(s) as the disclosed composition, so as to permit a lower dose to be taken, increase the effective bioavailability of one or both, or otherwise affect drug metabolism or pharmacokinetics. In some embodiments, the dose of a disclosed composition is adjusted when administered to a subject known to be a "poor metabolizer" of the active agent in the composition (e.g., having a genetic variation in CYP2D6, known to be the major metabolizer of the methylenedioxy moiety). In some embodiments, a genetic variation is an exclusion criteria for the administration of a disclosed compound.

In one embodiment, the genetic variation is a genetic variation in metabotropic glutamate receptor type 5 (mGluR5), which has been implicated in mood and anxiety symptoms in humans. In one embodiment the genetic variation is one or more single nucleotide polymorphisms (SNPs) in the FKBP5 gene that are associated with elevated levels of FKBP51 protein relative to persons lacking such SNPs. The FKBP5 gene has been implicated in responses to stress and trauma, and such SNPs are correlated with susceptibility to certain depression, PTSD, and anxiety disorders.

In one embodiment, the genetic variation is a genetic variation such as a SNP in a membrane transporter, such as SERT, DAT, NET, or VMAT.

In one embodiment, the mammal being treated has altered epigenetic regulation of a gene the expression of which is associated with a mental health condition or susceptibility to a mental health treatment, such as the SIGMAR1 gene for the non-opioid sigma-1 receptor.

E. Examples

Example 12: Synthesis of 2CB-2-$OCD_3$ (Compound I-B-31)

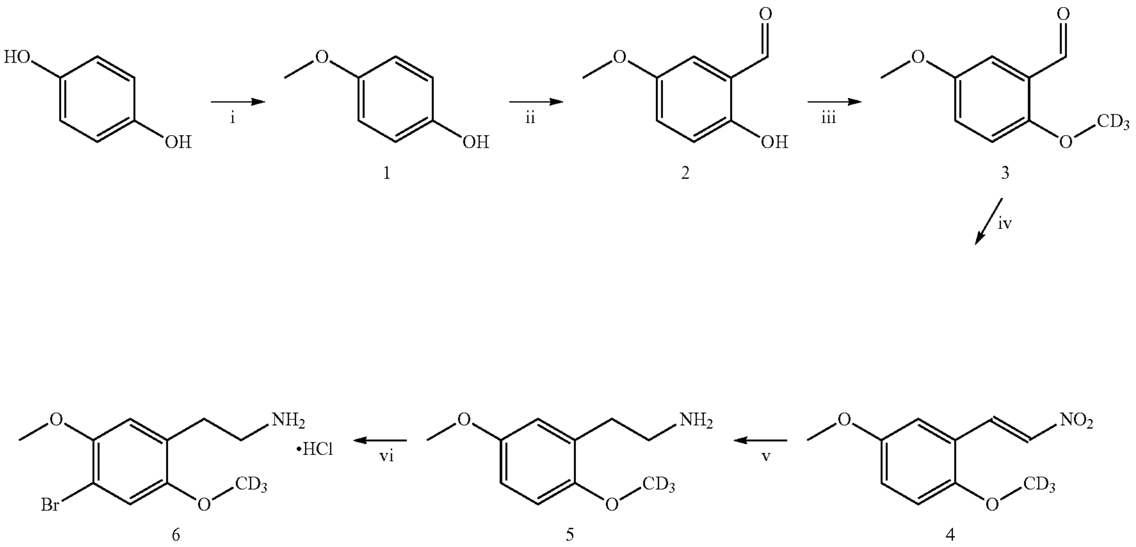

i: $NaNO_2$/MeOH/$H_2SO_4$; ii: NaOH/$CHCl_3$; iii: $K_2CO_3$/$CD_3I$; iv: EDDA/$CH_3NO_2$; v: LAH/$H_2SO_4$; vi: $Br_2$/$Na_2S_2O_3$/HCl 11 g hydroquinone (100 mmol), 345 mg $NaNO_2$ (5 mmol), 50 mL methanol (0.5 mL/mmol hydroquinone) were combined in a flask on a stir plate. 5.6 mL concentrated $H_2SO_4$ (100 mmol) was added dropwise and the solution allowed to stir. The reaction was monitored via GC-MS for the appearance of the target molecule and the disappearance of the starting substrate, and after approximately 3.5 hr, was quenched by pouring into 100 mL $H_2O$. The solution was then extracted with $CHCl_3$ (2×100 mL), dried with $Na_2SO_4$, and solvent removed under vacuum, leaving 12 g of partially crystalline crude 4-methoxyphenol (1).

12 g 4-methoxyphenol (1, 95.7 mmol), 32 g NaOH and 40 mL $H_2O$ (800 mmol) were combined in a flask on a stir plate with a condenser. 16 mL $CHCl_3$ (200 mmol) was added dropwise. After completion of the $CHCl_3$ addition, the solution was heated to reflux. After approximately 1 hr the reaction mixture was cooled to 10° C. with an ice bath, acidified to <pH 2 using 5M $H_2SO_4$, and extracted with EtOAc (2×100 mL). Organic layers were pooled, dried over $Na_2SO_4$, and the solvent removed under vacuum, leaving about 12.7 g as a dark mass. A silica column was used to separate the aldehyde, leaving about 6 g 2-hydroxy-5-methoxybenzaldehyde (2). 7.8 g (2) with 22.5 g $K_2CO_3$ (125 mmol) was suspended in 200 mL acetone on a stir-plate with a water-bath. 7.80 mL iodomethane-$d_3$ (50 mmol) was added dropwise, and the mixture brought to reflux. After 3.5 hrs, the reaction was cooled using a water-bath, poured into 200 mL $H_2O$, and extracted with EtOAc (2×200 mL). The organic layers were pooled, dried under $Na_2SO_4$, and the solvent was removed under vacuum, leaving ~6.8 g 5-methoxy-2-(methoxy-$d_3$)benzaldehyde (3).

To a stirred solution of 6.8 g 5-methoxy-2-(methoxy-$d_3$) benzaldehyde (3, 40 mmol), and 720 mg ethylenediamin-ediacetic acid (EDDA, 4 mmol) in 35 mL isopropyl alcohol (IPA), was added dropwise 2.6 mL nitromethane (48 mmol). Stirring was stopped, and the solvent was removed under vacuum, leaving a red oil which, upon standing, solidified as a bright orange mass weighing approximately 4 g (E)-4-methoxy-1-(methoxy-$d_3$)-2-(2-nitrovinyl)benzene (4).

To a chilled, stirred solution of 60 mL 1 M lithium aluminum hydride (LAH) in tetrahydrofuran (THF), was added dropwise 1.5 mL concentrated $H_2SO_4$, keeping the mixture below 10° C. After stirring for 10 min, 4.3 g (E)-4-methoxy-1-(methoxy-$d_3$)-2-(2-nitrovinyl)benzene (4, 20 mmol) in 30 mL THE was added dropwise and the solution was brought to reflux for 45 min. The solution was removed from heat and chilled to <10° C. $Na_2SO_4 \cdot 10\ H_2O$ was added until additional material no longer produced a reaction (approximately 3 g $Na_2SO_4 \cdot 10\ H_2O$ per g of LAH). The mixture was filtered, the filter cake washed with THF, and the solvent removed under vacuum, leaving approximately 4 g of 2-(5-methoxy-2-(methoxy-$d_3$)phenyl) ethan-1-amine (5) as an amber oil.

To a stirred solution of 4 g 2-(5-methoxy-2-(methoxy-$d_3$) phenyl)ethan-1-amine (5, 22 mmol) in 15 mL acetic acid was added dropwise 1.22 mL bromine (24 mmol) dissolved in 5 mL acetic acid. The solution was allowed to stir with gentle heating until solids formed. After solids formation, the reaction was quenched using 60 mL aqueous $Na_2S_2O_3$, the pH brought to >12 using 2M NaOH, and the mixture extracted with dichloromethane (3×40 mL). The organic layers were pooled, dried over $Na_2SO_4$, and the solvent was removed under vacuum. The oil was dissolved in IPA/$Et_2O$ and treated with concentrated aqueous HCl. Removal of solvent under vacuum gave the crude HCl salt, which after re-crystallization left approximately 2 g 2-(4-bromo-5-methoxy-2-(methoxy-$d_3$)phenyl)ethan-1-amine hydrochloride (6; 2CB-2-$OCD_3$; compound I-B-31).

Example 13: Synthesis of 2CB-5-$OCD_3$ (Compound I-A-31)

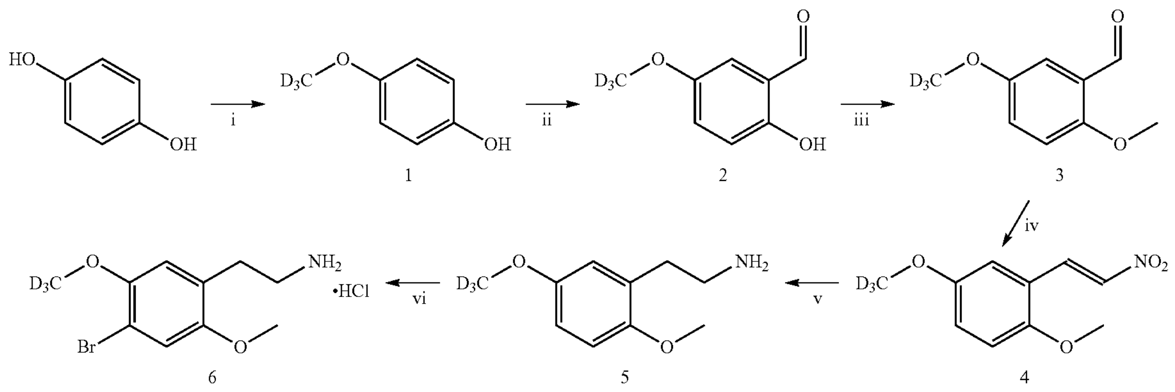

i: $NaNO_2$/MeOH/$H_2SO_4$; ii: NaOH/$CHCl_3$; iii: $K_2CO_3$/$CD_3I$; iv: EDDA/$CH_3NO_2$; v: LAH/$H_2SO_4$; vi: $Br_2$/$Na_2S_2O_3$/HCl 11 g hydroquinone (100 mmol), 345 mg $NaNO_2$ (5 mmol), 50 mL methanol-d4 (0.5 mL/mmol hydroquinone) were combined in a flask on a stir plate. 5.6 mL conc. $H_2SO_4$ (100 mmol) was added dropwise and the solution allowed to stir. The reaction was monitored via GC-MS for the appearance of the target molecule and the disappearance of the starting substrate, and after approximately 3.5 hrs, quenched by pouring into 100 mL $H_2O$. The solution was then extracted with $CHCl_3$ (2×100 mL), dried with $Na_2SO_4$, and solvent removed under vacuum, leaving 12.41 g of a partially crystalline crude solid with long needles of 4-(methoxy-$d_3$)phenol (1) of approximately 93% purity.

12.17 g 4-(methoxy-$d_3$)phenol (1, 95.7 mmol), 32 g NaOH and 40 mL $H_2O$ (800 mmol) were combined in a flask on a stir plate with a condenser. 16 mL $CHCl_3$ (200 mmol) was added dropwise. After completion of the $CHCl_3$ addition, the solution was heated to reflux. After approximately 1 hr, the reaction mixture was cooled to 10° C. with an ice bath, acidified to <pH 2 using 5M $H_2SO_4$, and extracted with EtOAc (2×100 mL). Organic layers were pooled, dried over $Na_2SO_4$, and the solvent removed under vacuum, leaving about 12.7 g as a dark mass. A silica column was used to separate the aldehyde, leaving 6.38 g of 2-hydroxy-5-(methoxy-$d_3$)benzaldehyde (2).

7.75 g 2-hydroxy-5-(methoxy-$d_3$)benzaldehyde (2, 50 mmol) and 22.5 g $K_2CO_3$ (125 mmol) were combined in 200 mL acetone on a stir-plate with a water-bath. 7.80 mL iodomethane was added dropwise, and the mixture brought to reflux. After 3.5 hr, the reaction was cooled using a water-bath, poured into 200 mL $H_2O$, and extracted with EtOAc (2×200 mL). The organic layers were pooled, dried under $Na_2SO_4$, and the solvent was removed under vacuum, leaving about 6.77 g of 2-methoxy-5-(methoxy-$d_3$)benzaldehyde (3).

To a stirred solution of 6.77 g 2-methoxy-5-(methoxy-$d_3$) benzaldehyde (3, 40 mmol), and 720 mg ethylenediaminediacetic acid (EDDA, 4 mmol) in 35 mL isopropyl alcohol (IPA), 2.6 mL nitromethane (48 mmol) was added dropwise. After a red color developed, stirring was stopped and the reaction was allowed to stand overnight, leaving (E)-1-methoxy-4-(methoxy-$d_3$)-2-(2-nitrovinyl)benzene (4) as a bright orange solid mass weighing approximately 4.24 g.

To a chilled, stirred solution of 60 mL 1 M lithium aluminum hydride (LAH) in tetrahydrofuran (THF) was added dropwise 1.5 mL concentrated $H_2SO_4$, keeping the mixture below 10° C. After stirring for 10 min, 4.24 g (E)-1-methoxy-4-(methoxy-$d_3$)-2-(2-nitrovinyl)benzene (4, 20 mmol) in 30 mL THF was added dropwise and the solution brought to reflux for 45 min. The solution was removed from heat and chilled to <10° C. $Na_2SO_4 \cdot 10H_2O$ was added until additional material no longer produced a reaction. The mixture was filtered, the filter cake washed with THF, and solvent removed under vacuum, leaving approximately 4 g of 2-(2-methoxy-5-(methoxy-$d_3$)phenyl) ethan-1-amine (5) as an amber oil.

To a stirred solution of 2 g 2-(2-methoxy-5-(methoxy-$d_3$) phenyl)ethan-1-amine (5, 10 mmol) in 10 mL acetic acid was added dropwise 515 μL bromine (10 mmol) dissolved in 5 mL acetic acid. The solution was allowed to stir with gentle heating until solids formed. After solids formation, the reaction was quenched using 30 mL aqueous $Na_2S_2O_3$, the pH brought to >12 using 2M NaOH and the mixture extracted with dichloromethane (3×40 mL). The organic layers were pooled, dried over $Na_2SO_4$, and solvent removed under vacuum. The oil was dissolved in IPA/$Et_2O$ and treated with concentrated HCl. Removal of solvent under vacuum, followed by recrystallization, gave approximately 1.26 g of 2-(4-bromo-2-methoxy-5-(methoxy-$d_3$) phenyl)ethan-1-amine hydrochloride (6; 2CB-5-OCD3, compound I-A-31).

Example 14: Synthesis of 2CB-5-OCF3 (Compound I-C-30)

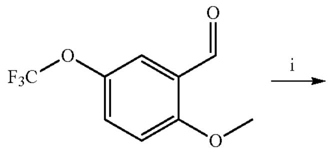

1

-continued

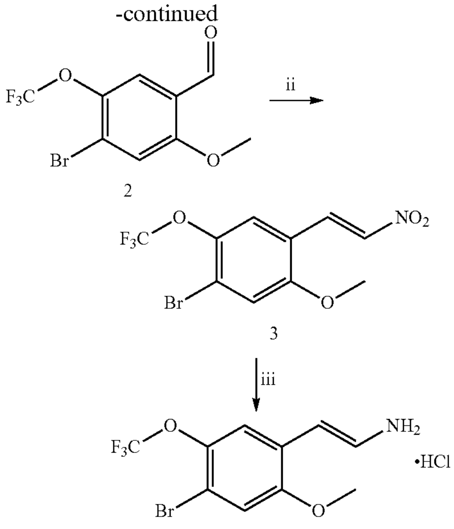

2

3

4 i: $H_2SO_4$/NBS; ii: $CH_3NO_2$/$NH_4CH_3CO_2$; iii: LAH/ $H_2SO_4$/HCl 5 g 2-methoxy-5-(trifluoromethoxy)benzaldehyde (1, 22.7 mmol), 20 mL THF, and 4 mL $H_2SO_4$ were slowly combined in a round-bottom flask with stirring. Over the next hour 6.06 g N-bromosuccinimide (NBS, 34.07 mmol) was added in small portions. The reaction was monitored via GC-MS for the appearance of the target and disappearance of the starting substrate. 1 hr after the completed addition of the NBS, the reaction mixture was slowly pipetted over 500 g ice with 200 mL saturated $NaHCO_3$ while mixing, at which point a chunky orange solid appeared and was washed into 200 mL $CH_2Cl_2$ (DCM). The aqueous layer was washed with an additional 100 mL DCM, the organic layers pooled and dried over $Na_2SO_4$, filtered and poured directly over a silica plug to strip color and residual NBS. Solvent was removed under vacuum, leaving 6.67 g 4-bromo-2-methoxy-5-(trifluoromethoxy)benzaldehyde (2, 98.5% yield).

3.25 g of 4-bromo-2-methoxy-5-(trifluoromethoxy)benzaldehyde (2, 10.87 mmol) was added to a stirring mixture of 5.4 mL nitromethane (100.87 mmol) and 77 g ammonium acetate (100.87 mmol). The reaction mixture volume was then brought to 50 mL using approximately 40 mL acetic acid. The solution was then heated to 78° C. for 4 hr. Solvents were removed under vacuum, 150 mL DCM was added and the solution was washed using aqueous $NaHCO_3$ (3×125 mL) followed by a brine wash (1×125 mL). The organic layer was dried over $Na_2SO_4$, then the solvent was removed under vacuum, leaving 3.57 g of (E)-1-bromo-5-methoxy-4-(2-nitrovinyl)-2-(trifluoromethoxy)benzene (3) as a brown-red oil.

To a purged, dry flask under $N_2$ atmosphere and chilled to <10° C., was added 30 mL 1 M lithium aluminum hydride (LAH; 30.54 mmol) in tetrahydrofuran (THF). 750 μL concentrated $H_2SO_4$ was added dropwise while maintaining the reaction at <10° C. and allowed to stir for 10 min. 3.48 g (E)-1-bromo-5-methoxy-4-(2-nitrovinyl)-2-(trifluoromethoxy)benzene (3), dissolved in 15 mL THE was added dropwise, and the reaction brought to reflux and monitored via GC-MS. After 3 hr, the reaction was quenched using $Na_2SO_4 \cdot 10H_2O$, filtered, and the filter cake washed with additional THF. Solvent was removed under vacuum, leaving 2.6 g of the free base. 400 mg of the free base was dissolved in 5 mL IPA and 5 mL $Et_2O$, then the solution was acidified with concentrated HCl. The solvents were removed under vacuum leaving 150 mg of crude 2-(4-bromo-2-methoxy-5-(trifluoromethoxy)phenyl)ethan-1-amine hydrochloride (4; 2CB-5-$OCF_3$, compound I-C-30).

Example 15: Synthesis of Compounds of Formula (I-D)

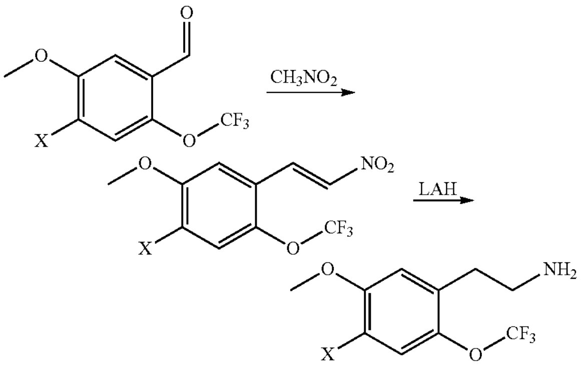

Certain compounds of Formula (I-D) are synthesized according to the following general procedure. In a first reaction step, a suitable precursor is reacted with nitromethane to produce a (E)-1-X-5-trifluoromethoxy-4-(2-nitrovinyl)-2-methoxybenzene intermediate. This reaction may proceed in the presence of a catalyst (e.g., ammonium acetate). The precursor may be commercially available. Alternatively, for certain compounds (e.g., wherein X=fluoro, chloro, bromo, iodo, or trifluoromethyl), the precursor is obtained by reacting 2-trifluoromethoxy-5-methoxybenzaldeyde precursor with a suitable reagent for directly substituting the benzene ring with a halogen or trifluoromethoxy group. For example, in the case where X is bromo, the precursor is obtained by reacting 2-trifluoromethoxy-5-methoxybenzaldehyde with a brominating agent (e.g., N-bromosuccinimide). In a second reaction step, the (E)-1-X-5-trifluoromethoxy-4-(2-nitrovinyl)-2-methoxybenzene intermediate is reacted with a reducing agent (e.g., lithium aluminum hydride) to yield a compound of Formula (1-D).

Example 16: Gas Chromatography Mass Spectrometry (GC-MS) Analysis of Disclosed Phenylalkylamines Throughout, reactions and final products were analyzed by GC/MS. Two instruments were used: GC1 was an HP 6890 GC with an HP 5973 single quadrupole mass spectrometer (MSD), running Agilent MSD Chemstation D.01.01; and GC2 was an HP 6890 with an Agilent 5973N MSD, running Agilent MSD Chemstation E.02.02. The spectrometers were tuned weekly using PFTBA (perfluorotertiarybutylamine), using the Agilent MSD Chemstation AutoTune routines. Samples were either free bases, or if crystalline salts, were dissolved in water, made basic, then extracted into DCM for GC injection as free bases. Sample concentrations were adjusted to approximately 1 mg/mL, and all sample injections were 1.0 μL, made with Agilent 7673 autosamplers.

GC1 was fitted with an Agilent Ultra-1, 0.20 mm×50 m×0.33 μM, 100% dimethylpolysiloxane column. The carrier gas was hydrogen at 9.0 psi, and an injector temperature of 250 C, operated in splitless mode. The purge time was 0.05 minutes, with a purge flow of 20.1 mL/min. The column oven ramp was initially at 50 C, with an 0.5 min hold, then ramped at 25.0 C/min to a final temperature of 320 C, which was held for 2.20 minutes. The MSD transfer line was set at 300 C, the MSD Source at 230 C, and the MSD Quads at 150 C. The MS was operated in full scan mode, from 40 to 500 amu.

GC2 was fitted with a J&W Scientific 122-1032, 0.10 mm×10 m×0.10 μM column, 100% dimethylpolysiloxane column. The carrier gas was hydrogen at 9.8 psi, and an injector temperature of 250 C, operated in split mode with a 20:1 split, split flow of 4.2 mL/min and total flow of 8.6 mL/min. The column oven ramp was initially at 45 C, with a 1.0 min hold, then ramped at 35.0 C/min to a final temperature of 280 C, which was held for 0.29 minutes. The MSD transfer line was set at 300 C, the MSD Source at 230 C, and the MSD Quads at 150 C. The MS was operated in full scan mode, from 40 to 400 amu.

GC-MS data for exemplary phenylalkylamines are provided in FIG. 1 to FIG. 4. The compounds had >98% purity by GC/MS, and the following fragments were observed:

FIG. 1 shows the experimental MS trace for 2C-B, for comparative purposes to aid in the identification of fragments. 2C-B (m/z): 44 (ethanamine fragment, 3.4%) 51 (14%) 63 (12%) 77 (benzene fragment, 35%) 91 (18%) 105 (16%) 121 (phenethylamine fragment, 9.5%) 133 (3.1%) 143 (5.2%) 157 (1.9%) 171 (4.3%) 186 (3.8%) 201 (10%) 215 (2-bromo-1,4-dimethoxy benzene fragment, 26%) 230 (1-bromo-5-methoxy-2-(methoxy)-4-methylbenzene fragment, 100%) 242 (0.9%) 259 (molecular ion, 13%).

Figure 2:
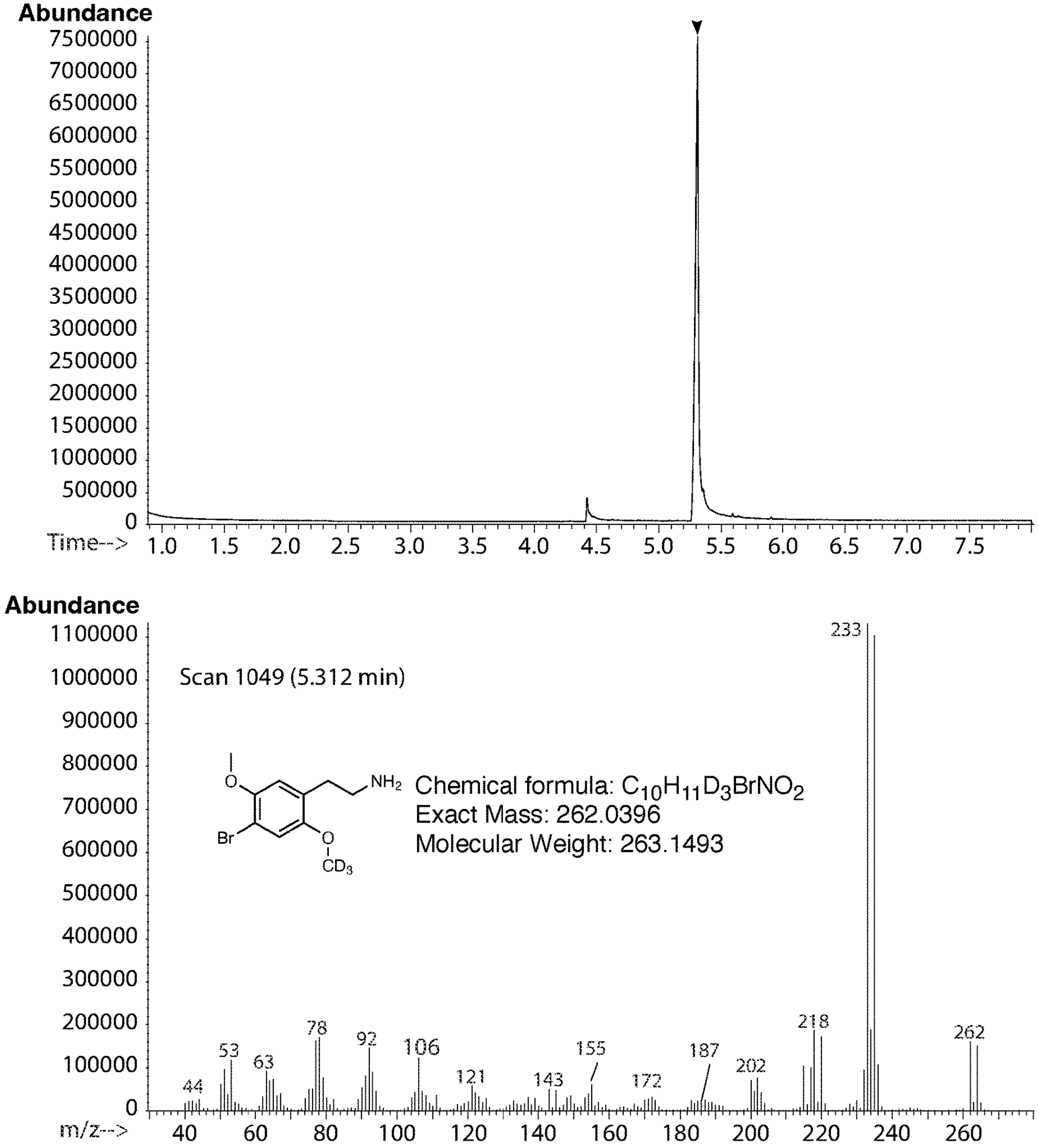
FIG. 2 shows the experimental MS data for 2C-B-2-$OCD_3$ (2-(4-bromo-2-(methoxy-$d_3$)-5-methoxyphenyl) ethanamine), which is referred to herein as compound I-B-31.

FIG. 2 shows the experimental MS trace for 2CB-2-$OCD_3$ (compound I-B-31) (m/z): 44 (ethanamine fragment, 2.0%) 53 (10%) 63 (8.1%) 78 (benzene fragment, 15%) 92 (13%) 106 (11%) 121 (phenethylamine fragment, 5.1%) 143 (4.4%) 155 (5.3%) 172 (2.8%) 187 (2.2%) 202 (6.7%) 218 (2-bromo-1-methoxy-4-(methoxy-$d_3$)benzene fragment, 16%) 233 (1-bromo-5-methoxy-2-(methoxy-$d_3$)-4-methylbenzene fragment, 100%) 262 (molecular ion, 14%).

Figure 3:
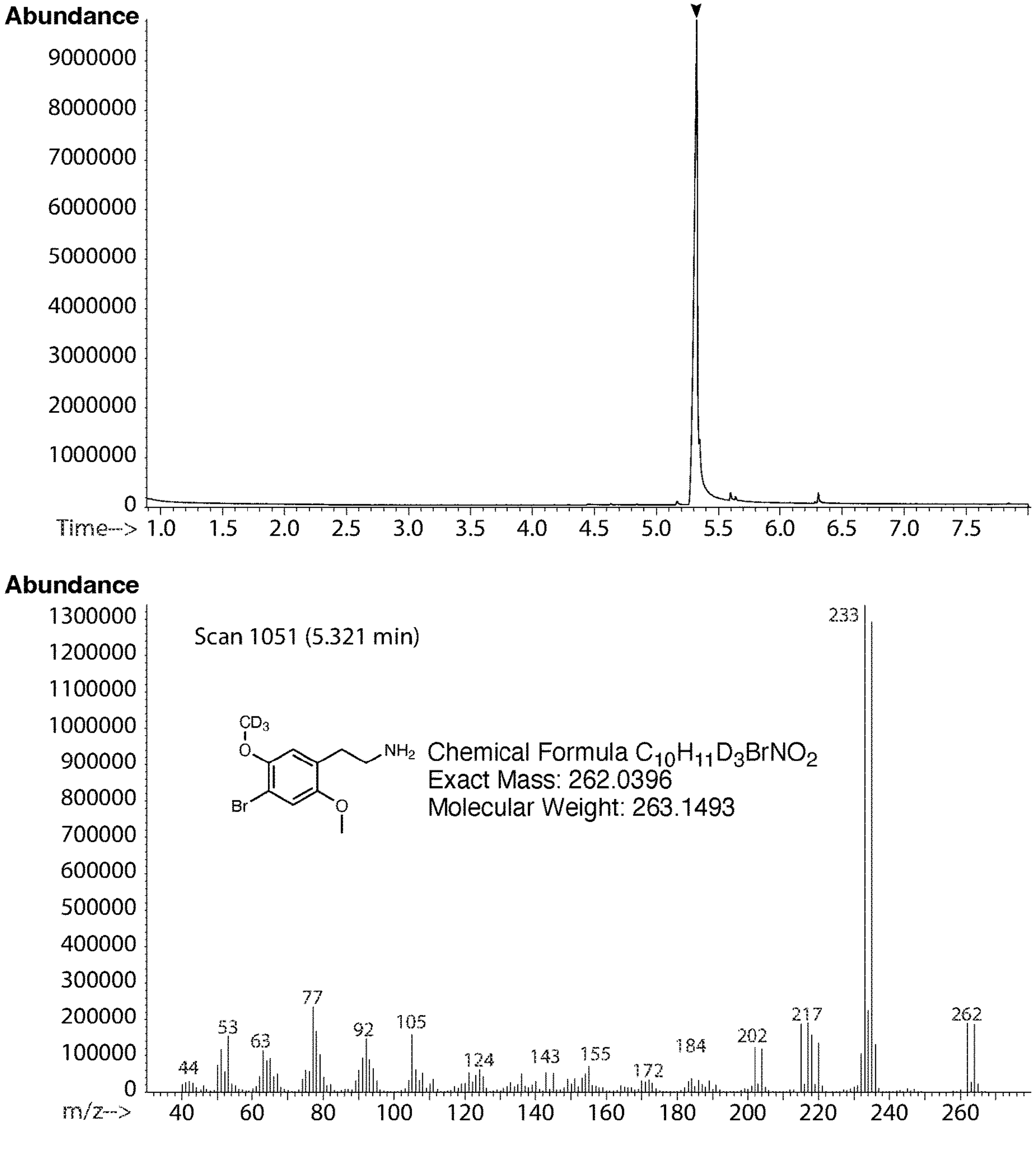
FIG. 3 shows the experimental MS data for 2C-B-5-$OCD_3$ (2-(4-bromo-2-methoxy-5-(methoxy-$d_3$)-phenyl) ethanamine), which is referred to herein as compound I-A-31.

FIG. 3 shows the experimental MS trace for 2CB-5-$OCD_3$ (compound I-A-31) (m/z): 44 (ethanamine fragment, 2.0%) 53 (11%) 63 (8.0%) 77 (17%) 92 (10%) 105 (11%) 124 (4.2%) 143 (3.7%) 155 (1-methoxy-4-(methoxy-d3)-2-methylbenzene fragment, 4.9%) 172 (2.5%) 184 (2.5%) 202 (8.8%) 217 (2-bromo-4-methoxy-1-(methoxy-$d_3$)benzene fragment, 14%) 233 (1-bromo-5-methoxy-2-(methoxy-$d_3$)-4-methylbenzene fragment, 100%) 262 (molecular ion, 14%).

Figure 4:
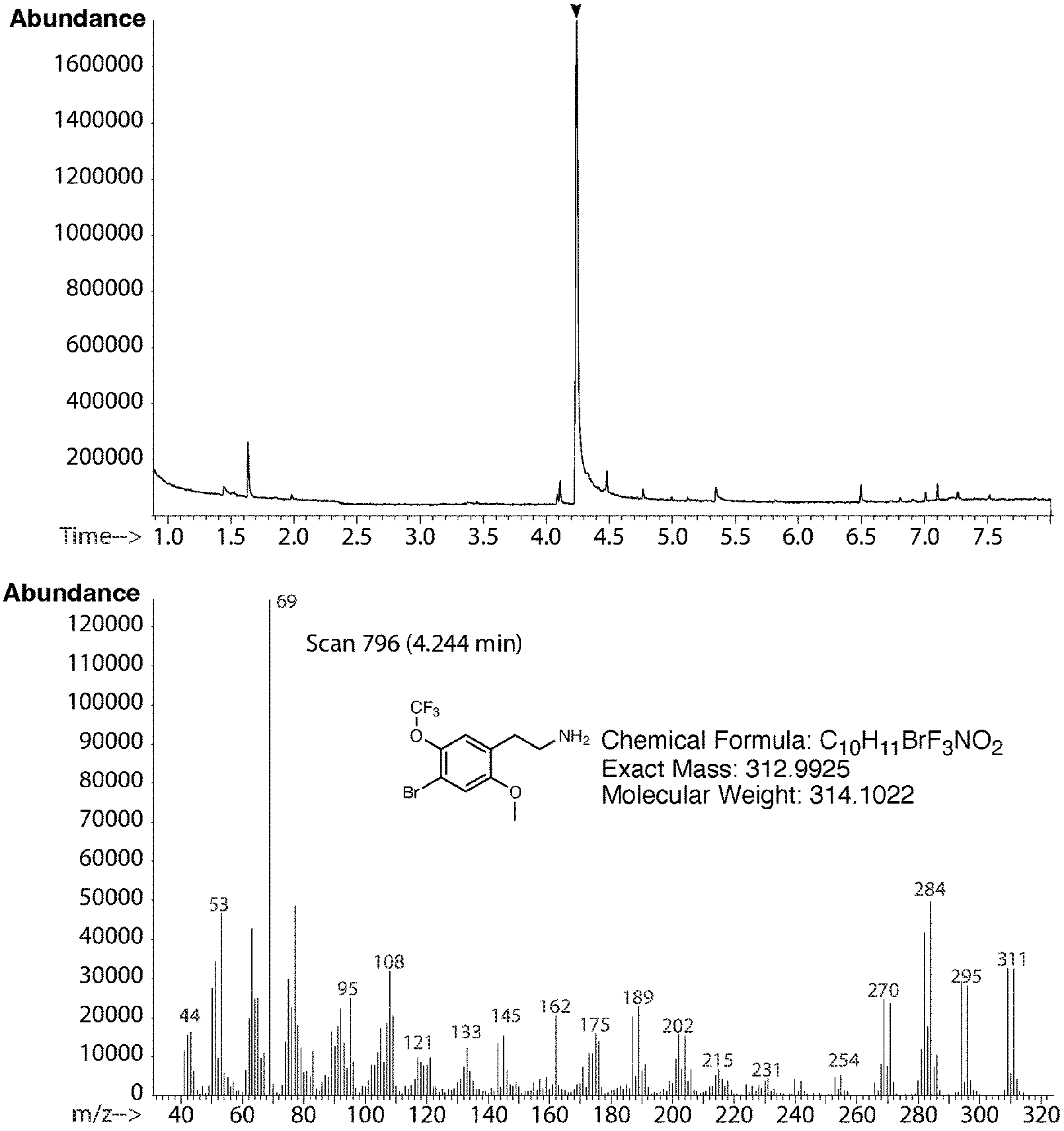
FIG. 4 shows the experimental MS data for 2C-B-5-$OCF_3$ (2-(4-bromo-2-methoxy-5-trifluoromethoxy-phenyl) ethanamine), which is referred to herein as compound I-C-30.
Figure 5:
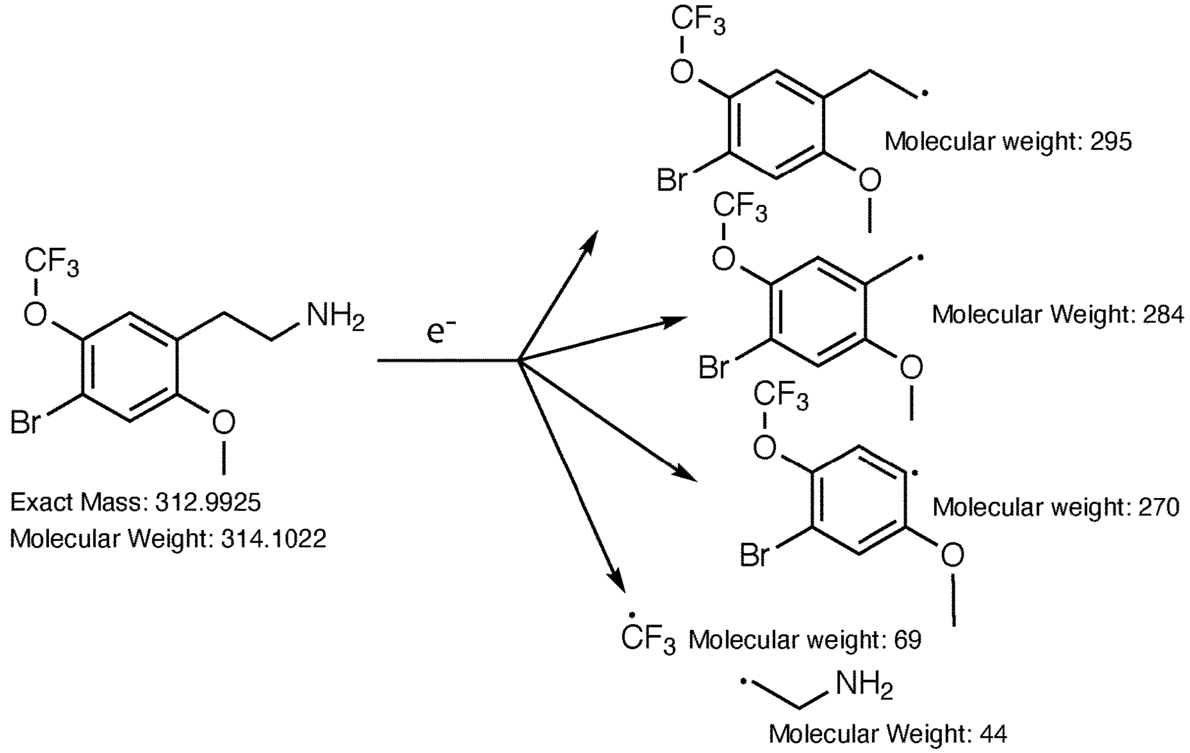
FIG. 5 is a schematic representation of the observed molecular fragments of 2C-B-5-$OCF_3$ (compound I-C-30).

FIG. 4 shows the experimental MS trace for 2CB-5-$OCF_3$ (compound I-C-30) (m/z): 44 (ethanamine fragment, 16%) 53 (36%) 69 (trifluoromethyl fragment, 100%) 95 (28%) 108 (33%) 121 (7.7%) 134 (5.0%) 145 (15%) 162 (22%) 175 (19%) 189 (24%) 202 (16%) 215 (6.0%) 231 (4.2%) 254 (1.2%) 270 (2-bromo-4-methoxy-1-(trifluoromethoxy)benzene fragment, 6.4%) 284 (57%) 295 (1-bromo-4-ethyl-5-methoxy-2-(trifluoromethoxy)benzene fragment, 3.6%) 311 (34%). FIG. 5 is a schematic representation of the observed fragmentation pattern of 2C-B-5-$OCF_3$ (compound I-C-30).

Example 17: Functional Activity of Disclosed Phenylalkylamines

Purpose: A comprehensive study is conducted to profile the interactions of disclosed phenylalkylamines with various receptors, including serotonin receptors, monoamine transporters, enzymes, such as monoamine oxidase A, and ion channels. Such activity is determined to assess potential neuromodulatory activity and safety liabilities.

Methods—Arrestin:

The PathHunter® β-Arrestin assay is used to assess activation of serotonin receptors, such as $HTR_{5A}$ and $HTR_6$. The assay monitors restoration of β-galactosidase (β-Gal) as a marker of GPCR activation and recruitment of β-Arrestin to the receptor.

To determine agonistic activity, cells are expanded from freezer stocks, seeded into multi-well plates, and incubated at 37° C. prior to addition of a test compound. 3.5 μL of concentrated sample is added to cells and incubated at 37° C. or room temperature for 90 to 180 minutes. Vehicle concentration is 1%.

Assay signal is generated through a single addition of 50% v/v of PathHunter Detection reagent cocktail, followed by a one hour incubation at room temperature. Microplates are read following signal generation with a plate reader set to detect chemiluminescent signals. Compound activity is analyzed using CBIS data analysis suite (ChemInnovation, CA).

Percentage activity is calculated using the following formula:

$$\%\ \text{Activity} = 100\%\times(\text{mean } RLU \text{ of test sample} - \text{mean } RLU \text{ of vehicle control})/(\text{mean MAX control ligand} - \text{mean } RLU \text{ of vehicle control}).$$

Methods—cAMP:

The HitHunter® cAMP assay is used to assess activity at neuromodulatory receptors, such as adrenergic and dopamine receptors. The assay monitors the activation of a GPCR via Gi and Gs secondary messenger signaling, using β-Gal as a functional reporter. To determine agonistic activity at Gi/Gs, cells are expanded from freezer stocks, seeded into multi-well plates, and incubated at 37° C. prior to addition of a test compound. To determine Gi/Gs agonism, media is aspirated from cells and replaced with 15 μL 2:1 HBSS/10 mM HEPES:cAMP XS+Ab reagent. Concentrated (4×) test compound in assay buffer is added to cells and incubated at 37° C. or room temp. for 30 or 60 minutes. For Gi agonist activation, cells are incubated with EC80 forskolin in addition to a test compound. Vehicle concentration is 1%.

Compound activity is analyzed using CBIS data analysis suite (ChemInnovation, CA). For Gs agonist mode assays, percentage activity is calculated using the following formula: % Activity=100%×(mean RLU of test sample−mean RLU of vehicle control)/(mean RLU of MAX control−mean RLU of vehicle control).

For Gi agonist mode assays, percentage activity is calculated using the following formula: % Activity=100%×(1−(mean RLU of test sample−mean RLU of MAX control)/(mean RLU of vehicle control−mean RLU of MAX control)).

Methods—Calcium Mobilization:

GPCR activity of serotonin receptors, for example, 2A ($HTR_{2A}$) and 2B ($HTR_{2B}$), among others, is measured using the Calcium No WashPLUS assay, which monitors calcium mobilization in cell lines expressing Gq-coupled GPCRs by loading a calcium-sensitive dye into cells. Activation of the GPCR results in the release of calcium from intracellular stores and an increase in dye fluorescence that can be measured.

Cell lines are expanded from freezer stocks and seeded into multi-well microplates. Then, the plates are incubated at 37° C. for an appropriate amount of time and loaded with Dye Loading buffer. To determine compound agonist activity, cells are incubated with the sample to induce a response, and HBSS/20 mM Hepes is added using a FLIPR Tetra (MDS). Activity is measured on a FLIPR Tetra. Calcium mobilization is monitored for 2 minutes.

To determine compound antagonist activity, cells are pre-incubated with the sample followed by a post-incubation administration of the compound with 3×EC80 agonist using FLIPR. Compound antagonist activity is measured on a FLIPR Tetra (MDS) and calcium mobilization is monitored for 2 minutes.

Compound activity is analyzed using CBIS data analysis suite (ChemInnovation, CA). For agonist mode assays, percentage activity is calculated using the following formula: % Activity=100%×(mean RFU of test sample−mean RFU of vehicle control)/(mean MAX RFU control ligand−mean RFU of vehicle control).

For antagonist mode assays, percentage inhibition is calculated using the following formula: % Inhibition=100%×(1−(mean RFU of test sample−mean RFU of vehicle control)/(mean RFU of EC80 control−mean RFU of vehicle control)).

Methods—Monoamine Transporter Assay:

Neurotransmitter uptake via transporters is measured using the Neurotransmitter Transporter Uptake Assay Kit from Molecular Devices. Dopamine (DAT), norepinephrine (NET), or serotonin transporter (SERT) activity in cells is detected using a homogeneous fluorescence based assay. Increased intracellular fluorescence intensity following uptake of biogenic amine neurotransmitters via transporters is measured and can be run in a kinetic or endpoint mode.

To determine percentage inhibition of neurotransmitter uptake via transporter, cell lines are expanded from freezer stocks, seeded into a multi-well microplate, and incubated at 37° C. Compound is added and the mixture is incubated. Following compound incubation, dye is added to the wells and the plate is re-incubated. Microplates are then transferred to a PerkinElmer Envision™ instrument for fluorescence signal detection.

Compound activity is analyzed using CBIS data analysis (ChemInnovation, CA). For blocker mode assays, percentage inhibition is calculated using the following formula: % Inhibition=100%×(1−(mean RLU of test sample−mean RLU of vehicle control)/(mean RLU of positive control−mean RLU of vehicle control)).

Methods—Enzyme Assays:

Enzymatic activity is determined by measuring either the consumption of substrate or production of product over time. For MAO-A (Sigma), enzyme and test compound are preincubated for 15 minutes at 37° C. before substrate addition. The reaction is initiated by addition of kynuramine and incubated at 37° C. for 30 minutes. The reaction is terminated by addition of NaOH. The amount of 4-hydroxyquinoline formed is determined through spectrofluorimetric readout with the emission detection at 380 nm and excitation wavelength 310 nm.

Methods—Ion Channel Assay:

Membrane potential changes are measured using the FLIPR® Membrane potential Assay Kit. A fluorescent indicator dye in combination with a quencher is used to reflect real-time membrane potential changes associated with ion channel activation and ion transporter proteins. Calcium channel CAV1.2, potassium channel hERG, and sodium channel NAV1.5 were tested.

To determine agonist and antagonist activity, cell lines are expanded from freezer stocks, seeded into multi-well microplates, and incubated at 37° C. Cells are then loaded with dye and incubated again.

For agonist determination, cells are incubated with the sample a different dilutions to induce a response. For antagonist determination, cells are pre-incubated with the sample at different dilutions. Following dye administration, the sample is added to the cells in the presence of EC80 agonist and then re-incubated at room temperature in the dark.

Compound activity is analyzed using CBIS data analysis suite (ChemInnovation, CA). For agonist mode assays, percentage activity is calculated using the following formula: % Activity=100%×(mean RLU of test sample−mean RLU of vehicle control)/(mean MAX control ligand−mean RLU of vehicle control).

For antagonist mode assays, percentage inhibition is calculated using the following formula: % Inhibition=100%×(1−(mean RLU of test sample−mean RLU of vehicle control)/(mean RLU of EC80 control−mean RLU of vehicle control)).

Results & Significance:

Serotonin Receptor Activity—

Disclosed phenylalkylamine compounds may exhibit agonist activity at $HTR_{2A}$. Such activity is indicative of potential hallucinogenic effects. See, e.g., Lŏpez-Gimenez & Gonzilez-Maeso, Curr Top Behav Neurosci. 2018; 36:45-73. Disclosed compounds may also show activity at other serotonin receptors (e.g., $HTR_{1A}$, $HTR_{1B}$, $HTR_{2B}$, $HTR_{5A}$, $HTR_6$, and $HTR_{7D}$).

Several therapeutic effects are mediated by the serotonin receptor system, including, for example, antidepressant and anxiolytic effects (Dos Santos et al., Journal of Psychopharmacology, 2021; 35(4):453-458), procognitive effects in the context of learning and memory (Woods et al., Br J Pharmacol. 2012; 167(2):436-449), and enhanced neural plasticity (Lukasiewicz et al., Front Mol Neurosci. 2021; 14:748359).

Additional Neuromodulatory Receptors—

Disclosed phenylalkylamine compounds may show antagonistic activity at at least one adrenergic receptor, such as $ADRA_{1A}$ or $ADRA_{2A}$. The adrenergic receptors are a class of GPCRs that are activated by catecholamines, such as norepinephrine and epinephrine. For reference, LSD and NBOMes have been shown to bind to adrenergic receptors with high affinity but appear to be associated with receptor activation and stimulatory effects (Rickli et al., Neuropharmacology, 2015; 99, 546-553).

Disclosed phenylalkylamine compounds may show agonistic activity for dopamine receptor D2 short isoform ($DRD_{2S}$). LSD has been shown to bind with high affinity (nanomolar $K_i$) to dopamine receptors D1, D2, and D3, whereas other psychoactive agents, such as psilocybin, DMT, and others have affinity at the micromolar level or effectively lack affinity for dopamine receptors (Rickli et al., Neuropsychopharmacol, 2016; 26(8), 1327-1337).

Disclosed phenylalkylamine compounds may show antagonistic effects at histamine receptor H1 (HRH). In relation to other psychedelics, certain NBOMe compounds have high affinity for HRH1 (nanomolar Ki) (Rickli et al., Neuropharmacol, 2015; 99, 546-553). The central histamine system is involved in many brain functions such as arousal and waking, pain perception, control of pituitary hormone secretion, appetite suppression, and cognitive functions. See, e.g., Nuutinen & Panula, Adv Exp Med Biol. 2010; 709:95-107.

Monoamine Transporter Inhibition—

Disclosed phenylalkylamine compounds may show potency for inhibiting uptake activity of SERT. Inhibiting the uptake activity of the monoamine transporter can increase circulating levels of serotonin and thereby increase neuromodulatory activity of the monoamine neurotransmitter. Inhibition of monoamine transporters DAT, NET, and SERT are known to produce antidepressive effects (Perona et al. Behav Pharmacol. 2008; 19(5-6):566-574).

MAO-A Inhibition—

Disclosed phenylalkylamine compounds may inhibit MAO-A. MAO-A is a member of the monoamine oxidase family of enzymes that oxidize monoamine neurotransmitters and structurally related compounds. The potential for oral bioavailability is one implication of disclosed compounds not acting as substrates for MAO-A. For context, DMT is known to be rapidly degraded by MAO enzymes, and oral bioavailability can be achieved by co-administering the compounds with monoamine oxidase inhibitors (MAOIs). Additionally, co-administration of agents that increase serotonin levels, such as SERT inhibitors and MAOIs have been shown to potentiate serotonin neuromodulation, a potential complication of which is serotonin syndrome. See, e.g., Izumi et al., Eur J Pharmacol. 2006; 532(3):258-64, Nakagawasai et al., Neurotoxicology. 2004; 25(1-2):223-32, and Tadano et al., J Pharmacol Exp Ther. 1989; 250(1):254-60.

Ion Channel Inhibition: Inhibition of calcium channel CAV1.2, hERG potassium channel, and sodium channel NAV1.5 may indicate possible cardiac liabilities, such as irregular heartbeat and complications thereof. See, e.g., Redfern et al., Cardiovasc Res. 2003; 58(1):32-45

Example 18: Metabolic Stability

Purpose:

To determine the metabolic stability of disclosed compounds. Metabolic stability assays measure the intrinsic clearance ($CL_{int}$) of a compound, providing data that can be used to calculate other key pharmacokinetic parameters such as bioavailability and half-life ($t_{1/2}$).

Methods:

A high-throughput assay is used to determine metabolic stability of disclosed compounds and undeuterated analogs thereof in various matrices, including human liver microsomes, using LCMS analysis to quantify the percent compound remaining after incubation. Briefly, the disclosed compound is mixed with liver microsomes and activated. Following this incubation, acetonitrile is added to terminate the reaction. Then, the samples are centrifuged and the supernatant is dried. The residue is reconstituted and analyzed using liquid chromatography-mass spectrometry. Pharmacokinetic parameters are calculated using a noncompartmental model. The half-life ($t_{1/2}$) is estimated from the slope of the initial linear range of the logarithmic curve of compound remaining (%) versus time, assuming first order kinetics.

Results & Significance:

Disclosed compounds may have increased clearance and reduced half-life relative to other psychedelic phenylalkylamines. Such features may provide advantages that facilitate use in the treatment applications described herein.

Figure 6:
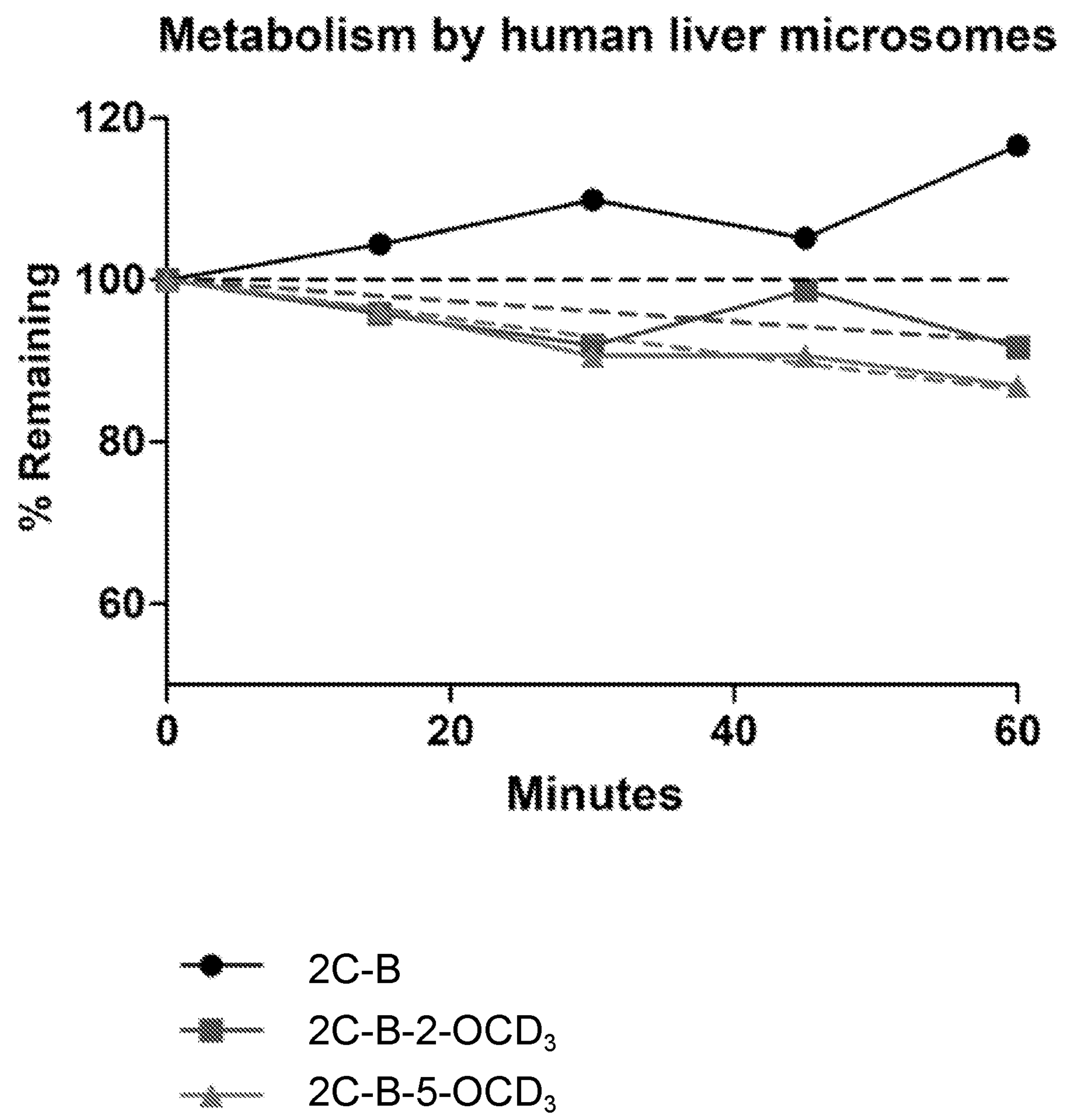
FIG. 6 shows the experimental data for in vitro metabolic stability of 2C-B compared with 2C-B-2-$OCD_3$ (compound I-B-31) and 2C-B-5-$OCD_3$ (compound I-A-31).

In one such assay of metabolic stability, percent of compound remaining was determined in human liver microsomes after 15, 30, 45, and 60 minutes of incubation, for 2C-B, 2C-B-2-$OCD_3$ (compound I-B-31), and 2C-B-5-$OCD_3$ (compound I-A-31). Results are provided in Table 29 below and in FIG. 6, and surprisingly demonstrate that both 2C-B-2-$OCD_3$ and 2C-B-5-$OCD_3$ are metabolized more quickly than 2C-B. Analysis via one-way ANOVA with Dunnett's post-test, compared to 2C-B as the control drug, is shown in Table 30 below, see, e.g., the results of Dunnett's multiple comparison test of 2-C—B to 2C-B-2-$OCD_3$ and 2C-B-5-$OCD_3$.

TABLE 29

| Percent of Compound Remaining Over Time | | | |
|---|---|---|---|
| Minutes | 2C-B | 2C-B-2-$OCD_3$ | 2C-B-5-$OCD_3$ |
| 0 | 100.0000 | 100.0000 | 100.0000 |
| 15 | 104.3970 | 95.8357 | 96.2535 |
| 30 | 109.8740 | 91.9169 | 90.6402 |
| 45 | 105.1500 | 98.7307 | 90.7021 |
| 60 | 116.6050 | 91.6972 | 86.9011 |

TABLE 30

Statistical Analysis of In Vitro Metabolic Stability Results

| One-way analysis of variance | |
|---|---|
| P value | 0.0022 |
| Significant (P < 0.05) | Yes |
| Number of groups | 3 |
| F | 10.64 |
| R square | 0.6395 |
| **Bartlett's test for equal variances** | |
| Bartlett's statistic (corrected) | 0.8842 |
| P value | 0.6427 |
| Significant (P < 0.05) | No |

| ANOVA Table | SS | df | MS |
|---|---|---|---|
| Treatment (between columns) | 576.7 | 2 | 288.3 |
| Residual (within columns) | 325.1 | 12 | 27.09 |
| Total | 901.7 | 14 | |

| Dunnett's Multiple Comparison Test | Mean Diff. | q | Significant (P < 0.05) | 95% CI of diff. |
|---|---|---|---|---|
| 2-C-B vs 2C-B-2-OCD3 | 11.57 | 3.514 | Yes | 3.332 to 19.81 |
| 2-C-B vs 2C-B-5-OCD3 | 14.31 | 4.346 | Yes | 6.068 to 22.54 |

Example 19: In Vitro Metabolic Profiling

Purpose:

To determine whether the disclosed compounds are metabolized and to identify metabolites thereof.

Methods:

An in vitro study is conducted to evaluate metabolism and metabolites of disclosed compounds in human liver microsomes, such as S9 hepatocytes. Briefly, disclosed compounds are incubated with human liver microsomes and/or various recombinant enzymes to determine metabolism and formation of metabolites. Following incubation, the supernatant is analyzed directly by ultra-high performance liquid chromatography-mass spectrometry.

Phase I and/or Phase II metabolites are identified using mass spectrometry (MS). The 00 compound remaining and half-life of the disclosed compound (parent compound) are determined. MS data, such as extracted ion chromatograms, show parent and major metabolites. Metabolic transformation for each observed metabolite is elucidated, and metabolite masses, peak areas, and retention times are determined.

Metabolic profiling may also be conducted according to the methods described in Muller & Rentsch, Anal Bioanal Chem, 2012; 402:2141-2151 and Pedersen et al., Drug Metab Dispos, 2013; 41:1247-1255.

Results & Significance:

Compounds that undergo metabolism in vivo may produce pharmacologically active or chemically reactive metabolites that produce unexpected effects or potential toxicities. The FDA Guidance for Industry on Safety Testing of Drug Metabolites highlights the relevance of in vitro metabolite profiling early in drug development, as metabolites which are unique to or disproportionate in humans may require additional toxicological studies.

Example 20: In Vitro CYP Enzyme Inhibition

Purpose:

To assess the interactions between disclosed compounds and cytochrome P450 (CYP450) enzymes. Such interactions will provide insight into metabolism-mediated drug-drug interactions, which can occur when a compound affects the pharmacokinetics, such as the absorption, distribution, metabolism, and excretion, of simultaneously administered drugs by altering the activities of drug metabolizing enzymes and/or drug transporters.

Methods:

An in vitro study is conducted to assess the inhibitory effect of the disclosed compound on recombinant human CYP450 isoenzymes. Recombinant human CYP450 isoenzymes are used to metabolize pro-fluorescent probe substrates to fluorescent products. Inhibition of human P450 isoforms is measured by reduced fluorescence following treatment with the disclosed compound at various concentrations.

Briefly, a disclosed compound is incubated in different concentrations in a mix containing buffer, enzymes, and substrate. Then, fluorescence is measured using a plate reader and percentage inhibition may be extrapolated out from the readings. Alternatively, the inhibitory effects of the disclosed compound on CYP enzymes may be assessed using high-performance liquid chromatography. Inhibition is evaluated using the Michaelis-Menten method. CYP enzyme inhibition may be conducted according to the methods described in Lin et al., J Pharm Sci. 2007 September; 96(9):2485-95 and Wójcikowski et al., Pharmacol Rep. 2020 June; 72(3):612-621.

Results & Significance:

Metabolizing enzymes in the liver, such as CYP450 enzymes, are responsible for the majority of drug metabolism that occurs in the body. Six CYP450 class enzymes metabolize 90 percent of drugs, and two of the most significant metabolizers are CYP3A4 and CYP2D6 (Lynch & Price, Am Fam Physician. 2007; 76(3):391-6). Compounds can interact with such enzymes by inhibiting their enzymatic activity (CYP inhibition) or by inducing their gene expression (CYP induction).

Example 21: In Vitro Evaluation of Membrane Permeability and Interactions with P-glycoprotein (P-gp) in MDCKII MDR1 Cells Purpose:

To assess the permeability and transport liability of disclosed compounds. Permeability is assessed using MDCK (Madin-Darby canine kidney) cells, and the effects of P-glycoprotein (P-gp) are evaluated to determine drug transport.

Methods:

A bidirectional permeability study (apical to basolateral [AB] and basolateral to apical [BA]) is conducted to evaluate the apparent permeability of the disclosed compound. Additionally, an evaluation to determine if the disclosed compound acts as a P-gp substrate in MDCKII-MDR1 and mock MDCKII cell lines is performed.

Briefly, the disclosed compound and reference compounds are evaluated in two directions in the absence and presence of a P-gp inhibitor. The MDCKII and MDCKII-MDR1 cells are incubated in a transport buffer on both apical [A] and basolateral [B] sides. Then, the disclosed compound is added to each side of the cells and incubated. The rate of transport of the disclosed compound is determined in the absence or presence of a P-gp inhibitor. Following incubation, where the disclosed compound will permeate the cells in both AB and BA directions, the permeability of the cells is measured using a LC MS/MS system. The efflux ratio of the disclosed compound is calculated to determine if it is a P-gp substrate.

Results & Significance:

This screening provides insight into the movement of the disclosed compound in a biological system. Compounds are classified as follows (Cambridge MedChem Consulting, ADME, 2019):

| Papp (nm/s) | Classification |
|---|---|
| >150 | High Permeability |
| 50-150 | Medium Permeability |
| <50 | Low Permeability |

Mass balance as a percentage (%) is calculated using the following equation:

$$\% \text{ Recovery} = 100 \times (CD(t) + CR(t)) / C_0$$

Where CD(t) is the measured concentration in the donor well at time t (expressed as IS ratio), CR(t) is the measured concentration in the receiver well at time t (expressed as IS ratio), Co is the initial concentration in the donor solution (expressed as IS ratio).

The percentage of cell integrity is calculated using the following equation:

$$\% \text{ Integrity} = 100 \times [1 - RFUbasolateral / RFUapical]$$

LY RFU values are normalized by background mean values. A test item is considered to be a P-gp substrate when the efflux ratio in the absence of the inhibitor is >2 and if the ratio is significantly reduced in the presence of a P-gp inhibitor.

Example 22: In Vitro Activity at Trace Amine-Associated Receptor 1 (TAAR1)

Purpose:

To assess the activity of disclosed compounds at trace amine-associated receptor 1, a target of psychoactive substances. See, e.g., Rickli et al., Neuropsychopharmacology, 2016; 26(8), 1327-1337, Simmler et al., Br J Pharmacol. 2013 January; 168(2): 458-470, and Simmler et al., Journal of Pharmacology and Experimental Therapeutics, 2016; 357(1):134-144.

Methods:

A radioligand binding assay is performed according to previously described methods, for example, by Rickli et al., Neuropsychopharmacology, 2016; 26(8), 1327-1337, using [3H] RO5166017 as a radiolabel and RO5166017 as a competitor. Briefly, membrane preparations of human embryonic kidney (HEK) 293 cells that overexpress TAAR1 receptors, for example, of human origin (Revel et al., PNAS, 2011; 108:8485-8490) are incubated with the radiolabeled selective ligand at concentrations equal to $K_d$. Ligand displacement by the compounds is then measured. Specific binding of the radioligand to the target receptor is defined as the difference between the total binding and nonspecific binding that is determined in the presence of selected competitors in excess.

Results & Significance:

Activation of TAAR1 has been shown to modulate monoaminergic neurotransmission. See, e.g., Revel et al., PNAS. 2011; 108(20):8485-8490. TAAR1 may be a promising target for the treatment of neuropsychiatric disorders. For example, the effects of TAAR1 activation on dopaminergic neurotransmission may provide therapeutic benefit for addiction, such as substance use disorders (Liu & Li, Front Pharmacol. 2018; 9:279).

Example 23: Head Twitch Response Assay

Purpose:

The mouse head-twitch response (HTR) is a behavioral test that reflects 5-$HT_{2A}$ receptor activation and can be predictive of psychedelic effects in humans (Halberstadt et al., J Psychopharmacol. 2011; 25(11): 1548-1561). The HTR is widely used as a behavioral surrogate for human psychedelic effects for its ability to reliably distinguish psychedelic from non-psychedelic 5-$HT_{2A}$ receptor agonists (Halberstadt & Geyer, Psychopharmacol (Berl). 2013; 227(4):727-3).

Methods:

An HTR assay is performed in accordance with the methods described in Klein et al., Neuropharmacol, 2018; 142:231-239 to assess the effects of disclosed compounds in mice. Male C57BL/6 J mice (6-8 weeks old) are obtained and housed in a vivarium that meets all requirements for care and treatment of laboratory animals. Mice are housed up to four per cage in a climate-controlled room on a reverse-light cycle (lights on at 1900 h, off at 0700 h) and are provided with ad libitum access to food and water, except during behavioral testing. Testing is conducted between 1000 and 1800 h. All animal experiments are conducted in accordance with applicable guidelines and are approved by an appropriate animal care committee.

A head-mounted magnet and a magnetometer detection coil will be used to assess HTR, as previously described (Halberstadt & Geyer, Psychopharmacol (Berl). 2013; 227 (4):727-3, Halberstadt & Geyer, Neuropharmacol, 2014; 77:200-7; Nichols et al., ACS Chem Neurosci. 2015; 6(7): 1165-1175). Briefly, mice are anesthetized and a small neodymium magnet is attached to the dorsal surface of the cranium using dental cement. Following a two-week recovery period, HTR experiments are carried out in a well-lit room with at least 7 days between sessions to avoid carry-over effects.

Test compounds are dissolved in a suitable solvent, e.g., water containing 5% Tween 80, and administered IP at a volume of 5 or 10 mL/kg body weight immediately prior to testing. Different doses are tested to produce a dose-response curve. Compound or vehicle are administered to mice by oral gavage, and HTR activity is recorded in a glass cylinder surrounded by a magnetometer coil for 30 min. Alternatively, compound may be administered by injection. Coil voltage is low-pass filtered (2e10 kHz cutoff frequency), amplified, and digitized (20 kHz sampling rate) using a Powerlab/8SP with LabChart v 7.3.2 (ADInstruments, Colorado Springs, CO, USA), then filtered off-line (40e200 Hz band-pass).

Head twitches are identified manually based on the following criteria: 1) sinusoidal wavelets; 2) evidence of at least two sequential head movements (usually exhibited as bipolar peaks) with frequency 40 Hz; 3) amplitude exceeding the level of background noise; 4) duration <0.15 s; and 5) stable coil voltage immediately preceding and succeeding each response.

Head twitch counts will be analyzed using one-way analyses of variance (ANOVA). Post hoc pairwise comparisons between selected groups are performed using Tukey's studentized range method. The entire recordings are examined for head twitches. In some cases a shorter block of time is analyzed to accommodate compounds with a brief duration-of-action, as potency calculations can be confounded by extended periods of inactivity. ED50 values and 95% confidence limits are calculated using nonlinear regression. Relationships between HTR potency and binding affinities are assessed using linear regression and ordinary least-squares regression. For all analyses, significance is demonstrated by surpassing an $\alpha$-level of 0.05.

Results & Significance:

Results can be represented as $ED_{50}$ (mg/kg). The magnitude of such effects is also evaluated and compared amongst compounds. The occurrence and frequency of head twitches following administration of disclosed compounds provides insight into time to onset of subjective effects and whether such compounds produce psychedelic effects in humans.

Example 24: Assessing Subjective Effects of Disclosed Compounds

Purpose:

To assess the subjective effects of disclosed phenylalkylamines, such as the duration of such effects, following administration to a subject.

Methods:

A disclosed compound is administered to a subject, e.g., orally administered. Subjects are interviewed at predetermined time points following administration and/or asked to document subjective effects to determine the onset and duration of psychedelic effects. The psychedelic experience elicited by the compound, including, for example, onset and duration thereof, is assessed with any of the Peak Experience Scale (PES), such as described in Reckweg et al., Front Pharmacol. 2021; 12:760671, the Mystical Experience Questionnaire (MEQ), the Ego Dissolution Inventory (EDI), the Challenging Experience Questionnaire (CEQ), and the 5-Dimensional Altered States of Consciousness Questionnaire (5D-ASC), the Subjective Drug Effects Questionnaire (SDEQ), and the List of Complaints (LC) questionnaire.

In some embodiments, the subject suffers from a condition, such as a disease or disorder. In some embodiments, the disease or disorder is a mental health condition, a neurodegenerative condition, pain, e.g., a pain disorder, or inflammation, e.g., an inflammatory disorder. Psychotherapy may be provided in conjunction with administration of a disclosed compound.

Results & Significance:

Administering a disclosed compound to a subject will provide insight into subjective effects, including the duration, intensity, and quality of any psychedelic effects. Results will also be useful for discerning therapeutic effects and safety.

Unless otherwise stated, all measurements, values, ratings, positions, magnitudes, sizes, locations, orientations, configurations, and other specifications that are set forth (either expressly or impliedly) in this specification, including in the figures and in the claims that follow, are approximate, and not exact. They are intended to have a reasonable range that is consistent with the functions to which they relate and with what is customary in the art to which they pertain.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise forms disclosed; obviously, many modifications and variations are possible in view of the above teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A compound of Formula (A):

(A)

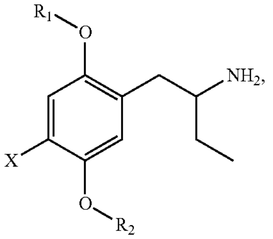

or an enantiomer or enantiomerically enriched mixture thereof, or a pharmaceutically acceptable salt, prodrug, hydrate, or solvate of any of the foregoing, wherein:

$R_1$ is —$CH_3$, —$CD_3$, or —$CF_3$;

$R_2$ is —$CH_3$, —$CD_3$, or —$CF_3$; and

X is —$CH_3$, —$CD_3$, or —$CF_3$;

provided that when both $R_1$ and $R_2$ are —$CH_3$, X is —$CD_3$ or —$CF_3$.

2. The compound of claim 1, having the structure of Formula (A-1), (A-2), or (A-3):

(A-1)

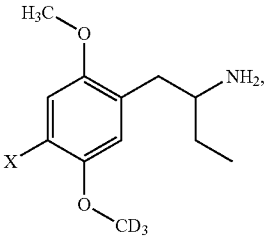

-continued (A-2)

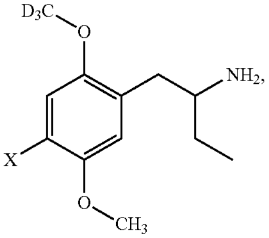

or (A-3)

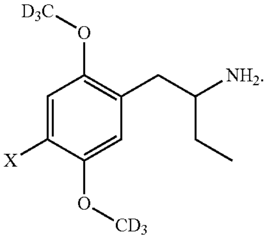

3. The compound of claim 1, having the structure of Formula (A-4), (A-5), or (A-6):

(A-4)

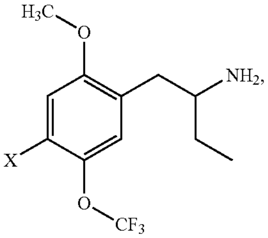

(A-5)

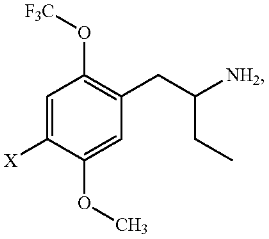

or (A-6)

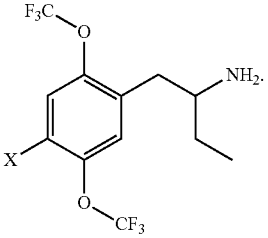

4. The compound of claim 1, having the structure of Formula (A-7) or (A-8):
(A-7)
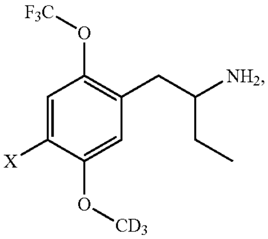
or
(A-8)
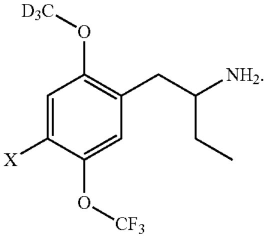
5. The compound of claim 1, having the structure of Formula (A-9):
(A-9)
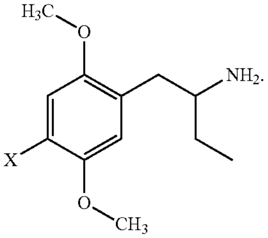
6. The compound of claim 2, having the structure of:
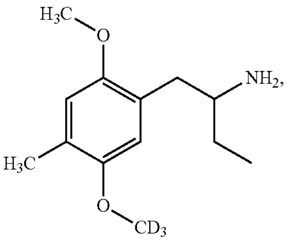
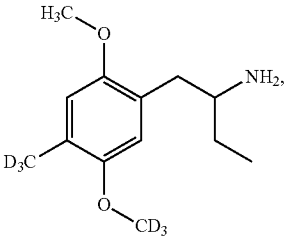
or
-continued
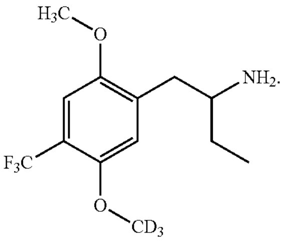
7. The compound of claim 2, having the structure of:
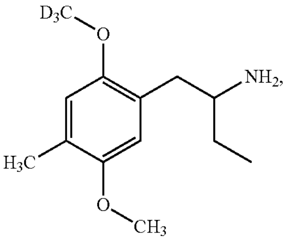
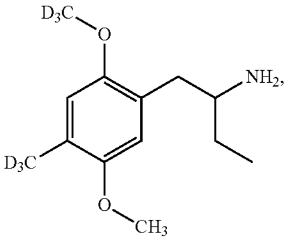
or
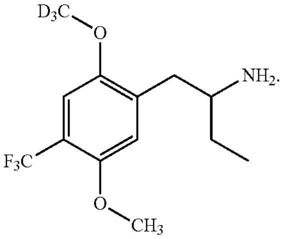
8. The compound of claim 2, having the structure of:
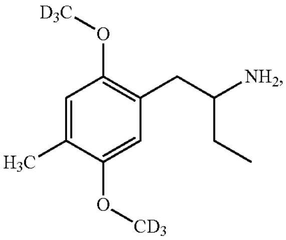
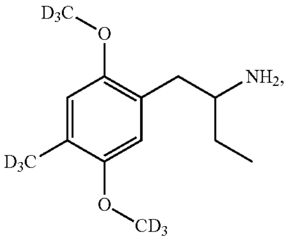
or -continued
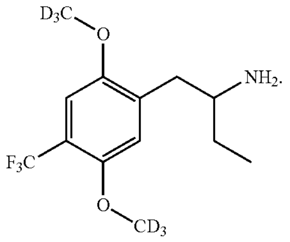
9. The compound of claim 3, having the structure of:
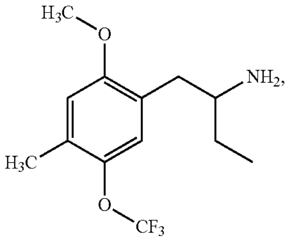
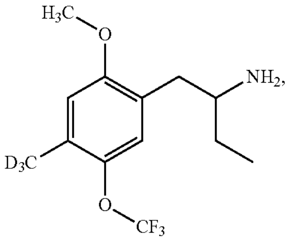
or
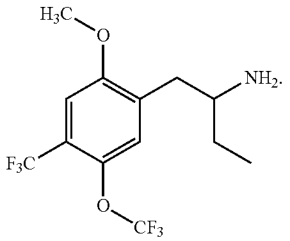
10. The compound of claim 3, having the structure of:
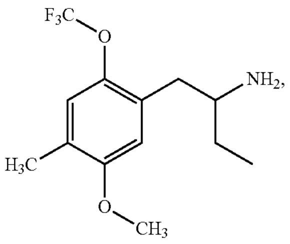
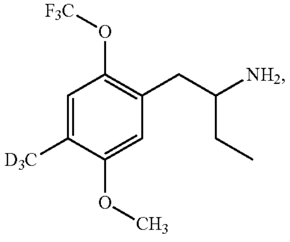
or
-continued
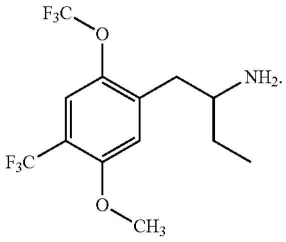
11. The compound of claim 3, having the structure of:
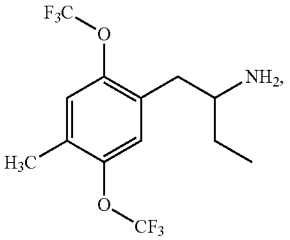
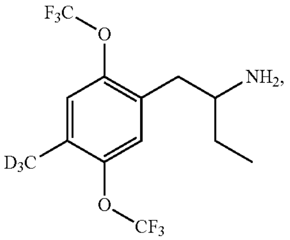
or
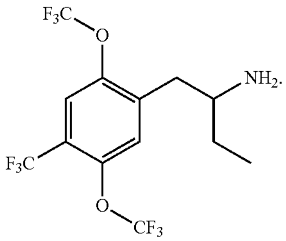
12. The compound of claim 4, having the structure of:
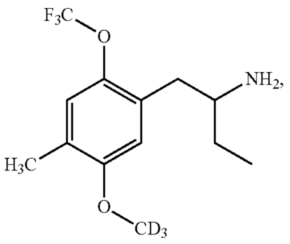
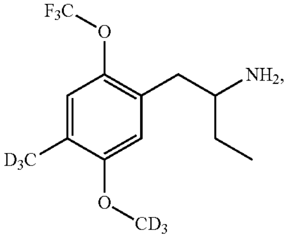
or -continued

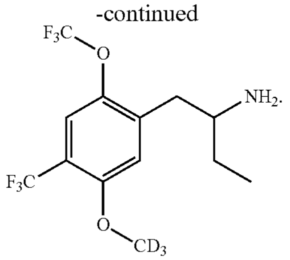

13. The compound of claim 4, having the structure of:

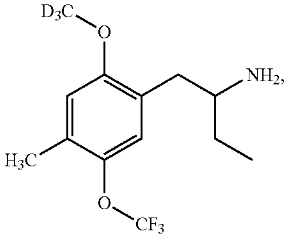

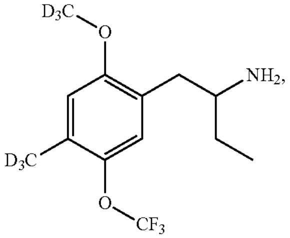 or

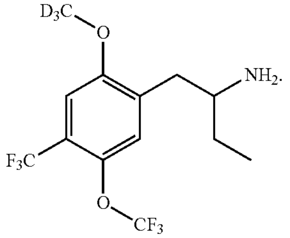

14. The compound of claim 5, having the structure of:

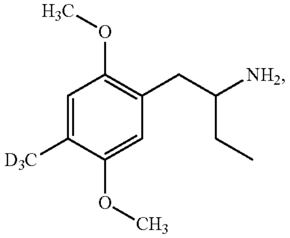 or

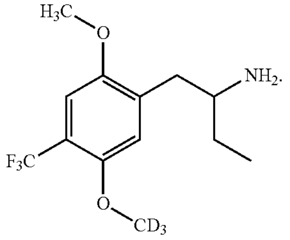

15. The compound of claim 2, having the structure of an (R)-enantiomer of Formula (A-1), (A-2), or (A-3):

(R)-(A-1)

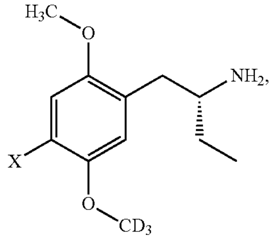

(R)-(A-2)

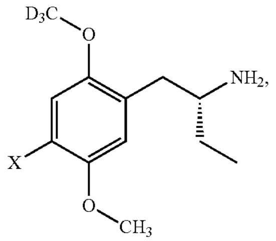 or (R)-(A-3)

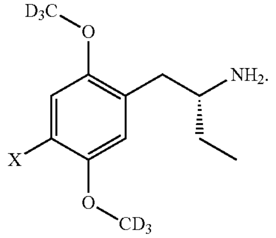

16. A pharmaceutical composition comprising a therapeutically effective amount of the compound of claim 1, and a pharmaceutically acceptable carrier, diluent, or excipient.

17. The pharmaceutical composition of claim 16, wherein the composition is in a unit dosage form.

18. The pharmaceutical composition of claim 17, wherein the unit dosage form is an immediate release formulation, a modified release formulation, a controlled release formulation, an extended release formulation, a sustained release formulation, or a delayed release formulation.

19. The pharmaceutical composition of claim 16, wherein the composition is formulated for oral, buccal, sublingual, inhalation, intranasal, injectable, or transdermal administration.

20. The pharmaceutical composition of claim 19, wherein the injectable administration is subcutaneous, intramuscular, or intravenous administration.

* * * * *